United States Patent
Heron et al.

(10) Patent No.: US 10,221,450 B2
(45) Date of Patent: Mar. 5, 2019

(54) ENZYME STALLING METHOD

(71) Applicant: OXFORD NANOPORE TECHNOLOGIES LIMITED, Oxford (GB)

(72) Inventors: Andrew John Heron, Oxford (GB); David Antoni Alves, Oxford (GB); James Anthony Clarke, Oxford (GB); Marion Louise Crawford, Oxford (GB); Daniel Ryan Garalde, Oxford (GB); Graham Hall, Oxford (GB); Daniel John Turner, Oxford (GB); James White, Oxford (GB)

(73) Assignee: Oxford Nanopore Technologies Ltd., Oxford (GB)

( * ) Notice: Subject to any disclaimer, the term of this patent is extended or adjusted under 35 U.S.C. 154(b) by 401 days.

(21) Appl. No.: 14/773,164

(22) PCT Filed: Jan. 22, 2014

(86) PCT No.: PCT/GB2014/050175
§ 371 (c)(1),
(2) Date: Sep. 4, 2015

(87) PCT Pub. No.: WO2014/135838
PCT Pub. Date: Sep. 12, 2014

(65) Prior Publication Data
US 2016/0010147 A1 Jan. 14, 2016

Related U.S. Application Data

(60) Provisional application No. 61/774,694, filed on Mar. 8, 2013.

(30) Foreign Application Priority Data

| Aug. 16, 2013 | (GB) | 1314695.6 |
| Oct. 18, 2013 | (GB) | 1318464.3 |
| Oct. 18, 2013 | (GB) | 1318465.0 |

(51) Int. Cl.
C12Q 1/68 (2018.01)
C12Q 1/6869 (2018.01)
(Continued)

(52) U.S. Cl.
CPC ............ *C12Q 1/6869* (2013.01); *C12N 9/14* (2013.01); *C12N 13/00* (2013.01); *C12Q 1/6827* (2013.01); *C12Y 306/04012* (2013.01)

(58) Field of Classification Search
None
See application file for complete search history.

(56) References Cited

U.S. PATENT DOCUMENTS 5,561,043 A 10/1996 Cantor et al.
5,777,078 A 7/1998 Bayley et al.
(Continued)

FOREIGN PATENT DOCUMENTS

CN 102245760 11/2011
EP 2682460 A1 1/2014
(Continued)

OTHER PUBLICATIONS

Suhasini et al, Cell Cycle, vol. 9, pp. 2317-2329, published online Jun. 15, 2010.*
(Continued)

*Primary Examiner* — Robert T. Crow
(74) *Attorney, Agent, or Firm* — Wolf, Greenfield & Sacks, P.C.

(57) ABSTRACT

The invention relates to new methods of moving helicases past spacers on polynucleotides and controlling the loading
(Continued)

of helicases on polynucleotides. The invention also relates to new methods of characterizing target polynucleotides using helicases.

12 Claims, 22 Drawing Sheets

Specification includes a Sequence Listing.

(51) Int. Cl.
*C12Q 1/6827* (2018.01)
*C12N 9/14* (2006.01)
*C12N 13/00* (2006.01)

(56) References Cited

U.S. PATENT DOCUMENTS

| | | | |
|---|---|---|---|
| 5,795,782 | A | 8/1998 | Church et al. |
| 5,817,771 | A | 10/1998 | Bayley et al. |
| 5,866,328 | A | 2/1999 | Bensimon et al. |
| 5,985,834 | A | 11/1999 | Engel et al. |
| 6,015,714 | A | 1/2000 | Baldarelli et al. |
| 6,087,099 | A | 7/2000 | Gupte et al. |
| 6,123,819 | A | 9/2000 | Peeters |
| 6,127,166 | A | 10/2000 | Bayley et al. |
| 6,251,610 | B1 | 6/2001 | Gupte et al. |
| 6,362,002 | B1 | 3/2002 | Denison et al. |
| 6,426,231 | B1 | 7/2002 | Bayley et al. |
| 6,451,563 | B1 | 9/2002 | Wittig et al. |
| 6,627,067 | B1 | 9/2003 | Branton et al. |
| 6,787,308 | B2 | 9/2004 | Balasubramanian et al. |
| 6,824,659 | B2 | 11/2004 | Bayley et al. |
| 6,863,833 | B1 | 3/2005 | Bloom et al. |
| 6,916,665 | B2 | 7/2005 | Bayley et al. |
| 6,927,070 | B1 | 8/2005 | Bayley et al. |
| 7,087,729 | B1 | 8/2006 | Prive |
| 7,189,503 | B2 | 3/2007 | Akeson et al. |
| 7,361,466 | B2 | 4/2008 | Korlach et al. |
| 7,507,575 | B2 | 3/2009 | Bedingham et al. |
| 8,105,846 | B2 | 1/2012 | Bayley et al. |
| 8,143,030 | B2 | 3/2012 | Maxham et al. |
| 8,343,746 | B2 | 1/2013 | Rank et al. |
| 8,383,369 | B2 | 2/2013 | Maxham et al. |
| 8,628,940 | B2 | 1/2014 | Sorenson et al. |
| 8,652,779 | B2 | 2/2014 | Turner et al. |
| 8,785,211 | B2 | 7/2014 | Bayley et al. |
| 8,822,160 | B2 | 9/2014 | Bayley et al. |
| 8,889,348 | B2 | 11/2014 | Ju |
| 9,057,102 | B2 | 6/2015 | Turner et al. |
| 9,116,118 | B2 | 8/2015 | Turner et al. |
| 9,145,623 | B2 | 9/2015 | Kavanagh et al. |
| 9,542,527 | B2 | 1/2017 | Travers et al. |
| 9,546,400 | B2 | 1/2017 | Turner et al. |
| 9,551,023 | B2 | 1/2017 | Turner et al. |
| 9,556,480 | B2 | 1/2017 | Turner et al. |
| 9,678,056 | B2 | 6/2017 | Turner et al. |
| 9,738,929 | B2 | 8/2017 | Turner et al. |
| 9,797,009 | B2 | 10/2017 | Heron et al. |
| 2002/0028458 | A1 | 3/2002 | Lexow |
| 2002/0094526 | A1 | 7/2002 | Bayley et al. |
| 2002/0098530 | A1 | 7/2002 | Pfeifer et al. |
| 2002/0197618 | A1 | 12/2002 | Sampson |
| 2003/0044816 | A1 | 3/2003 | Denison et al. |
| 2003/0059778 | A1 | 3/2003 | Berlin et al. |
| 2003/0087232 | A1 | 5/2003 | Christians et al. |
| 2003/0099951 | A1 | 5/2003 | Akeson et al. |
| 2003/0108902 | A1 | 6/2003 | Abarzua |
| 2003/0118595 | A1 | 6/2003 | Niemeyer et al. |
| 2003/0165936 | A1 | 9/2003 | Rabbani et al. |
| 2003/0166137 | A1 | 9/2003 | Zuker et al. |
| 2003/0211502 | A1 | 11/2003 | Sauer et al. |
| 2003/0215881 | A1 | 11/2003 | Bayley et al. |
| 2004/0055901 | A1 | 3/2004 | Petersen et al. |
| 2004/0214177 | A1 | 10/2004 | Bension |
| 2004/0229315 | A1 | 11/2004 | Lee et al. |
| 2005/0053961 | A1 | 3/2005 | Akeson et al. |
| 2005/0142559 | A1 | 6/2005 | Makrigiorgos |
| 2005/0221316 | A1 | 10/2005 | Pedersen et al. |
| 2005/0227239 | A1 | 10/2005 | Joyce |
| 2005/0260655 | A1 | 11/2005 | Liu et al. |
| 2006/0063171 | A1 | 3/2006 | Akeson et al. |
| 2006/0086626 | A1 | 4/2006 | Joyce |
| 2006/0141516 | A1 | 6/2006 | Kobold et al. |
| 2006/0292611 | A1 | 12/2006 | Berka et al. |
| 2007/0015182 | A1 | 1/2007 | Abarzua |
| 2007/0122885 | A1 | 5/2007 | Reeves et al. |
| 2007/0224613 | A1 | 9/2007 | Strathmann |
| 2008/0166724 | A1 | 7/2008 | Gerber et al. |
| 2008/0206252 | A1 | 8/2008 | Pennica et al. |
| 2008/0311582 | A1 | 12/2008 | Bayley et al. |
| 2009/0256116 | A1 | 10/2009 | Shumaker-Parry et al. |
| 2009/0280538 | A1 | 11/2009 | Patel et al. |
| 2009/0298075 | A1 | 12/2009 | Travers et al. |
| 2010/0003560 | A1 | 1/2010 | Shibata |
| 2010/0035260 | A1 | 2/2010 | Olasagasti et al. |
| 2010/0075309 | A1 | 3/2010 | Maxham et al. |
| 2010/0092960 | A1* | 4/2010 | Fehr .................... C12Q 1/6869 435/6.11 |
| 2010/0120098 | A1 | 5/2010 | Grunenwald et al. |
| 2010/0221212 | A1 | 9/2010 | Stagliano et al. |
| 2010/0276588 | A1 | 11/2010 | Syms |
| 2010/0331194 | A1 | 12/2010 | Turner et al. |
| 2011/0019186 | A1 | 1/2011 | Himmelhaus et al. |
| 2011/0136676 | A1 | 6/2011 | Greene |
| 2011/0177498 | A1 | 7/2011 | Clarke et al. |
| 2011/0214991 | A1 | 9/2011 | Kim et al. |
| 2011/0229877 | A1 | 9/2011 | Jayasinghe et al. |
| 2011/0281768 | A1 | 11/2011 | Travers et al. |
| 2011/0311965 | A1 | 12/2011 | Maglia et al. |
| 2012/0010085 | A1 | 1/2012 | Rava et al. |
| 2012/0058468 | A1 | 3/2012 | Mckeown |
| 2012/0100530 | A1 | 4/2012 | Moysey et al. |
| 2012/0107802 | A1 | 5/2012 | Stoddart et al. |
| 2013/0017978 | A1 | 1/2013 | Kavanagh et al. |
| 2013/0078624 | A1 | 3/2013 | Holmes et al. |
| 2013/0143802 | A1 | 6/2013 | Chilkoti |
| 2013/0195908 | A1 | 8/2013 | Leonetti et al. |
| 2013/0327644 | A1 | 12/2013 | Turner et al. |
| 2014/0051069 | A1 | 2/2014 | Jayasinghe et al. |
| 2014/0134629 | A1 | 5/2014 | Turner et al. |
| 2014/0186823 | A1 | 7/2014 | Clarke et al. |
| 2014/0206842 | A1 | 7/2014 | Majeed et al. |
| 2014/0255921 | A1 | 9/2014 | Moysey et al. |
| 2014/0262784 | A1 | 9/2014 | Clarke et al. |
| 2014/0296089 | A1 | 10/2014 | Holmes et al. |
| 2014/0308661 | A1 | 10/2014 | Holmes et al. |
| 2014/0335512 | A1 | 11/2014 | Moysey et al. |
| 2015/0008126 | A1 | 1/2015 | Maglia et al. |
| 2015/0031020 | A1 | 1/2015 | Jayasinghe et al. |
| 2015/0045257 | A1 | 2/2015 | Kavanagh et al. |
| 2015/0065354 | A1 | 3/2015 | Moysey et al. |
| 2015/0152492 | A1 | 6/2015 | Brown et al. |
| 2015/0167075 | A1 | 6/2015 | Turner et al. |
| 2015/0175663 | A1 | 6/2015 | Yokoi et al. |
| 2015/0191709 | A1 | 7/2015 | Heron et al. |
| 2015/0197796 | A1 | 7/2015 | White et al. |
| 2015/0218629 | A1 | 8/2015 | Heron et al. |
| 2015/0265994 | A1 | 9/2015 | Hyde et al. |
| 2015/0285781 | A1 | 10/2015 | Heron et al. |
| 2015/0307934 | A1 | 10/2015 | Turner et al. |
| 2016/0010148 | A1 | 1/2016 | Turner et al. |
| 2016/0011169 | A1 | 1/2016 | Turner et al. |
| 2016/0194677 | A1 | 7/2016 | Stoddart et al. |
| 2016/0257942 | A1 | 9/2016 | Bruce et al. |
| 2016/0281159 | A1 | 9/2016 | Brown et al. |
| 2016/0362739 | A1 | 12/2016 | Brown et al. |
| 2017/0002406 | A1 | 1/2017 | Bowen et al. |
| 2017/0067101 | A1 | 3/2017 | Clarke et al. |
| 2017/0240955 | A1 | 8/2017 | White |

(56) References Cited

U.S. PATENT DOCUMENTS

| | | |
|---|---|---|
| 2017/0321266 A1 | 11/2017 | Mckeown |
| 2018/0037874 A9 | 2/2018 | Bruce et al. |

FOREIGN PATENT DOCUMENTS

| | | |
|---|---|---|
| GB | 2130219 | 5/1984 |
| GB | 2237390 | 5/1991 |
| GB | 2453377 | 4/2009 |
| JP | H11-137260 | 5/1999 |
| WO | WO 94/23065 | 10/1994 |
| WO | WO 99/05167 | 2/1999 |
| WO | 00/028312 A1 | 5/2000 |
| WO | WO 01/40516 | 6/2001 |
| WO | WO 01/42782 | 6/2001 |
| WO | WO 01/59453 | 8/2001 |
| WO | 02/42496 | 5/2002 |
| WO | WO 03/095669 | 11/2003 |
| WO | WO 2005/056750 | 6/2005 |
| WO | 2005/124888 A1 | 12/2005 |
| WO | WO 2005/118877 | 12/2005 |
| WO | WO 2006/020775 | 2/2006 |
| WO | 2006/028508 A2 | 3/2006 |
| WO | 2006/100484 A2 | 9/2006 |
| WO | 2007/057668 A1 | 5/2007 |
| WO | WO 2007/075987 | 7/2007 |
| WO | WO 2007/084103 | 7/2007 |
| WO | WO 2007/146158 | 12/2007 |
| WO | WO 2008/045575 | 4/2008 |
| WO | WO 2008/083554 | 7/2008 |
| WO | 2008102120 A1 | 8/2008 |
| WO | 2008102121 A1 | 8/2008 |
| WO | WO 2008/124107 | 10/2008 |
| WO | 2009/035647 A1 | 3/2009 |
| WO | 2009/044170 A1 | 4/2009 |
| WO | 2009/077734 A2 | 6/2009 |
| WO | 2010/004265 A1 | 1/2010 |
| WO | 2010/004273 A1 | 1/2010 |
| WO | WO 2010/034018 | 3/2010 |
| WO | WO 2010/048605 A1 | 4/2010 |
| WO | WO 2010/051773 | 5/2010 |
| WO | 2010/086602 A1 | 8/2010 |
| WO | 2010/086603 A1 | 8/2010 |
| WO | WO 2010/086622 | 8/2010 |
| WO | WO 2010/094040 | 8/2010 |
| WO | 2010/109197 A2 | 9/2010 |
| WO | WO 2010/109107 A1 | 9/2010 |
| WO | 2010/122293 A1 | 10/2010 |
| WO | 2011/067559 A1 | 6/2011 |
| WO | WO 2012/033524 A2 | 3/2012 |
| WO | WO 2012/061832 | 5/2012 |
| WO | WO 2012/083249 A2 | 6/2012 |
| WO | WO 2012/098561 A2 | 7/2012 |
| WO | WO 2012/098562 A2 | 7/2012 |
| WO | WO 2012/103545 A1 | 8/2012 |
| WO | WO 2012/107778 A2 | 8/2012 |
| WO | 2012/164270 A1 | 12/2012 |
| WO | 2013014451 A1 | 1/2013 |
| WO | WO 2013/041878 A1 | 3/2013 |
| WO | 2013/057495 A2 | 4/2013 |
| WO | 2013/098561 A1 | 7/2013 |
| WO | 2013/098562 A2 | 7/2013 |
| WO | WO 2013/131962 A2 | 9/2013 |
| WO | 2013153359 A1 | 10/2013 |
| WO | WO 2013/185137 A1 | 12/2013 |
| WO | 2014/013259 A1 | 1/2014 |
| WO | 2014/013260 A1 | 1/2014 |
| WO | 2014/013262 A1 | 1/2014 |
| WO | WO 2014/108810 A2 | 7/2014 |
| WO | 2014/135838 A1 | 9/2014 |
| WO | WO 2015/022544 A1 | 2/2015 |
| WO | WO 2015/031909 A | 3/2015 |
| WO | WO 2015/055981 A2 | 4/2015 |
| WO | WO 2015/056028 A1 | 4/2015 |
| WO | WO 2015/110777 A1 | 7/2015 |
| WO | WO 2015/110813 A1 | 7/2015 |
| WO | WO 2015/189636 A1 | 12/2015 |
| WO | WO 2015/200609 A1 | 12/2015 |
| WO | WO 2016/003814 A1 | 1/2016 |

OTHER PUBLICATIONS

Lohman et al, Ann. Rev. Biochem, vol. 65, pp. 169-214 (1996).*
Fu et al, Cell, vol. 146, pp. 931-941, published Sep. 16, 2011.*
Activating signal cointegrator 1 complex subunit 3-like [Strongylocentrotus purpuratus]Database accession No. XP_003728286 abstract.
Altschul S. F., "A Protein Alignment Scoring System Sensitive at All Evolutionary Distances," Journal of Molecular Evolution, vol. 36, pp. 290-300 (1993).
Altschul, S.F., et al. "Basic Local Alignment Search Tool," J Mol Biol, vol. 215, pp. 403-410 (1990).
Braha, O. et al., "Designed Protein Pores as Components for Biosensors," Chemistry & Biology, vol. 4(7), pp. 497-505 (1997).
Cheng, Y. et al.,"Functional Characterization of the Multidomain F Plasmid TraI Relaxase-Helicase," The Journal of Biological Chemistry, vol. 286(14), pp. 12670-12682 (Apr. 8, 2001).
Database accession No. B4KAC8 sequence.
DEAD/DEAN box helicase Database accession No. I3D0E7 sequence.
Devereux, J. et al., "A Comprehensive Set of Sequence Analysis Programs for the VAX," Nucleic Acids Research, vol. 12 (1), pp. 387-395 (1984).
Fairman-Williams. M. E. et al., "SF1 and SF2 Helicases: family matters," Current Opinion in Structural Biology, vol. 20, pp. 313-324 (2010).
Garcillán-Barcia, M.P. et al., "The diversity of conjugative relaxases and its application in plasmid classification," FEMS Microbiol Rev. vol. 33(3), pp. 657-687 (2009).
Gonzalez-Perez, A. et al., "Biomimetic Triblock Copolymer Membrane Arrays: A Stable Template for Functional Membrane Proteins," Langmuir, vol. 25(18), pp. 10447-10450 (2009).
Grant, G. P. et al., "A facile method for attaching nitroxide spin labels at the 5' terminus of nucleic acids," Nucleic Acids Research, vol. 35(10), e77 (2007).
Green, N. et al., "Quantitative evaluation of the lengths of homobifunctional protein cross-linking reagents used as molecular rulers," Protein Science, vol. 10, pp. 1293-1304 (2001).
Hammerstein, A. et al., "Subunit Dimers of alpha-Hemolysin Expand the Engineering Toolbox for Protein Nanopores," The Journal of Biological Chemistry, vol. 286(16), pp. 14324-14334 (2001).
Holden, M. et al., "Functional Bionetworks from Nanoliter Water Droplets," J Am. Chem. Soc., vol. 129(27), pp. 8650-8655 (2007).
International Preliminary Report on Patentability, PCT/GB2014/050175, dated Sep. 8, 2015, pp. 1-7.
Ivanov, A.P. et al., "DNA Tunneling Detector Embedded in a Nanopore," Nano Letters, vol. 11(1), pp. 279-285 (2011).
Keyser, U.F., "Controlling Molecular Transport Through Nanopores," The Journal of Soc. Interface, vol. 8, pp. 1369-1378 (2011).
Kumar, A. et al., Nonradioactive Labeling of Synthetic Oligonucleotide Probes with Terminal Deoxynucleotidyl Transferase, Analytical Biochemistry, vol. 169, pp. 376-382 (1988).
Lieberman, K.R. et al., "Processive Replication of Single DNA Molecules in a Nanopore Catalyzed by phi29 DNA Polymerase," J. Am. Chem. Soc., vol. 132(50), pp. 17961-17972 (2010).
Liu, C. C. et al., "Adding New Chemistries to the Genetic Code," Annu. Rev. Biochem., vol. 79, pp. 413-444 (2010).
Liu, H. et al., "Structure of the DNA Repair Helicase XPD," Cell, vol. 133(5), pp. 801-812 (May 30, 2008).
Lohman, T. et al., "Non-hexameric DNA helicases and translocases: mechanisms and regulation," Nature Reviews Molecular Cell Biology, vol. 9, pp. 391-401 (2008).
Holden, M. et al., "Direct Introduction of Single Protein Channels and Pores into Lipid Bilayers," J. Am. Chem. Soc., vol. 127(18), pp. 6502-6503 (2005).
Montal, M. et al., "Formation of Bimolecular Membranes from Lipid Monolayers and a Study of Their Electrical Properties," PNAS, USA, vol. 69(12), pp. 3561-3566 (1972).

(56) References Cited

OTHER PUBLICATIONS

Nikolov, V. et al., "Behavior of Giant Vesicles with Anchored DNA Molecules," Biophysical Journal, vol. 92(12), pp. 4356-4368 (2007).
O'Shea, E. et al., "X-ray Structure of the GCN4 Leucine Zipper, a Two-Stranded, Parallel Coiled Coil," Science, vol. 254, pp. 539-544 (1991).
Pfeiffer, I. et al., "Bivalent cholesterol-based coupling of Oligonucletides to lipid membrane assemblies." J Am Chem Soc, vol. 126(33), pp. 10224-10225 (2004).
Predicted protein Database accession No. A4S1E1 sequence.
Press release: "Oxford Nanopore introduces DNA 'strand sequencing' on the high-throughput GridION platform and presents MinION, a sequencer the size of a USB memory stick," Feb. 2012.
Putative ski2-type helicase; EC=3.6.4.—Database accession No. E1QUS6 sequence.
Remaut, H. et al., "Protein-protein interaction through beta-strand addition," Trends in Biochemical Sciences, vol. 31 (8), pp. 436-444 (2006).
Richards, J. et al., "Structure of the DNA Repair Helicase Hel308 Reveals DNA Binding and Autoinhibitory Domains," The Journal of Biochemistry, vol. 283 (8), pp. 5118-5128 (2008).
Satapathy, A.K. et al., "ATPase activity of RecD is essential for growth of the Antarctic Pseudomonas Syringae Lz4W at low Temperature," The FEBS Journal, vol. 275(8), pp. 1835-1851 (2008).
Schneider, G. et al, "DNA Sequencing with Nanopores," Nature Biotechnology, vol. 30(4), pp. 326-328 (2012).
Soni G.V. et al., "Synchronous optical and electrical detection of biomolecules traversing through solid-state nanopores," Review of Scientific Instruments, vol. 81 (014301) 8 pages (2010).
Stoddart, D. et al., "Single-nucleotide discrimination in immobilized DNA oligonucleotides with a biological nanopore," PNAS, vol. 106(19), p. 7702-7707 (2009).
Troutt, A. B. et al., "Litigation-anchored PCR: A simple amplification technique with single-sided Specificity," PNAS, USA, vol. 89(20), pp. 9823-9825 (1992).
Tuteja, N. et al., "Unraveling DNA Helicases," Eur. J. Biochem, vol. 271, pp. 1849-1863 (2004).
Van Heel, M. et al., "Single-particle electron cryo-microscopy: towards atomic resolution," Quarterly Reviews of Biophysics, vol. 33 (4), pp. 307-369 (2000).
Van Lengerich, B. et al., "Covalent attachment of lipid vesicles to a fluid-supported bilayer allows observation of DNA-mediated vesicle interactions," Langmuir, vol. 26(11), pp. 8666-8672 (2010).
Venkatesan, B. et al., "Nanapore Sensors for Nucleic Acid Analysis," Nature Nanotechnology, vol. 6, pp. 615-624 (2011).
Vinson, V. et al., "Proteins in Motion," Science, vol. 324, p. 197 (2009).
Xiang, M. et al. "Bright functional rotaxanes," Chemical Society Reviews, vol. 39, pp. 70-80 (2010).
Yoshina-Ishii, C., et al., "Arrays of Mobile Tethered Vesicles on Supported Lipid Bilayers," J. Am. Chem. Soc., vol. 125 (13), pp. 3696-3697 (2003).
International Search Report and Written Opinion, PCT/GB2014/050175, May 9, 2014, 1-11.
[No Author Listed] HyperMu(TM)TransposonTools HyperMu(TM)<CHL-1>InsertionKit. Jan. 1, 2011. Retrieved from http://arb-ls.com/download/epi protocol/search/document/197p10611.pdf on Oct. 8, 2014.
[No Author Listed] Nucleic acid double helix, Wikipedia.com (accessed May 24, 2016).
[No Author Listed] PreCR Repair Mix—Product Information, FAQs, Protocols, Other Tools & Resources, Related Products etc. Jan. 1, 2010. Retrieved from https://www.neb.com/products/m0309-preer-repair-mix on Oct. 8, 2014.
[No Author Listed] Thermo Scientific Mutation Generation System Kit. Technical Manual. 2012.

Akeson et al., Microsecond time-scale discrimination among polycytidylic acid, polyadenylic acid, and polyuridylic acid as homopolymers or as segments within single RNA molecules. Biophys J. Dec. 1999;77(6):3227-33.
Alzubutas et al., MuA Transposase enzyme enables fast and easy DNA library preparation for next generation sequencing. Thermo Fisher Scientific. Jan. 1, 2012. Retrieved from URL:http://www.gene-quantification.de/qpcr-ngs-2013/posters/P013-qPCR-NGS-2013.pdf on May 18, 2017.
Amblard et al., Cu(I)-catalyzed Huisgen azide-alkyne 1,3-dipolar cycloaddition reaction in nucleoside, nucleotide, and oligonucleotide chemistry. Chem Rev. Sep. 2009;109(9):4207-20. doi:10.1021/cr9001462.
Ashkenasy et al., Recognizing a single base in an individual DNA strand: a step toward DNA sequencing in nanopores. Angew Chem Int Ed Engl. Feb. 18, 2005;44(9):1401-4.
Ashkenasy et al., Single Nucleobase Sensitivity of a-Hemolysin (a-HL) Transmembrane Protein Pore: Toward Single DNA Sequencing. ACS National Meeting. 2005;45(13), Abstract No. 74.
Astier et al., Stochastic detection of motor protein-RNA complexes by single-channel current recording. Chemphyschem. Oct. 22, 2007;8(15):2189-94.
Astier et al., Toward single molecule DNA sequencing: direct identification of ribonucleoside and deoxyribonucleoside 5'-monophosphates by using an engineered protein nanopore equipped with a molecular adapter. J Am Chem Soc. Feb. 8, 2006;128(5):1705-10.
Avrameas, Coupling of enzymes to proteins with glutaraldehyde. Use of the conjugates for the detection of antigens and antibodies. Immunochemistry. Jan. 1969;6(1):43-52.
Baker, De novo genome assembly: what every biologist should know. Nature methods. Apr. 2012;9(4):333-337.
Bayley et al., Stochastic sensors inspired by biology. Nature. Sep. 13, 2001;413(6852):226-30.
Bayley, Sequencing single molecules of DNA. Curr Opin Chem Biol. Dec. 2006;10(6):628-37. Epub Nov. 20, 2006.
Benner et al., Sequence-specific detection of individual DNA polymerase complexes in real time using a nanopore. Nat Nanotechnol. Nov. 2007;2(11):718-24. doi: 10.1038/nnano.2007.344. Epub Oct. 28, 2007.
Bowie et al., Deciphering the message in protein sequences: tolerance to amino acid substitutions. Science. Mar. 16, 1990;247(4948):1306-10.
Braha et al., Carriers versus adapters in stochastic sensing. Chemphyschem. May 2005;6(5):889-92.
Branton et al., The potential and challenges of nanopore sequencing. Nat Biotechnol. Oct. 2008;26(10):1146-53. doi:10.1038/nbt.1495.
Braslavsky et al., Sequence information can be obtained from single DNA molecules. Proc Natl Acad Sci U S A. Apr. 1, 2003;100(7):3960-4. Epub Mar. 21, 2003.
Budanova et al., Heptakis(6-amino-6-deoxy)-beta-cyclodextrin as a chiral selector for the separation of anionic analyte enantiomers by capillary electrophoresis. Electrophoresis. Aug. 2004;25(16):2795-800.
Burgess et al., Possible dissociation of the heparin-binding and mitogenic activities of heparin-binding (acidic fibroblast) growth factor-1 from its receptor-binding activities by site-directed mutagenesis of a single lysine residue. J Cell Biol. Nov. 1990;111(5 Pt 1):2129-38.
Busam, Structure of *Escherichia coli* exonuclease I in complex with thymidine 5'-monophosphate. Acta Crystallogr D Biol Crystallogr. Feb. 2008;64(Pt 2):206-10. doi: 10.1107/S090744490706012X. Epub Jan. 16, 2008.
Butler et al., Determination of RNA orientation during translocation through a biological nanopore. Biophys J. Jan. 1, 2006;90(1):190-9. Epub Oct. 7, 2005.
Butler et al., Single-molecule DNA detection with an engineered MspA protein nanopore. Proc Natl Acad Sci U S A. Dec. 30, 2008;105(52):20647-52. doi: 10.1073/pnas.0807514106. Epub Dec. 19, 2008.
Chan, Advances in sequencing technology. Mutat Res. Jun 3, 2005;573(1-2):13-40.

(56) References Cited

OTHER PUBLICATIONS

Cheley et al., A functional protein pore with a "retro" transmembrane domain. Protein Sci. Jun. 1999;8(6):1257-67.
Cheley et al., A genetically encoded pore for the stochastic detection of a protein kinase. Chembiochem. Dec. 2006;7(12):1923-7.
Cheley et al., Spontaneous oligomerization of a Staphylococcal alpha-hemolysin conformationally constrained by removal of residues that form the transmembrane beta-barrel. Protein Eng. Dec. 1997;10(12):1433-43.
Cheley et al., Stochastic sensing of nanomolar inositol 1,4,5-trisphosphate with an engineered pore. Chem Biol. Jul. 2002;9(7):829-38.
Chen et al., Atomic Layer Deposition to Fine-Tune the Surface Properties and Diameters of Fabricated Nanopores. Nano Lett. Jun 25, 2004;4(7):1333-1337.
Chen et al., Outer membrane protein G: Engineering a quiet pore for biosensing. Proc Natl Acad Sci U S A. Apr. 29, 2008;105(17):6272-7. doi: 10.1073/pnas.0711561105. Epub Apr. 28, 2008.
Clarke et al., Continuous base identification for single-molecule nanopore DNA sequencing. Nat Nanotechnol. Apr. 2009;4(4):265-70. doi: 10.1038/nnano.2009.12. Epub Feb. 22, 2009.
Cockroft et al., A single-molecule nanopore device detects DNA polymerase activity with single-nucleotide resolution. J Am Chem Soc. Jan. 23, 2008 ;130(3):818-20. doi: 10.1021/ja077082c. Epub Jan. 1, 2008.
Comai et al., Protein engineering modulates the transport properties and ion selectivity of the pores formed by Staphylococcal gamma-haemolysins in lipid membranes. Mol Microbiol. Jun. 2002 ;44(5):1251-67.
Comer et al., Microscopic mechanics of hairpin DNA translocation through synthetic nanopores. Biophys J. Jan. 2009;96(2):593-608. doi: 10.1016/j.bpj.2008.09.023.
Coros et al., Effect of mutations in the Mu-host junction region on transpososome assembly. J Mol Biol. Jul. 6, 2001;310(2):299-309.
Cudic et al., Binding of Nucleotides in Water by Phenathridinium Bis(intercaland) Receptor Molecules. J. Chem. Soc., Chem. Commun., pp. 1073-1075 (1995).
Dapprich, Single-molecule DNA digestion by lambda-exonuclease. Cytometry. Jul. 1, 1999;36(3):163-8.
Deamer et al., Characterization of nucleic acids by nanopore analysis. Acc Chem Res. Oct. 2002;35(10):817-25.
Deamer et al., Nanopores and nucleic acids: prospects for ultrarapid sequencing. Trends Biotechnol. Apr. 2000;18(4):147-51.
Deamer et al., Three decades of nanopore sequencing. Nat Biotechnol. May 6, 2016;34(5):51824. doi: 10.1038/nbt.3423.
Derrington et al., Nanopore DNA sequencing with MspA. Proc Natl Acad Sci U S A. Sep. 14, 2010;107(37):16060-5. doi: 10.1073/pnas.1001831107. Epub Aug. 26, 2010.
Dorre et al., Techniques for single molecule sequencing. Bioimaging, vol. 5:139-152 (1997).
Eid et al., Real-time DNA sequencing from single polymerase molecules. Science. Jan. 2, 2009;323(5910):133-8. doi:10.1126/science.1162986. Epub Nov. 20, 2008.
Eliseev et al., Aminocyclodextrins as Selective Hosts with Several Binding Sites for Nucleotides. Angew. Chem. Int. Ed. Engl., vol. 32(9):1331-1333 (1993).
Eliseev et al., Molecular Recognition of Nucleotides, Nucleosides, and Sugars by Aminocyclodextrins. J. Am. Chem. Soc., vol. 116:6081-6088 (1994).
El-Sagheer et al., Synthesis and polymerase chain reaction amplification of DNA strands containing an unnatural triazole linkage. J Am Chem Soc. Mar. 25, 2009;131(11):3958-64. doi: 10.1021/ja8065896.
Erie et al., A dumbbell-shaped, double-hairpin structure of DNA: a thermodynamic investigation. Biochemistry. Nov. 3, 1987;26(22):7150-9.
Flicek et al., Sense from sequence reads: methods for alignment and assembly. Nat Methods. Nov. 2009;6(11 Suppl):S6-S12. doi: 10.1038/nmeth.1376.
Flomenbom et al., Single stranded DNA translocation through a nanopore: a master equation approach. Phys Rev E Stat Nonlin Soft Matter Phys. Oct. 2003;68(4 Pt 1):041910. Epub Oct. 14, 2003.
Flusberg et al., Direct detection of DNA methylation during single-molecule, real-time sequencing. Nat Methods. Jun. 2010;7(6):461-5. doi: 10.1038/nmeth.1459. Epub May 9, 2010.
Genschel et al., Interaction of *E. coli* single-stranded DNA binding protein (SSB) with exonuclease I. The carboxy-terminus of SSB is the recognition site for the nuclease. Biol Chem. Mar. 2000;381(3):183-92.
Gershow et al., Recapturing and trapping single molecules with a solid-state nanopore. Nat Nanotechnol. Dec. 2007;2(12):775-9. doi:10.1038/nnano.2007.381. Epub Dec. 2, 2007.
Ghosal, Electrokinetic-flow-induced viscous drag on a tethered DNA inside a nanopore. Phys Rev E Stat Nonlin Soft Matter Phys. Dec. 2007;76(6 Pt 1):061916. Epub Dec. 26, 2007.
Gu et al., Capture of a single molecule in a nanocavity. Science. Jan. 26, 2001;291(5504):636-40.
Gu et al., Electroosmotic enhancement of the binding of a neutral molecule to a transmembrane pore. Proc Natl Acad Sci U S A. Dec. 23, 2003;100(26):15498-503. Epub Dec. 15, 2003.
Gu et al., Prolonged residence time of a noncovalent molecular adapter, beta-cyclodextrin, within the lumen of mutant alpha-hemolysin pores. J Gen Physiol. Nov. 2001;118(5):481-94.
Gu et al., Reversal of charge selectivity in transmembrane protein pores by using noncovalent molecular adapters. Proc Natl Acad Sci U S A. Apr. 11, 2000;97(8):3959-64.
Gu et al., Single molecule sensing by nanopores and nanopore devices. Analyst. Mar. 2010;135(3):441-51. doi: 10.1039/b907735a. Epub Dec. 22, 2009.
Gu et al., Stochastic sensing of organic analytes by a pore-forming protein containing a molecular adapter. Nature. Apr. 22, 1999;398(6729):686-90.
Guan et al., Stochastic sensing of TNT with a genetically engineered pore. Chembiochem. Oct. 2005;6(10):1875-81.
Gui-Jiang et al., Advances in next-generation sequencing technologies. Progress in Modern Biomedicine. 2012;12(19):3789-3793.
Han et al., Characterization and optimization of an entropic trap for DNA separation. Anal Chem. Jan. 15, 2002;74(2):394-401.
Han et al., RecJ exonuclease: substrates, products and interaction with SSB. Nucleic Acids Res. Feb. 18, 2006;34(4):1084-91. Print 2006.
Haque et al., Solid-State and Biological Nanopore for Real-Time Sensing of Single Chemical and Sequencing of DNA. Nano Today. Feb. 2013;8(1):56-74.
Heger, Nanopore Sequencing Makes Strides in 2010 as Technology Improves, Investment Grows. GenomeWeb. Jan. 11, 2011. Retrieved from https://www.genomeweb.com/sequencing/nanopore-sequencing-makes-strides-2010-technology-improves-investment-grows on Oct. 4, 2017.
Hein et al., Click chemistry, a powerful tool for pharmaceutical sciences. Pharm Res. Oct. 2008;25(10):2216-30. doi: 10.1007/s11095-008-9616-1. Epub May 29, 2008.
Henrickson et al., Driven DNA transport into an asymmetric nanometer-scale pore. Phys Rev Lett. Oct. 2, 2000;85(14):3057-60.
Heredia et al., In vitro double transposition for DNA identification. Anal Biochem. Apr. 1, 2010;399(1):78-83. doi:10.1016/j.ab.2009.11.030. Epub Nov. 26, 2009.
Hornblower et al., Single-molecule analysis of DNA-protein complexes using nanopores. Nat Methods. Apr. 2007;4(4):315-7. Epub Mar. 4, 2007.
Howorka et al., DNA Duplex Formation of Individual DNA Strands within a Single Protein Pore. Biophysical Journal, vol. 82{1, pt. 2):508a, No. 2482-Plat (2002).
Howorka et al., Improved protocol for high-throughput cysteine scanning mutagenesis. Biotechniques. Nov. 1998;25(5):764-6, 768, 770 passim.
Howorka et al., Kinetics of duplex formation for individual DNA strands within a single protein nanopore. Proc Natl Acad Sci U S A. Nov. 6, 2001;98(23):12996-3001. Epub Oct. 23, 2001.
Howorka et al., Probing distance and electrical potential within a protein pore with tethered DNA. Biophys J. Dec. 2002 ;83(6):3202-10.

(56) References Cited

OTHER PUBLICATIONS

Howorka et al., Sequence-specific detection of individual DNA strands using engineered nanopores. Nat Biotechnol. Jul. 2001;19(7):636-9.

Hu et al., Theory of DNA translocation through narrow ion channels and nanopores with charged walls. Phys Rev E Stat Nonlin Soft Matter Phys. Sep. 2008;78(3 Pt 1):032901. Epub Sep. 10, 2008.

Hwang et al., Electrical behavior of droplet interface bilayer networks: experimental analysis and modeling. J Am Chem Soc. Sep. 26, 2007;129(38):11854-64. Epub Sep. 1, 2007.

Jayasinghe et al., The leukocidin pore: evidence for an octamer with four LukF subunits and four LukS subunits alternating around a central axis. Protein Sci. Oct. 2005;14(10):2550-61.

Jung et al., The internal cavity of the Staphylococcal alpha-hemolysin pore accommodates approximately 175 exogenous amino acid residues. Biochemistry. Jun. 28, 2005;44(25):8919-29.

Kalisch et al., Covalently linked sequencing primer linkers (splinkers) for sequence analysis of restriction fragments. Gene. 1986;44(2-3):263-70.

Kanan et al., Reaction discovery enabled by DNA-templated synthesis and in vitro selection. Nature. Sep. 30, 2004;431(7008):545-9.

Kang et al., Single protein pores containing molecular adapters at high temperatures. Angew Chem Int Ed Engl. Feb. 25, 2005;44(10):1495-9.

Kasianowicz et al., Characterization of individual polynucleotide molecules using a membrane channel. Proc Natl Acad Sci U S A. Nov. 26, 1996;93(24):13770-3.

Khulbe et al., DNA translocation through a-hemolysin nanopores with potential application to macromolecular data storage. Journal Applied Physics, vol. 97(104317):1-7 (2005).

Kocalka et al., Rapid and efficient DNA strand cross-linking by click chemistry. Chembiochem. May 23, 2008;9(8):1280-5. doi:10.1002/cbic.200800006.

Kolb et al., Click Chemistry: Diverse Chemical Function from a Few Good Reactions. Angew Chem Int Ed Engl. Jun. 1, 2001;40(11):2004-2021.

Kovall et al., Toroidal structure of lambda-exonuclease. Science. Sep. 19, 1997;277(5333):1824-7.

Langecker et al., Synthetic lipid membrane channels formed by designed DNA nanostructures. Science. Nov. 16, 2012;338(6109):932-6. doi: 10.1126/science.1225624.

Lazar et al., Transforming growth factor alpha: mutation of aspartic acid 47 and leucine 48 results in different biological activities. Mol Cell Biol. Mar. 1988;8(3):1247-52.

Lee et al., Importance of the conserved CA dinucleotide at Mu termini. J Mol Biol. Nov. 30, 2001;314(3):433-44.

Li et al., DNA molecules and configurations in a solid-state nanopore microscope. Nat Mater. Sep. 2003;2(9):611-5. Epub Aug. 24, 2003.

Li et al., DNA Sequencing Method Based on Electro-Mechanical Effects Between DNA and Nano-Structures. Advances in Mechanics. Nov. 25, 2011;41(6):722-729.

Lodish et al., Molecular Cell Biology. Fourth Edition. New York: W.H. Freeman; 2000. Section 4.1, Structure of Nucleic Acids, pp. 101-110.

Lovett et al., Identification and purification of a single-stranded-DNA-specific exonuclease encoded by the recJ gene of *Escherichia coli*. Proc Natl Acad Sci U S A. Apr. 1989;86(8):2627-31.

Lovrinovic et al., Rapid synthesis of DNA-cysteine conjugates for expressed protein ligation. Biochem Biophys Res Commun. Sep. 30, 2005;335(3):943-8.

Luo et al., Influence of polymer-pore interactions on translocation. Phys Rev Lett. Oct. 5, 2007;99(14):148102. Epub Oct. 1, 2007.

Lutz et al., Efficient construction of therapeutics, bioconjugates, biomaterials and bioactive surfaces using azide-alkyne "click" chemistry. Adv Drug Deliv Rev. Jun. 10, 2008;60(9):958-70. doi: 10.1016/j.addr.2008.02.004. Epub Mar. 4, 2008.

Maglia et al., Analysis of single nucleic acid molecules with protein nanopores. Methods Enzymol. 2010;475:591-623. doi: 10.1016/S0076-6879(10)75022-9.

Maglia et al., Enhanced translocation of single DNA molecules through alpha-hemolysin nanopores by manipulation of internal charge. Proc Natl Acad Sci U S A. Dec. 16, 2008;105(50):19720-5. doi:10.1073/pnas.0808296105. Epub Dec. 5, 2008.

Martin et al., Nanoscale protein pores modified with PAMAM dendrimers. J Am Chem Soc. Aug. 8, 2007;129(31):9640-9. Epub Jul. 18, 2007.

Martínez et al., The mRNA cap structure stimulates rate of poly(A) removal and amplifies processivity of degradation. J Biol Chem. Jul. 27, 2001;276(30):27923-9. Epub May 18, 2001.

Marziali et al., New DNA sequencing methods. Annu Rev Biomed Eng. 2001;3:195-223.

Mathé et al., Orientation discrimination of single-stranded DNA inside the alpha-hemolysin membrane channel. Proc Natl Acad Sci U S A. Aug. 30, 2005;102(35):12377-82. Epub Aug. 19, 2005.

Matsuura et al., Real-time observation of a single DNA digestion by lambda exonuclease under a fluorescence microscope field. Nucleic Acids Res. Aug. 15, 2001;29(16):E79.

Meller et al., Rapid nanopore discrimination between single polynucleotide molecules. Proc Natl Acad Sci U S A. Feb. 1; 2000;97(3):1079-84.

Meller et al., Single molecule measurements of DNA transport through a nanopore. Electrophoresis. Aug. 2002;23(16):2583-91.

Meller, Dynamics of polynucleotide transport through nanometre-scale pores. Journal Physics: Condensed Matter, vol. 15:R581-R607 (2003).

Merzlyak et al., Conductance and ion selectivity of a mesoscopic protein nanopore probed with cysteine scanning mutagenesis. Biophys J. Nov. 2005;89(5):3059-70. Epub Aug. 5, 2005.

Miles et al., Single molecule sensing with solid-state nanopores: novel materials, methods, and applications. Chem Soc Rev. Jan. 7, 2013;42(1):15-28. doi: 10.1039/c2cs35286a. Epub Sep. 19, 2012.

Mitchell et al., Chemical tags facilitate the sensing of individual DNA strands with nanopores. Angew Chem Int Ed Engl. 2008;47(30):5565-8. doi:10.1002/anie.200800183.

Mohammad et al., Controlling a single protein in a nanopore through electrostatic traps. J Am Chem Soc. Mar. 26, 2008;130(12):4081-8. doi: 10.1021/ja710787a. Epub Mar. 6, 2008.

Mol et al., Structure and function of the multifunctional DNA-repair enzyme exonuclease III. Nature. Mar. 23, 1995;374(6520):381-6.

Movileanu et al., Detecting protein analytes that modulate transmembrane movement of a polymer chain within a single protein pore. Nat Biotechnol. Oct. 2000;18(10):1091-5.

Movileanu et al., Location of a constriction in the lumen of a transmembrane pore by targeted covalent attachment of polymer molecules. J Gen Physiol. Mar. 2001;117(3):239-52.

Muller et al., DNA-directed assembly of artificial multienzyme complexes. Biochem Biophys Res Commun. Dec. 5, 2008;377(1):62-7. doi:10.1016/j.bbrc.2008.09.078. Epub Sep. 25, 2008.

Nakane et al., A nanosensor for transmembrane capture and identification of single nucleic Acid molecules. Biophys J. Jul. 2004;87(1):615-21. Erratum in: Biophys J. Nov. 2004;87(5):3618.

Nakane et al., Nanopore sensors for nucleic acid analysis. J. Phys.: Condens. Matter, vol. 15: R1365-R1393 (2003).

Niemeyer et al., DNA-directed assembly of bienzymic complexes from in vivo biotinylated NAD(P)H:FMN oxidoreductase and luciferase. Chembiochem. Mar. 1, 2002:3(2-3):242-5.

Nwe et al., Growing applications of "click chemistry" for bioconjugation in contemporary biomedical research. Cancer Biother Radiopharm. Jun. 2009;24(3):289-302. doi: 10.1089/cbr.2008.0626.

Paner et al., Studies of DNA dumbbells. III. Theoretical analysis of optical melting curves of dumbbells with a 16 base-pair duplex stem and Tn end loops (n=2, 3, 4, 6, 8, 10, 14). Biopolymers. Jul. 1992;32(7):881-92.

Paner et al., Studies of DNA dumbbells. VI. Analysis of optical melting curves of dumbbells with a sixteen-base pair duplex stem and end-loops of variable size and sequence. Biopolymers. Dec. 1996;39(6):779-93.

Phoenix et al., OmpF-Lpp signal sequence mutants with varying charge hydrophobicity ratios provide evidence for a phosphatidylglycerol-signal sequence interaction during protein translocation across the *Escherichia coli* inner membrane. J Biol Chem. Aug. 15, 1993;268(23):17069-73.

(56) References Cited

OTHER PUBLICATIONS

Pinero-Fernandez et al., Indole transport across *Escherichia coli* membranes. J Bacteriol. Apr. 2011;193(8):1793-8. doi:10.1128/JB.01477-10. Epub Feb. 4, 2011.

Purnell et al., Nucleotide identification and orientation discrimination of DNA homopolymers immobilized in a protein nanopore. Nano Lett. Sep. 2008;8(9):3029-34. doi: 10.1021/n1802312f. Epub Aug. 13, 2008.

Saariaho et al., Characteristics of MuA transposase-catalyzed processing of model transposon end DNA hairpin substrates. Nucleic Acids Res. Jun. 6, 2006;34(10):3139-49. Print 2006.

Sanchez-Quesada et al., Cyclic Peptides as Molecular Adapters for a Pore-Forming Protein. Journal American Chemical Society, vol. 122(48):11757-11766 (2000).

Sanchez-Quesada et al., Single DNA rotaxanes of a transmembrane pore protein. Angew Chem Int Ed Engl. Jun. 7, 2004;43(23):3063-7.

Sanderson, Personal genomes: Standard and pores. Nature. Nov. 6, 2008;456(7218):23-5. doi: 10.1038/456023a.

Sauer-Budge et al., Unzipping kinetics of double-stranded DNA in a nanopore. Phys Rev Lett. Jun. 13, 2003;90(23):238101. Epub Jun. 9, 2003.

Savilahti et al., The phage Mu transpososome core: DNA requirements for assembly and function. EMBO J. Oct. 2, 1995;14(19):4893-903.

Seeman, Nucleic acid junctions and lattices. J Theor Biol. Nov. 21, 1982;99(2):237-47.

Seo et al., Click chemistry to construct fluorescent oligonucleotides for DNA sequencing. J Org Chem. Jan. 24, 2003;68(2):609-12.

Seol et al., Stretching of homopolymeric RNA reveals single-stranded helices and base-stacking. Phys Rev Lett. Apr. 13, 2007;98(15):158103. Epub Apr. 12, 2007.

Shank et al., Redesigning channel-forming peptides: amino acid substitutions that enhance rates of supramolecular self-assembly and raise ion transport activity. Biophys J. Mar. 15, 2006;90(6):2138-50. Epub Dec. 30, 2005.

Shin et al., Kinetics of a reversible covalent-bond-forming reaction observed at the single-molecule level. Angew Chem Int Ed Engl. Oct. 4, 2002;41(19):3707-9; 3523.

Smeets et al., Salt dependence of ion transport and DNA translocation through solid-state nanopores. Nano Lett. Jan. 2006;6(1):89-95.

Song et al., Structure of Staphylococcal alpha-hemolysin, a heptameric transmembrane pore. Science. Dec. 13, 1996;274(5294):1859-66.

Stoddart et al., Multiple base-recognition sites in a biological nanopore: two heads are better than one. Angew Chem Int Ed Engl. 2010;49(3):556-9. doi: 10.1002/anie.200905483.

Sutherland et al., An analysis of mismatched duplex DNA unzipping through a bacterial nanopore. Biochem Cell Biol. Jun. 2004;82(3):407-12.

Tadey et al., Capillary electrophoretic separation of nucleotide isomers via complexation with cyclodextrin and borate. J Chromatogr B Biomed Appl. Jul. 15, 1994;657(2):365-72.

Thomas et al., Processivity of DNA exonucleases. J Biol Chem. Jan. 25, 1978;253(2):424-9.

Tohda et al., "Channel Mimetic Sensing Membranes for Nucleotides Based on Multitopic Hydrogen Bonding," Israel Journal of Chemistry, vol. 37:267-275 (1997).

Travers et al., A flexible and efficient template format for circular consensus sequencing and SNP detection. Nucleic Acids Res. Aug. 2010;38(15):e159. doi: 10.1093/nar/gkq543. Epub Jun. 22, 2010.

Tung et al., Preparation and applications of peptide-oligonucleotide conjugates. Bioconjug Chem. Sep.-Oct. 2000;11(5):605-18.

UniProt Database accession No. k0im99 sequence. Nov. 28, 2012.

Van De Goor, Nanopore Detection: Threading DNA Through a Tiny Hole. PharmaGenomics, vol. 4 (3):28-30 (2004).

Walker et al., Key residues for membrane binding, oligomerization, and pore forming activity of Staphylococcal alpha-hemolysin identified by cysteine scanning mutagenesis and targeted chemical modification. J Biol Chem. Sep. 29, 1995;270(39):23065-71.

Wang et al., Bioconjugation by copper(I)-catalyzed azide-alkyne [3+2] cycloaddition. J Am Chem Soc. Mar. 19, 2003;125(11):3192-3.

Wang et al., Nanopores with a spark for single-molecule detection. Nat Biotechnol. Jul. 2001;19(7):622-3.

Wanunu et al., DNA translocation governed by interactions with solid-state nanopores. Biophys J. Nov. 15, 2008;95(10):4716-25. doi: 10.1529/biophysj.108.140475. Epub Aug. 15, 2008.

Wemmer et al., Preparation and melting of single strand circular DNA loops. Nucleic Acids Res. Dec. 9, 1985;13(23):8611-21.

Winters-Hilt et al., Highly accurate classification of Watson-Crick basepairs on termini of single DNA molecules. Biophys J. Feb. 2003;84(2 Pt 1):967-76.

Wolfe et al., Catalyzing the translocation of polypeptides through attractive interactions. J Am Chem Soc. Nov. 14, 2007;129(45):14034-41. Epub Oct. 19, 2007.

Wong et al., Polymer capture by electro-osmotic flow of oppositely charged nanopores. J Chem Phys. Apr. 28, 2007;126(16):164903.

Woodman et al., Archaeal Hel308 domain V couples DNA binding to ATP hydrolysis and positions DNA for unwinding over the helicase ratchet. J Mal Biol. Dec. 14, 2007;374(5):1139-44. Epub Oct. 10, 2007.

Wu et al., Protein nanopores with covalently attached molecular adapters. J Am Chem Soc. Dec. 26, 2007;129(51):16142-8. Epub Nov. 30, 2007.

Xie et al., Single-molecule observation of the catalytic subunit of cAMP-dependent protein kinase binding to an inhibitor peptide. Chem Biol. Jan. 2005;12(1):109-20.

Yamagata et al., Overexpression, purification and characterization of RecJ protein from Thermus thermophilus HB8 and its core domain. Nucleic Acids Res. Nov. 15, 2001;29(22):4617-24.

U.S. Appl. No. 14/415,533, filed Jan. 16, 2015, Andrew Heron.
U.S. Appl. No. 14/415,459, filed Jan. 16, 2015, James White.
U.S. Appl. No. 14/415,453, filed Jan. 16, 2015, Andrew Heron.
U.S. Appl. No. 14/369,024, filed Jun. 26, 2014, Ruth Moysey.
U.S. Appl. No. 14/369,072, filed Jun. 26, 2014, Ruth Moysey.
U.S. Appl. No. 14/351,038, filed Apr. 10, 2014, Ruth Moysey.
U.S. Appl. No. 13/260,178, filed Jan. 17, 2012, David Stoddart.
U.S. Appl. No. 13/147,159, filed Nov. 15, 2011, Brian Mckeown.
U.S. Appl. No. 14/234,698, filed Apr. 25, 2014, Clive Gavin Brown.
U.S. Appl. No. 14/122,573, filed Apr. 16, 2014, James Clarke.
U.S. Appl. No. 14/334,285, filed Jul. 17, 2014, Giovanni Maglia.
U.S. Appl. No. 13/984,628, filed Feb. 27, 2014, James Clarke.
U.S. Appl. No. 13/002,717, filed Mar. 30, 2011, James Clarke.
U.S. Appl. No. 14/858,138, filed Sep. 18, 2015, Lakmal Jayasinghe.
U.S. Appl. No. 14/455,394, filed Aug. 8, 2014, Lakmal Jayasinghe.
U.S. Appl. No. 13/968,778, filed Aug. 16, 2013, Lakmal Jayasinghe.
U.S. Appl. No. 13/338,794, filed Dec. 28, 2011, Hagan Bayley.
U.S. Appl. No. 12/093,610, filed Jul. 28, 2008, Hagan Bayley.
U.S. Appl. No. 15/704,395, filed Sep. 14, 2017, Heron et al.
U.S. Appl. No. 15/944,365, filed Apr. 3, 2018, Brown et al.
U.S. Appl. No. 15/906,964, filed Feb. 27, 2018, McKeown.

Eoff et al., Chemically modified DNA substrates implicate the importance of electrostatic interactions for DNA unwinding by Dda helicase. Biochemistry. Jan. 18, 2005;44(2):666-74.

Hobbs et al., SSB protein limits RecOR binding onto single-stranded DNA. J Biol Chem. Apr. 13, 2007;282(15):11058-67. Epub Feb. 1, 2007.

Kozlov et al., Regulation of single-stranded DNA binding by the C termini of *Escherichia coli* single-stranded DNA-binding (SSB) protein. J Biol Chem. May 28, 2010;285(22):17246-52. doi: 10.1074/jbc.M110.118273. Epub Apr. 1, 2010.

Tackett et al., Unwinding of unnatural substrates by a DNA helicase. Biochemistry. Jan. 16, 2001;40(2):543-8.

United States District Court for the District of Delaware Order. Pacific Biosciences of California, Inc. v. Oxford Nanopore Technolgoies, Inc. Civil Action No. 17-275-RGA. Nov. 9, 2017.

Case 1:17-cv-01353-LPS Document 15. Plaintiff's response to Oxford Nanopore Techologies, Inc.'s Motion to Dismiss and Request for Scheduling Conference. Nov. 30, 2017.

Case 1:17-cv-01353-LPS Document 13. First Amended Complaint for Patent Infringement. Nov. 30, 2017.

(56) References Cited

OTHER PUBLICATIONS

Case 1:17-cv-01353-RGA Document 10. Oxford's opening brief in support of its motion to partially dismiss Pacbio's complaint for patent infringement. Nov. 16, 2017.
Case 1:17-cv-00275-LPS Document 19. Oxford Nanopore Technologies, Inc.'s response to Pacific Biosciences of California, Inc.'s notice of subsequent events. Oct. 24, 2017.
Case 1:17-cv-00275-LPS Document 18. Notice of subsequent events relating to Oxford's motion to dismiss (D.I. 9). Oct. 18, 2017.
Case 1:17-cv-00275-RGA Document 16. Oxford's reply brief in support of its motion to dismiss PacBio's complaint for patent infringement. Jun. 26, 2017.
Case 1:17-cv-00275-RGA Document 14. PacBio's response to Oxford's motion to dismiss. Jun. 5, 2017.
Case 1:17-cv-00275-RGA Document 10. Oxford's opening brief in support of its motion to dismiss PacBio's complaint for patent infringement. May 8, 2017.

\* cited by examiner

Figure 5
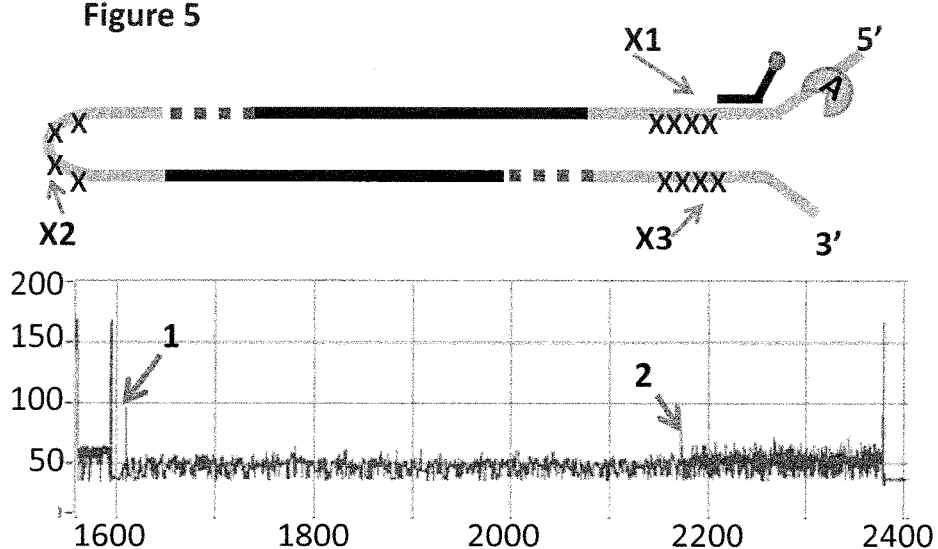
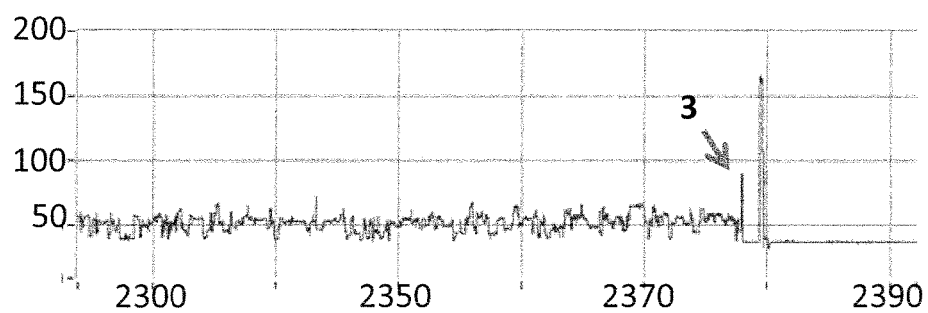

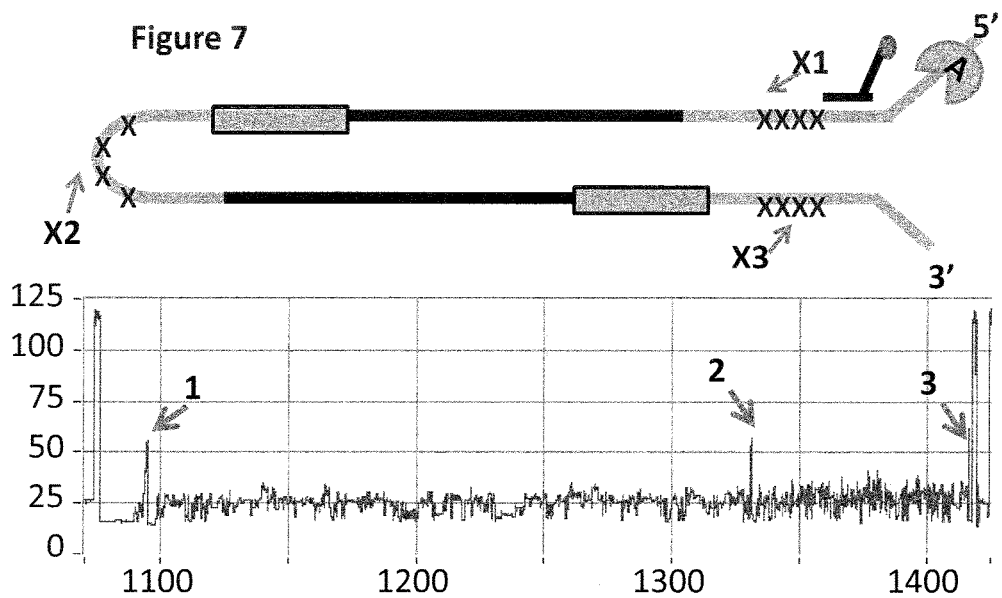
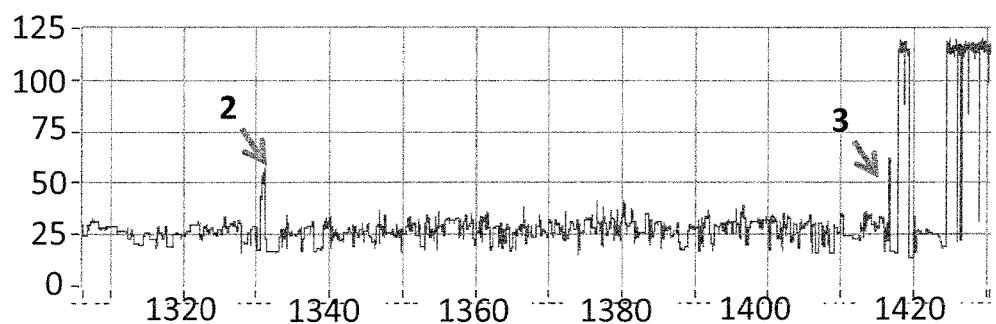
Figure 7

ENZYME STALLING METHOD

CROSS REFERENCE TO RELATED APPLICATIONS

This application is a 35 U.S.C. 371 national stage filing of International Application No. PCT/GB2014/050175, filed on Jan. 22, 2014, which claims priority to, and the benefit of, U.S. Application No. 61/774,694, filed on Mar. 8, 2013. PCT/GB2014/050175 also claims priority to United Kingdom Patent Application Nos. 1314695.6, filed on Aug. 16, 2013; 1318464.3, filed on Oct. 18, 2013; and 1318465.0, filed on Oct. 18, 2013. The contents of the aforementioned applications are hereby incorporated by reference in their entireties.

FIELD OF THE INVENTION

The invention relates to new methods of moving helicases past spacers on polynucleotides and controlling the loading of helicases on polynucleotides. The invention also relates to new methods of characterising target polynucleotides using helicases.

BACKGROUND OF THE INVENTION

There is currently a need for rapid and cheap polynucleotide (e.g. DNA or RNA) sequencing and identification technologies across a wide range of applications. Existing technologies are slow and expensive mainly because they rely on amplification techniques to produce large volumes of polynucleotide and require a high quantity of specialist fluorescent chemicals for signal detection.

Transmembrane pores (nanopores) have great potential as direct, electrical biosensors for polymers and a variety of small molecules. In particular, recent focus has been given to nanopores as a potential DNA sequencing technology.

When a potential is applied across a nanopore, there is a change in the current flow when an analyte, such as a nucleotide, resides transiently in the barrel for a certain period of time. Nanopore detection of the nucleotide gives a current change of known signature and duration. In the "strand sequencing" method, a single polynucleotide strand is passed through the pore and the identities of the nucleotides are derived. Strand sequencing can involve the use of a nucleotide handling protein, such as a helicase, to control the movement of the polynucleotide through the pore.

SUMMARY OF THE INVENTION

Spacers in polynucleotides are typically capable of stalling helicases, i.e. preventing helicases from moving further along the polynucleotides past the spacers. The inventors have surprisingly demonstrated that it is possible to move one or more stalled helicases past a spacer in a polynucleotide by contacting the helicase and polynucleotide with a transmembrane pore and applying a potential. Since the helicase is typically too large to fit through the pore, the force of the polynucleotide moving through the pore along the potential moves the helicase past the spacer. This has important applications for controlling the movement of polynucleotides and characterising, such as sequencing, polynucleotides. The inventors have also surprisingly demonstrated that it is possible to control the loading of one or more helicases on a polynucleotide using one or more spacers.

The invention therefore provides a method of moving one or more stalled helicases past one or more spacers in a target polynucleotide, comprising contacting (a) the one or more stalled helicases and the target polynucleotide with a transmembrane pore and (b) applying a potential across the pore and thereby moving the one or more helicases past the one or more spacers on the target polynucleotide.

The invention also provides:

a method of controlling the movement of a target polynucleotide through a transmembrane pore, comprising (a) providing the target polynucleotide with one or more spacers; (b) contacting the target polynucleotide with one or more helicases such that the one or more helicases stall at the one or more spacers; (c) contacting the target polynucleotide and the one or more stalled helicases with the pore; and (d) applying a potential across the pore such that the one or more helicases move past the one or more spacers and control the movement of the target polynucleotide through the pore;

a method of characterising a target polynucleotide, comprising (a) carrying out the method of controlling the movement of a target polynucleotide through a transmembrane pore of the invention; and (b) taking one or more measurements as the polynucleotide moves with respect to the pore wherein the measurements are indicative of one or more characteristics of the polynucleotide and thereby characterising the target polynucleotide;

a method of controlling the loading of one or more helicases on a target polynucleotide, comprising (a) providing the polynucleotide with one or more spacers; and (b) contacting the polynucleotide provided in (a) with the one or more helicases such that the one or more helicases bind to the polynucleotide and stall at each spacer;

an adaptor for controlling the movement of a target polynucleotide, wherein the adaptor comprises (a) (L-S-D)n or (D-S-L)n in the 5' to 3' direction, wherein L is a single stranded polynucleotide or a non-hybridised polynucleotide, S is a spacer and D is a double stranded polynucleotide and wherein n is a whole number and (b) one or more helicases stalled on each adaptor; and a kit for controlling the movement of a target polynucleotide, wherein the kit comprises (a) one or more spacers, (b) one or more helicases and (c) a transmembrane pore.

DESCRIPTION OF THE FIGURES

FIG. 5 shows example current traces (y-axis label=Current (pA), x-axis label=Time (s) for both upper and lower traces) of when a helicase (Trwc Cba (SEQ ID NO: 9) controls the translocation of the Lambda DNA construct (shown in FIG. 4b) through a nanopore (MS(B1-G75S/G77S/L88N/Q126R)8 MspA (SEQ ID NO: 2 with mutations G75S/G77S/L88N/Q126R)). The upper trace shows helicase controlled DNA movement of the entire lambda DNA construct through the nanopore, the first iSpC3 spacer labelled X1 produces the spike in current labelled 1 and the second iSpC3 spacers labelled X2 produces the spike in current labelled 2. The lower trace shows a zoomed in region of the end of the helicase controlled DNA movement through the nanopore, the third iSpcC3 spacer labelled X3 produces the spike in current labelled 3.

FIG. 7 shows example current traces (y-axis label=Current (pA), x-axis label=Time (s) for both upper and lower traces) of when a helicase (Trwc Cba (SEQ ID NO: 17) controls the translocation of the Lambda DNA construct (shown in FIG. 6b) through a nanopore (MS(B1-G75S/G77S/L88N/Q126R)8 MspA (SEQ ID NO: 2 with mutations G75S/G77S/L88N/Q126R)). The upper trace shows helicase controlled DNA movement of the entire lambda DNA construct through the nanopore, the first iSpC3 spacer labelled X1 produces the spike in current labelled 1, the second iSpC3 spacer labelled X2 produces the spike in current labelled 2 and the third iSpC3 spacer labelled X3 produces the spike in current labelled 3. The lower trace shows a zoomed in region of the second half of the helicase controlled DNA movement through the nanopore, the second iSpC3 spacer labelled X2 produces the spike in current labelled 2 and the third iSpC3 spacer labelled X3 produces the spike in current labelled 3.

Figure 16:
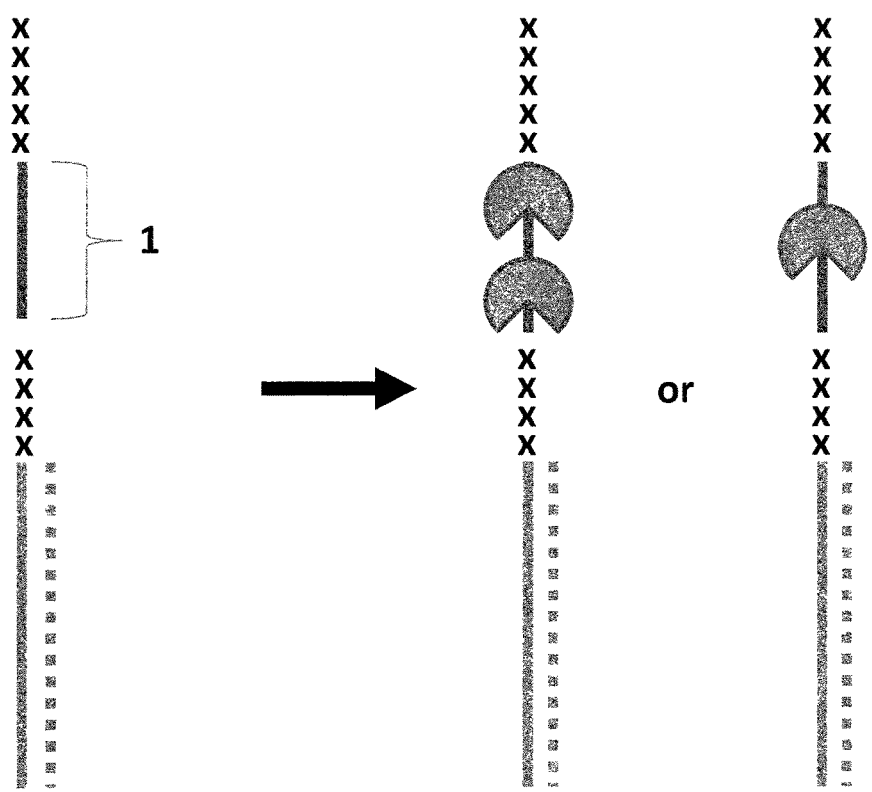

FIG. 16 shows the standard DNA construct used in Example 9. The x's represent spacer groups onto which the helicase cannot bind. The length of the region labelled 1 can be altered in order to control the number of helicases which can bind to that region. The figure shows, as an example, the binding of one or two helicases in region 1.

Figure 17:
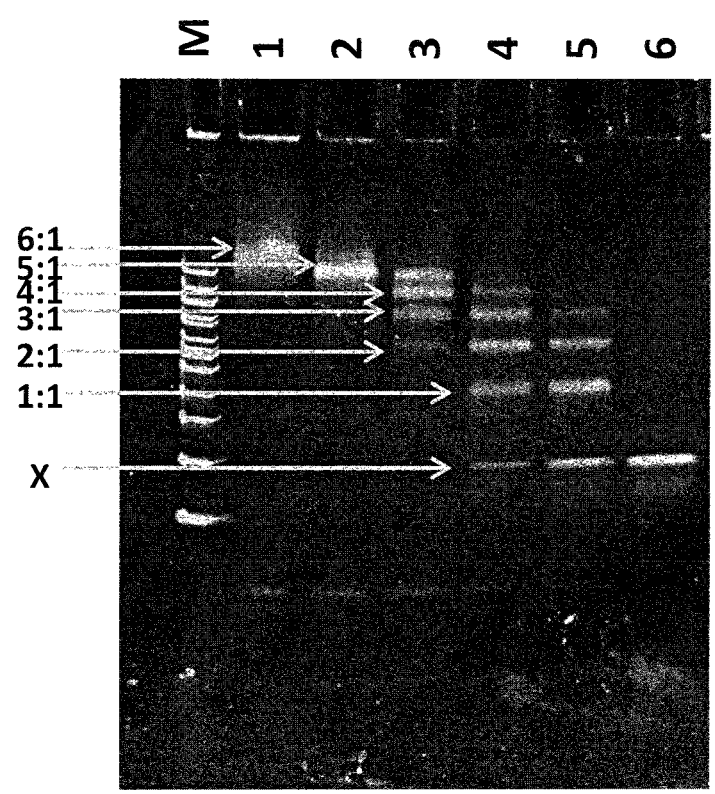

FIG. 17 shows an example gel assay of the DNA construct labelled 3 in Table 12 (Five iSpC3 spacers attached to the 5' end of SEQ ID NO: 9, which is attached at its 3' end to four iSpC3 spacers which are attached to the 5' end of SEQ ID NO: 36 which is hybridised to SEQ ID NO: 35). The lane labelled M shows a DNA ladder for reference (bands correspond from lowest mass (bottom of the gel) to highest mass (top of the gel) 200 bp (base pairs), 300 bp, 400 bp, 500/517 bp, 600 bp, 700 bp, 800 bp, 900 bp, 1000 bp, 1200 bp and 1517 bp). Lanes 1-6 correspond to different concentrations of T4 Dda-E94C/A360C—1=5000 nM, 2=2500 nM, 3=1250 nM, 4=625 nM, 5=312.5 nM and 6=0 nM). The band observed at level X corresponds to the unbound dsDNA construct. The numbers on the left-hand side of the gel relate to the number of enzymes bound to the DNA. For this DNA construct it was possible to bind up to 6 helicases at the highest concentration of enzyme added. The numbers shown at the top of the gel correspond to the concentration of T4 Dda-E94C/A360C) added.

Figure 18:
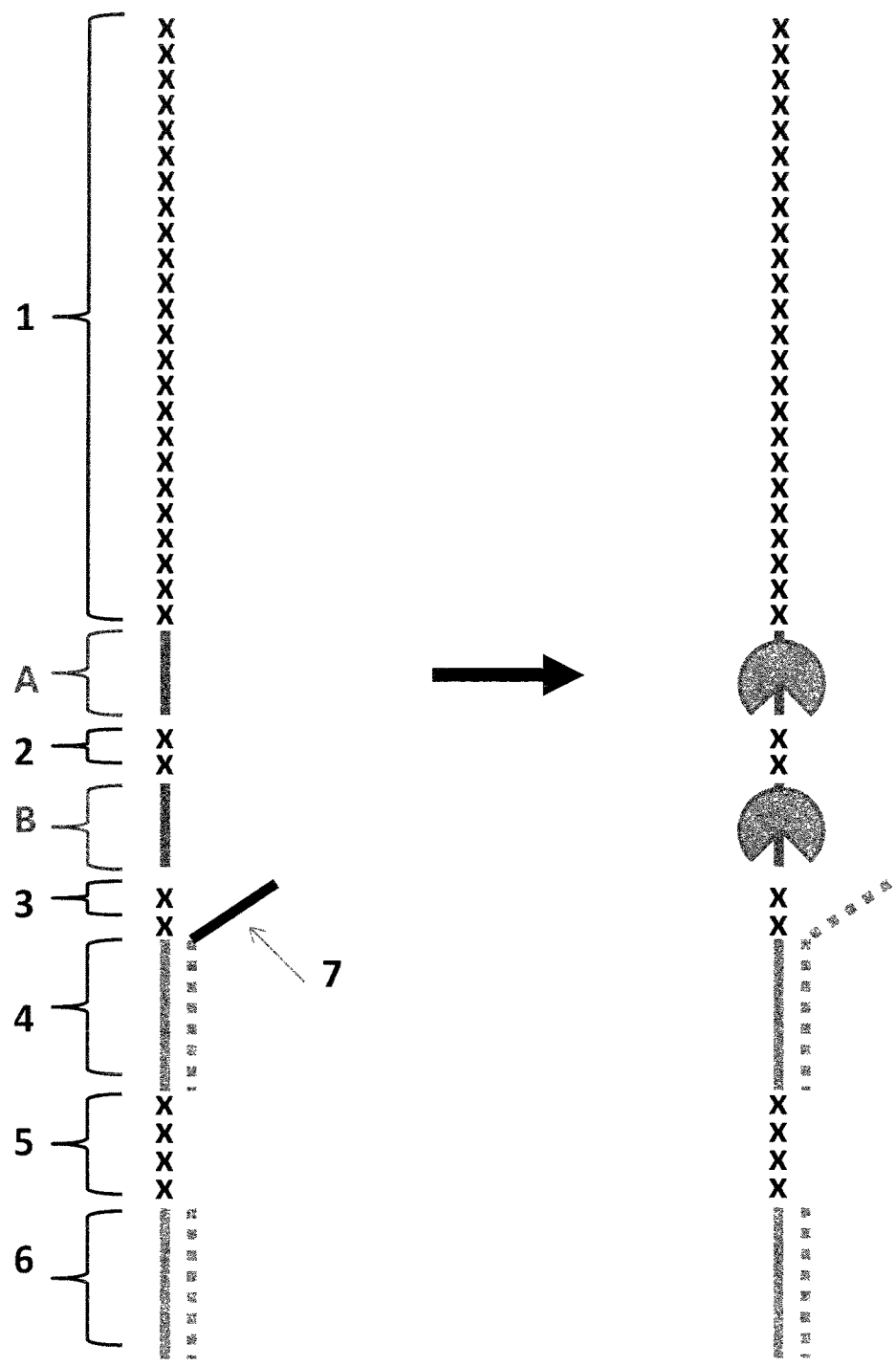

FIG. 18 shows the DNA construct used in example 9. Regions labelled A and B are short strands of DNA (SEQ ID NO: 37) which have been designed so that one helicase can bind to each region (as shown on the right-hand side). Region 1 corresponds to 25 SpC3 spacers, region 2 corresponds to two iSp18 spacers, region 3 corresponds to two iSp18 spacers, region 4 is a section of DNA (SEQ ID NO: 10) which hybridises to another strand of DNA which may or may not be made up of forked DNA (e.g. SEQ ID NO: 42=non-forked (missing fragment labelled 7) and SEQ ID NO: 12 attached to six iSp18 spacers (shown as fragment labelled 7) forked), region 5 corresponds to four 5-nitroindoles and region 6 corresponds to another region of DNA (SEQ ID NO: 41) which is hybridised to its complement (SEQ ID NO: 43).

Figure 19:
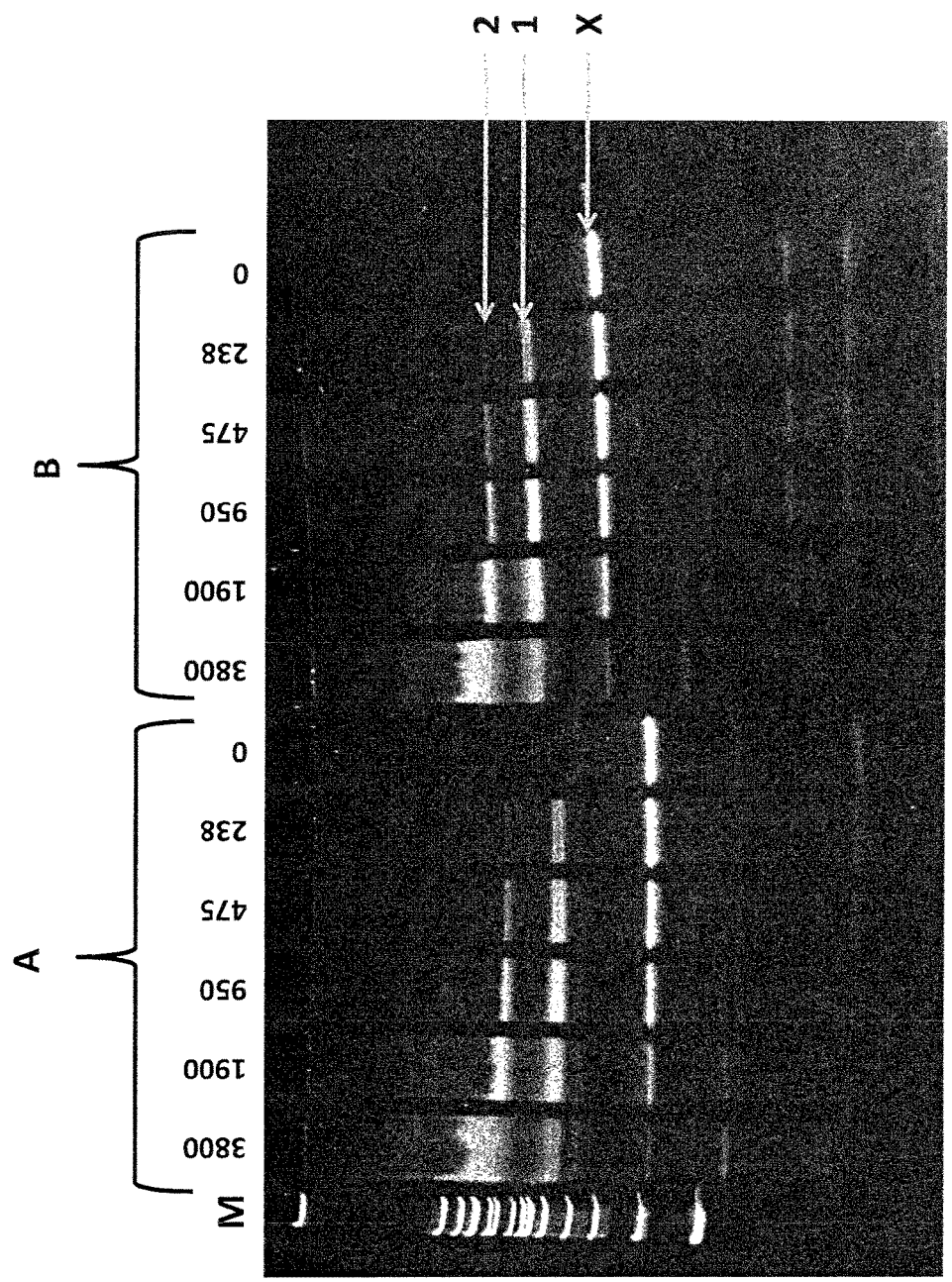

FIG. 19 shows a gel assay of the DNA construct described and shown in FIG. 18. The band observed at level X corresponds to the unbound dsDNA construct. The lane labelled M shows a DNA ladder for reference (bands correspond from lowest mass (bottom of the gel) to highest mass (top of the gel) 200 bp (base pairs), 300 bp, 400 bp, 500/517 bp, 600 bp, 700 bp, 800 bp, 900 bp, 1000 bp, 1200 bp and 1517 bp). The numbers on the left-hand side of the gel relate to the number of enzymes bound to the DNA. For this DNA construct it was possible to observe binding of two helicases (one at region A and the second at region B as shown in FIG. 18) from a concentration of 475 nM enzyme and above. The numbers shown at the top of the gel correspond to the concentration of T4 Dda-E94C/A360C) added.

Figure 20:
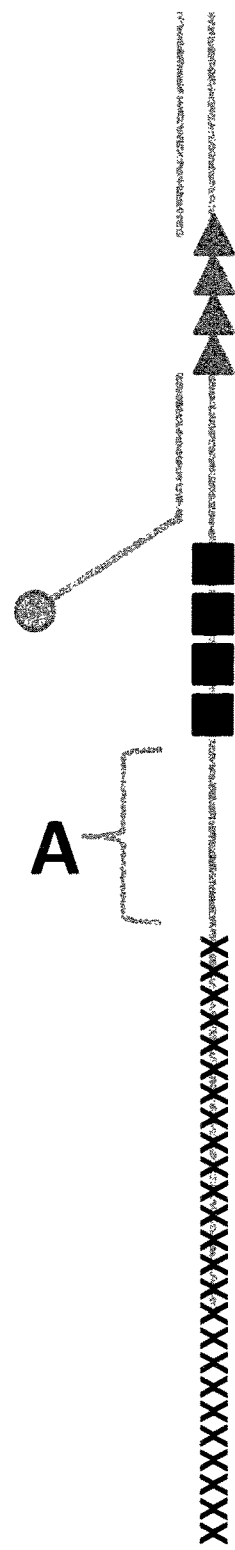

FIG. 20 shows the DNA construct used in Example 10 (referred to as DNA construct X1). There are 25 SpC3 spacers (shown as x's) attached to the 5' end of SEQ ID NO: 38 which is attached at its 3' end to 4 iSp18 spacers (shown as black squares). The four iSp18 spacers are attached to the 5' end of SEQ ID NO: 10 which is attached at its 3' end to four 5-nitroindoles (shown as grey triangles). The four nitroindoles are then attached to the 5' end of SEQ ID NO: 41. The complementary DNA strand which hybridises to SEQ ID NO: 41 is SEQ ID NO: 43. The complementary DNA strand which hybridises to SEQ ID NO: 10 is SEQ ID NO: 12 (attached to SEQ ID NO: 12's 3' end is six iSp18 spacers attached to two thymine residues and a 3' cholesterol TEG (shown as a grey circle)). The region labelled A corresponds to the region of the construct where T4 Dda-E94C/A360C is able to bind.

Figure 21:
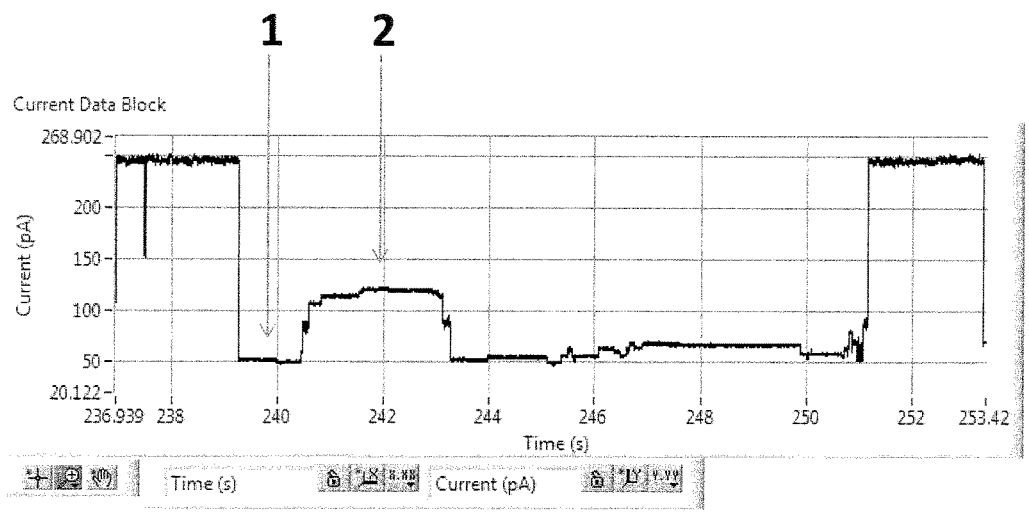

FIG. 21 shows an example current trace (y-axis label=Current (pA, 50 to 250), x-axis label=Time (s, 238 to 252)) of when a helicase (T4 Dda-E94C/A360C) controls the translocation of the DNA construct (0.1 nM, see FIG. 20 description) through a nanopore (MspA-B2C). The region labelled 1 shows the helicase controlled translocation of the polyT region (SEQ ID NO: 38, that the enzyme bound onto) through the nanopore. The region labelled 2 corresponds to the helicase controlled translocation of the iSp18 spacers through the nanopore.

Figure 22:
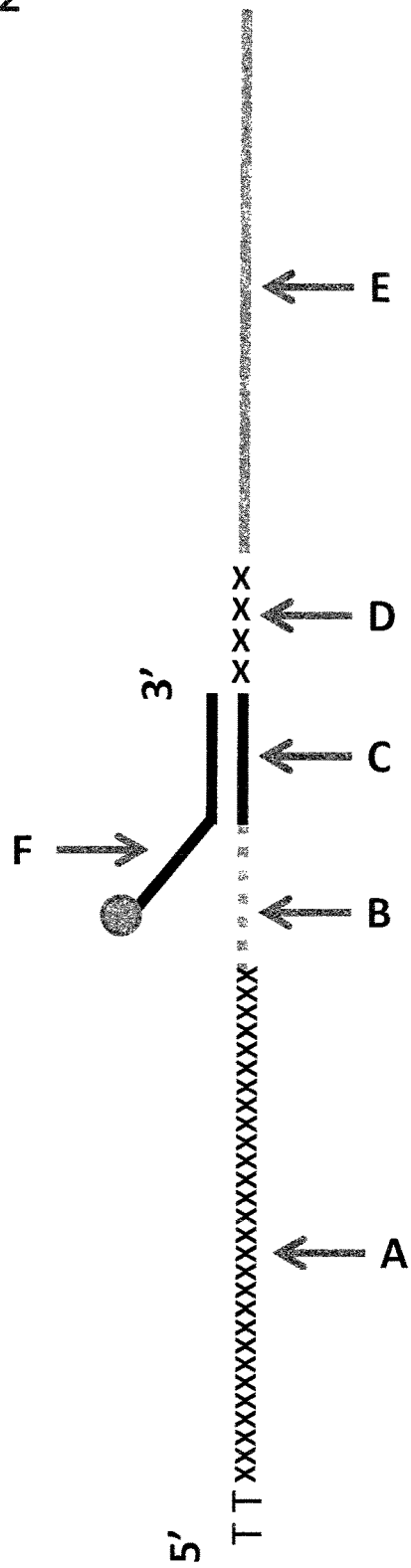

FIG. 22 shows a diagram of the DNA construct used in Example 4. Two thymines are attached at the 3' end to 28 iSpC3 spacers (labelled A). The 28 iSpC3 spacers are attached at the other end to the 5' end of SEQ ID NO: 23 (sequence corresponds to region B=polyT section and region C=sequence complementary to the tether sequence (SEQ ID NO: 12)). The 3' end of SEQ ID NO: 23 is attached to four iSpC3 spacers (labelled D). The other end of the 4 iSpC3 spacers is attached to the 5' end of SEQ ID NO: 24. The tether sequence (SEQ ID NO: 12) is attached at its 3' end to six iSp18 spacers attached to two thymine residues and a 3' cholesterol TEG.

DESCRIPTION OF THE SEQUENCE LISTING

SEQ ID NO: 1 shows the codon optimised polynucleotide sequence encoding the MS-B1 mutant MspA monomer. This mutant lacks the signal sequence and includes the following mutations: D90N, D91N, D93N, D118R, D134R and E139K.

SEQ ID NO: 2 shows the amino acid sequence of the mature form of the MS-B1 mutant of the MspA monomer. This mutant lacks the signal sequence and includes the following mutations: D90N, D91N, D93N, D118R, D134R and E139K.

SEQ ID NO: 3 shows the polynucleotide sequence encoding one monomer of a-hemolysin-E111N/K147N (α-HL-NN; Stoddart et al., PNAS, 2009; 106(19): 7702-7707).

SEQ ID NO: 4 shows the amino acid sequence of one monomer of α-HL-NN.

SEQ ID NOs: 5 to 7 show the amino acid sequences of MspB, C and D.

SEQ ID NO: 8 shows the amino acid sequence of the helicase Dda 1993 from Enterobacteria phage T4.

SEQ ID NO: 9 shows a polynucleotide sequence used in Example 1, 2, 3, 7 and 8.

SEQ ID NO: 10 shows a polynucleotide sequence used in Example 1 and 9.

SEQ ID NO: 11 shows a polynucleotide sequence used in Example 1. SEQ ID NO: 11 is attached by its 5' end to three iSpC3 spacers which are attached to the 3' end of SEQ ID NO: 10.

SEQ ID NO: 12 shows a polynucleotide sequence used in Examples 1 and 9. In Example 1 SEQ ID NO: 12 is attached at its 3' end to six iSp18 spacers attached to two thymine residues and a 3' cholesterol TEG. In Example 9 SEQ ID NO: 12 is attached at its 3' end to six iSp18 spacers only.

SEQ ID NO: 13 shows the polynucleotide sequence of the Enterobacteria phage X. The sequence contains an additional 12 base overhang attached at the 5' end of the sense strand. The sequence shown here is that of the sense strand only.

SEQ ID NO: 14 shows a polynucleotide sequence used in Examples 2 and 3. SEQ ID NO: 14 is attached at its 3' end to the 5' end of SEQ ID NO: 15 by four iSpC3 spacer units.

SEQ ID NO: 15 shows a polynucleotide sequence used in Examples 2 and 3. SEQ ID NO: 15 is attached at its 5' end to the 3' end of SEQ ID NO: 14 by four iSpC3 spacer units.

SEQ ID NO: 16 shows a polynucleotide sequence used in Example 2 and 3 which at the 3' end of the sequence has six iSp18 spacers attached to two thymine residues and a 3' cholesterol TEG.

SEQ ID NO: 17 shows the amino acid sequence of the Trwc Cba helicase.

SEQ ID NO: 18 shows a polynucleotide sequence used in Example 3. SEQ ID NO: 18 is attached at its 3' end to the 5' end of SEQ ID NO: 9 by four iSpC3 spacer units. This sequence has a phosphate attached to its 5' end and 5 deoxyinosines at positions 1 to 5.

SEQ ID NO: 19 shows a polynucleotide sequence used in Example 2.

SEQ ID NO: 20 shows a polynucleotide sequence used in Example 2.

SEQ ID NOs: 21 and 22 are placeholders to maintain the numbering of the following sequences.

SEQ ID NO: 23 shows the polynucleotide sequence used in Example 4. Attached to the 5' end of this sequence is 28 iSpC3 spacers units the last of which has an additional two T's attached to the 5' end of the spacer group. Attached to the 3' end of this sequence is four iSpC3 spacer units which are attached to the 5' end of SEQ ID NO: 24.

SEQ ID NO: 24 shows the polynucleotide sequence used in Example 9. Attached to the 5' end of this sequence is four iSpC3 spacer units, the last of which is attached to SEQ ID NO: 23. Attached to the 5' end of SEQ ID NO: 23 is 28 iSpC3 spacer units the last of which has an additional two T's attached to the 5' end of the spacer group.

SEQ ID NO: 25 shows a polynucleotide sequence used in Example 5. It has a carboxyfluorescein (FAM) base at its 5' end.

SEQ ID NO: 26 shows a polynucleotide sequence used in Example 5 and 6. It has a black-hole quencher (BHQ-1) base at its 3' end.

SEQ ID NO: 27 shows a polynucleotide sequence used in Examples 5 and 6.

SEQ ID NO: 28 shows the amino acid sequence of Hel308 Mbu.

SEQ ID NO: 29 shows a polynucleotide sequence used in Example 5. This sequence is connected to SEQ ID NO: 27 at its 5' end by either one or four iSp9 spacer groups.

SEQ ID NO: 30 shows a polynucleotide sequence used in Example 6. This sequence is connected to SEQ ID NO: 27 at its 5' end by one idSp group.

SEQ ID NO: 31 shows a polynucleotide sequence used in Example 6. This sequence is connected to SEQ ID NO: 27 at its 5' end by four idSp groups.

SEQ ID NO: 32 shows a polynucleotide sequence used in Example 6. It has a carboxyfluorescein (FAM) base at its 5' end.

SEQ ID NO: 33 shows a polynucleotide sequence used in Example 6. It has a carboxyfluorescein (FAM) base at its 5' end.

SEQ ID NO: 34 shows a polynucleotide sequence used in Example 7.

SEQ ID NO: 35 shows a polynucleotide sequence used in Example 7 and 8. It has a carboxyfluorescein (FAM) base at its 5' end.

SEQ ID NO: 36 shows a polynucleotide sequence used in Example 7 and 8.

SEQ ID NO: 37 shows a polynucleotide sequence used in Example 7, 8 and 9.

SEQ ID NO: 38 shows a polynucleotide sequence used in Example 8 and 10.

SEQ ID NO: 39 shows a polynucleotide sequence used in Example 8.

SEQ ID NO: 40 shows a polynucleotide sequence used in Example 8.

SEQ ID NO: 41 shows a polynucleotide sequence used in Example 9.

SEQ ID NO: 42 shows a polynucleotide sequence used in Example 9.

SEQ ID NO: 43 shows a polynucleotide sequence used in Example 9.

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "a polynucleotide" includes two or more polynucleotides, reference to "a spacer" includes two or more spacers, reference to "a helicase" includes two or more helicases, reference to "a transmembrane pore" includes two or more pores, and the like.

All publications, patents and patent applications cited herein, whether supra or infra, are hereby incorporated by reference in their entirety.

Methods of Moving Helicases Past Spacers

The invention provides a method of moving one or more stalled helicases past one or more spacers in a target polynucleotide. A helicase is stalled if it has stopped moving along the polynucleotide. Each spacer typically stalls the one or more helicases. Methods for determining whether or not one or more helicases are stalled are discussed below. The one or more helicases may be stalled before a spacer. The one or more helicases may be stalled by a spacer. The one or more helicases may be stalled on a spacer. The invention concerns moving the one or more stalled helicases past, i.e. beyond, the one or more spacers.

The one or more stalled helicases and the target polynucleotide are contacted with a transmembrane pore and a potential is applied. As described in more detail below, the target polynucleotide moves through the pore with the field resulting from the applied potential. The one or more helicases are typically too large to move through the pore. When a part of the target polynucleotide enters the pore and moves through the pore along the field resulting from the applied potential, the one or more helicases are moved past the spacer by the pore as the target polynucleotide moves through the pore. This is because the target polynucleotide (including the one or more spacers) moves through the pore and the one or more helicases remain on top of the pore.

This allows the position of the one or more helicases on the target polynucleotide to be controlled. Before the one or more stalled helicases and the target polynucleotide are contacted with a transmembrane pore and the potential is applied, the one or more helicases remain in the position where they are stalled. Even in the presence of the necessary components to facilitate helicase movement (e.g. ATP and $Mg^{2+}$), the one or more helicases will not move past a spacer on the target polynucleotide and will not move along the portion of the target polynucleotide on other side of the spacer until they are in the presence of the transmembrane pore and the applied potential.

The one or more helicases will also remain in the position where they are stalled in the presence of the transmembrane pore, but in the absence of the applied potential. In this instance, the application of a potential moves the one or more helicases past a spacer. The application of a potential can therefore be used to instigate the movement of the the one or more helicases past a spacer and along the portion of the target polynucleotide on other side of the spacer. For instance, an increase in voltage may be used to move the one or more helicases past the spacer.

The invention also provides a method of controlling the movement of a target polynucleotide through a transmembrane pore. The target polynucleotide is provided with one or more spacers. The target polynucleotide is contacted with one or more helicases and the one or more helicases stall at the one or more spacers. This ensures that the one or more helicases remain at one or more specific positions on the polynucleotide. This is discussed in more detail below. The target polynucleotide and the one or more stalled helicases are contacted with a transmembrane pore. Once a potential is applied, the one or more helicases move past the one or more spacers and along the portion of the polynucleotide on other side of the spacer(s). This allows the one or more helicases to control the movement of the polynucleotide through the pore. The potential is also typically used to thread the polynucleotide into the pore.

Helicases can control the movement of polynucleotides in at least two active modes of operation (when the helicase is provided with all the necessary components to facilitate movement, e.g. ATP and $Mg^{2+}$) and one inactive mode of operation (when the helicase is not provided with the necessary components to facilitate movement). When provided with all the necessary components to facilitate movement, the helicase moves along the polynucleotide in a 5' to 3' or a 3' to 5' direction (depending on the helicase), but the orientation of the polynucleotide in the pore (which is dependent on which end of the polynucleotide is captured by the pore) means that the helicase can be used to either move the polynucleotide out of the pore against the applied field or move the polynucleotide into the pore with the applied field. When the end of the polynucleotide towards which the helicase moves is captured by the pore, the helicase works against the direction of the field resulting from the applied potential and pulls the threaded polynucleotide out of the pore and into the cis chamber. However, when the end away from which the helicase moves is captured in the pore, the helicase works with the direction of the field resulting from the applied potential and pushes the threaded polynucleotide into the pore and into the trans chamber.

When the helicase is not provided with the necessary components to facilitate movement it can bind to the polynucleotide and act as a brake slowing the movement of the polynucleotide when it is pulled into the pore by the field resulting from the applied potential. In the inactive mode, it does not matter which end of the polynucleotide is captured, it is the applied field which pulls the polynucleotide into the pore towards the trans side with the helicase acting as a brake. When in the inactive mode, the movement control of the polynucleotide by the helicase can be described in a number of ways including ratcheting, sliding and braking.

In the method of the invention, the one or more helicases preferably control the movement of the target polynucleotide through the pore with the field resulting from the applied potential. In one preferred embodiment, the one or more helicases are used in the active mode and the end away from which the one or more helicases move is captured by the pore such that the one or more helicases work with the field resulting from the applied potential and push the polynucleotide through the pore. If the one or more helicases move in the 5' to 3' direction, the 5' end of the target polynucleotide is preferably captured by the pore. In such embodiments, the one or more helicases are moved past the one or more spacers in the 5' to 3' direction. If the one or more helicases move in the 3' to 5' direction, the 3' end of the target polynucleotide is preferably captured by the pore. In such embodiments, the one or more helicases are moved past the one or more spacers in the 3' to 5' direction.

In another preferred embodiment, the one or more helicases are used in the inactive mode such that the applied field pulls the target polynucleotide through the pore and the one or more helicases act as a brake. In the method of the invention, the one or more helicases preferably slow or brake the movement of the target polynucleotide through the pore with the field resulting from the applied potential. In either case, the one or more helicases are typically too large to move through the pore and the pore pushes the one or more helicases past the one or more spacers on the polynucleotide as the polynucleotide moves through the pore with the field resulting from the applied potential.

The method of controlling the movement of a target polynucleotide through a transmembrane pore can be helpful during characterisation of the polynucleotide using the pore, for instance during strand sequencing. The invention also provides a method of characterising a target polynucleotide. The target polynucleotide is provided with one or more spacers. The target polynucleotide is contacted with one or more helicases and the one or more helicases stall at the one or more spacers. This ensures that the one or more helicases remain at one or more specific positions on the polynucleotide. This is discussed in more detail below. The target polynucleotide and the one or more stalled helicases are contacted with a transmembrane pore. Once a potential is applied, the one or more helicases move past the one or more spacers and along the portion of the polynucleotide on other side of the spacer(s). This allows the one or more helicases to control the movement of the polynucleotide through the pore. The method also comprises taking one or more measurements as the polynucleotide moves with respect to the pore. The measurements are indicative of one or more characteristics of the polynucleotide.

The ability to stall one or more helicases on the target polynucleotide and move the one or more helicases past the one or more spacers using a transmembrane pore and an applied potential is advantageous because it allows effective characterisation, such as sequencing, of the target polynucleotide. For instance, the one or more helicases can be stalled towards one end of the target polynucleotide in a leader sequence which is designed to be captured by the pore and does not need to be characterised (as described below). The stalling of the one or more helicases in the leader sequence means that the one or more helicases do not move away from the leader sequence along the part of the polynucleotide to be characterised until it/they are contacted with the pore and a potential is applied. Once the one or more helicases and the polynucleotide are contacted with the pore and a potential is applied, the leader sequence is typically captured by the pore and moves through the pore. This movement moves the one or more helicases past the spacer(s) and along the part of polynucleotide to be characterised (as described above). The one or more helicases may then control the movement of the part of the polynucleotide to be characterised.

If the one or more helicases are not stalled in the leader sequence, it/they would move along the polynucleotide away from the leader sequence and along the part of the polynucleotide to be characterised. When the one or more helicases and the polynucleotide are contacted with the pore and a potential is applied under these circumstances, the leader sequence and some, if not all, of the polynucleotide to be characterised will move in an uncontrolled manner through the pore along the field resulting from the applied potential. Only once the one or more helicases come into contact with the pore will it/they begin to control the movement of the part of the polynucleotide to be characterised as discussed above. Any part of the polynucleotide which moves through the pore in an uncontrolled manner cannot be characterised as described below. If the one or more helicases move away from the leader sequence and along most of the rest of the target polynucleotide little, if any, of the polynucleotide will be characterised.

The use of one or more spacers in accordance with the invention also allows the number and position of the one or more helicases on the target polynucleotide to be controlled as discussed in more detail below. For instance, a specific number of helicases may be stalled at specific positions on adaptors which may be ligated to the target polynucleotide before characterisation. Such adaptors are provided by the invention and may be provided in a kit for characterisation. The use of one or more spacers ensures that the helicases remain where they supposed to be until the characterisation is begun, even if the adaptor and/or target polynucleotide before characterisation are in the presence of the components necessary to facilitate helicase movement (e.g. ATP and $Mg^{2+}$).

Polynucleotide

A polynucleotide, such as a nucleic acid, is a macromolecule comprising two or more nucleotides. The polynucleotide or nucleic acid may comprise any combination of any nucleotides. The nucleotides can be naturally occurring or artificial. One or more nucleotides in the polynucleotide can be oxidized or methylated. One or more nucleotides in the polynucleotide may be damaged. For instance, the polynucleotide may comprise a pyrimidine dimer. Such dimers are typically associated with damage by ultraviolet light and are the primary cause of skin melanomas. One or more nucleotides in the polynucleotide may be modified, for instance with a label or a tag. Suitable labels are described below.

A nucleotide typically contains a nucleobase, a sugar and at least one phosphate group. The nucleobase and sugar form a nucleoside.

The nucleobase is typically heterocyclic. Nucleobases include, but are not limited to, purines and pyrimidines and more specifically adenine (A), guanine (G), thymine (T), uracil (U) and cytosine (C).

The sugar is typically a pentose sugar. Nucleotide sugars include, but are not limited to, ribose and deoxyribose. The sugar is preferably a deoxyribose.

The nucleotide in the polynucleotide is typically a ribonucleotide or deoxyribonucleotide.

The polynucleotide may comprise the following nucleosides: adenosine, uridine, guanosine and cytidine. The nucleotide is preferably a deoxyribonucleotide. The polynucleotide preferably comprises the following nucleosides: deoxyadenosine (dA), deoxyuridine (dU) and/or thymidine (dT), deoxyguanosine (dG) and deoxycytidine (dC).

The nucleotide typically contains a monophosphate, diphosphate or triphosphate. Phosphates may be attached on the 5' or 3' side of a nucleotide.

Suitable nucleotides include, but are not limited to, adenosine monophosphate (AMP), guanosine monophosphate (GMP), thymidine monophosphate (TMP), uridine monophosphate (UMP), cytidine monophosphate (CMP), cyclic adenosine monophosphate (cAMP), cyclic guanosine monophosphate (cGMP), deoxyadenosine monophosphate (dAMP), deoxyguanosine monophosphate (dGMP), deoxythymidine monophosphate (dTMP), deoxyuridine monophosphate (dUMP) and deoxycytidine monophosphate (dCMP). The nucleotides are preferably selected from AMP, TMP, GMP, CMP, UMP, dAMP, dTMP, dGMP, dCMP and dUMP. The nucleotides are most preferably selected from dAMP, dTMP, dGMP, dCMP and dUMP. The polynucleotide preferably comprises the following nucleotides: dAMP, dUMP and/or dTMP, dGMP and dCMP.

The nucleotides in the polynucleotide may be attached to each other in any manner. The nucleotides are typically attached by their sugar and phosphate groups as in nucleic acids. The nucleotides may be connected via their nucleobases as in pyrimidine dimers.

The polynucleotide can be a nucleic acid. The polynucleotide may be any synthetic nucleic acid known in the art, such as peptide nucleic acid (PNA), glycerol nucleic acid (GNA), threose nucleic acid (TNA), locked nucleic acid (LNA) or other synthetic polymers with nucleotide side chains. The PNA backbone is composed of repeating N-(2-aminoethyl)-glycine units linked by peptide bonds. The GNA backbone is composed of repeating glycol units linked by phosphodiester bonds. The TNA backbone is composed of repeating threose sugars linked together by phosphodiester bonds. LNA is formed from ribonucleotides as discussed above having an extra bridge connecting the 2' oxygen and 4' carbon in the ribose moiety.

The polynucleotide is most preferably ribonucleic nucleic acid (RNA) or deoxyribonucleic acid (DNA).

The polynucleotide preferably does not comprise any abasic nucleotides (i.e. nucleotides which lack a nucleobase), except in the one or more spacers. The polynucleotide preferably does not comprise any C3 spacers (i.e. nucleotide which lack a nucleobase and a sugar), except in the one or more spacers.

The polynucleotide may be any length. For example, the polynucleotide can be at least 10, at least 50, at least 100, at least 150, at least 200, at least 250, at least 300, at least 400 or at least 500 nucleotides in length. The polynucleotide can be 1000 or more nucleotides, 5000 or more nucleotides in length or 100000 or more nucleotides in length.

The helicase may move along the whole or only part of the target polynucleotide in the method of the invention. The whole or only part of the target polynucleotide may be characterised using the method of the invention.

The target polynucleotide may be single stranded. At least a portion of the target polynucleotide is preferably double stranded. Helicases typically hind to single stranded polynucleotides. If at least a portion of the target polynucleotide is double stranded, the target polynucleotide preferably comprises a single stranded region or a non-hybridised region. The one or more helicases are capable of binding to the single stranded region or one strand of the non-hybridised region. The target polynucleotide preferably comprises one or more single stranded regions or one or more non-hybridised regions.

The one or more spacers are preferably included in the single stranded region or the non-hybridised region of the target polynucleotide. The target polynucleotide may comprise more than one single stranded region or more than one non-hybridised region. The target polynucleotide may comprise a single stranded region or a non-hybridised region within its sequence and/or at one or both ends. The one or more spacers may be included in the double stranded region of the target polynucleotide.

If the one or more helicases used in the method move in the 5' to 3' direction, the target polynucleotide preferably comprises a single stranded region or a non-hybridised region at its 5' end. If the one or more helicases used in the method move in the 3' to 5' direction, the target polynucleotide preferably comprises a single stranded region or a non-hybridised region at its 3' end. If the one or more helicases are used in the inactive mode (i.e. as a brake), it does not matter where the single stranded region or the non-hybridised region is located.

The single stranded region preferably comprises a leader sequence which preferentially threads into the pore. The leader sequence facilitates the method of the invention. The leader sequence is designed to preferentially thread into the transmembrane pore and thereby facilitate the movement of target polynucleotide through the pore. The leader sequence typically comprises a polymer. The polymer is preferably negatively charged. The polymer is preferably a polynucleotide, such as DNA or RNA, a modified polynucleotide (such as abasic DNA), PNA, LNA, polyethylene glycol (PEG) or a polypeptide. The leader preferably comprises a polynucleotide and more preferably comprises a single stranded polynucleotide. The leader sequence can comprise any of the polynucleotides discussed above. The single stranded leader sequence most preferably comprises a single strand of DNA, such as a poly dT section. The leader sequence preferably comprises the one or more spacers.

The leader sequence can be any length, but is typically 10 to 150 nucleotides in length, such as from 20 to 150 nucleotides in length. The length of the leader typically depends on the transmembrane pore used in the method.

If at least a portion of the target polynucleotide is double stranded, the two strands of the double stranded portion are preferably linked using a bridging moiety, such as a hairpin. This facilitates characterisation method of the invention. Linking the two strands of the target polynucleotide by a bridging moiety allows both strands of the polynucleotide to be characterised, such as sequenced, by the transmembrane pore. The two strands dehybridise as the polynucleotide moves though the pore as a single stranded polynucleotide. This method is advantageous because it doubles the amount of information obtained from a single double stranded target polynucleotide. Moreover, because the sequence in the complementary 'antisense' strand is necessarily orthogonal to the sequence of the 'sense' strand, the information from the two strands can be combined informatically. Thus, this mechanism provides an orthogonal proof-reading capability that provides higher confidence observations.

Any of the embodiments disclosed in International Application No. PCT/GB2012/051786 (published as WO 2013/014451) may be used. The bridging moiety typically covalently links the two strands of the polynucleotide. The bridging moiety can be anything that is capable of linking the two strands of the target polynucleotide, provided that the bridging moiety does not interfere with movement of the polynucleotide through the transmembrane pore. Suitable bridging moieties include, but are not limited to a polymeric linker, a chemical linker, a polynucleotide or a polypeptide. Preferably, the bridging moiety comprises DNA, RNA, modified DNA (such as abasic DNA), RNA, PNA, LNA or polyetheylone glycol (PEG). The bridging moiety is more preferably DNA or RNA. The bridging moiety may comprise the one or more spacers.

The bridging moiety is most preferably a hairpin loop. The hairpin loop may be formed from any of the polynucleotides disclosed above. The hairpin loop or the loop of the hairpin loop is typically from about 4 to about 100 nucleotides in length, preferably from about 4 to about 8 nucleotides in length.

The bridging moiety is linked to the two strands of the target polynucleotide by any suitable means known in the art. The bridging moiety may be synthesized separately and chemically attached or enzymatically ligated to the target polynucleotide. Alternatively, the bridging moiety may be generated in the processing of the target polynucleotide.

The bridging moiety is linked to the target polynucleotide at or near one end of the target polynucleotide. The bridging moiety is preferably linked to the target polynucleotide within 10 nucleotides of the end of the polynucleotide.

The one or more spacers are preferably positioned such that it/they stall(s) the one or more helicases and prevents it/them from moving along the target polynucleotide to be controlled or characterised. For instance, the one or more spacers are preferably located between a leader sequence and the target polynucleotide to be controlled or characterised, for instance within a leader sequence at one end of the polynucleotide. The leaders sequence typically enters the pore with the field resulting from the applied potential and the one or more helicases are moved past the one or more spacers as the polynucleotide moves through the pore. The one or more helicases may then control the movement of the remainder of the target polynucleotide through the pore and facilitate its characterisation.

In the most preferred embodiment, the target polynucleotide comprises a double stranded portion which is linked at one end by a bridging moiety, such as a hairpin loop, and a single stranded portion at the at the other end from the bridging moiety which comprises a leader sequence. The one or more spacers may be present in the leader sequence and/or the bridging moiety.

The target polynucleotide is present in any suitable sample. The invention is typically carried out on a sample that is known to contain or suspected to contain the target polynucleotide. The invention may be carried out on a sample to confirm the identity of one or more target polynucleotides whose presence in the sample is known or expected.

The sample may be a biological sample. The invention may be carried out in vitro on a sample obtained from or extracted from any organism or microorganism. The organism or microorganism is typically archaeal, prokaryotic or eukaryotic and typically belongs to one of the five kingdoms: plantae, animalia, fungi, monera and protista. The invention may be carried out in vitro on a sample obtained from or extracted from any virus. The sample is preferably a fluid sample. The sample typically comprises a body fluid of the patient. The sample may be urine, lymph, saliva, mucus or amniotic fluid but is preferably blood, plasma or serum. Typically, the sample is human in origin, but alternatively it may be from another mammal animal such as from commercially farmed animals such as horses, cattle, sheep or pigs or may alternatively be pets such as cats or dogs. Alternatively a sample of plant origin is typically obtained from a commercial crop, such as a cereal, legume, fruit or vegetable, for example wheat, quinoa, barley, oats, canola, maize, soya, rice, bananas, apples, tomatoes, potatoes, grapes, tobacco, beans, lentils, sugar cane, cocoa, cotton.

The sample may be a non-biological sample. The non-biological sample is preferably a fluid sample. Examples of a non-biological sample include surgical fluids, water such as drinking water, sea water or river water, and reagents for laboratory tests.

The sample is typically processed prior to being assayed, for example by centrifugation or by passage through a membrane that filters out unwanted molecules or cells, such as red blood cells. The sample may be measured immediately upon being taken. The sample may also be typically stored prior to assay, preferably below −70° C.

Spacer(s)

The one or more spacers are included in the target polynucleotide. The one or more spacers are preferably part of the target polynucleotide, for instance it/they interrupt(s) the polynucleotide sequence. The one or more spacers are preferably not part of one or more blocking molecules, such as speed bumps, hybridised to the target polynucleotide.

There may be any number of spacers in the target polynucleotide, such as 1, 2, 3, 4, 5, 6, 7, 8, 9, 10 or more spacers. There are preferably two, four or six spacers in the target polynucleotide. There may be spacer in different regions of the target polynucleotide, such as a spacer in the leader sequence and a spacer in the hairpin loop.

The one or more spacers each provides an energy barrier which the one or more helicases cannot overcome even in the active mode. The one or more spacers may stall the one or more more helicases by by reducing the traction of the helicase (for instance by removing the bases from the nucleotides in the target polynucleotide) or physically blocking movement of the one or more helicases (for instance using a bulky chemical group).

The one or more spacers may comprise any molecule or combination of molecules that stalls the one or more helicases. The one or more spacers may comprise any molecule or combination of molecules that prevents the one or more helicases from moving along the target polynucleotide. It is straightforward to determine whether or not the one or more helicases are stalled at one or more spacers in the absence of a transmembrane pore and an applied potential. For instance, this can be assayed as shown in the Examples, for instance the ability of a helicase to move past a spacer and displace a complementary strand of DNA can be measured by PAGE.

The one or more spacers typically comprise a linear molecule, such as a polymer. The one or more spacers typically have a different structure from the target polynucleotide. For instance, if the target polynucleotide is DNA, the one or more spacers are typically not DNA. In particular, if the target polynucleotide is deoxyribonucleic acid (DNA) or ribonucleic acid (RNA), the one or more spacers preferably comprise peptide nucleic acid (PNA), glycerol nucleic acid (GNA), threose nucleic acid (TNA), locked nucleic acid (LNA) or a synthetic polymer with nucleotide side chains.

The one or more spacers preferably comprises one or more nitroindoles, such as one or more 5-nitroindoles, one or more inosines, one or more acridines, one or more 2-aminopurines, one or more 2-6-diaminopurines, one or more 5-bromo-deoxyuridines, one or more inverted thymidines (inverted dTs), one or more inverted dideoxy-thymidines (ddTs), one or more dideoxy-cytidines (ddCs), one or more 5-methylcytidines, one or more 5-hydroxymethylcytidines, one or more 2'-O-Methyl RNA bases, one or more Iso-deoxycytidines (Iso-dCs), one or more Iso-deoxyguanosines (Iso-dGs), one or more iSpC3 groups (i.e. nucleotides which lack sugar and a base), one or more photo-cleavable (PC) groups, one or more hexandiol groups, one or more spacer 9 (iSp9) groups, one or more spacer 18 (iSp18) groups, a polymer or one or more thiol connections. The one or more spacers may comprise any combination of these groups. Many of these groups are commercially available from IDT® (Integrated DNA Technologies®).

The one or more spacers may contain any number of these groups. For instance, for 2-aminopurines, 2-6-diaminopurines, 5-bromo-deoxyuridines, inverted dTs, ddTs, ddCs, 5-methylcytidines, 5-hydroxymethylcytidines, 2'-O-Methyl RNA bases, Iso-dCs, Iso-dGs, iSpC3 groups, PC groups, hexandiol groups and thiol connections, the one or more spacers preferably comprise 2, 3, 4, 5, 6, 7, 8, 9, 10, 11, 12 or more. The one or more spacers preferably comprise 2, 3, 4, 5, 6, 7, 8 or more iSp9 groups. The one or more spacers preferably comprise 2, 3, 4, 5 or 6 or more iSp18 groups. The most preferred spacer is four iSp18 groups.

The polymer is preferably a polypeptide or a polyethylene glycol (PEG). The polypeptide preferably comprises 2, 3, 4, 5, 6, 7, 8, 9, 10, 11, 12 or more amino acids. The PEG preferably comprises 2, 3, 4, 5, 6, 7, 8, 9, 10, 11, 12 or more monomer units.

The one or more spacers preferably comprise one or more abasic nucleotides (i.e. nucleotides lacking a nucleobase), such as 2, 3, 4, 5, 6, 7, 8, 9, 10, 11, 12 or more abasic nucleotides. The nucleobase can be replaced by —H (idSp) or —OH in the abasic nucleotide.

Abasic spacers can be inserted into target polynucleotides by removing the nucleobases from one or more adjacent nucleotides. For instance, polynucleotides may be modified to include 3-methyladenine, 7-methylguanine, 1,N6-ethenoadenine inosine or hypoxanthine and the nucleobases may be removed from these nucleotides using Human Alkyladenine DNA Glycosylase (hAAG). Alternatively, polynucleotides may be modified to include uracil and the nucleobases removed with Uracil-DNA Glycosylase (UDG). In one embodiment, the one or more spacers do not comprise any abasic nucleotides.

The one or more helicases may be stalled by (i.e. before) or on each linear molecule spacers. If linear molecule spacers are used, the target polynucleotide is preferably provided with a double stranded region of polynucleotide adjacent to the end of each spacer past which the one or more helicases are to be moved. The double stranded region typically helps to stall the one or more helicases on the adjacent spacer. The presence of the double stranded region(s) is particularly preferred if the method is carried out at at a salt concentration of about 100 mM or lower. Each double stranded region is typically at least 10, such as at least 12, nucleotides in length. If the target polynucleotide used in the invention is single stranded, a double stranded region may formed by hybridising a shorter polynucleotide to a region adjacent to a spacer. The shorter polynucleotide is typically formed from the same nucleotides as the target polynucleotide, but may be formed from different nucleotides. For instance, the shorter polynucleotide may be formed from LNA.

If linear molecule spacers are used, the target polynucleotide is preferably provided with a blocking molecule at end of each spacer opposite to end past which the one or more helicases are to be moved. This can help to ensure that the one or more helicases remain stalled on each spacer. It may also help retain the one or more helicases on the target polynucleotide in the case that it/they diffuse(s) off in solution. The blocking molecule may be any of the chemical groups discussed below which physically cause the one or more helicases to stall. The blocking molecule may be a double stranded region of polynucleotide.

The one or more spacers preferably comprise one or more chemical groups which physically cause the one or more helicases to stall. The one or more chemical groups are preferably one or more pendant chemical groups. The one or more chemical groups may be attached to one or more nucleobases in the target polynucleotide. The one or more chemical groups may be attached to the target polynucleotide backbone. Any number of these chemical groups may be present, such as 2, 3, 4, 5, 6, 7, 8, 9, 10, 11, 12 or more. Suitable groups include, but are not limited to, fluorophores, streptavidin and/or biotin, cholesterol, methylene blue, dinitrophenols (DNPs), digoxigenin and/or anti-digoxigenin and dibenzyicyclooctyne groups.

Different spacers in the target polynucleotide may comprise different stalling molecules. For instance, one spacer may comprise one of the linear molecules discussed above and another spacer may comprise one or more chemical groups which physically cause the one or more helicases to stall. A spacer may comprise any of the linear molecules discussed above and one or more chemical groups which physically cause the one or more helicases to stall, such as one or more abasics and a fluorophore.

Suitable spacers can be designed depending on the type of target polynucleotide and the conditions under which the method of the invention is carried out. Most helicases bind and move along DNA and so may be stalled using anything that is not DNA. Suitable molecules are discussed above.

The method of the invention is preferably carried out in the presence of free nucleotides and/or the presence of a helicase cofactor. This is discussed in more detail below. In the absence of the transmembrane pore and an applied potential, the one or more spacers are preferably capable of stalling the one or more helicases in the presence of free nucleotides and/or the presence of a helicase cofactor.

If the method of the invention is carried out in the presence of five nucleotides and a helicase cofactor as discussed below (such that the one of more helicases are in the active mode), one or more longer spacers are typically used to ensure that the one or more helicases are stalled on the target polynucleotide before they are contacted with the transmembrane pore and a potential is applied. One or more shorter spacers may be used in the absence of free nucleotides and a helicase cofactor (such that the one or more helicases are in the inactive mode).

The salt concentration also affects the ability of the one or more spacers to stall the one or more helicases. In the absence of the transmembrane pore and an applied potential, the one or more spacers are preferably capable of stalling the one or more helicases at a salt concentration of about 100 mM or lower. The higher the salt concentration used in the method of the invention, the shorter the one or more spacers that are typically used and vice versa.

Preferred combinations of features are shown in Table 1 below.

| Target poly-nucleotide | Spacer compo-sition* | Spacer length (i.e. number of*) | Salt [ ] | Free nucle-otides? | Helicase cofactor? |
| --- | --- | --- | --- | --- | --- |
| DNA | iSpC3 | 4 | 1M | Yes | Yes |
| DNA | iSp18 | 4 | 100-1000 mM | Yes | Yes |
| DNA | iSp18 | 6 | <100-1000 mM | Yes | Yes |
| DNA | iSp18 | 2 | 1M | Yes | Yes |
| DNA | iSpC3 | 12 | <100-1000 mM | Yes | Yes |
| DNA | iSpC3 | 20 | <100-1000 mM | Yes | Yes |
| DNA | iSp9 | 6 | 100-1000 mM | Yes | Yes |
| DNA | idSp | 4 | 1M | Yes | Yes |

As discussed in more detail below, the method may concern moving two or more helicases past a spacer. In such instances, the length of the spacer is typically increased to prevent the trailing helicase from pushing the leading helicase past the spacer in the absence of the pore and applied potential. If the method concerns moving two or more helicases past one or more spacers, the spacer lengths discussed above may be increased at least 1.5 fold, such 2 fold, 2.5 fold or 3 fold. For instance, if the method concerns moving two or more helicases past one or more spacers, the spacer lengths in the third column of Table 1 above may be increased 1.5 fold, 2 fold, 2.5 fold or 3 fold.

The two or more helicases may also be separated such that each has its own one or more spacers. This is discussed in more detail below.

Helicase(s)

Any helicase may be used in the invention. The helicase may be or be derived from a Hel308 helicase, a RecD helicase, such as TraI helicase or a TrwC helicase, a XPD helicase or a Dda helicase. The helicase may be any of the helicases, modified helicases or helicase constructs disclosed in International Application Nos. PCT/GB2012/052579 (published as WO 2013/057495); PCT/GB2012/053274 (published as WO 2013/098562); PCT/GB2012/053273 (published as WO2013098561); PCT/GB2013/051925; PCT/GB2013/051924 and PCT/GB2013/051928; and in UK Application No. 1318464.3 filed on 18 Oct. 2013).

The helicase preferably comprises the sequence shown in SEQ ID NO: 17 (Trwc Cba) or as variant thereof, the sequence shown in SEQ ID NO: 28 (Hel308 Mbu) or a variant thereof or the sequence shown in SEQ ID NO: 8 (Dda) or a variant thereof. Variants may differ from the native sequences in any of the ways discussed below for transmembrane pores. A preferred variant of SEQ ID NO: 8 comprises E94C/A360C and then ($\Delta$M1)G1G2 (i.e. deletion of M1 and then addition G1 and G2).

Any number of helicases may be moved past the one or more spacers in accordance with the invention. For instance, 1, 2, 3, 4, 5, 6, 7, 8, 9, 10 or more helicases may be moved past the one or more spacer. In some embodiments, different numbers of helicases may be moved past each spacer. For instance, if two helicases are stalled using two separate spacers, one helicase (the first helicase) may be moved past the first spacer, but two helicases (the first and second helicases) may be moved past the second spacer.

The method of the invention preferably comprises moving two or more, such as three or more or four or more, stalled helicases past one or more spacers. The two or more helicases are typically the same helicases. The two or more helicases may be different helicases.

The two or more helicases may be any combination of the helicases mentioned above. The two or more helicases may be two or more Dda helicases. The two or more helicases may be one or more Dda helicases and one or more TrwC helicases. The two or more helicases may be different variants of the same helicase.

The two or more helicases are preferably attached to one another. The two or more helicases are more preferably covalently attached to one another. The helicases may be attached in any order and using any method. Preferred helicase constructs for use in the invention are described in International Application Nos. PCT/GB2013/051925; PCT/GB2013/051924 and PCT/GB2013/051928; and in UK Application No. 1318464.3 filed on 18 Oct. 2013.

Conditions and Transmembrane Pores

The method comprises applying a potential across the pore. The applied potential may be a voltage potential. The method may comprise applying a voltage potential across the pore. The method may comprise increasing the voltage applied across the pore. In this embodiment, the initial voltage potential is typically not sufficient to move the one or more helicases past the one or more spacer and the increased voltage potential is typically sufficient to move the one or more helicases past the one or more spacers. Alternatively, the applied potential may be a chemical potential. An example of this is using a salt gradient across an amphiphilic layer. A salt gradient is disclosed in Holden et al., J Am Chem Soc. 2007 Jul. 11; 129(27):8650-5. In some instances, the current passing through the pore as the target polynucleotide moves with respect to the pore is used to determine the sequence of the target polynucleotide. This is strand sequencing.

A transmembrane pore is a structure that crosses the membrane to some degree. It permits hydrated ions driven by an applied potential to flow across or within the membrane. The transmembrane pore typically crosses the entire membrane so that hydrated ions may flow from one side of the membrane to the other side of the membrane. However, the transmembrane pore does not have to cross the membrane. It may be closed at one end. For instance, the pore may be a well in the membrane along which or into which hydrated ions may flow.

Any transmembrane pore may be used in the invention. The pore may be biological or artificial. Suitable pores include, but are not limited to, protein pores, polynucleotide pores and solid state pores.

Any membrane may be used in accordance with the invention. Suitable membranes are well-known in the art. The membrane is preferably an amphiphilic layer. An amphiphilic layer is a layer formed from amphiphilic molecules, such as phospholipids, which have both at least one hydrophilic portion and at least one lipophilic or hydrophobic portion. The amphiphilic molecules may be synthetic or naturally occurring. Non-naturally occurring amphiphiles and amphiphiles which form a monolayer are known in the art and include, for example, block copolymers (Gonzalez-Perez et al., Langmuir, 2009, 25, 10447-10450). Block copolymers are polymeric materials in which two or more monomer sub-units that are polymerized together to create a single polymer chain. Block copolymers typically have properties that are contributed by each monomer sub-unit. However, a block copolymer may have unique properties that polymers formed from the individual sub-units do not possess. Block copolymers can be engineered such that one of the monomer sub-units is hydrophobic (i.e. lipophilic), whilst the other sub-unit(s) are hydrophilic whilst in aqueous media. In this case, the block copolymer may possess amphiphilic properties and may form a structure that mimics a biological membrane. The block copolymer may be a diblock (consisting of two monomer sub-units), but may also be constructed from more than two monomer sub-units to form more complex arrangements that behave as amphiphiles. The copolymer may be a triblock, tetrablock or pentablock copolymer.

The amphiphilic layer may be a monolayer or a bilayer. The amphiphilic layer is typically a planar lipid bilayer or a supported bilayer.

The amphiphilic layer is typically a lipid bilayer. Lipid bilayers are models of cell membranes and serve as excellent platforms for a range of experimental studies. For example, lipid bilayers can be used for in vitro investigation of membrane proteins by single-channel recording. Alternatively, lipid bilayers can be used as biosensors to detect the presence of a range of substances. The lipid bilayer may be any lipid bilayer. Suitable lipid bilayers include, but are not limited to, a planar lipid bilayer, a supported bilayer or a liposome. The lipid bilayer is preferably a planar lipid bilayer. Suitable lipid bilayers are disclosed in International Application No. PCT/GB08/000563 (published as WO 2008/102121), International Application No. PCT/GB08/004127 (published as WO 2009/077734) and International Application No. PCT/GB2006/001057 (published as WO 2006/100484).

Methods for forming lipid bilayers are known in the art. Suitable methods are disclosed in the Examples. Lipid bilayers are commonly formed by the method of Montal and Mueller (Proc. Natl. Acad. Sci. USA., 1972; 69: 3561-3566), in which a lipid monolayer is carried on aqueous solution/air interface past either side of an aperture which is perpendicular to that interface.

The method of Montal & Mueller is popular because it is a cost-effective and relatively straightforward method of forming good quality lipid bilayers that are suitable for protein pore insertion. Other common methods of bilayer formation include tip-dipping, painting bilayers and patch-clamping of liposome bilayers.

In a preferred embodiment, the lipid bilayer is formed as described in International Application No. PCT/GB08/004127 (published as WO 2009/077734).

In another preferred embodiment, the membrane is a solid state layer. A solid-state layer is not of biological origin. In other words, a solid state layer is not derived from or isolated from a biological environment such as an organism or cell, or a synthetically manufactured version of a biologically available structure. Solid state layers can be formed from both organic and inorganic materials including, but not limited to, microelectronic materials, insulating materials such as $Si_3N_4$, $Al_2O_3$, and SiO, organic and inorganic polymers such as polyamide, plastics such as Teflon® or elastomers such as two-component addition-cure silicone rubber, and glasses. The solid state layer may be formed from monatomic layers, such as graphene, or layers that are only a few atoms thick. Suitable graphene layers are disclosed in International Application No. PCT/US2008/010637 (published as WO 2009/035647).

The method is typically carried out using (i) an artificial amphiphilic layer comprising a pore, (ii) an isolated, naturally-occurring lipid bilayer comprising a pore, or (iii) a cell having a pore inserted therein. The method is typically carried out using an artificial amphiphilic layer, such as an artificial lipid bilayer. The layer may comprise other transmembrane and/or intramembrane proteins as well as other molecules in addition to the pore. Suitable apparatus and conditions are discussed below. The method of the invention is typically carried out in vitro.

The target polynucleotide is preferably coupled to the membrane. This may be done using any known method. If the membrane is an amphiphilic layer, such as a lipid bilayer (as discussed in detail above), the target polynucleotide is preferably coupled to the membrane via a polypeptide present in the membrane or a hydrophobic anchor present in the membrane. The hydrophobic anchor is preferably a lipid, fatty acid, sterol, carbon nanotube or amino acid.

The target polynucleotide may be coupled directly to the membrane. It may be coupled to the membrane using any of the ways disclosed in International Application Number No. PCT/GB2012/051191 (published as WO 2012/164270). The target polynucleotide is preferably coupled to the membrane via a linker. Preferred linkers include, but are not limited to, polymers, such as polynucleotides, polyethylene glycols (PEGs) and polypeptides. If a target polynucleotide is coupled directly to the membrane, then some data will be lost as the characterising run cannot continue to the end of the polynucleotide due to the distance between the membrane and the pore and/or helicase. If a linker is used, then the target polynucleotide can be processed to completion. If a linker is used, the linker may be attached to the target polynucleotide at any position. The linker is typically attached to the target polynucleotide at the tail polymer.

The coupling may be stable or transient. For certain applications, the transient nature of the coupling is preferred. If a stable coupling molecule were attached directly to either the 5' or 3' end of a polynucleotide, then some data will be lost as the characterising run cannot continue to the end of the polynucleotide due to the distance between the membrane and the pore and/or helicase. If the coupling is transient, then when the coupled end randomly becomes free of the membrane, then the polynucleotide can be processed to completion. Chemical groups that form stable or transient links with the membrane are discussed in more detail below. The polynucleotide may be transiently coupled to an amphiphilic layer, such as a lipid bilayer using cholesterol or a fatty acyl chain. Any fatty acyl chain having a length of from 6 to 30 carbon atoms, such as hexadecanoic acid, may be used.

In preferred embodiments, the polynucleotide is coupled to an amphiphilic layer. Coupling of polynucleotides to synthetic lipid bilayers has been carried out previously with various different tethering strategies. These are summarised in Table 2 below.

TABLE 2

| Attachment group | Type of coupling | Reference |
|---|---|---|
| Thiol | Stable | Yoshina-Ishii, C. and S. G. Boxer (2003). "Arrays of mobile tethered vesicles on supported lipid bilayers." J Am Chem Soc 125(13): 3696-7. |
| Biotin | Stable | Nikolov, V., R, Lipowsky, et al. (2007). "Behavior of giant vesicles with anchored DNA molecules," Biophys J 92(12): 4356-68 |
| Cholesterol | Transient | Pfeiffer, I. and F. Hook (2004). "Bivalent cholesterol-based coupling of oligonucletides to lipid membrane assemblies." J Am Chem Soc 126(33): 10224-5 |
| Lipid | Stable | van Lengerich, B., R. J, Rawle, et al. "Covalent attachment of lipid vesicles to a fluid-supported bilayer allows observation of DNA-mediated vesicle interactions." Langmuir 26(11): 8666-72 |

Polynucleotides may be functionalized using a modified phosphoramidite in the synthesis reaction, which is easily compatible for the addition of reactive groups, such as thiol, cholesterol, lipid and biotin groups. These different attachment chemistries give a suite of attachment options for polynucleotides. Each different modification group tethers the polynucleotide in a slightly different way and coupling is not always permanent so giving different dwell times for the polynucleotide to the membrane. The advantages of transient coupling are discussed above.

Coupling of polynucleotides can also be achieved by a number of other means provided that a reactive group can be added to the polynucleotide. The addition of reactive groups to either end of DNA has been reported previously. A thiol group can be added to the 5' of ssDNA using polynucleotide kinase and ATPγS (Grant, G. P. and P. Z. Qin (2007). "A facile method for attaching nitroxide spin labels at the 5' terminus of nucleic acids." *Nucleic Acids Res* 35(10): e77). A more diverse selection of chemical groups, such as biotin, thiols and fluorophores, can be added using terminal transferase to incorporate modified oligonucleotides to the 3' of ssDNA (Kumar, A., P. Tehen, et al. (1988). "Nonradioactive labeling of synthetic oligonucleotide probes with terminal deoxynucleotidyl transferase." *Anal Biochem* 169(2): 376-82).

Alternatively, the reactive group could be considered to be a short region in the polynucleotide to one already coupled to the membrane, so that attachment can be achieved via hybridisation. The region could be part of the polynucleotide or ligated to it. Ligation of short pieces of ssDNA have been reported using T4 RNA ligase I (Troutt, A. B., M. G. McHeyzer-Williams, et al. (1992). "Ligation-anchored PCR: a simple amplification technique with single-sided specificity." Proc Natl Acad Sci USA 89(20): 9823-5).

Most preferably, the polynucleotide is coupled to the membrane using a cholesterol-tagged polynucleotide which hybridises to the polynucleotide.

The transmembrane pore is preferably a transmembrane protein pore. A transmembrane protein pore is a polypeptide or a collection of polypeptides that permits hydrated ions, such as analyte, to flow from one side of a membrane to the other side of the membrane. In the present invention, the transmembrane protein pore is capable of forming a pore that permits hydrated ions driven by an applied potential to flow from one side of the membrane to the other. The transmembrane protein pore preferably permits analyte such as nucleotides to flow from one side of the membrane, such as a lipid bilayer, to the other. The transmembrane protein pore allows a polynucleotide or nucleic acid, such as DNA or RNA, to be moved through the pore.

The transmembrane protein pore may be a monomer or an oligomer. The pore is preferably made up of several repeating subunits, such as 6, 7, 8 or 9 subunits. The pore is preferably a hexameric, heptameric, octameric or nonameric pore.

The transmembrane protein pore typically comprises a barrel or channel through which the ions may flow. The subunits of the pore typically surround a central axis and contribute strands to a transmembrane β barrel or channel or a transmembrane α-helix bundle or channel.

The barrel or channel of the transmembrane protein pore typically comprises amino acids that facilitate interaction with analyte, such as nucleotides, polynucleotides or nucleic acids. These amino acids are preferably located near a constriction of the barrel or channel. The transmembrane protein pore typically comprises one or more positively charged amino acids, such as arginine, lysine or histidine, or aromatic amino acids, such as tyrosine or tryptophan. These amino acids typically facilitate the interaction between the pore and nucleotides, polynucleotides or nucleic acids.

Transmembrane protein pores for use in accordance with the invention can be derived from β-barrel pores or α-helix bundle pores. β-barrel pores comprise a barrel or channel that is formed from β-strands. Suitable β-barrel pores include, but are not limited to, β-toxins, such as α-hemolysin, anthrax toxin and leukocidins, and outer membrane proteins/porins of bacteria, such as *Mycobacterium smegmatis* porin (Msp), for example MapA, MspB, MspC or MspD, lysening, outer membrane porin F (OmpF), outer membrane porin G (OmpG), outer membrane phospholipase A and *Neisseria* autotransporter lipoprotein (NalP). α-helix bundle pores comprise a barrel or channel that is formed from α-helices. Suitable α-helix bundle pores include, but are not limited to, inner membrane proteins and α outer membrane proteins, such as WZA and ClyA toxin. The transmembrane pore may be derived from lysenin. Suitable pores derived from lysenin are disclosed in International Application No. PCT/GB2013/050667 (published as WO 2013/153359). The transmembrane pore may be derived from Msp or from α-hemolysin (α-HL).

The transmembrane protein pore is preferably derived from Msp, preferably from MspA. Such a pore will be oligomeric and typically comprises 7, 8, 9 or 10 monomers derived from Map. The pore may be a homo-oligomeric pore derived from Msp comprising identical monomers. Alternatively, the pore may be a hetero-oligomeric pore derived from Msp comprising at least one monomer that differs from the others. Preferably the pore is derived from MspA or a homolog or paralog thereof.

A monomer derived from Msp typically comprises the sequence shown in SEQ ID NO: 2 or a variant thereof. SEQ ID NO: 2 is the MS-(B1)8 mutant of the MspA monomer. It includes the following mutations: D90N, D91N, D93N, D118R, D134R and E139K. A variant of SEQ ID NO: 2 is a polypeptide that has an amino acid sequence which varies from that of SEQ ID NO: 2 and which retains its ability to form a pore. The ability of a variant to form a pore can be assayed using any method known in the art. For instance, the variant may be inserted into an amphiphilic layer along with other appropriate subunits and its ability to oligomerise to form a pore may be determined. Methods are known in the art for inserting subunits into membranes, such as amphiphilic layers. For example, subunits may be suspended in a purified form in a solution containing a lipid bilayer such that it diffuses to the lipid bilayer and is inserted by binding to the lipid bilayer and assembling into a functional state. Alternatively, subunits may be directly inserted into the membrane using the "pick and place" method described in M. A. Holden, H. Bayley. J. Am. Chem. Soc. 2005, 127, 6502-6503 and International Application No. PCT/GB2006/001057 (published as WO 2006/100484).

Over the entire length of the amino acid sequence of SEQ ID NO: 2, a variant will preferably be at least 50% homologous to that sequence based on amino acid identity. More preferably, the variant may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 2 over the entire sequence. There may be at least 80%, for example at least 85%, 90% or 95%, amino acid identity over a stretch of 100 or more, for example 125, 150, 175 or 200 or more, contiguous amino acids ("hard homology").

Standard methods in the art may be used to determine homology. For example the UWGCG Package provides the BESTFIT program which can be used to calculate homology, for example used on its default settings (Devereux et al (1984) *Nucleic Acids Research* 12, p 387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F et al (1990) J Mol Biol 215:403-10. Software for performing BLAST analyses is publicly available through the National Center for Biotechnology Information (http://www.ncbi.nlm.nih.gov/).

SEQ ID NO: 2 is the MS-(B1)8 mutant of the MspA monomer. The variant may comprise any of the mutations in the MspB, C or D monomers compared with MspA. The mature forms of MspB, C and D are shown in SEQ ID NOs: 5 to 7. In particular, the variant may comprise the following substitution present in MspB: A138P. The variant may comprise one or more of the following substitutions present in MspC: A96G, N102E and A138P. The variant may comprise one or more of the following mutations present in MspD: Deletion of G1, L2V, E5Q, L8V, D13O, W21A, D22E, K47T, I49H, I68V, D91G, A96Q, N102D, S103T, V104I, S136K and G141A. The variant may comprise combinations of one or more of the mutations and substitutions from Map B, C and D. The variant preferably comprises the mutation L88N. A variant of SEQ ID NO: 2 has the mutation L88N in addition to all the mutations of MS-(B1)8 and is called MS-(B2)8. The pore used in the invention is preferably MS-(B2)8. The further preferred variant comprises the mutations G75S/G77S/L88N/Q126R. The variant of SEQ ID NO: 2 has the mutations G75S/G77S/L88N/Q126R in addition to all the mutations of MS-(B1)8 and is called MS-(B2C)8. The pore used in the invention is preferably MS-(B2)8 or MS-(B2C)8.

Amino acid substitutions may be made to the amino acid sequence of SEQ ID NO: 2 in addition to those discussed above, for example up to 1, 2, 3, 4, 5, 10, 20 or 30 substitutions. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid. Conservative amino acid changes are well-known in the art and may be selected in accordance with the properties of the 20 main amino acids as defined in Table 3 below. Where amino acids have similar polarity, this can also be determined by reference to the hydropathy scale for amino acid side chains in Table 4.

TABLE 3

Chemical properties of amino acids

| Ala | aliphatic, hydrophobic, neutral | Met | hydrophobic, neutral |
| --- | --- | --- | --- |
| Cys | polar, hydrophobic, neutral | Asn | polar, hydrophilic, neutral |
| Asp | polar, hydrophilic, charged (−) | Pro | hydrophobic, neutral |
| Glu | polar, hydrophilic, charged (−) | Gln | polar, hydrophilic, neutral |
| Phe | aromatic, hydrophobic, neutral | Arg | polar, hydrophilic, charged (+) |
| Gly | aliphatic, neutral | Ser | polar, hydrophilic, neutral |
| His | aromatic, polar, hydrophilic, charged (+) | Thr | polar, hydrophilic, neutral |
| Ile | aliphatic, hydrophobic, neutral | Val | aliphatic, hydrophobic, neutral |
| Lys | polar, hydrophilic, charged(+) | Trp | aromatic, hydrophobic, neutral |
| Leu | aliphatic, hydrophobic, neutral | Tyr | aromatic, polar, hydrophobic |

TABLE 4

Hydropathy scale

| Side Chain | Hydropathy |
| --- | --- |
| Ile | 4.5 |
| Val | 4.2 |
| Leu | 3.8 |
| Phe | 2.8 |
| Cys | 2.5 |
| Met | 1.9 |
| Ala | 1.8 |
| Gly | −0.4 |
| Thr | −0.7 |
| Ser | −0.8 |
| Trp | −0.9 |
| Tyr | −1.3 |
| Pro | −1.6 |
| His | −3.2 |
| Glu | −3.5 |
| Gln | −3.5 |
| Asp | −3.5 |
| Asn | −3.5 |
| Lys | −3.9 |
| Arg | −4.5 |

One or more amino acid residues of the sequence of SEQ ID NO: 2 may additionally be deleted from the polypeptides described above. Up to 1, 2, 3, 4, 5, 10, 20 or 30 residues may be deleted, or more.

Variants may include fragments of SEQ ID NO: 2. Such fragments retain pore forming activity. Fragments may be at least 50, 100, 150 or 200 amino acids in length. Such fragments may be used to produce the pores. A fragment preferably comprises the pore forming domain of SEQ ID NO: 2. Fragments must include one of residues 88, 90, 91, 105, 118 and 134 of SEQ ID NO: 2. Typically, fragments include all of residues 88, 90, 91, 105, 118 and 134 of SEQ ID NO: 2.

One or more amino acids may be alternatively or additionally added to the polypeptides described above. An extension may be provided at the amino terminal or carboxy terminal of the amino acid sequence of SEQ ID NO: 2 or polypeptide variant or fragment thereof. The extension may be quite short, for example from 1 to 10 amino acids in length. Alternatively, the extension may be longer, for example up to 50 or 100 amino acids. A carrier protein may be fused to an amino acid sequence according to the invention. Other fusion proteins are discussed in more detail below.

As discussed above, a variant is a polypeptide that has an amino acid sequence which varies from that of SEQ ID NO: 2 and which retains its ability to form a pore. A variant typically contains the regions of SEQ ID NO: 2 that are responsible for pore formation. The pore forming ability of Msp, which contains a β-barrel, is provided by β-sheets in each subunit. A variant of SEQ ID NO: 2 typically comprises the regions in SEQ ID NO: 2 that form β-sheets. One or more modifications can be made to the regions of SEQ ID NO: 2 that form β-sheets as long as the resulting variant retains its ability to form a pore. A variant of SEQ ID NO: 2 preferably includes one or more modifications, such as substitutions, additions or deletions, within its α-helices and/or loop regions.

The monomers derived from Msp may be modified to assist their identification or purification, for example by the addition of histidine residues (a his tag), aspartic acid residues (an asp tag), a streptavidin tag or a flag tag, or by the addition of a signal sequence to promote their secretion from a cell where the polypeptide does not naturally contain such a sequence. An alternative to introducing a genetic tag is to chemically react a tag onto a native or engineered position on the pore. An example of this would be to react a gel-shift reagent to a cysteine engineered on the outside of the pore. This has been demonstrated as a method for separating hemolysin hetero-oligomers (Chem Biol. 1997 July; 4(7):497-505).

The monomer derived from Msp may be labelled with a revealing label. The revealing label may be any suitable label which allows the pore to be detected. Suitable labels are described below.

The monomer derived from Msp may also be produced using D-amino acids. For instance, the monomer derived from Msp may comprise a mixture of L-amino acids and D-amino acids. This is conventional in the art for producing such proteins or peptides.

The monomer derived from Msp contains one or more specific modifications to facilitate nucleotide discrimination. The monomer derived from Msp may also contain other non-specific modifications as long as they do not interfere with pore formation. A number of non-specific side chain modifications are known in the art and may be made to the side chains of the monomer derived from Msp. Such modifications include, for example, reductive alkylation of amino acids by reaction with an aldehyde followed by reduction with $NaBH_4$, amidination with methylacetimidate or acylation with acetic anhydride.

The monomer derived from Msp can be produced using standard methods known in the art. The monomer derived from Msp may be made synthetically or by recombinant means. For example, the pore may be synthesized by in vitro translation and transcription (IVTT). Suitable methods for producing pores are discussed in International Application Nos. PCT/GB09/001690 (published as WO 2010/004273), PCT/GB09/001679 (published as WO 2010/004265) or PCT/GB10/000133 (published as WO 2010/086603). Methods for inserting pores into membranes are discussed.

The transmembrane protein pore is also preferably derived from a-hemolysin (α-HL). The wild type α-HL pore is formed of seven identical monomers or subunits (i.e. it is heptameric). The sequence of one monomer or subunit of α-hemolysin-NN is shown in SEQ ID NO: 4. The transmembrane protein pore preferably comprises seven monomers each comprising the sequence shown in SEQ ID NO: 4 or a variant thereof. Amino acids 1, 7 to 21, 31 to 34, 45 to 51, 63 to 66, 72, 92 to 97, 104 to 111, 124 to 136, 149 to 153, 160 to 164, 173 to 206, 210 to 213, 217, 218, 223 to 228, 236 to 242, 262 to 265, 272 to 274, 287 to 290 and 294 of SEQ ID NO: 4 form loop regions. Residues 113 and 147 of SEQ ID NO: 4 form part of a constriction of the barrel or channel of α-HL.

In such embodiments, a pore comprising seven proteins or monomers each comprising the sequence shown in SEQ ID NO: 4 or a variant thereof are preferably used in the method of the invention. The seven proteins may be the same (homo-heptamer) or different (hetero-heptamer).

A variant of SEQ ID NO: 4 is a protein that has an amino acid sequence which varies from that of SEQ ID NO: 4 and which retains its pore forming ability. The ability of a variant to form a pore can be assayed using any method known in the art. For instance, the variant may be inserted into an amphiphilic layer, such as a lipid bilayer, along with other appropriate subunits and its ability to oligomerise to form a pore may be determined. Methods are known in the art for inserting subunits into amphiphilic layers, such as lipid bilayers. Suitable methods are discussed above.

The variant may include modifications that facilitate covalent attachment to or interaction with the helicase. The variant preferably comprises one or more reactive cysteine residues that facilitate attachment to the helicase. For instance, the variant may include a cysteine at one or more of positions 8, 9, 17, 18, 19, 44, 45, 50, 51, 237, 239 and 287 and/or on the amino or carboxy terminus of SEQ ID NO: 4. Preferred variants comprise a substitution of the residue at position 8, 9, 17, 237, 239 and 287 of SEQ ID NO: 4 with cysteine (A8C, T9C, N17C, K237C, S239C or E287C). The variant is preferably any one of the variants described in International Application No. PCT/GB09/001690 (published as WO 2010/004273), PCT/GB09/001679 (published as WO 2010/004265) or PCT/GB10/000133 (published as WO 2010/086603).

The variant may also include modifications that facilitate any interaction with nucleotides.

The variant may be a naturally occurring variant which is expressed naturally by an organism, for instance by a *Staphylococcus* bacterium. Alternatively, the variant may be expressed in vitro or recombinantly by a bacterium such as *Escherichia coli*. Variants also include non-naturally occurring variants produced by recombinant technology. Over the entire length of the amino acid sequence of SEQ ID NO: 4, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 4 over the entire sequence. There may be at least 80%, for example at least 85%, 90% or 95%, amino acid identity over a stretch of 200 or more, for example 230, 250, 270 or 280 or more, contiguous amino acids ("hard homology"). Homology can be determined as discussed above.

Amino acid substitutions may be made to the amino acid sequence of SEQ ID NO: 4 in addition to those discussed above, for example up to 1, 2, 3, 4, 5, 10, 20 or 30 substitutions. Conservative substitutions may be made as discussed above.

One or more amino acid residues of the amino acid sequence of SEQ ID NO: 4 may additionally be deleted from the polypeptides described above. Up to 1, 2, 3, 4, 5, 10, 20 or 30 residues may be deleted, or more.

Variants may be fragments of SEQ ID NO: 4. Such fragments retain pore-forming activity. Fragments may be at least 50, 100, 200 or 250 amino acids in length. A fragment preferably comprises the pore-forming domain of SEQ ID NO: 4. Fragments typically include residues 119, 121, 135. 113 and 139 of SEQ ID NO: 4.

One or more amino acids may be alternatively or additionally added to the polypeptides described above. An extension may be provided at the amino terminus or carboxy terminus of the amino acid sequence of SEQ ID NO: 4 or a variant or fragment thereof. The extension may be quite short, for example from 1 to 10 amino acids in length. Alternatively, the extension may be longer, for example up to 50 or 100 amino acids. A carrier protein may be fused to a pore or variant.

As discussed above, a variant of SEQ ID NO: 4 is a subunit that has an amino acid sequence which varies from that of SEQ ID NO: 4 and which retains its ability to form a pore. A variant typically contains the regions of SEQ ID NO: 4 that are responsible for pore formation. The pore forming ability of α-HL, which contains a β-barrel, is provided by β-strands in each subunit. A variant of SEQ ID NO: 4 typically comprises the regions in SEQ ID NO: 4 that form β-strands. The amino acids of SEQ ID NO: 4 that form β-strands are discussed above. One or more modifications can be made to the regions of SEQ ID NO: 4 that form β-strands as long as the resulting variant retains its ability to form a pore. Specific modifications that can be made to the p-strand regions of SEQ ID NO: 4 are discussed above.

A variant of SEQ ID NO: 4 preferably includes one or more modifications, such as substitutions, additions or deletions, within its a-helices and/or loop regions. Amino acids that form α-helices and loops are discussed above.

The variant may be modified to assist its identification or purification as discussed above.

Pores derived from α-HL can be made as discussed above with reference to pores derived from Msp.

In some embodiments, the transmembrane protein pore is chemically modified. The pore can be chemically modified in any way and at any site. The transmembrane protein pore is preferably chemically modified by attachment of a molecule to one or more cysteines (cysteine linkage), attachment of a molecule to one or more lysines, attachment of a molecule to one or more non-natural amino acids, enzyme modification of an epitope or modification of a terminus. Suitable methods for carrying out such modifications are well-known in the art. The transmembrane protein pore may be chemically modified by the attachment of any molecule. For instance, the pore may be chemically modified by attachment of a dye or a fluorophore.

Any number of the monomers in the pore may be chemically modified. One or more, such as 2, 3, 4, 5, 6, 7, 8, 9 or 10, of the monomers is preferably chemically modified as discussed above.

The reactivity of cysteine residues may be enhanced by modification of the adjacent residues. For instance, the basic groups of flanking arginine, histidine or lysine residues will change the pKa of the cysteines thiol group to that of the more reactive $S^-$ group. The reactivity of cysteine residues may be protected by thiol protective groups such as dTNB. These may be reacted with one or more cysteine residues of the pore before a linker is attached.

The molecule (with which the pore is chemically modified) may be attached directly to the pore or attached via a linker as disclosed in International Application Nos. PCT/GB09/001690 (published as WO 2010/004273), PCT/GB09/001679 (published as WO 2010/004265) or PCT/GB10/000133 (published as WO 2010/086603).

The helicase may be covalently attached to the pore. The helicase is preferably not covalently attached to the pore.

Any of the proteins described herein may be modified to assist their identification or purification, for example by the addition of histidine residues (a his tag), aspartic acid residues (an asp tag), a streptavidin tag, a flag tag, a SUMO tag, a GST tag or a MBP tag, or by the addition of a signal sequence to promote their secretion from a cell where the polypeptide does not naturally contain such a sequence. An alternative to introducing a genetic tag is to chemically react a tag onto a native or engineered position on the helicase or pore. An example of this would be to react a gel-shift reagent to a cysteine engineered on the outside of the pore. This has been demonstrated as a method for separating hemolysin hetero-oligomers (Chem Biol. 1997 July; 4 (7):497-505).

The target polynucleotide, helicase or pore may be labelled with a revealing label. The revealing label may be any suitable label which can be detected. Suitable labels include, but are not limited to, fluorescent molecules, radio-isotopes, e.g. $^{125}I$, $^{35}S$, enzymes, antibodies, antigens, polynucleotides and ligands such as biotin.

Proteins may be made synthetically or by recombinant means. For example, proteins may be synthesized by in vitro translation and transcription (IVTT). The amino acid sequence of the protein may be modified to include non-naturally occurring amino acids or to increase the stability of the protein. When a protein is produced by synthetic means, such amino acids may be introduced during production. Proteins may also be altered following either synthetic or recombinant production.

Proteins may also be produced using D-amino acids. For instance, the pore or helicase may comprise a mixture of L-amino acids and D-amino acids. This is conventional in the art for producing such proteins or peptides.

The proteins used in the invention may also contain other non-specific modifications as long as they do not interfere with the proteins' function. A number of non-specific side chain modifications are known in the art and may be made to the side chains of the protein(s). Such modifications include, for example, reductive alkylation of amino acids by reaction with an aldehyde followed by reduction with $NaBH_4$, amidination with methylacetimidate or acylation with acetic anhydride.

Polynucleotide sequences encoding a protein may be derived and replicated using standard methods in the art. Polynucleotide sequences encoding a protein may be expressed in a bacterial host cell using standard techniques in the art. The protein may be produced in a cell by in situ expression of the polypeptide from a recombinant expression vector. The expression vector optionally carries an inducible promoter to control the expression of the polypeptide. These methods are described in Sambrook, J. and Russell, D. (2001). Molecular Cloning: A Laboratory Manual, 3rd Edition. Cold Spring Harbor Laboratory Press, Cold Spring Harbor, N.Y.

The gene encoding the sequence of interest may be amplified using PCR involving specific primers. The amplified sequences may then be incorporated into a recombinant replicable vector such as a cloning vector. The vector may be used to replicate the polynucleotide in a compatible host cell. Thus polynucleotide sequences may be made by introducing a polynucleotide encoding the sequence of interest into a replicable vector, introducing the vector into a compatible host cell, and growing the host cell under conditions which bring about replication of the vector. The vector may be recovered from the host cell. Suitable host cells for cloning of polynucleotides are known in the art and described in more detail below.

The polynucleotide sequence may be cloned into a suitable expression vector. In an expression vector, the polynucleotide sequence is typically operably linked to a control sequence which is capable of providing for the expression of the coding sequence by the host cell. Such expression vectors can be used to express a construct.

The term "operably linked" refers to a juxtaposition wherein the components described are in a relationship permitting them to function in their intended manner. A control sequence "operably linked" to a coding sequence is ligated in such a way that expression of the coding sequence is achieved wider conditions compatible with the control sequences. Multiple copies of the same or different polynucleotide may be introduced into the vector.

The expression vector may then be introduced into a suitable host cell. Thus, a construct can be produced by inserting a polynucleotide sequence encoding a construct into an expression vector, introducing the vector into a compatible bacterial host cell, and growing the host cell under conditions which bring about expression of the polynucleotide sequence.

The vectors may be for example, plasmid, virus or phage vectors provided with an origin of replication, optionally a promoter for the expression of the said polynucleotide sequence and optionally a regulator of the promoter. The vectors may contain one or more selectable marker genes, for example an ampicillin resistance gene. Promoters and other expression regulation signals may be selected to be compatible with the host cell for which the expression vector is designed. A T7, tre, lac, ara or $\lambda_L$ promoter is typically used.

The host cell typically expresses the construct at a high level. Host cells transformed with a polynucleotide sequence will be chosen to be compatible with the expression vector used to transform the cell. The host cell is typically bacterial and preferably E. coli. Any cell with a λ DE3 lysogen, for example Rosetta2(DE3)pLys, C41 (DE3), BL21 (DE3), JM109 (DE3), B834 (DE3), TUNER, Origami and Origami B, can express a vector comprising the T7 promoter.

Proteins may be produced in large scale following purification by any protein liquid chromatography system from protein producing organisms or after recombinant expression. Typical protein liquid chromatography systems include FPLC, AKTA systems, the Bio-Cad system, the Bio-Rad BioLogic system and the Gilson HPLC system.

The method of the invention involves measuring one or more characteristics of the target polynucleotide. The method may involve measuring two, three, four or five or more characteristics of the target polynucleotide. The one or more characteristics are preferably selected from (i) the length of the target polynucleotide, (ii) the identity of the target polynucleotide, (iii) the sequence of the target polynucleotide, (iv) the secondary structure of the target polynucleotide and (v) whether or not the target polynucleotide is modified. Any combination of (i) to (v) may be measured in accordance with the invention.

For (i), the length of the polynucleotide may be measured for example by determining the number of interactions between the target polynucleotide and the pore or the duration of interaction between the target polynucleotide and the pore.

For (ii), the identity of the polynucleotide may be measured in a number of ways. The identity of the polynucleotide may be measured in conjunction with measurement of the sequence of the target polynucleotide or without measurement of the sequence of the target polynucleotide. The former is straightforward; the polynucleotide is sequenced and thereby identified. The latter may be done in several ways. For instance, the presence of a particular motif in the polynucleotide may be measured (without measuring the remaining sequence of the polynucleotide). Alternatively, the measurement of a particular electrical and/or optical signal in the method may identify the target polynucleotide as coming from a particular source.

For (iii), the sequence of the polynucleotide can be determined as described previously. Suitable sequencing methods, particularly those using electrical measurements, are described in Stoddart D et al., Proc Natl Acad Sci, 12; 106(19):7702-7, Lieberman K R et al, J Am Chem Soc. 2010; 132(50):17961-72, and International Application WO 2000/28312.

For (iv), the secondary structure may be measured in a variety of ways. For instance, if the method involves an electrical measurement, the secondary structure may be measured using a change in dwell time or a change in current flowing through the pore. This allows regions of single-stranded and double-stranded polynucleotide to be distinguished.

For (v), the presence or absence of any modification may be measured. The method preferably comprises determining whether or not the target polynucleotide is modified by methylation, by oxidation, by damage, with one or more proteins or with one or more labels, tags or spacers. Specific modifications will result in specific interactions with the pore which can be measured using the methods described below. For instance, methylcytosine may be distinguished from cytosine on the basis of the current flowing through the pore during its interaction with each nucleotide.

A variety of different types of measurements may be made. This includes without limitation: electrical measurements and optical measurements. Possible electrical measurements include: current measurements, impedance measurements, tunneling measurements (Ivanov A P et al., Nano Lett. 2011 Jan. 12; 11(1):279-85), and FET measurements (International Application WO 2005/124888). Optical measurements may be combined with electrical measurements (Soni G V et al., Rev Sci Instrum. 2010 January; 81(1): 014301). The measurement may be a transmembrane current measurement such as measurement of ionic current flowing through the pore.

Electrical measurements may be made using standard single channel recording equipment as describe in Stoddart D et al., Proc Natl Acad Sci, 12; 106(19):7702-7, Lieberman K R et al, J Am Chem Soc. 2010; 132(50):17961-72, and International Application WO-2000/28312. Alternatively, electrical measurements may be made using a multi-channel system, for example as described in International Application WO-2009/077734 and International Application WO-2011/067559.

The methods may be carried out using any apparatus that is suitable for investigating a membrane/pore system in which a pore is present in a membrane. The method may be carried out using any apparatus that is suitable for transmembrane pore sensing. For example, the apparatus comprises a chamber comprising an aqueous solution and a barrier that separates the chamber into two sections. The barrier typically has an aperture in which the membrane containing the pore is formed. Alternatively the barrier forms the membrane in which the pore is present.

The methods may be carried out using the apparatus described in International Application No. PCT/GB08/000562 (WO 2008/102120).

The methods may involve measuring the current passing through the pore as the polynucleotide moves with respect to the pore. Therefore the apparatus may also comprise an electrical circuit capable of applying a potential and measuring an electrical signal across the membrane and pore. The methods may be carried out using a patch clamp or a voltage clamp. The methods preferably involve the use of a voltage clamp.

The methods of the invention may involve the measuring of a current passing through the pore as the polynucleotide moves with respect to the pore. Suitable conditions for measuring ionic currents through transmembrane protein pores are known in the art and disclosed in the Examples. The method is typically carried out with a voltage applied across the membrane and pore. The voltage used is typically from +2 V to −2 V, typically −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 100 mV to 240 mV and most preferably in the range of 120 mV to 220 mV. It is possible to increase discrimination between different nucleotides by a pore by using an increased applied potential.

The methods are typically carried out in the presence of any charge carriers, such as metal salts, for example alkali metal salt, halide salts, for example chloride salts, such as alkali metal chloride salt. Charge carriers may include ionic liquids or organic salts, for example tetramethyl ammonium chloride, trimethylphenyl ammonium chloride, phenyltrimethyl ammonium chloride, or 1-ethyl-3-methyl imidazolium chloride. In the exemplary apparatus discussed above, the salt is present in the aqueous solution in the chamber. Potassium chloride (KCl), sodium chloride (NaCl), caesium chloride (CsCl) or a mixture of potassium ferrocyanide and potassium ferricyanide is typically used. KCl, NaCl and a mixture of potassium ferrocyanide and potassium ferricyanide are preferred. The salt concentration may be at saturation. The salt concentration may be 3 M or lower and is typically from 0.1 to 2.5 M, from 0.3 to 1.9 M, from 0.5 to 1.8 M, from 0.7 to 1.7 M, from 0.9 to 1.6 M or from 1 M to 1.4 M. The salt concentration is preferably from 150 mM to 1 M. Hel308, XPD, RecD, TraI and Dda helicases surprisingly work under high salt concentrations. The method is preferably carried out using a salt concentration of at least 0.3 M, such as at least 0.4 M, at least 0.5 M, at least 0.6 M, at least 0.8 M, at least 1.0 M, at least 1.5 M, at least 2.0 M, at least 2.5 M or at least 3.0 M. High salt concentrations provide a high signal to noise ratio and allow for currents indicative of the presence of a nucleotide to be identified against the background of normal current fluctuations.

The methods are typically carried out in the presence of a buffer. In the exemplary apparatus discussed above, the buffer is present in the aqueous solution in the chamber. Any buffer may be used in the method of the invention. Typically, the buffer is phosphate buffer. Other suitable buffers are HEPES and Tris-HCl buffer. The methods are typically carried out at a pH of from 4.0 to 12.0, from 4.5 to 10.0, from 5.0 to 9.0, from 5.5 to 8.8, from 6.0 to 8.7 or from 7.0 to 8.8 or 7.5 to 8.5. The pH used is preferably about 7.5.

The methods may be carried out at from 0° C. to 100° C., from 15° C. to 95° C., from 16° C. to 90° C., from 17° C. to 85° C., from 18° C. to 80° C., 19° C. to 70° C., or from 20° C. to 60° C. The methods are typically carried out at room temperature. The methods are optionally carried out at a temperature that supports helicase function, such as about 37° C.

The method may be carried out in the presence of free nucleotides or free nucleotide analogues and/or a helicase cofactor that facilitates the action of the helicase. The method may also be carried out in the absence of free nucleotides or free nucleotide analogues and in the absence of a helicase cofactor. The free nucleotides may be one or more of any of the individual nucleotides discussed above. The free nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP). The free nucleotides are preferably selected from AMP, TMP, GMP, CMP, UMP, dAMP, dTMP, dGMP or dCMP. The free nucleotides are preferably adenosine triphosphate (ATP).

The helicase cofactor is a factor that allows the helicase or construct to function. The helicase cofactor is preferably a divalent metal cation. The divalent metal cation is preferably $Mg^{2+}$, $Mn^{2+}$, $Ca^{2+}$ or $Co^{2+}$. The helicase cofactor is most preferably $Mg^{2+}$.

Methods of Controlling the Loading of One or More Helicases on a Target Polynucleotide The invention also provides a method of controlling the loading of one or more helicases on a target polynucleotide. The method comprises providing the target polynucleotide with one or more spacers. The method preferably comprises modifying the target polynucleotide so that it comprises one or more spacers. All of the spacer embodiments discussed above equally apply to this method.

The method also comprises contacting the target polynucleotide with the one or more helicases such that the one or more helicases bind to the target polynucleotide and one or more helicases stall at each spacer. The stalling of helicases at spacers may be assayed as discussed above.

The target polynucleotide may comprise any number of spacers as discussed above. The target polynucleotide preferably comprises two or more spacers, such as 3, 4, 5, 6, 7, 8, 9, 10 or more spacers. Any number of helicases may be stalled at each spacer as discussed above. In this way, it is possible to control where and how many helicases are loaded on the target polynucleotide and thereby facilitate characterisation of the target polynucleotide. The one or more helicases may be moved past the one or more spacers using any of the methods discussed above.

The target polynucleotide is preferably provided with one or more spacers S and one or more single stranded regions or one or more non-hybridised regions L (L is for loading site). The length of each region L depends on the number of helicases that should bind to each L and be stalled at each spacer S. The one or more spacers S and one or more regions L may be adjacent to (i.e. next to) one another or may be separated by part of the target polynucleotide. Each spacer is typically located at or near the end of each region L towards which the helicase moves. For instance, if the helicase is a 5' to 3' helicase, each spacer is typically located at or near the 3' end of each region, i.e 5'-L-S-3'. If the helicase is a 3' to 5' helicase, each spacer is typically located at or near the 5' end of each region, i.e 5'-S-L-3'.

The target polynucleotide is preferably provided with (L-S)n or (S-L)n in the 5' to 3' direction, wherein L is a single stranded polynucleotide or a non-hybridised polynucleotide, S is a spacer and n is a whole number, such as 1, 2, 3, 4, 5, 6, 7, 8, 9, 10 or more. n is preferably 1, 2, 3 or 4. The 5' to 3' direction refers to the target polynucleotide.

The target polynucleotide is preferably provided with one or more single stranded regions or one or more non-hybridised regions L each of which has a spacer S at or near either end, i.e. provided with (S-L-S)n.

In a preferred embodiment, the spacer is adjacent to a double stranded region D as discussed above, i.e. 5'-L-S-D-3' for 5' to 3' helicases or helicases used in the inactive mode or 5'-D-S-L-3' for 3' to 5' helicases or helicases used in the inactive mode. The target polynucleotide is preferably provided with (L-S-D)n or (D-S-L)n in the 5' to 3' direction, wherein L is a single stranded polynucleotide or a non-hybridised polynucleotide, S is a spacer, D is a double stranded polynucleotide and n is a whole number, such as 1, 2, 3, 4, 5, 6, 7, 8, 9, 10 or more. n is preferably 1, 2, 3 or 4. L may be the same type of polynucleotide as D or may be a different type of polynucleotide from D. L and/or D may be the same type of polynucleotide as the target polynucleotide or may be a different type of polynucleotide from the target polynucleotide.

In a preferred embodiment, a blocking molecule B is provided at the end of each spacer opposite to the end past which the one or more helicases are to be moved, i.e. 5'-B-L-S-3' for 5' to 3' helicases or helicases used in the inactive mode or 5'-S-L-B-3' for 3' to 5' helicases. The target polynucleotide is preferably provided with (B-L-S)n or (S-L-B)n in the 5' to 3' direction, wherein L is a single stranded polynucleotide or a non-hybridised polynucleotide, S is a spacer, B is blocking molecule and n is a whole number, such as 1, 2, 3, 4, 5, 6, 7, 8, 9, 10 or more. n is preferably 1, 2, 3 or 4.

In the most preferred embodiment, the target polynucleotide is provided with both D and B, i.e 5'-B-L-S-D-3' for 5' to 3' helicases or helicases used in the inactive mode or 5'-D-S-L-B-3' for 3' to 5' helicases. The target polynucleotide is most preferably provided with (B-L-S-D)n or (D-S-L-B)n in the 5' to 3' direction, wherein L is a single stranded polynucleotide or a non-hybridised polynucleotide, S is a spacer, B is blocking molecule, D is a double stranded polynucleotide and n is a whole number, such as 1, 2, 3, 4, 5, 6, 7, 8, 9, 10 or more. n is preferably 1, 2, 3 or 4.

The target polynucleotide may be provided with any number of these spacer-containing units. For instance, the target polynucleotide may be provided with (5'-L-S-3')n, (5'-S-L-3')n, (S-L-S)n, (5'-L-S-D-3')n, (5'-D-S-L-3')n, (5'-B-L-S-3')n, (5'-S-L-B-3')n, (5'-B-L-S-D-3')n or (5'-D-S-L-B-3')n, where n is 2 or more, such as such as 3, 4, 5, 6, 7, 8, 9, 10 or more. Such embodiments allow multiple helicases to be stalled on the target polynucleotide.

The target polynucleotide may be provided with all of the embodiments discussed above with reference to L, S, D and B by ligating an adaptor of the invention to the target polynucleotide.

In a preferred embodiment, the target polynucleotide is contacted with the one or more helicases such that one helicase (i.e. only one helicase) stalls at each spacer. This can be achieved by providing the target polynucleotide with one or more spacers S and one or more single stranded regions or one or more non-hybridised regions $L^1$ each of which is only long enough for one helicase to bind. The target polynucleotide is preferably provided with ($L^1$-S)n or (S-$L^1$)n in the 5' to 3' direction, wherein $L^1$ is a single stranded polynucleotide or a non-hybridised polynucleotide which is only long enough for one helicase to bind, S is a spacer and n is a whole number, such as 1, 2, 3, 4, 5, 6, 7, 8, 9, 10 or more. n is preferably 1, 2, 3 or 4.

The length of region $L^1$ depends on the footprint of the helicase and can be calculated in a straightforward manner. Region $L^1$ may be part of the target polynucleotide or may be added to the target polynucleotide, for instance as part of an adaptor of the invention. Region $L^1$ is typically 8, 9, 10, 12, 13, 14 or 15 nucleotides in length. The one or more spacers S and one or more $L^1$ regions may be adjacent to (i.e. next to) one another or may be separated by part of the target polynucleotide. Each spacer S is typically located at or near the end of each region $L^1$ towards which the helicase moves. For instance, if the helicase is a 5' to 3' helicase, each spacer S is typically located at or near the 3' end of each region $L^1$, i.e 5'-$L^1$-S-3'. If the helicase is a 3' to 5' helicase, each spacer S is typically located at or near the 5' end of each region $L^L$, i.e 5'-S-$L^1$-3'. The target polynucleotide is preferably provided with one or more single stranded regions or one or more non-hybridised regions $L^1$ each of which is only long enough for one helicase to bind and each of which has a spacer S at or near either end, i.e. (S-$L^1$-S)n.

The target polynucleotide may be provided with (5'-$L^1$-S-3')n, (5'-S-$L^1$-3')n, (S-$L^1$-S)n, (5'-$L^1$-S-D-3')n, (5'-D-S-$L^1$-3')n, (5'-B-L-S-3')n, (5'-S-$L^1$-B-3')n, (5'-B-$L^1$-S-D-3')n or (5'-D-S-$L^1$-B-3')n, where n is a whole number, such as 1, 2, 3, 4, 5, 6, 7, 8, 9, 10 or more. n is preferably 1, 2, 3 or 4. Such embodiments allow n helicases to be stalled on the target polynucleotide. One helicase is stalled by each spacer.

In another preferred embodiment, the target polynucleotide is contacted with the one or more helicases such that two helicases (i.e. only two helicases) stall at each spacer. This can be achieved by providing the target polynucleotide with one or more spacers S and one or more single stranded regions or one or more non-hybridised regions $L^2$ each of which is only long enough for two helicases to bind. The target polynucleotide is preferably provided with ($L^2$-S)n or (S-$L^2$)n in the 5' to 3' direction, wherein L is a single stranded polynucleotide or a non-hybridised polynucleotide which is only long enough for two helicases to bind, S is a spacer and n is a whole number, such as 1, 2, 3, 4, 5, 6, 7, 8, 9, 10 or more. n is preferably 1, 2, 3 or 4.

The length of region $L^2$ depends on the footprint of the helicases and can be calculated in a straightforward manner. Region L may be part of the target polynucleotide or may be added to the target polynucleotide, for instance as part of an adaptor of the invention. Region $L^2$ is typically 16, 17, 18, 19, 20, 21 or 22 nucleotides in length. The one or more spacers S and one or more regions $L^2$ may be adjacent to (i.e. next to) one another or may be separated by part of the polynucleotide. Each spacer is typically located at or near the end of each region towards which the helicase moves. For instance, if the helicase is a 5' to 3' helicase, each spacer is typically located at or near the 3' end of each region. The polynucleotide is preferably provided with one or more single stranded regions or one or more non-hydrisied regions $L^2$ each of which is only long enough for two helicases to bind and each of which has a spacer S at or near either end, i.e. (S-$L^2$-S)n.

The target polynucleotide may be provided with (5'-$L^2$-S-3')n, (5'-S-$L^2$-3')n, (S-$L^2$-S)n, (5'-$L^2$-S-D-3')n, (5'-D-S-$L^2$-3')n, (5'-B-$L^2$-S-3')n, (5'-S-$L^2$-B-3')n, (5'-B-$L^2$-S-D-3')n or (5'-D- S-$L^2$-B-3')n, where n is a whole number, such as 1, 2, 3, 4, 5, 6, 7, 8, 9, 10 or more. n is preferably 1, 2, 3 or 4. Such embodiments allow 2n helicases to be stalled on the target polynucleotide. Two helicases are stalled by each spacer.

The two helicases stalled at each spacer are preferably different from one another. This can be controlled in several ways. For instance, two different helicases may be attached to one another, such as covalently attached to one another, and then stalled at each spacer. Suitable constructs are discussed above. Alternatively, blocking polynucleotides may be used to ensure that different helicases are stalled by each spacer. If the method comprises providing the polynucleotide with one or more spacers S and one or more single stranded regions or one or more non-hydrisied regions $L^2$ each of which is only long enough for two helicases to bind, the method preferably comprises hybridising a blocking polynucleotide to part of each region $L^2$ so that the remaining (i.e. non-blocked) part of each region is only long enough to bind one helicase. Blocking polynucleotides are typically 2, 3, 4, 5, 6, 7 or 8 nucleotides in length. The blocking polynucleotide prevents two helicases from binding to the same region at the same time. The polynucleotide comprising the blocking polynucleotides is preferably contacted with one or more helicases such that one helicase binds to the remaining (i.e. non-blocked) part of each region $L^2$. Each helicase may then be used to remove each blocking polynucleotide. The one or more bound helicases are preferably provided with free nucleotides and a helicase cofactor such that they remove each blocking polynucleotide and stall at each spacer S. The polynucleotide produced in in this way is then preferably contacted with one or more helicases which are different from the helicases used earlier in the method such that one different helicase binds to each region and is stalled by the spacer and the other stalled helicase.

The method preferably comprises (a) providing the target polynucleotide with $(L^2-S)n$ or $(S-L^2)n$ in the 5' to 3' direction, wherein L is a single stranded polynucleotide or a non-hybridised polynucleotide which is only long enough for two helicases to bind, S is a spacer and n is a whole number, such as 1, 2, 3, 4, 5, 6, 7, 8, 9, 10 or more; (b) hybridising a blocking polynucleotide to part of each region $L^2$ so that the remaining part of each region $L^2$ is only long enough to bind one helicase; (c) contacting the target polynucleotide produced in (b) with one or more helicases such that one helicase binds to the remaining part of each region $L^2$; (d) providing the one or more bound helicases in (c) with free nucleotides and a helicase cofactor such that they remove each blocking polynucleotide and stall at each spacer S; and (e) contacting the target polynucleotide produced in (d) with one or more helicases which are different from those used in (c) such that one different helicase binds to each region $L^2$ and is stalled by each spacer and each helicase stalled in (d). n is preferably 1, 2, 3 or 4. Other arrangements of S and $L^2$, such $(S-L^2-S)n$, $(5'-L^2-S-D-3')n$, $(5'-D-S-L^2-3')n$, $(5'-B-L^2-S-3')n$, $(5'-S-L^2-B-3')n$, $(5'-B-L^2-S-D-3')n$ and $(5'-D-S-L^2-B-3')n$ as discussed above, may also be used in this embodiment.

As discussed above, the length of a spacer may be used to control the number of helicases that are stalled and/or the number of helicases which may be moved past the spacer. Longer spacers may be used to stall more helicases. Trains of two or more helicases, such as 3, 4 or 5 helicases, may also move past longer spacers because trailing helicases may push leading helicases past the spacer. The embodiments with reference to $L^1$ and $L^2$ above can be modified such that 3, 4 or 5 helicases are stalled at each spacer. For instance, the polynucleotide may be provided with one or more spacers S and one or more single stranded regions or one or more non-hybridised regions each of which is only long enough for three ($L^3$), four ($L^4$) or five ($L^5$) helicases to bind.

Adaptor

The invention also provides an adaptor for controlling the movement of a target polynucleotide. The adaptor is preferably for characterising a target polynucleotide. The adaptor comprises (a) $(L-S-D)n$ or $(D-S-L)n$ in the 5' to 3' direction, wherein L is a single stranded polynucleotide or a non-hybridised polynucleotide, S is a spacer and D) is a double stranded polynucleotide and wherein n is a whole number, such as 1, 2, 3, 4, 5, 6, 7, 8, 9, 10 or more, and (b) one or more helicases stalled on each adaptor. n is preferably 1, 2, 3 or 4. The 5' to 3' direction refers to the direction of the L and D polynucleotides in the adaptor.

The one or more helicases may be stalled before the spacer S, by the spacer S or on the spacer S.

The adaptor may be ligated to a target polynucleotide such that the target polynucleotide may be used in any of the method discussed above.

L may be $L^1$ or $L^2$ as discussed above. An adaptor may comprise a combination of $L^1$ and $L^2$.

All of the spacer embodiments discussed above equally apply to this method.

Any of the embodiments discussed above with reference to L, S and D equally apply to the adaptors of the invention. The adaptor may comprise $(5'-L^1-S-D-3')n$, $(5'-D-S-L^1-3')n$, $(5'-B-L^1-S-D-3')n$ or $(5'-D-S-L^1-B-3')n$, $(5'-1-S-D-3')n$, $(5'-D-S-L^2-3')n$, $(5'-B-L^2-S-D-3')n$ or $(5'-D-S-L^2-B-3')n$ in the 5' to 3' direction, where n is a whole number, such as 1, 2, 3, 4, 5, 6, 7, 8, 9, 10 or more. n is preferably 1, 2, 3 or 4. $L^1$ or $L^2$ may be replaced with $L^3$, $L^4$ or $L^5$.

Most preferably n is 1 and one or two helicases are stalled one the adaptor.

Kit

The invention also provides a kit for controlling the movement of a target polynucleotide.

The kit is preferably for characterising a target polynucleotide. The kit comprises (a) one or more spacers, (b) one or more helicases and (c) a transmembrane pore. All of the spacer embodiments discussed above with reference to the methods of the invention equally apply to the kits of the invention. For instance, the one or more spacers may be part of a polynucleotide adaptor, preferably a single stranded polynucleotide adaptor, which may be ligated to to the target polynucleotide and which comprises a leader sequence which preferentially threads into the pore. The kit may comprise any of the helicases and pores discussed above.

The one or more spacers and the one or more helicases may be part of an adaptor of the invention.

The kit may further comprise the components of a membrane, such as the phospholipids needed to form an amphiphilic layer, such as a lipid bilayer.

The kit of the invention may additionally comprise one or more other reagents or instruments which enable any of the embodiments mentioned above to be carried out. Such reagents or instruments include one or more of the following: suitable buffer(s) (aqueous solutions), means to obtain a sample from a subject (such as a vessel or an instrument comprising a needle), means to amplify and/or express polynucleotides, a membrane as defined above or voltage or patch clamp apparatus. Reagents may be present in the kit in a dry state such that a fluid sample resuspends the reagents. The kit may also, optionally, comprise instructions to enable the kit to be used in the method of the invention or details regarding which patients the method may be used for. The kit may, optionally, comprise the components necessary to facilitate helicase movement (e.g. ATP and $Mg^{2+}$). The following Examples illustrate the invention.

EXAMPLES

Example 1

This example describes how a T4 Dda-E94C/A360C (SEQ ID NO: 8 with mutations E94C/A360C and then (ΔM1)G1G2) helicase can control the movement of intact DNA strands through a single MspA nanopore (MS(B1-G75S/G77S/L88N/Q126R)8 (MspA-B2C) (SEQ ID NO: 2 with mutations G75S/G77S/L88N/Q126R). The iSpC3 spacers in the lambda DNA construct (SEQ ID NO: 9 attached by its 3' end to four iSpC3 spacers which are attached to the 5' end of SEQ ID NO: 10 which is attached to three iSpC3 spacers which are attached to the 3' end to SEQ ID NO: 11, the SEQ ID NO: 10 region of this construct is hybridised to SEQ ID NO: 12 (which has attached to its 3' end, six iSp18 spacers attached to two thymine residues and a 3' cholesterol TEG)) are used to stall the enzyme until the construct is captured by the nanopore. Upon capture the force of the applied potential moves the enzyme T4 Dda-E94C/A360C past the stalling spacer and allows enzyme controlled DNA movement of the lambda construct through the nanopore.

Materials and Methods

Prior to setting up the experiment, the Lambda DNA construct (SEQ ID NO: 9 attached by its 3' end to four iSpC3 spacers which are attached to the 5' end of SEQ ID NO: 10 which is attached at its 3' end to SEQ ID NO: 11, the SEQ ID NO: 10 region of this construct is hybridised to SEQ ID NO: 12 (which has a 3' cholesterol tether)) and T4 Dda-E94C/A360C were pre-incubated together for 15 minutes at 23° C. in buffer (20 mM CAPS, pH 10.0, 500 mM NaCl, 5% Glycerol, 2 mM DTT).

Electrical measurements were acquired at 20° C. (by placing the experimental system on a cooler plate) from single MspA nanopores (MspA-B2C) inserted in block co-polymer in buffer (600 mM KCl, 25 mM potassium phosphate, 75 mM Potassium Ferrocyanide (II), 25 mM Potassium ferricyanide (III), pH 8). After achieving a single pore inserted in the block co-polymer, then buffer (1 mL, 600 mM KCl, 25 mM potassium phosphate, 75 mM Potassium Ferrocyanide (II), 25 mM Potassium ferricyanide (II), pH 8) was flowed through the system to remove any excess MspA nanopores (MspA-B2C) and finally experimental buffer was flowed into the system (2 mL 960 mM KCl, 25 mM potassium phosphate, 3 mM Potassium Ferrocyanide (II), 1 mM Potassium ferricyanide (III), pH 8). MgCl$_2$ (10 mM final concentration) and ATP (1 mM final concentration) were mixed together with buffer (960 mM KCl, 25 mM potassium phosphate, 3 mM Potassium Ferrocyanide (II), 1 mM Potassium ferricyanide (III), pH 8) and then added to the Lambda DNA construct (0.2 nM final concentration), T4 Dda-E94C/A360C (10 nM final concentration) buffer (20 mM CAPS, pH 10.0, 500 mM NaCl, 5% Glycerol, 2 mM DTT) pre-mix. The pre-mix was then added to the single nanopore experimental system. Experiments were carried out for four hours following a potential flip process (+100 mV for 2 s, then 0 V for 2 s, then −120 mV for 14500 s applied at the cis side) and helicase-controlled DNA movement was monitored.

Results and Discussion

Figure 1:
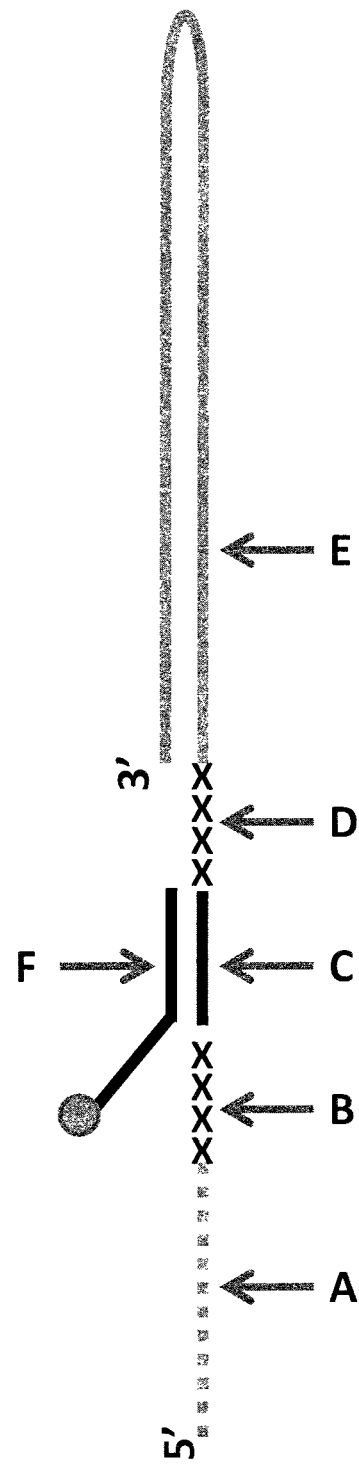
FIG. 1 shows a diagram of the lambda DNA construct used in Example 1. SEQ ID NO: 9 (labelled A) is attached at its 3' end to four iSpC3 spacers (labelled B). The four iSpC3 spacers are attached to the 5' end of SEQ ID NO: 10 (labelled C). SEQ ID NO: 10 is attached to four iSpC3 spacers (labelled D) which are attached to SEQ ID NO: 11 (labelled E) at its 5' end. SEQ ID NO: 10 is hybridised to SEQ ID NO: 12 (labelled F, which has a 3' cholesterol tether).
Figure 2:
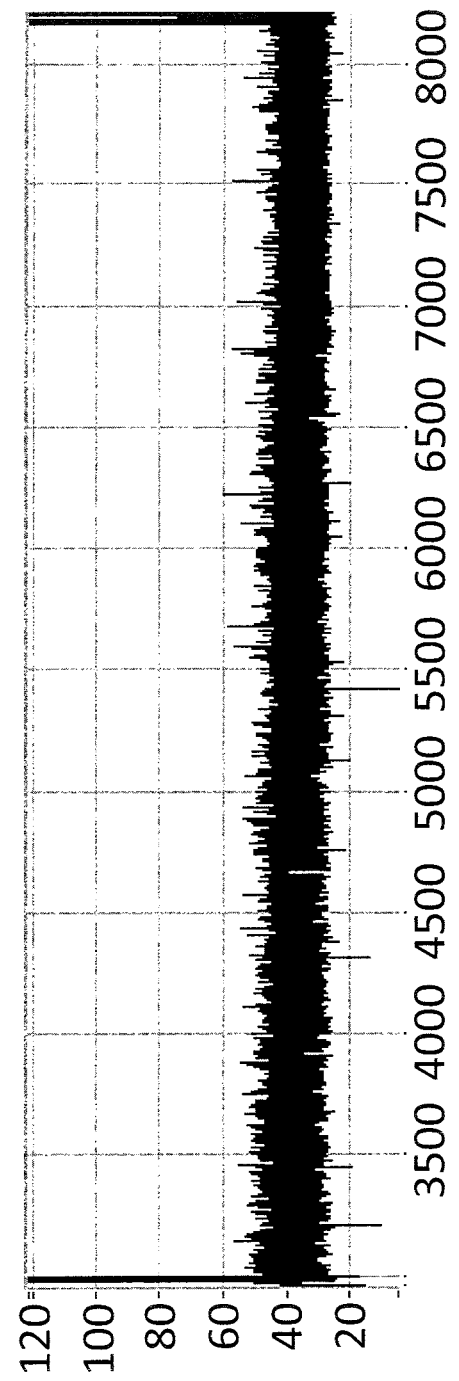
FIG. 2 shows an example current trace (y-axis label=Current (pA, 20 to 120), x-axis label=Time (s, 3500 to 8000)) of when a helicase (T4 Dda-E94C/A360C (SEQ ID NO: 8 with mutations E94C/A360C and then (ΔM1) G1G2))) controls the translocation of the Lambda DNA construct (0.2 nM as described and illustrated in FIG. 1) through a nanopore (MS(B1-G75S/G77S/L88N/Q126R))8 MspA (MspA-B2C) (SEQ ID NO: 2 with mutations G75S/G77S/L88N/Q126R)).
Figure 3:
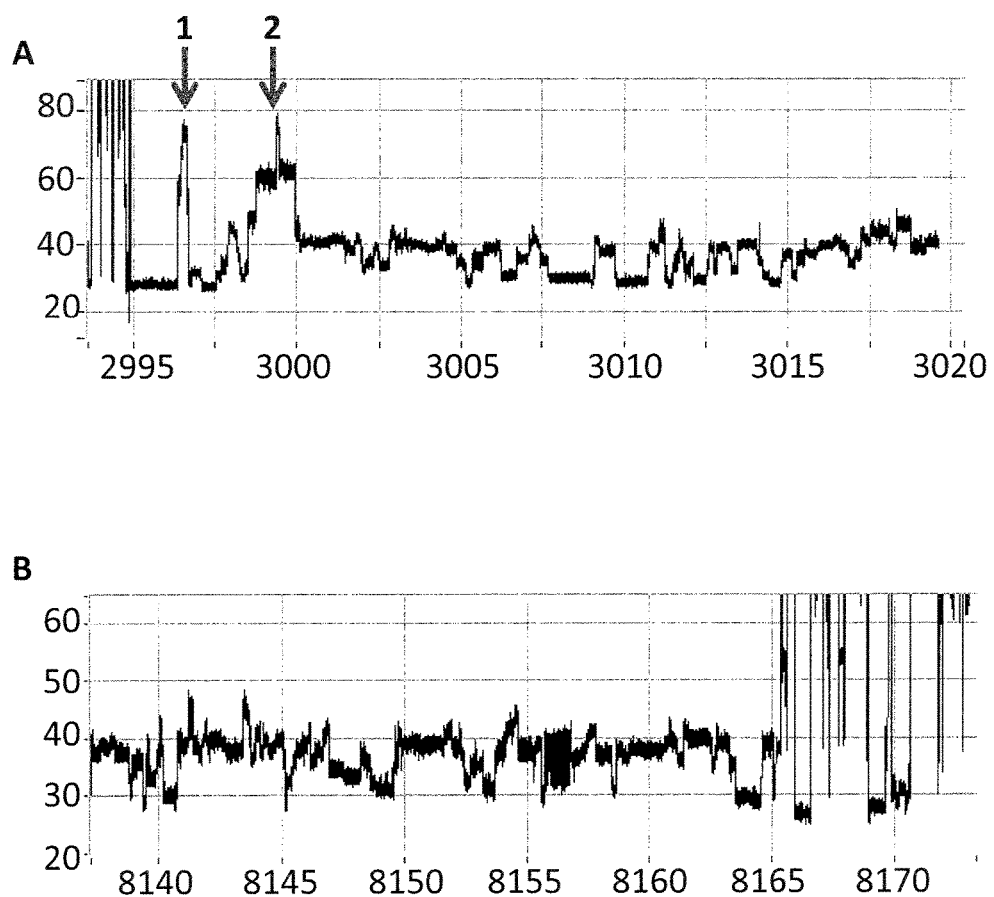
FIG. 3 shows zoomed in regions of the helicase-controlled DNA movement shown in the current trace in FIG. 2 (y-axis label=Current (pA, upper trace 20 to 80, lower trace 20 to 60), x-axis label=Time (s, upper trace 2995 to 3020, lower trace 8140 to 8170) for both the upper and lower traces). A) shows the beginning of the helicase-controlled DNA movement and B) shows the end of the helicase controlled DNA movement. The arrow labelled 1 corresponds to when the first four iSpC3 spacers (which is used to stall the movement of the enzyme prior to capture by the nanopore) moves through the nanopore. The arrow labelled 2 corresponds to a second group of four iSpC3 spacers moving through the nanopore.

The DNA construct is shown in FIG. 1. The T4 Dda-E94C/A360C is able to bind on to the region of the construct labelled A (SEQ ID NO: 9) when pre-incubated with the DNA construct. However, the enzyme is not able to motor past the stalling groups when in free solution (labelled B and D in FIG. 1). Therefore, the enzyme is stalled at the iSpC3 spacers (labelled B in FIG. 1) until the DNA construct is captured by the nanopore. Once captured by the nanopore, the force of the applied potential moves the enzyme T4 Dda-E94C/A360C past the stalling spacer and allows enzyme controlled DNA movement of the lambda construct through the nanopore. An example of a helicase-controlled DNA movement is shown in FIG. 2. The helicase-controlled DNA movement was 5170 seconds long and corresponds to the translocation of approximately 30 kB of the lambda construct through the nanopore. FIG. 3 shows zoomed in regions of the beginning (a) and end (b) of the helicase-controlled DNA movement, 1 and 2 show when the iSpC3 spacers translocate through the nanopore under control of the helicase.

Example 2

Figure 4:
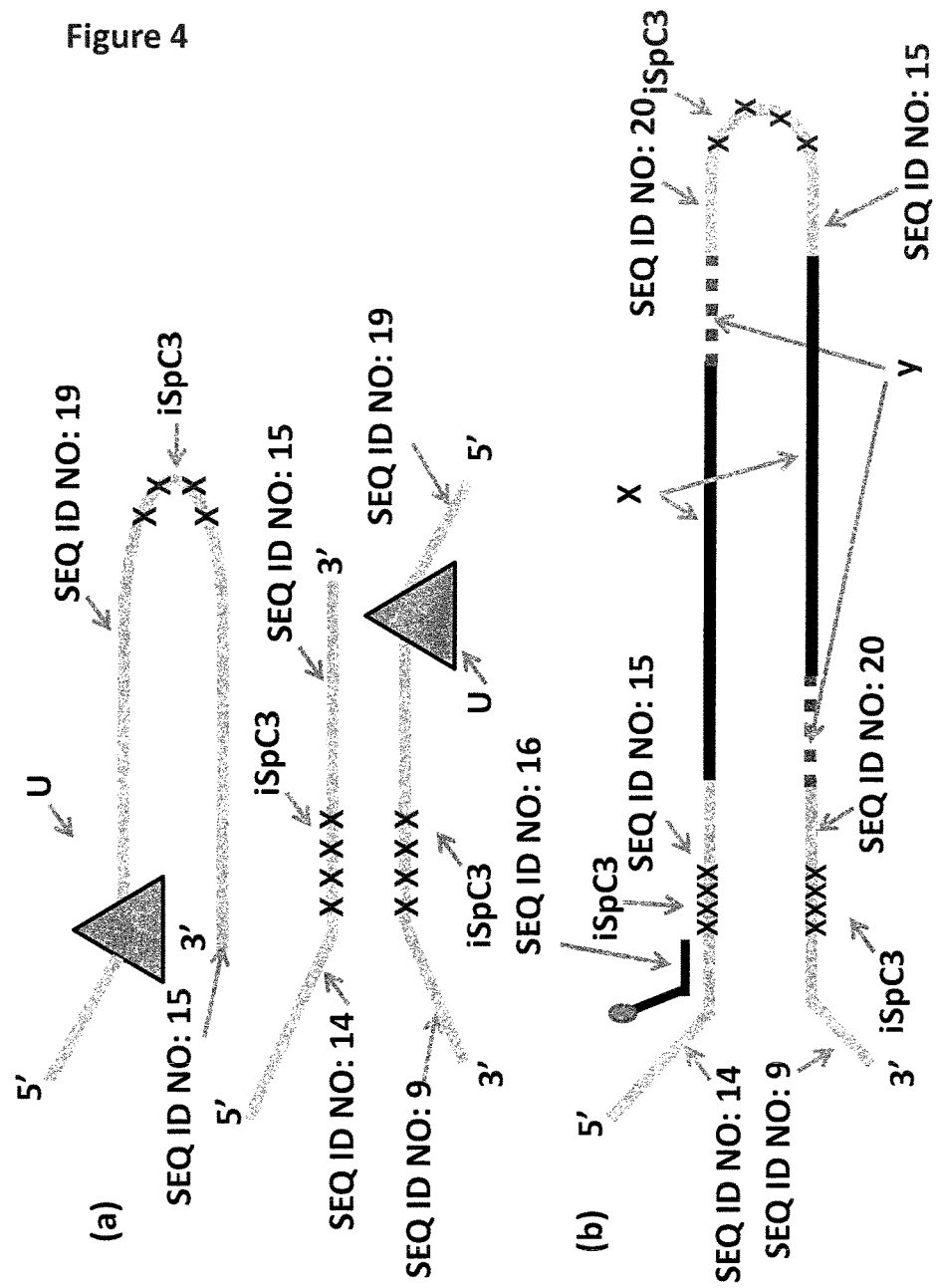
FIG. 4(a) shows the hairpin and Y-shaped MuA substrate designs used in Example 2. The dUMP in SEQ ID NO: 19 is highlighted as a triangle and the iSpC3 spacers are shown as x's.
FIG. 4(b) shows the Lambda DNA construct produced during the sample preparation procedure detailed in Example 2. The 5-10 kB fragment of Lambda DNA is labelled X, the fragment of DNA filled in by the polymerase and joined to the rest of the construct by the ligase is labelled y (and is shown as a dotted line) and the iSpC3 spacers are shown as x's. A tether sequence (SEQ ID NO: 16) is hybridised to the DNA construct as shown. Attached t the 3' end of SEQ ID NO: 16 is six iSp18 spacers attached to two thymine residues and a 3' cholesterol TEG (shown as a grey circle).

The DNA construct used in this example was produced by fragmentation of Lambda DNA into ~5-10 kB fragments using MuA. The fragments which were produced by the sample prep were then passed through a nanopore, with their movement controlled by a helicase enzyme. The helicase was moved past the dsDNA region (where the tether hybridises to the construct) and the spacers by the force of the applied potential across the nanopore. The observance of characteristic blocks produced by the helicase controlled movement of the markers through the nanopore showed the sample preparation procedure had been successful and that the enzyme had been stalled as shown in FIG. 4(b). This meant that the enzyme had a defined start point and was unable to move past the dsDNA region (where the tether hybridises to the construct) and spacers until captured by the nanopore.

Materials and Methods 2.1 Anneal of DNA Strands to Form Y-Shaped and Hairpin MuA Substrates The Y-shaped and hairpin MuA substrates were prepared as shown in Table 5 below. The sample mixtures which contained the DNA to form the Y-shaped and hairpin MuA substrates were then heated to 95° C. for 2 minutes and then cooled to 16° C. at a rate of 2° C. per minute. This allowed SEQ ID NOs: 14 and 15 (where SEQ ID NO: 14 is attached at its 3' end to the 5' end of SEQ ID NO: 15 by four iSpC3 spacer units) to anneal to SEQ ID NO: 19 and 9 (where SEQ ID NO: 19 is attached at its 3' end to the 5' end of SEQ ID NO: 9 by four iSpC3 spacer units) to form the Y-shaped MuA substrate and for SEQ ID NO: 19 and 20 (where SEQ ID NO: 19 is attached at its 3' end to the 5' end of SEQ ID NO: 15 by four iSpC3 spacer units) to form a hairpin loop MuA substrate. The DNA substrate designs of the two MuA substrates formed are shown in FIG. 4(a).

TABLE 5

| Reagent | Y-shaped | Hairpin | Final Concentrations |
|---|---|---|---|
| Water | 12 uL | 14 uL | |
| 0.5M NaCl | 2 uL | 2 uL | 50 mM |
| 0.1M Tris pH 7.5 | 2 uL | 2 uL | 10 mM |
| SEQ ID NO: 14 and 15 (where SEQ ID NO: 14 is attached at its 3' end to the 5' end of SEQ ID NO: 15 by four iSpC3 spacer units) (100 uM) | 2 uL | | 10 uM |
| SEQ ID NO: 19 and 9 (where SEQ ID NO: 19 is attached at its 3' end to the 5' end of SEQ ID NO: 9 by four iSpC3 spacer units) (100 uM) | 2 uL | | 10 uM |
| SEQ ID NO: 19 and 20 (where SEQ ID NO: 19 is attached at its 3' end to the 5' end of SEQ ID NO: 15 by four iSpC3 spacer units) (100 uM) | | 2 uL | 10 uM |
| Total | 20 uL | 20 uL | |

2.2 Fragmentation of the DNA Template Using the MuA Transposase

Double-stranded Lambda DNA (SEQ ID NO: 13 corresponds to the sequence of the sense strand) was fragmented into approximately 5-10 kB length strands using a MuA transposase. The MuA transposase inserted the MuA substrates (the Y-shaped and the hairpin MuA substrates) which were annealed in section 3.1. The sample was prepared as shown in Table 6 below. The sample was then incubated at 30° C. for 1 hour and heat inactivated at 75° C. for 10 minutes. The sample was then further purified using a QIAQUICK™ PCR Purification kit (Qiagen) and eluted in 26 μL.

TABLE 6

| Reagent | Sample Volume 1 | Final Concentrations |
|---|---|---|
| Water | 17.7 uL | |
| Lambda DNA (90 ng/uL) (SEQ ID NO: 13 shows the sense strand sequence only) | 22.3 uL | 2 μg |
| Y-shaped MuA substrate (1 uM) | 8 uL | 100 nM |
| Hairpin MuA substrate (1 uM) | 8 uL | 100 nM |
| 5x Buffer (125 mM Tris (pH 8.0), 50 mM MgCl$_2$, 550 mM NaCl, 0.25% Triton X-100 and 50% Glycerol) | 16 uL | 1x |
| MuA (4 uM, Thermo, catalogue No. F-750C) | 8 uL | 400 nM |
| Total | 80 uL | |

2.3 USER™ (Uracil-Specific Excision Reagent) Digest of Fragmented Lambda DNA with Inserted MuA Substrates Purified sample volume 1 from step 3.2 was then treated with USER™ (Uracil-Specific Excision Reagent) digest in order to remove the dUMP from SEQ ID NOs: 19. See Table 7 below for appropriate volumes and concentrations. The sample was then incubated at 37° C. for 30 minutes before it was cooled in an ice block.

TABLE 7

| Reagent | Sample Volume 2 | Final Concentrations |
|---|---|---|
| Sample Volume 1 | 26 uL | 8 pmol of U |
| 10x DNA ligase buffer | 3 uL | 1x |
| USER (1 U/uL) | 1 uL | 1 U |
| Total | 30 uL | |

2.4 Repair of Single-Stranded Gap in the Double-Stranded Lambda DNA Construct Fragments Sample Volume 2 produced after treatment with USER™ (Uracil-Specific Excision Reagent) was then treated with DNA polymerase and ligase in order to close the single-stranded gap. Sample volume 3 (see table 8 below for appropriate volumes and concentrations) was incubated for 30 minutes at 16° C. and then EDTA (0.5 M, 10 μL) was added to sample volume 3. A QIAQUICK™ PCR Purification kit was then used to purify each sample, which was run on an Agilent 12000 chip to quantify the sample and Tris-HCl and NaCl (pH 7.5) until were added to the rest of the sample until the concentrations were 10 mM and 50 mM respectively. Finally, SEQ ID NO: 16 (3' end of the sequence has six iSp19 spacers attached to two thymine residues and a 3' cholesterol TEG, 0.5 μM) was annealed to the purified sample.

TABLE 8

| Reagent | Sample Volume 3 | Final Concentrations |
|---|---|---|
| Water | 6.2 uL | |
| Sample Volume 2 | 30 uL | |

TABLE 8-continued

| Reagent | Sample Volume 3 | Final Concentrations |
|---|---|---|
| 10x DNA ligase buffer | 1 uL | 1x |
| dNTPs (10 mM) | 0.8 uL | 200 uM |
| T4 DNAP exo(□) (Lucigen) | 1 uL | |
| Ligase (NEB; M0202M) | 1 uL | 1x |
| Total | 40 uL | |

2.5 Electrophysiology Experiment Showing Helicase Controlled DNA Movement of the Purified and Fragmented Lambda DNA Construct Prior to setting up the experiment, the Lambda DNA construct (0.2 nM, 5-10 kB fragments of Lambda DNA which have had the Y-shaped MuA substrates and the hairpin MuA substrates attached to either end of the fragments by the MuA transposase (see FIG. 4(b) for an example construct)) and Trwc Cba (SEQ ID NO: 9, 1 μM) were pre-incubated together for 1 hour in buffer (50 mM CAPS, pH 10.0 (pH altered to pH 10.0 by addition of NaOH), 100 mM NaCl).

Electrical measurements were acquired from single MspA nanopores (MspA-B2C) inserted in block co-polymer in buffer (600 mM KCl, 25 mM KH2PO4, 75 mM Potassium Ferrocyanide (II), 25 mM Potassium ferricyanide (II), pH 8). After achieving a single pore in the bilayer, then buffer (1 mL, 600 mM KCl, 25 mM KH2PO4, 75 mM Potassium Ferrocyanide (II), 25 mM Potassium ferricyanide (III), pH 8) was flowed through the system to remove any excess MspA nanopores (MspA-B2C) and the experimental system was placed on a cooler plate set to 8° C. which gave a system temperature of ~15° C. MgCl$_2$ (10 mM) and dTTP (5 mM) were mixed together with buffer (600 mM KCl, 25 mM KH2PO4, 75 mM Potassium Ferrocyanide (II), 25 mM Potassium ferricyanide (III), pH 8) and then added to the Lambda DNA construct (0.2 nM), Trwc Cha (SEQ ID NO: 9, 1 μM) buffer (50 mM CAPS, pH 10.0 (pH altered to pH 10.0 by addition of NaOH), 100 mM NaCl) pre-mix. The pre-mix was then added to the single nanopore experimental system. Experiments were carried out for two hours following a potential flip process (+120 mV for 30 mins, then −100 mV for 2 seconds and then 0 mV for 2 seconds) and helicase-controlled DNA movement was monitored.

2.6 Results and Discussion

Helicase controlled DNA movement was observed for the Lambda DNA construct, an example of a helicase-controlled DNA movement is shown in FIG. 5. The iSpC3 spacers present in the Lambda DNA construct produced a characteristic block level highlighted by the numbers 1, 2 and 3 in FIG. 5. The Y-shaped MuA substrate has four iSpC3 spacers in either strand and the hairpin MuA substrate also has four iSpC3 spacers, each iSpC3 spacer allows more current to flow as that region of the Lambda DNA construct translocates through the nanopore. If the sample preparation has occurred successfully then the iSpC3 spacer events will be observed at the beginning of the Lambda DNA construct, in the middle (marking the transition between sense and antisense sequences) and at the end. FIG. 5 clearly shows three instances of increased current flow which correspond to the iSpC3 spacer regions. Therefore, the sample preparation procedure effectively introduced MuA substrates into the Lambda DNA to produce the Lambda DNA constructs shown in FIG. 4(b). Upon capture of the DNA by the nanopore, the enzyme (labelled A) is moved past the dsDNA region (where the tether hybridises to the construct) and the spacers by the force of the applied potential across the nanopore.

Example 3

The DNA construct used in this example was produced by fragmentation of Lambda DNA into ~5-10 kB fragments using MuA. This example is similar to the one described in Example 2, however, the sample preparation procedure is different (steps 2.3 and 2.4 as described above are not required) as the transposase sequences contain inosines in this example. The enzyme was moved past the dsDNA region and the spacers by the force of the applied potential across the nanopore.

Figure 6:
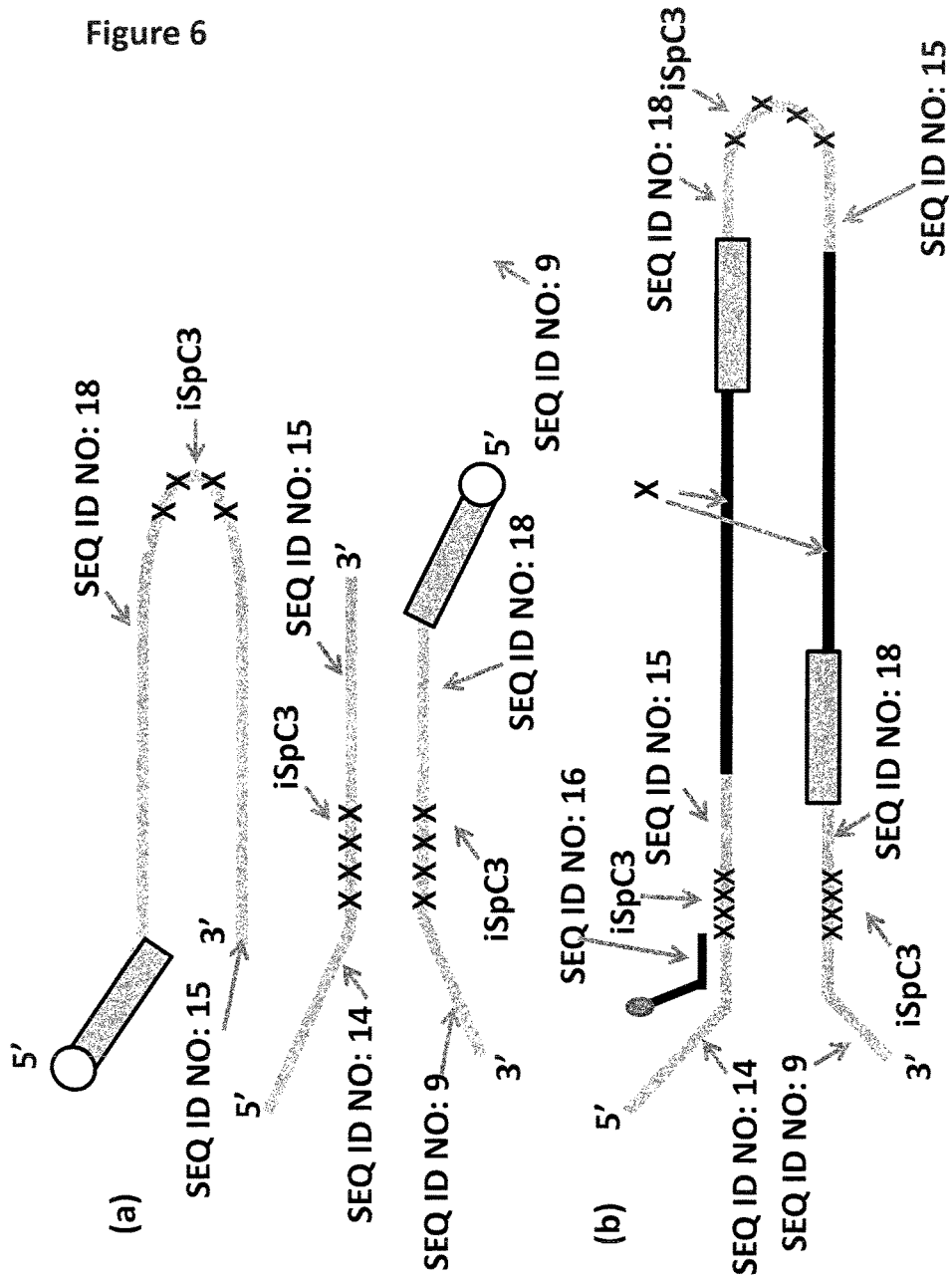
FIG. 6(a) shows the hairpin and Y-shaped MuA substrates designs used in Example 3. The 5' phosphate is labelled as a circle, the inosines in SEQ ID NO: 18 are highlighted as a rectangle and the iSpC3 spacers are shown as x's.
FIG. 6(b) shows the Lambda DNA construct produced during the sample preparation procedure detailed in Example 3. The 5-10 kB fragment of Lambda DNA is labelled X, the inosines which have now been attached to x are labelled as a rectangle and the ISpC3 spacers are shown as x's. A tether sequence (SEQ ID NO: 16) is hybridised to the DNA construct as shown. Attached t the 3' end of SEQ ID NO: 16 is six iSp18 spacers attached to two thymine residues and a 3' cholesterol TEG (shown as a grey circle).

Materials and Methods 3.1 Anneal of DNA Strands to Form Y-Shaped and Hairpin MuA Substrates The Y-shaped 2 and hairpin 2 MuA substrates were prepared as described in Example 2.1 above. Volumes, concentrations and sequences that were used in this example are detailed in table 9 below. The DNA substrate designs of the two constructs formed are shown in FIG. 6 (a).

TABLE 9

| Reagent | Y-shaped 2 | Hairpin 2 | Final Concentrations |
|---|---|---|---|
| Water | 12 uL | 14 uL | |
| 0.5M NaCl | 2 uL | 2 uL | 50 mM |
| 0.1M Tris pH 7.5 | 2 uL | 2 uL | 10 mM |
| SEQ ID NO: 14 and 15 (where SEQ ID NO: 14 is attached at its 3' end to the 5' end of SEQ ID NO: 15 by four iSpC3 spacer units) (100 uM) | 2 uL | | 10 uM |
| SEQ ID NO: 18 and 9 (where SEQ ID NO: 18 is attached at its 3' end to the 5' end of SEQ ID NO: 9 by four iSpC3 spacer units) (100 uM) | 2 uL | | 10 uM |
| SEQ ID NO: 18 and 15 (where SEQ ID NO: 18 is attached at its 3' end to the 5' end of SEQ ID NO: 15 by four iSpC3 pacer units) (100 uM) | | 2 uL | 10 uM |
| Total | 20 uL | 20 uL | |

3.2 Fragmentation of the DNA Template Using the MuA Transposase

Double-stranded Lambda DNA (SEQ ID NO: 13 shows the sequence of the sense strand only) was fragmented into approximately 5-10 kB length strands using a MuA transposase. The MuA transposase inserted the MuA substrates (the Y-shaped 2 and the hairpin 2 MuA substrates) which were annealed in section 3.1. The sample was prepared by an analogous procedure as that described in Section 2.2 and table 6 above except the MuA substrates used were the Y-shaped 2 and the hairpin 2 MuA substrates. In this case the purified sample X was eluted in a volume of 20 μL.

3.3 Nick Repair in the Double-Stranded Lambda DNA Construct Fragments

Once the Y-shaped 2 and the hairpin 2 MuA substrates have been inserted into the fragmented Lambda DNA it is necessary to repair the nick in the strand and join the inosines to the Lambda DNA fragment to produce a complete double-stranded Lambda DNA fragment. One reaction was assembled on ice as described in Table 10 below. The sample was incubated at 16° C. for 60 mins before EDTA (10 μL, 0.5 M) was added to the sample. The resultant sample mixture was purified using a QIAQUICK™ PCR Purification kit and was eluted in 50 μL of water. An aliquot of the purified sample (1 μL) was run on an Agilent 12000 chip to quantify the sample and Tris-HCl and NaCl (pH 7.5) were added to the rest of the sample until the concentrations were 10 mM and 50 mM respectively. Finally, SEQ ID NO: 16 (3' end of the sequence has six iSp18 spacers attached to two thymine residues and a 3' cholesterol TEG, 0.5 μM) was annealed to the purified Lambda DNA construct.

TABLE 10

| Reagent | Sample Z | Final Concentrations |
|---|---|---|
| Sample X | 16 uL | |
| 2x DNA ligase buffer | 20 uL | 1x |
| Ligase (NEB; M0202M) | 4 uL | |
| Total | 40 uL | |

3.4 Electrophysiology Experiment Showing Helicase Controlled DNA Movement of the Purified and Fragmented Lambda DNA Construct Prior to setting up the experiment, the Lambda DNA construct (0.2 nM, 5-10 kB fragments of Lambda DNA which have had the Y-shaped 2 and the hairpin 2 MuA substrates attached to either end of the fragments by the MuA transposase (see FIG. 6(b) for an example construct)) and Trwc Cba (SEQ ID NO: 17, 1 μM) were pre-incubated together for 1 hour in buffer (50 mM CAPS, pH 10.0 (pH altered to pH 10.0 by addition of NaOH), 100 mM NaCl).

Electrical measurements were acquired from single MspA nanopores (MspA-B2C) inserted in block co-polymer in buffer (600 mM KCl, 25 mM KH2PO4, 75 mM Potassium Ferrocyanide (II), 25 mM Potassium ferricyanide (III), pH 8). After achieving a single pore in the bilayer, then buffer (3 mL, 600 mM KCl, 25 mM KH2PO4, 75 mM Potassium Ferrocyanide (II), 25 mM Potassium ferricyanide (III), pH 8) was flowed through the system to remove any excess MspA nanopores (MspA-B2C) and the experimental system was placed on a cooler plate set to 8° C. which gave a system temperature of ~15° C. MgCl$_2$ (10 mM) and dTTP (5 mM) were mixed together with buffer (600 mM KCl, 25 mM KH2PO4, 75 mM Potassium Ferrocyanide (II), 25 mM Potassium ferricyanide (III), pH 8) and then added to the Lambda DNA construct (0.2 nM), Trwc Cba (SEQ ID NO: 17, 1 μM) buffer (50 mM CAPS, pH 10.0 (pH altered to pH 10.0 by addition of NaOH), 100 mM NaCl) pre-mix. The pre-mix was then added to the single nanopore experimental system. Experiments were carried out for two hours following a potential flip process (+120 mV for 30 mins, then −100 mV for 2 seconds and then 0 mV for 2 seconds) and helicase-controlled DNA movement was monitored.

3.5 Results and Discussion

Helicase controlled DNA movement was observed for the Lambda DNA construct, an example of a helicase-controlled DNA movement is shown in FIG. 7. The iSpC3 spacers present in the Lambda DNA construct produced a characteristic block level highlighted by numbers 1-3 in FIG. 7. The Y-shaped 2 MuA substrate has four iSpC3 spacers in either strand and the hairpin 2 MuA substrate also has four iSpC3 spacers, each iSpC3 spacer allows more current to flow as that region of the Lambda DNA construct translocates through the nanopore. If the sample preparation occurred successfully then the iSpC3 spacer events will be observed at the beginning of the Lambda DNA construct, in the middle (making the transition between the sense and antisense sequences) and at the end. FIG. 7 clearly shows three instances of increased current flow which correspond to the iSpC3 spacer regions. Therefore, the sample preparation procedure effectively introduced MuA substrates into the Lambda DNA to produce the Lambda DNA constructs shown in FIG. 6(b). Upon capture of the DNA by the nanopore, the enzyme (labelled A) is past the dsDNA region (where the tether hybridises to the construct) and the spacers by the force of the applied potential across the nanopore. Owing to the use of the inosines in the Y-shaped 2 and the hairpin 2 MuA substrates, the steps in the sample preparation procedure were reduced as once the MuA substrates had been inserted all that was necessary was to close the nicks in the double-stranded DNA constructs.

Example 4

This Example compares the ability of a TrwC Cba monomer (SEQ ID NO: 17), to control the movement of intact DNA strands (attached to the 5' end of SEQ ID NO: 23 is 28 iSpC3 spacers units the last of which has an additional two T's attached to the 5' end of the spacer group, attached to the 3' end of SEQ ID NO: 23 is a further four iSpC3 spacers which are attached to the 5' end of SEQ ID NO: 24, where SEQ ID NO: 12 is hybridised to a region of SEQ ID NO: 23) through a nanopore, to that of the TrwC Cba Q276C-3.4 kDa dimer (where each monomer unit comprises SEQ ID NO: 17 with the mutation Q276C, with one monomer unit being linked to the other via position 276 of each monomer unit using a 3.4 kDa PEG linker). The DNA construct used in this example is shown in FIG. 22 (the helicase is capable of binding to the region labelled B). When the DNA construct is captured by the nanopore, the applied potential across the nanopore moves the enzyme past the dsDNA region (where the tether hybridises to the construct) and spacers and helicase controlled DNA movement is observed.

Upon comparison of the helicase controlled movement of the monomer with the dimer, it was observed that the dimer resulted in a greater percentage of long dwell helicase-controlled DNA movement (a long dwell movement is a helicase-controlled DNA movement which is more than three standard deviations away from the mean of the major population of helicase-controlled DNA movements) than the monomer.

Materials and Methods

Prior to setting up the experiment, the DNA (1 nM, attached to the 5' end of SEQ ID NO: 23 is 28 iSpC3 spacers units the last of which has an additional two T's attached to the 5' end of the spacer group, attached to the 3' end of SEQ ID NO: 23 is a further four iSpC3 spacers which are attached to the 5' end of SEQ ID NO: 24, where SEQ ID NO: 12 is hybridised to a region of SEQ ID NO: 23) and the enzyme (either a TrwC Cba monomer (1 nM, SEQ ID NO: 17) or TrwC Cba Q276C-3.4 kDa dimer (0.3 nM, where each monomer unit comprises SEQ ID NO: 17 with the mutation Q276C, with one monomer unit being linked to the other via position 276 of each monomer unit using a 3.4 kDa PEG linker)) were pre-incubated together for >16 hours.

Electrical measurements were acquired from single MspA nanopores MS(G75S/G77S/L88N/Q126R)8 MspA (SEQ ID NO: 2 with the mutations G75S/G77S/1.88N/Q126R) inserted in block copolymer in buffer (625 mM KCl, 100 mM Hepes, 75 mM Potassium Ferrocyanide (II), 25 mM Potassium ferricyanide (III), pH 8). MgCl$_2$ (10 mM) and dTTP (5 mM) were mixed together with buffer (625 mM KCl, 100 mM Hepes, 75 mM Potassium Ferrocyanide (II), 25 mM Potassium ferricyanide (III), pH 8) and then added to the DNA (construct described previously), enzyme pre-mix (either a TrwC Cba monomer (I nM, SEQ ID NO: 17) or TrwC Cba Q276C-3.4 kDa dimer (I nM, where each monomer unit comprises SEQ ID NO: 17 with the mutation Q276C, with one monomer unit being linked to the other via position 276 of each monomer unit using a 3.4 kDa PEG linker)). After achieving a single pore in the bilayer, the pre-mix was added to the single nanopore experimental system. Experiments were carried out at a constant potential of +120 mV and helicase-controlled DNA movement was monitored.

Results and Discussion

Helicase controlled DNA movement was observed for the helicase TrwC Cba monomer (SEQ ID NO: 17) and TrwC Cba Q276C-3.4 kDa dimer (where each monomer unit comprises SEQ ID NO: 17 with the mutation Q276C, with one monomer unit being linked to the other via position 276 of each monomer unit using a 3.4 kDa PEG linker). Upon capture of the DNA construct by the nanopore the helicase was moved past the dsDNA region (where the tether hybridises to the construct) and the spacers and helicase controlled movement was observed.

Of the helicase-controlled DNA movements observed there is a major population which accounts for around 95% of movements detected, however, there is a small percentage of movements which are significantly longer in dwell time (more than three standard deviations away from the mean of the major population of helicase-controlled DNA movements). These longer movements allow improved data analysis. When the TrwC Cba Q276C-3.4 kDa dimer (1 nM) was used to control DNA movement then a much higher percentage (20% for the TrwC Cba Q276C-3.4 kDa dimer in comparison to and 5% for the TrwC Cba monomer) of these longer dwell time movements (more than three standard deviations away from the mean of the major population of helicase-controlled DNA movements) was observed. The use of the dimer helicase provides an advantage over the monomer as it allows improved data analysis in the nanopore sequencing system.

Example 5

This Example illustrates that Sp9 spacer units can be used to stall the movement of Hel308 Mbu (SEQ ID NO: 28) (when provided with both ATP and MgCl2) in a fluorescence based assay for testing enzyme activity.

Materials and Methods

Three different custom fluorescent substrates (A=(control strands containing no spacers) SEQ ID NOs: 25 and 26, B=(strand containing a single Sp9 spacer) SEQ ID NO: 27 attached at its 3' end by one Sp9 spacers to the 5' end of SEQ ID NO: 29 and hybridised to SEQ ID NO: 26, C=(strand containing four Sp9) SEQ ID NO: 27 attached at its 3' end by four Sp9 spacers to the 5' end of SEQ ID NO: 29 and hybridised to SEQ ID NO: 26) were used to assay the ability of Hel308 Mbu (SEQ ID NO: 28) to displace hybridised dsDNA. FAM labelled DNA (for fluorescent substrate A=SEQ ID NO: 25, B=SEQ ID NO: 27 attached by its 3' end to one sp9 spacer which is attached to the 3' end of SEQ ID NO: 29, C=SEQ ID NO: 27 attached by its 3' end to four sp9 spacers which are attached to the 3' end of SEQ ID NO: 29) is annealed to the partially complementary strand which has a black-hole quencher attached to its 3' end (SEQ ID NO: 26) in a one to one ratio (1 uM of each strand) in 400 mM KCl, 100 mM HEPES pH8, 10 mM MgCl$_2$, 1 mg/ml BSA. The strands were annealed at room temperature for 30 minutes. The annealed DNA (A=SEQ ID NOs: 25 and 26, B=SEQ ID NO: 27 attached at its 3' end by one Sp9 spacers to the 5' end of SEQ ID NO: 29 and hybridised to SEQ ID NO: 26, C=SEQ ID NO: 27 attached at its 3' end by four Sp9 spacers to the 5' end of SEQ ID NO: 29 and hybridised to SEQ ID NO: 26) was diluted to 50 nM in 400 mM KCl, 100 mM HEPES pH8, 10 mM MgCl$_2$, 1 mg/ml BSA, 1 mM ATP (1 uM capture DNA (SEQ ID NO: 27 also present). A sample of Hel308 Mbu (SEQ ID NO: 28) was diluted to 475 nM in 400 mM KCl, 100 mM HEPES pH8, 10 mM MgCl$_2$, 1 mg/ml BSA. Hel308 Mbu (12 nM) was then assayed (as described below and shown in FIGS. 8 and 9) against 48.75 nM annealed DNA in 400 mM KCl, 100 mM HEPES pH8, 10 mM MgCl$_2$, 1 mg/ml BSA, 0.975 mM ATP (0.975 uM capture DNA also present).

Figure 8:
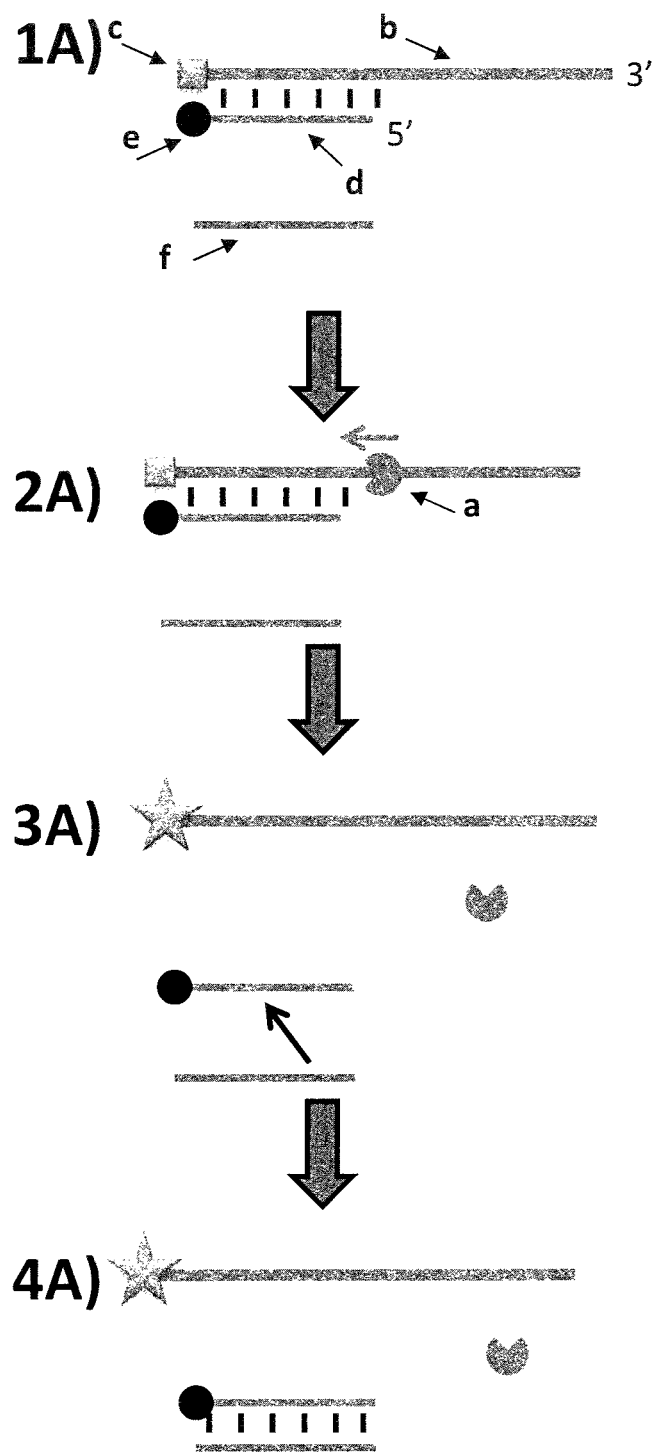
FIG. 8 Fluorescence assay for testing enzyme activity. A custom fluorescent substrate was used to assay the ability of the helicase (labelled a) to displace hybridised dsDNA. 1) The fluorescent substrate strand (48.75 nM final, SEQ ID NO: 25 and 26) has a 3' ssDNA overhang (20 bases), and a 40 base section of hybridised dsDNA. The upper strand (b) has a carboxyfluorescein base (c) at the 5' end of SEQ ID NO: 25, and the hybridised complement (d) has a black-hole quencher (BHQ-1) base (e) at the 3' end of SEQ ID NO: 26. When hybridised, the fluorescence from the fluorescein is quenched by the local BHQ-1, and the substrate is essentially non-fluorescent. 0.975 μM of a capture strand (f, SEQ ID NO: 27) that is part-complementary to the lower strand of the fluorescent substrate is included in the assay. 2) In the presence of ATP (0.975 mM) and MgCl$_2$ (10 mM), helicase Hel308 Mbu (12 nM, SEQ ID NO: 28) binds to the 3' overhang of the fluorescent substrate, moves along the upper strand, and displaces the complementary strand (d) as shown. 3) Once the complementary strand with BHQ-1 is fully displaced the fluorescein on the major strand fluoresces (shown as a star shape). 4) The displaced lower strand (d) preferentially anneals to an excess of capture strand (f) to prevent re-annealing of initial substrate and loss of fluorescence.
Figure 9:
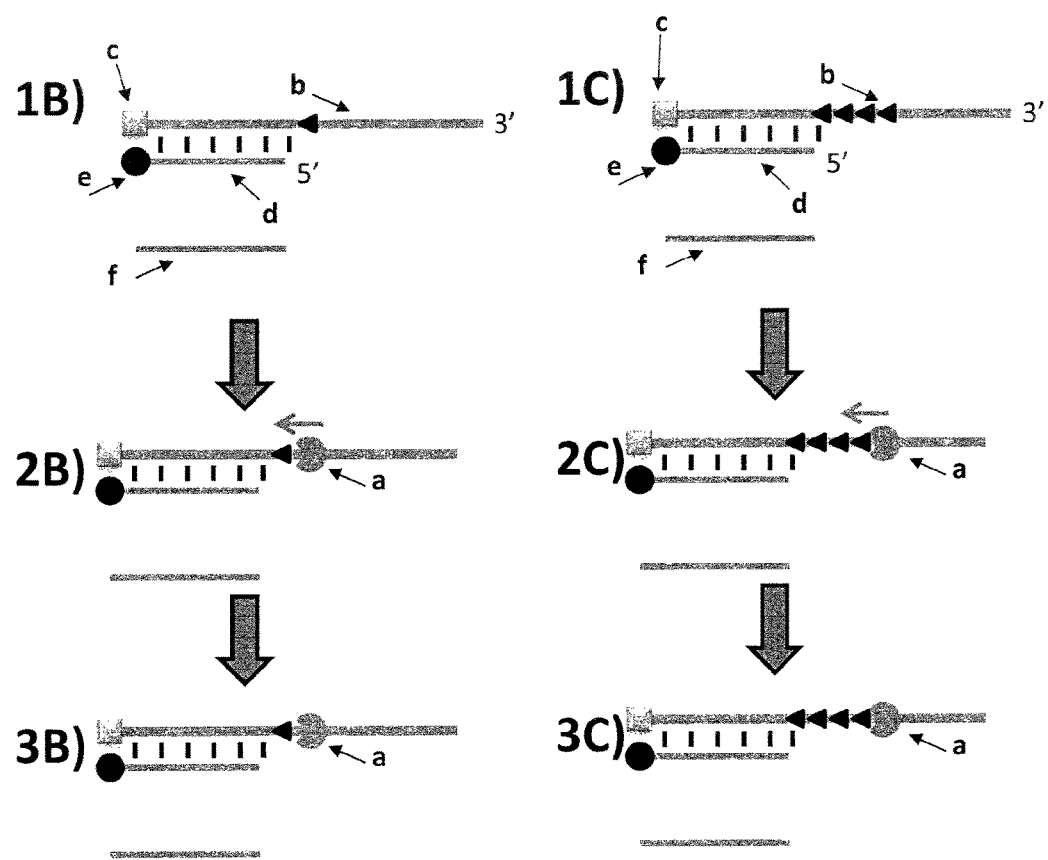
FIG. 9 Fluorescence assay for testing enzyme activity. Two possible fluorescent substrates were used to assay the ability of the helicase (labelled a) to displace hybridised dsDNA, these are shown in FIG. 9(a) (labelled 1C-3C) has four Sp9 spacers (shown as a black triangle) connecting the 3' end of SEQ ID NO: 27 to the 3' end of SEQ ID NO: 29 and (b) (labelled 1B-3B) has one Sp9 spacer (shown as a black triangle) connecting the 3' end of SEQ ID NO: 27 to the 3' end of SEQ ID NO: 29. The fluorescent substrate strand (48.75 nM final either a) or b) described previously) has a 3' ssDNA overhang (20 bases), and a 40 base section of hybridised dsDNA. The upper strand (b) has a carboxyfluorescein base (c) at the 5' end of SEQ ID NO: 27, and the hybridised complement (d) has a black-hole quencher (BHQ-1) base (e) at the 3' end of SEQ ID NO: 26. When hybridised, the fluorescence from the fluorescein is quenched by the local BHQ-1, and the substrate is essentially non-fluorescent. 1 μM of a capture strand (f, SEQ ID NO: 27) that is part-complementary to the lower strand of the fluorescent substrate is included in the assay. 2 a and b) In the presence of ATP (0.975 mM) and MgCl$_2$ (10 mM), helicase Hel308 Mbu (SEQ ID NO: 28) binds to the 3' overhang of the fluorescent substrate, moves along the upper strand up to the Sp9 group(s). The sp9 group (1 in B and 4 in C) stops the helicase from moving past it and the helicase does not displace the complementary strand (SEQ ID NO: 26). Therefore, the fluorescein and black hole quencher remain in close proximity to each other and fluorescence is not observed.

The control strand A is shown in FIG. 8, where in 1A) the fluorescent substrate strand (48.75 nM final) has a 3' ssDNA overhang, and a 40 base section of hybridised dsDNA. The upper strand, containing the 3' ssDNA overhang, has a carboxyfluorescein base attached to the 5' end of SEQ ID NO: 25, and the hybrised complement has a black-hole quencher (BHQ-1) base attached to the 3' end of SEQ ID NO: 26. When hybridised the fluorescence from the fluorescein is quenched by the local BHQ-1, and the substrate is essentially non-fluorescent. 1 µM of a capture strand (SEQ ID NO: 27) that is part-complementary to the lower strand of the fluorescent substrate is included in the assay. As shown in 2A), in the presence of ATP (0.975 mM) and MgCl$_2$ (10 mM), helicase (12 nM) added to the substrate binds to the 3' tail of the fluorescent substrate, moves along the upper strand, and displaces the complementary strand. As shown in 3A), once the complementary strand with BHQ-1 is fully displaced the fluorescein on the major strand fluoresces. As shown in 4A), the displaced strand preferentially anneals to an excess of capture strand to prevent re-annealing of initial substrate and loss of fluorescence. FIG. 9 shows the steps of the assay for strands B (1B-3B) and C (1C-3C), for these strands the Sp9 spacers stall the helicase and prevent it from separating the strand with the fluorescein attached from the strand with the black hole quencher attached.

Results and Discussion

Figure 10:
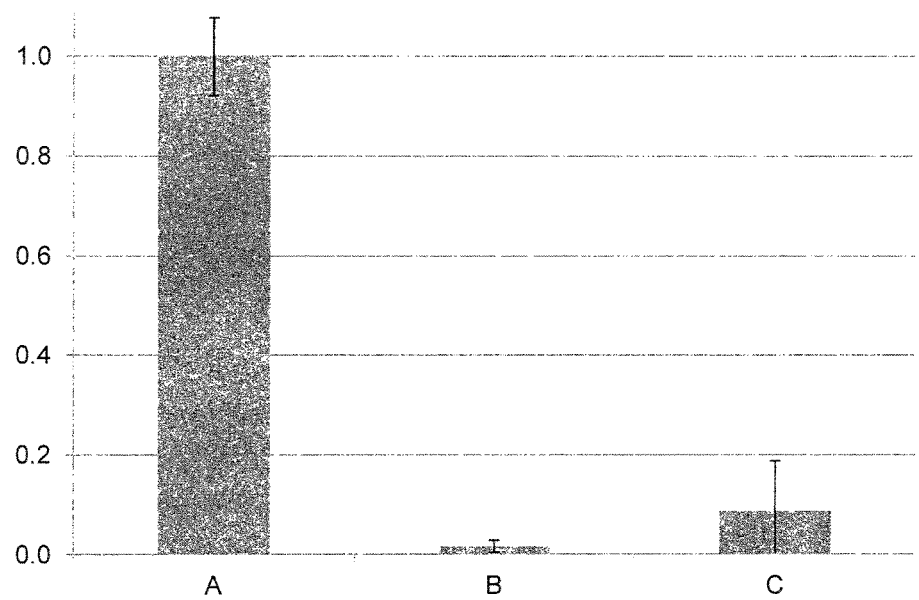
FIG. 10 Graph (y-axis=Relative dsDNA turnover, x-axis=fluorescent substrate) of the relative dsDNA turnover rate in buffer solutions (100 mM HEPES pH8, 0.975 mM ATP, 10 mM MgCl$_2$, 1 mg/mL BSA, 48.75 nM fluorescent substrate DNA (A=SEQ ID NOs: 25 and 26, B=SEQ ID NO: 27 attached at its 3' end by one Sp9 spacers to the 5' end of SEQ ID NO: 29 and hybridised to SEQ ID NO: 26, C=SEQ ID NO: 27 attached at its 3' end by four Sp9 spacers to the 5' end of SEQ ID NO: 29 and hybridised to SEQ ID NO: 26), 0.975 µM capture DNA (SEQ ID NO: 27)) for the Hel308 Mbu helicase (labeled A, SEQ ID NO: 28) at 400 mM of KCl.

The graph in FIG. 10 shows the initial rate of activity in buffer solution (100 mM Hopes pH8.0, 0.975 mM ATP, 10 mM MgCl$_2$, 1 mg/ml BSA, 48.75 nM fluorescent substrate DNA (substrates A, B and C as discussed above), 0.975 µM capture DNA (SEQ ID NO: 27)) for the Hel308 Mbu (labeled A in FIGS. 8 and 9; SEQ ID NO: 28) at 400 mM of KCl. At the salt concentration investigated the Hel308 Mbu (SEQ ID NO: 28) exhibited dsDNA turnover of the control strand A. However, FIG. 10 clearly indicates that for both constructs which have Sp9 spacers in the sequence (B (one Sp9 spacer) and C (four Sp9 spacers)) the dsDNA turnover was abolished. This indicates that in the presence of ATP and MgCl2 the Sp9 spacers stall the Hel308 Mbu enzyme in free solution.

Example 6

This Example illustrates that idSp groups can be used to stall the movement of Hel308 Mbu (SEQ ID NO: 28) (when provided with both ATP and MgCl2) in a fluorescence based assay for testing enzyme activity.

Materials and Methods

Four different custom fluorescent substrates (D=(control strand containing no spacers) SEQ ID NOs: 32 and 26, E+(strand containing a single idSp spacer) SEQ ID NO: 27 attached at its 3' end by one idSp group to the 5' end of SEQ ID NO: 30 and hybridised to SEQ ID NO: 26, F=(strand containing four idSp) SEQ ID NO: 27 attached at its 3' end by four idSp groups to the 5' end of SEQ ID NO: 31 and hybridised to SEQ ID NO: 26 and G=(second control strand containing no spacers) SEQ ID NOs: 33 and 26) were used to assay the ability of Hel308 Mbu (SEQ ID NO: 28) to displace hybridised dsDNA. FAM labelled DNA (for fluorescent substrate D=SEQ ID NO: 32, E=SEQ ID NO: 27 attached by its 3' end to one idSp group which is attached to the 3' end of SEQ ID NO: 30, F=SEQ ID NO: 27 attached by its 3' end to four idSp groups which are attached to the 3' end of SEQ ID NO: 31 and G=SEQ ID NO: 33) is annealed to the partially complementary strand which has a black-hole quencher attached to its 3' end (SEQ ID NO: 26) in a 1 to 1.2 ratio (1:1.2 µM) in 400 mM KCl, 100 mM HEPES pH8, 10 mM MgCl$_2$, 1 mg/ml BSA. The strands were annealed at room temperature for 15 minutes. The annealed DNA (D=SEQ ID NOs: 32 and 26, E=SEQ ID NO: 27 attached at its 3' end by one idSp group to the 5' end of SEQ ID NO: 30 and hybridised to SEQ ID NO: 26, F=SEQ ID NO: 27 attached at its 3' end by four idSp groups to the 5' end of SEQ ID NO: 31 and hybridised to SEQ ID NO: 26 and G=SEQ ID NOs: 33 and 26) was diluted to 50 nM in 400 mM KCl, 100 mM HEPES pH8, 10 mM MgCl$_2$, 1 mg/ml BSA, 1 mM ATP (1 uM capture DNA (SEQ ID NO: 27 also present). Hel308 Mbu (12 nM) was then assayed (as described previously in Example 5 (except the DNA constructs are different and contain idSp groups instead of Sp9 spacers) and shown in FIGS. 8 and 9 (again where the Sp9 groups in these figures are replaced with idSp groups)) against 48.75 nM annealed DNA in 400 mM KCl, 100 mM HEPES pH8, 10 mM MgCl$_2$, 1 mg/ml BSA, 0.975 mM ATP (0.975 uM capture DNA also present).

Results and Discussion

Figure 11:
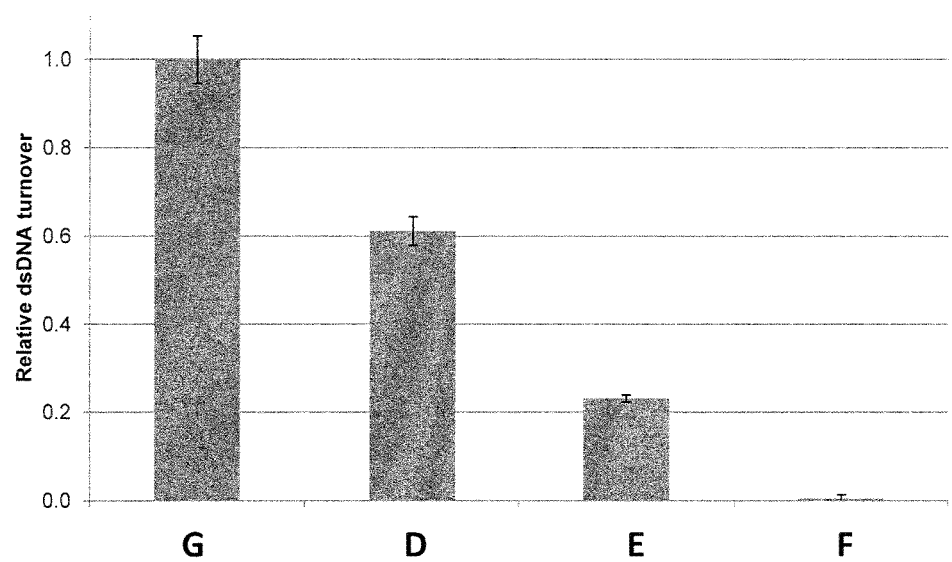
FIG. 11 Graph (y-axis=Relative dsDNA turnover, x-axis=fluorescent substrate) of the relative dsDNA turnover rate in buffer solutions (100 mM HEPES pH8, 0.975 mM ATP, 10 mM $MgCl_2$, 1 mg/mL BSA, 48.75 nM fluorescent substrate DNA (D=SEQ ID NOs: 32 and 26, E=SEQ ID NO: 27 attached at its 3' end by one idSp groups to the 5' end of SEQ ID NO: 30 and hybridised to SEQ ID NO: 26, F=SEQ ID NO: 27 attached at its 3' end by four idSp groups to the 5' end of SEQ ID NO: 31 and hybridised to SEQ ID NO: 26 and G=SEQ ID NO: 33 hybridised to SEQ ID NO: 26), 0.975 µM capture DNA (SEQ ID NO: 27)) for the Hel308 Mbu helicase (labeled A, SEQ ID NO: 28) at 400 mM of KCl.

The graph in FIG. 11 shows the initial rate of activity in buffer solution (100 mM Hepes pH 8.0, 0.975 mM ATP, 10 mM MgCl$_2$, 1 mg/ml BSA, 48.75 nM fluorescent substrate DNA (substrates D, E, F and 0 as discussed above), 0.975 µM capture DNA (SEQ ID NO: 27)) for the Hel308 Mbu (labelled A in FIGS. 8 and 9; SEQ ID NO: 28) at 400 mM of KCl. At the salt concentration investigated the Hel308 Mbu (SEQ ID NO: 28) exhibited dsDNA turnover of the control strands D and G. However, FIG. 11 clearly indicates that for the construct which has four idSp spacers in the sequence (F) the dsDNA turnover was abolished. This indicates that in the presence of ATP and MgCl2 the four idSp groups stall the Hel308 Mbu enzyme in free solution.

Example 7

This Example illustrates a gel based assay that was used to measure the ability of iSpC3 spacers and iSp18 spacers to stall the movement of T4 Dda-E94C/A360C.

Materials and Methods

The annealed DNA complexes (sequences tested are shown in table 11 below) were mixed in a ratio of (1:1, v/v) with T4 Dda-E94C/A360C in 25 mM phosphate pH 8.0, 200 mM KCl giving final concentrations of T4 Dda-E94C/A360C (2000 nM) and DNA (100 nM). The helicase was allowed to bind to the DNA for 2 hours at ambient temperature. Capture strand (SEQ ID NO: 37, 20 µM) was added to each sample to bind any unbound enzyme and the samples incubated at ambient temperature for 30 mins. Buffer was added to the samples (DNA construct from table 11-50 nM, capture DNA (SEQ ID NO: 37)=10 µM and T4 Dda-E94C/A360C=1000 nM) and they were incubated at ambient temperature for one hour (either Buffer 1=25 mM phosphate pH 8.0, 200 mM KCl, 20 mM MgCl2, 10 mM ATP or Buffer 2=25 mM phosphate pH 8.0, 1 M KCl, 25 mM potassium ferricyanide(III), 75 mM potassium ferrocyanide, 20 mM MgCl2, 10 mM ATP). Loading buffer (25 mM Phosphate pH8.0, 151.5 mM KCl, 25% Glycerol, 125 mM EDTA) is added to each sample to quench the helicase activity. The samples were loaded onto 4-20% TBE gel and the gel run at 160 V for 1.5 hours. The Gel was then stained with SYBR gold in order to observe the DNA bands.

TABLE 11

| DNA construct Number | DNA sequences which make up the construct |
|---|---|
| 1 (positive control, no spacers) | SEQ ID NO: 34 hybridised to SEQ ID NO: 35 |
| 2 (4 x iSpC3 spacers) | SEQ ID NO: 9 attached at its 3' end to four iSpC3 spacers which are attached to the 5' end of SEQ ID NO: 36 hybridised to SEQ ID NO: 35 |
| 3 (8 x iSpC3 spacers) | SEQ ID NO: 9 attached at its 3' end to eight iSpC3 spacers which are attached to the 5' end of SEQ ID NO: 36 hybridised to SEQ ID NO: 35 |
| 4 (12 x iSpC3 spacers) | SEQ ID NO: 9 attached at its 3' end to twelve iSpC3 spacers which are attached to the 5' end of SEQ ID NO: 36 hybridised to SEQ ID NO: 35 |
| 5 (1 x iSp18 spacer) | SEQ ID NO: 9 attached at its 3' end to one iSp18 spacer which are attached to the 5' end of SEQ ID NO: 36 hybridised to SEQ ID NO: 35 |
| 6 (2 x iSp18 Spacer) | SEQ ID NO: 9 attached at its 3' end to two iSp18 spacers which are attached to the 5' end of SEQ ID NO: 36 hybridised to SEQ ID NO: 35 |
| 7 (3 x iSp18 spacer) | SEQ ID NO: 9 attached at its 3' end to three iSp18 spacers which are attached to the 5' end of SEQ ID NO: 36 hybridised to SEQ ID NO: 35 |
| 8 (4 x iSp18 spacer) | SEQ ID NO: 9 attached at its 3' end to four iSp18 spacers which are attached to the 5' end of SEQ ID NO: 36 hybridised to SEQ ID NO: 35 |
| 9 (5 x iSp18 spacer) | SEQ ID NO: 9 attached at its 3' end to five iSp18 spacers which are attached to the 5' end of SEQ ID NO: 36 hybridised to SEQ ID NO: 35 |

Results and Discussion

Figure 12:
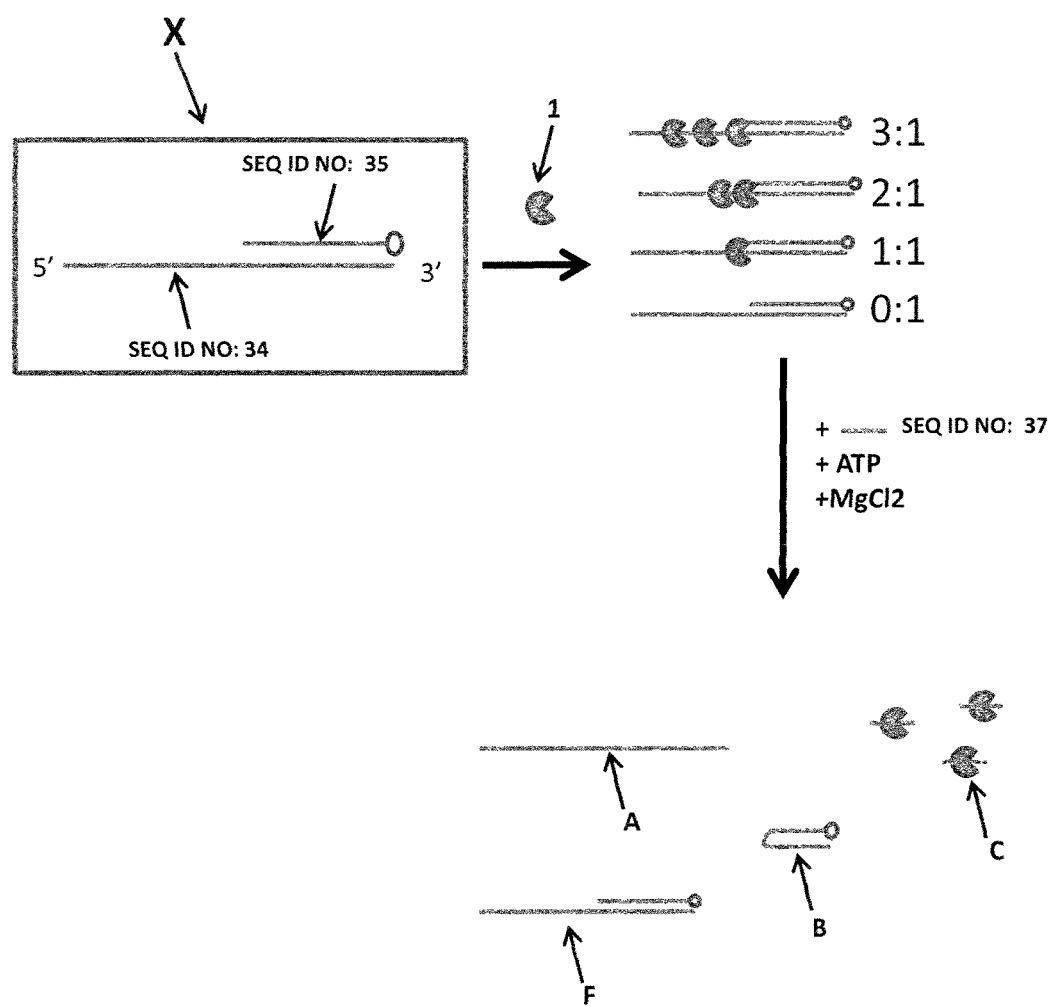
FIG. 12 shows the experimental steps for the control strand which does not contain ISpC3 or iSp18 spacers which stall the helicase (labelled 1). The control strand (SEQ ID NO: 34) contains no spacers or blocking groups and is hybridised to a shorter complementary strand of DNA (SEQ ID NO: 35, which has a carboxyfluorescein attached to its 5' end, shown as a grey circle). This produces a partially double stranded construct which has a 50 nucleotide overhang. The construct (SEQ ID NO: 34 hybridised to SEQ ID NO: 35) is pro incubated with T4 Dda-E94C/A360C to allow the enzyme to bind to the overhang. Owing to the length of the overhang more than one enzyme can bind to it as shown. The enzyme is then provided with the necessary components to promote helicase movement (ATP and MgCl2). Additional capture strand (SEQ ID NO: 37) is also added with the ATP and MgCl2. The helicase then translocates along the control strand, displacing the shorter complementary strand, leaving the control strand with no helicase or complementary strand bound (labelled A). The complementary strand then forms a hairpin so that it cannot re-anneal to the control strand (labelled B). Helicase which is free in solution or has moved along the control DNA and fallen off at the end is then bound by the excess of capture strand (SEQ ID NO: 37, complex labelled C) as shown. Any DNA which does not bind a helicase remains intact (remains as species F). The sample mixture is then run on a gel and the separate species identified by the bands they produce on the gel.
Figure 14:
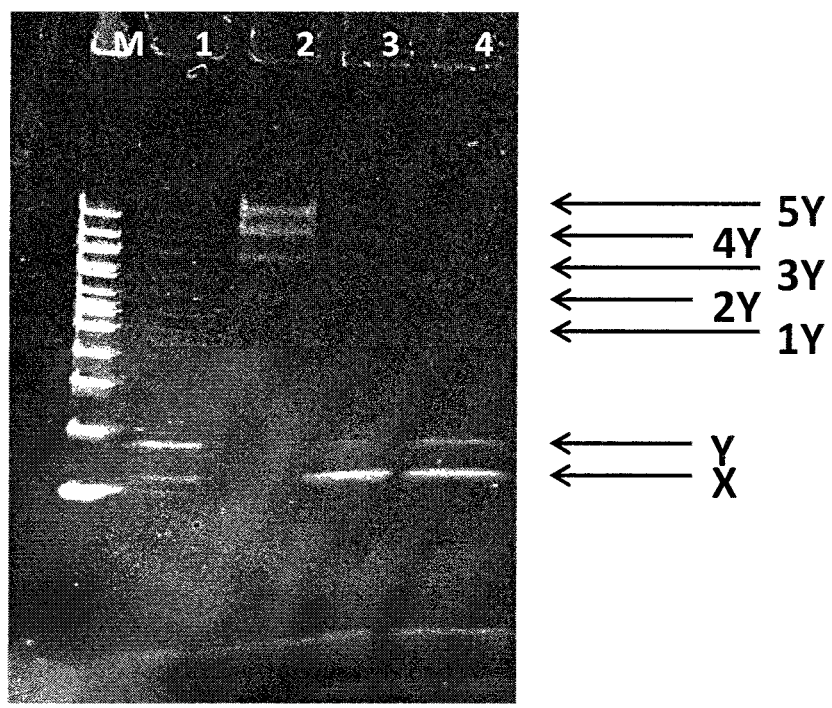
FIG. 14 shows the gel assay which was run for the control strand (1 in table 11). The lane labelled M shows a DNA ladder for reference (bands correspond from lowest mass (bottom of the gel) to highest mass (top of the gel) 200 bp (base pairs), 300 bp, 400 bp, 500/517 bp, 600 bp, 700 bp, 800 bp, 900 bp, 1000 bp, 1200 bp and 1517 bp). Lane 1 contains annealed DNA only (SEQ ID NO: 34 hybridised to SEQ ID NO: 35). Lane 2 contains the helicase (T14 Dda-E94C/A360C) pre-bound to control strand (no fuel added). Lane 3 shows the control strand after fuel (ATP and MgCl2) has been added in buffer 1. Lane 4 shows the control strand after fuel (ATP and MgCl2) has been added in buffer 2. Band X corresponds to SEQ ID NO: 34 only and band Y corresponds to SEQ ID NO: 34 hybridised to SEQ ID NO: 35. The region labelled 1Y corresponds to one helicase bound to SEQ ID NO: 34 hybridised to SEQ ID NO: 35. The region labelled 2Y corresponds to two helicases bound to SEQ ID NO: 34 hybridised to SEQ ID NO: 35. The region labelled 3Y corresponds to three helicases bound to SEQ ID NO: 34 hybridised to SEQ ID NO: 35. The region labelled 4Y corresponds to four helicases bound to SEQ ID NO: 34 hybridised to SEQ ID NO: 35. The region labelled 5Y corresponds to five helicases bound to SEQ ID NO: 34 hybridised to SEQ ID NO: 35.

FIG. 12 show the gel of the positive control experiment where the DNA construct contains no spacers to stall the helicase (T4 Dda-E94C/A360C). Lane 2 of FIG. 14 shows that the up to 5 helicase enzymes can bind onto the single-stranded section of SEQ ID NO: 34. Upon the addition of ATP and MgCl2, the higher bands corresponding to the dsDNA construct bound to multiple enzymes disappears and band corresponding to the ssDNA construct (labelled X and corresponding to SEQ ID NO: 34 only) increases in intensity. This indicates that when the helicase is provided with fuel it moves along the DNA and displaces the hybridised complementary strand (SEQ ID NO: 35).

Figure 13:
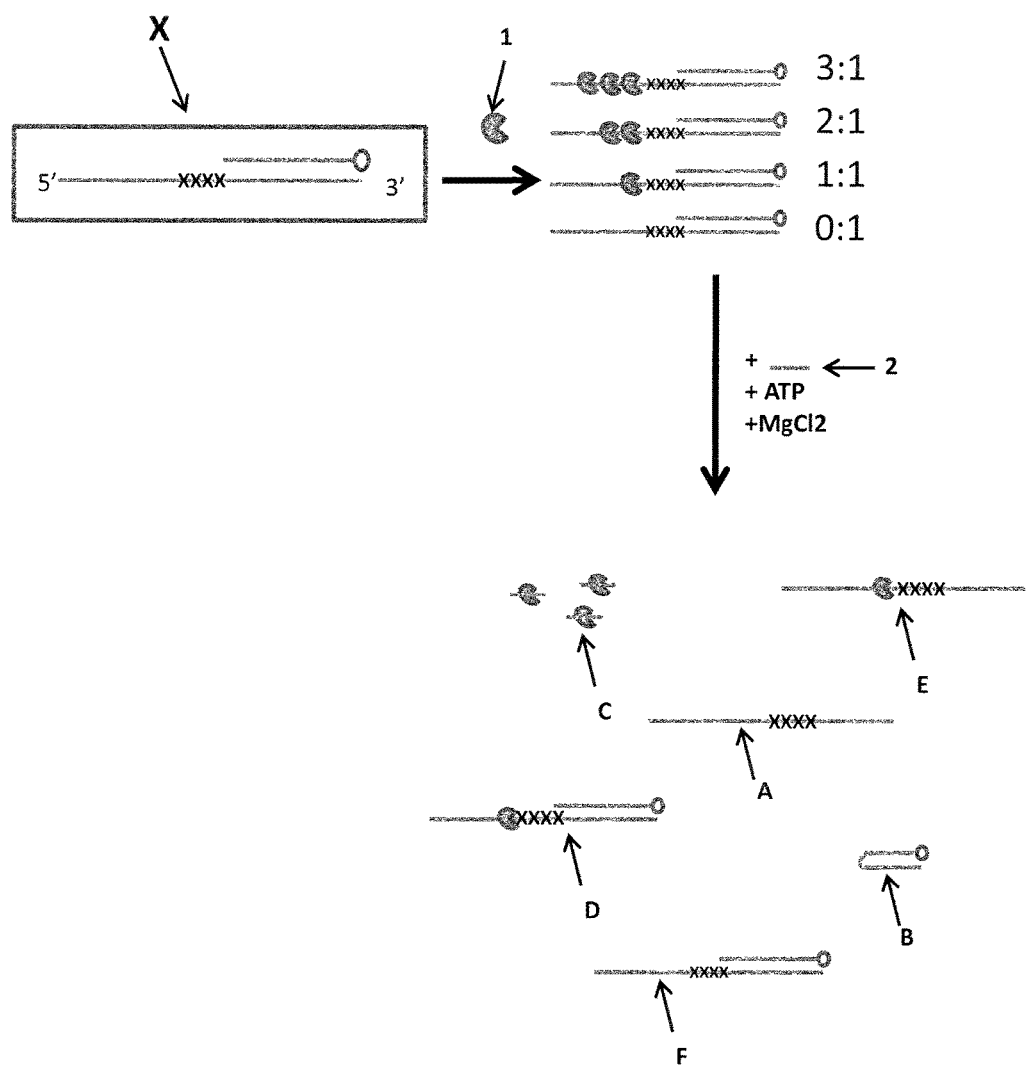
FIG. 13 shows the experimental steps for a strand which contains iSpC3 or iSp18 spacers (shown as X's in the figure) in order to stall the helicase (labelled 1). The same procedure was carried out as shown in FIG. 12, the enzyme was pre-incubated with the DNA construct (the shorter complementary strand has a carboxyfluorescein attached to its 5' end). The spacer groups are located in front of the double stranded region and the helicase is capable of binding to the DNA as shown. Upon the addition of ATP, MgCl2 and capture DNA (labelled 2) the helicase is then provided with the necessary components to promote helicase movement. If the spacers are capable of stalling the helicase then it will remain bound to the DNA construct which still contains the short complementary strand (labelled D). If the spacers are not capable of stalling the helicase then it will move past the spacer and displace the complementary strand (labelled B) leaving species A with no helicase bound. The free enzyme will then bind to the excess capture strand (labelled C) and the displaced complementary strand will form a hairpin (labelled B). If the spacers are able to stall one helicase but not two helicases then the first helicase will be pushed past the spacers by the helicase behind and will displace the complementary stand. However, the second helicase will not be able to move past the spacers resulting in the complex labelled E. Any DNA which does not bind a helicase remains intact with no helicase bound (species F) The sample mixture is then run on a gel and the separate species identified by the bands they produce on the gel.
Figure 15:
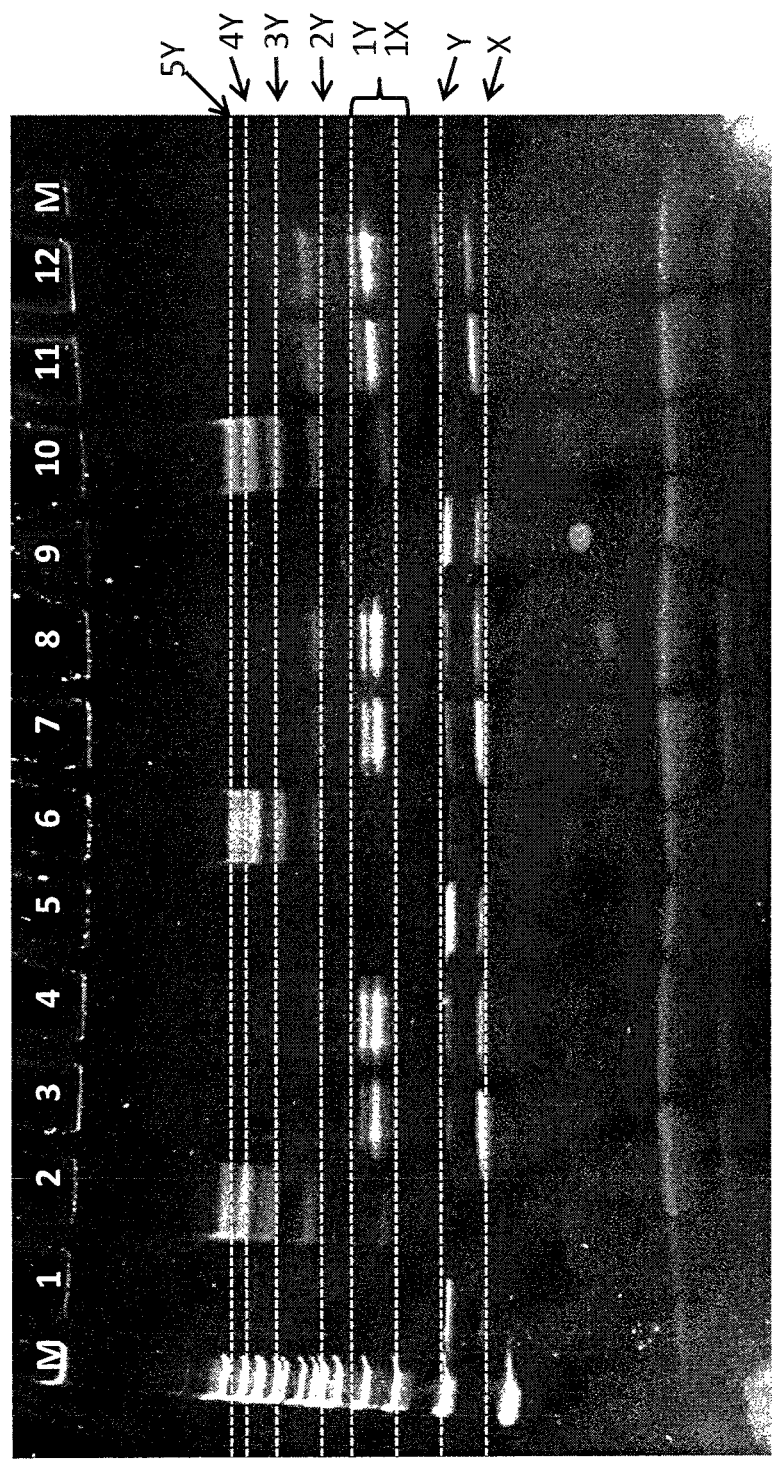
FIG. 15 shows the gel assay which was run for the DNA constructs containing 3 (7 in table 11, corresponding lanes=1-4), 4 (8 in table 11, corresponding lanes=5-8) and 5 iSp18 spacers (9 in table 11, corresponding lanes=9-12) at the junction between ssDNA and dsDNA. The lanes labelled M show a DNA ladder for reference (bands correspond from lowest mass (bottom of the gel) to highest mass (top of the gel) 200 bp (base pairs), 300 bp, 400 bp, 500/517 bp, 600 bp, 700 bp, 800 bp, 900 bp, 1000 bp, 1200 bp and 1517 bp). Lane 1 contains annealed DNA only (SEQ ID NO: 9 attached at its 3' end to three iSp18 spacers which are attached to the 5' end of SEQ ID NO: 36 hybridised to SEQ ID NO: 35). Lane 2 contains the helicase (T4 Dda-E94C/A360C) pre-bound to the DNA construct with no fuel added (SEQ ID NO: 9 attached at its 3' end to three iSp18 spacers which are attached to the 5' end of SEQ ID NO: 36 hybridised to SEQ ID NO: 35). Lane 3 shows the DNA construct (SEQ ID NO: 9 attached at its 3' end to three iSp18 spacers which are attached to the 5' end of SEQ ID NO: 36 hybridised to SEQ ID NO: 35) after fuel (ATP and MgCl2) has been added in buffer 1. Lane 4 shows the DNA construct (SEQ ID NO: 9 attached at its 3' end to three iSp18 spacers which are attached to the 5' end of SEQ ID NO: 36 hybridised to SEQ ID NO: 35) after fuel (ATP and MgCl2) has been added in buffer 2. Lane 5 contains annealed DNA only (SEQ ID NO: 9 attached at its 3' end to four iSp18 spacers which are attached to the 5' end of SEQ ID NO: 36 hybridised to SEQ ID NO: 35). Lane 6 contains the helicase (T4 Dda-E94C/A360C) pre-bound to the DNA construct with no fuel added (SEQ ID NO: 9 attached at its 3' end to four iSp18 spacers which are attached to the 5' end of SEQ ID NO: 36 hybridised to SEQ ID NO: 35). Lane 7 shows the DNA construct (SEQ ID NO: 9 attached at its 3' end to four iSp18 spacers which are attached to the 5' end of SEQ ID NO: 36 hybridised to SEQ ID NO: 35) after fuel (ATP and MgCl2) has been added in buffer 1. Lane 8 shows the DNA construct (SEQ ID NO: 9 attached at its 3' end to four iSp18 spacers which are attached to the 5' end of SEQ ID NO: 36 hybridised to SEQ ID NO: 35) after fuel (ATP and MgCl2) has been added in buffer 2. Lane 9 contains annealed DNA only (SEQ ID NO: 9 attached at its 3' end to five iSp18 spacers which are attached to the 5' end of SEQ ID NO: 36 hybridised to SEQ ID NO: 35). Lane 10 contains the helicase (T4 Dda-E94C/A360C) pre-bound to the DNA construct with no fuel added (SEQ ID NO: 9 attached at its 3' end to five iSp18 spacers which are attached to the 5' end of SEQ ID NO: 36 hybridised to SEQ ID NO: 35). Lane 11 shows the DNA construct (SEQ ID NO: 9 attached at its 3' end to five iSp18 spacers which are attached to the 5' end of SEQ ID NO: 36 hybridised to SEQ ID NO: 35) after fuel (ATP and MgCl2) has been added in buffer 1. Lane 12 shows the DNA construct (SEQ ID NO: 9 attached at its 3' end to five iSp18 spacers which are attached to the 5' end of SEQ ID NO: 36 hybridised to SEQ ID NO: 35) after fuel (ATP and MgCl2) has been added in buffer 2. Band X corresponds to ssDNA construct only (e.g. SEQ ID NO: 9 attached at its 3' end to three four or five iSp18 spacers which are attached to the 5' end of SEQ ID NO: 36) only and Band Y corresponds to the dsDNA construct only (SEQ ID NO: 9 attached at its 3' end to three, four or five iSp18 spacers which are attached to the 5' end of SEQ ID NO: 36 hybridised to SEQ ID NO: 35). The region labelled 1X corresponds to one helicase bound to SEQ ID NO: 9 attached at its 3' end to three, four or five iSp18 spacers which are attached to SEQ ID NO: 36. The region labelled 1Y corresponds to one helicase bound to SEQ ID NO: 9 attached at its 3' end to three, four or five iSp18 spacers which are attached to SEQ ID NO: 36 hybridised to SEQ ID NO: 35. The region labelled 2Y corresponds to two helicases bound to SEQ ID NO: 9 attached at its 3' end to three, four or five iSp18 spacers which are attached to SEQ ID NO: 36 hybridised to SEQ ID NO: 35. The region labelled 3Y corresponds to three helicases bound to SEQ ID NO: 9 attached at its 3' end to three, four or five iSp18 spacers which are attached to SEQ ID NO: 36 hybridised to SEQ ID NO: 35. The region labelled 4Y corresponds to four helicases bound to SEQ ID NO: 9 attached at its 3' end to three, four or five iSp18 spacers which are attached to SEQ ID NO: 36 hybridised to SEQ ID NO: 35. The region labelled 5Y corresponds to five helicases bound to SEQ ID NO: 9 attached at its 3' end to three, four or five iSp18 spacers which are attached to SEQ ID NO: 36 hybridised to SEQ ID NO: 35.

FIG. 15 shows an example of a gel showing the enzyme activity experiment for DNA constructs 7-9 of table 11 (e.g. DNA which has three, four or five iSp18 spacers just before the ssDNA/dsDNA junction). Lanes 1-4 correspond to three iSp18 spacers, lanes 5-7 correspond to four iSp18 spacers and lanes 9-12 correspond to five iSp18 spacers. Lanes 2, 6 and 10 show that, similarly to the control, up to five helicase enzymes can bind onto the single-stranded section of the DNA constructs 7-9 in table 11. Upon the addition of ATP and MgCl2 the helicases will be provided with the necessary components in order to move along the DNA strand. Lanes 3-4, 7-8 and 11-12 show the various DNA constructs under two different buffer conditions (buffer 1 and 2) after the addition of ATP and MgCl2. Two bands are clearly visible at the region labelled 1Y and 1X. 1Y corresponds to the dsDNA construct with one helicase stalled and bound. This shows that three, four and five iSP18 spacers are able to stall the helicase under the conditions tested. 1X corresponds to the ssDNA construct with one helicase stalled and bound. This band has resulted from multiple helicases binding to the DNA construct and the helicases pushing the front helicase past the stalling groups, thus displacing the short complementary strand (SEQ ID NO: 35). However, this band still has one helicase bound as a single helicase cannot move past the iSp18 spacers (e.g. species E in FIG. 13 results). In the case of 4 and 5 iSp18 spacers being used to stall the helicase there are faint bands at level 2Y. This shows that under the conditions tested, when 4/5 iSp18 spacers are used it is possible to stall the movement of up to two helicases.

Of the other spacer combinations investigated (entries 2-6 of table 11) in at least one of the buffer conditions tested both iSpC3 and iSp18 spacers were capable of stalling one helicase. Of the two buffer conditions tested, generally more efficient stalling was observed for buffer 2 than buffer 1. The greater the number of spacers included the more efficient the stalling of the helicases under the conditions tested.

Example 8

This Example investigates the number of bases needed to control the binding of only one or two T4 Dda-E94C/A360C helicases in a particular region.

Materials and Methods

DNA constructs (1 µM or 100 nM final concentration) detailed below in Table 12 were incubated in appropriate buffer with serially diluted T4 Dda-E94C/A360C. The samples were then loaded on 4-20% TBE gels and run at 160 V for 90 minutes. The gels containing entries 1-6 were then stained using SYBR. FIG. 16 shows the type of DNA construct used in this experiment. The length of the region labelled 1 is varied from 2 to 50 to optimise conditions so that it is possible to control the number of T4 Dda-E94C/A360C helicases which can bind to the DNA.

TABLE 12

| Entry | DNA Construct | Buffer | Incubation Conditions | Concentrations of T4 Dda - E94C/A360C |
|---|---|---|---|---|
| 1 | 1 µM, Five iSpC3 spacers attached to the 5' end of SEQ ID NO: 37, which is attached at its 3' end to four iSpC3 spacers which are attached to the 5' end of SEQ ID NO: 36 which is hybridised to SEQ ID NO: 35. | 25 mM phosphate, 151.5 mM KCl pH 8.0 | overnight at room temperature | 5000 nM, 2500 nM, 1250 nM, 625 nM, 312.5 nM, 0M |
| 2 | 1 µM, Five iSpC3 spacers attached to the 5' end of SEQ ID NO: 38, which is attached at its 3' end to four iSpC3 spacers which are attached to the 5' end of SEQ ID NO: 36 which is hybridised to SEQ ID NO: 35. | 25 mM phosphate, 151.5 mM KCl pH 8.0 | overnight at room temperature | 5000 nM, 2500 nM, 1250 nM, 625 nM, 312.5 nM, 0M |
| 3 | 1 µM, Five iSpC3 spacers attached to the 5' end of SEQ ID NO: 9, which is attached at its 3' end to four iSpC3 spacers which are attached to the 5' end of SEQ ID NO: 36 which is hybridised to SEQ ID NO: 35. | 25 mM phosphate, 151.5 mM KCl pH 8.0 | overnight at room temperature | 5000 nM, 2500 nM, 1250 nM, 625 nM, 312.5 nM, 0M |
| 4 | 1 µM, Five iSpC3 spacers attached to the 5' end of two thymines, which are attached at the 3' end to four iSpC3 spacers which are attached to the 5' end of SEQ ID NO: 36 which is hybridised to SEQ ID NO: 35. | 25 mM phosphate, 151.5 mM KCl pH 8.0 | 1.5 hours at room temperature | 3750 nM, 1875 nM, 938 nM, 469 nM, 235 nM, 0M |
| 5 | 1 µM, Five iSpC3 spacers attached to the 5' end of four thymines, which are attached at the 3' end to four iSpC3 spacers which are attached to the 5' end of SEQ ID NO: 36 which is hybridised to SEQ ID NO: 35. | 25 mM phosphate, 151.5 mM KCl pH 8.0 | 1.5 hours at room temperature | 3750 nM, 1875 nM, 938 nM, 469 nM, 235 nM, 0M |
| 6 | 1 µM, Five iSpC3 spacers attached to the 5' end of eight thymines, which are attached at the 3' end to four iSpC3 spacers which are attached to the 5' end of SEQ ID NO: 36 which is hybridised to SEQ ID NO: 35. | 25 mM phosphate, 151.5 mM KCl pH 8.0 | 1.5 hours at room temperature | 3750 nM, 1875 nM, 938 nM, 469 nM, 235 nM, 0M |
| 7 | 100 nM, Five iSpC3 spacers attached to the 5' end of SEQ ID NO: 39, which is attached at its 3' end to four iSp18 spacers which are attached to the 5' end of SEQ ID NO: 36 which is hybridised to SEQ ID NO: 35. | 25 mM phosphate, 151.5 mM KCl pH 8.0 | Overnight at room temperature | 2700 nM, 1350 nM, 675 nM, 337.5 nM, 169 nM, 0M |
| 8 | 100 nM, Five iSpC3 spacers attached to the 5' end of SEQ ID NO: 40, which is attached at its 3' end to four iSp18 spacers which are attached to the 5' end of SEQ ID NO: 36 which is hybridised to SEQ ID NO: 35. | 25 mM phosphate, 151.5 mM KCl pH 8.0 | Overnight at room temperature | 2700 nM, 1350 nM, 675 nM, 338 nM, 169 nM, 0M |

Results and Discussion

Each of the DNA constructs listed in Table 12 were investigated to determine how many enzymes can bind to region 1 (shown in FIG. 16) which has been varied from 2 bases to 50 bases. For each of the DNA constructs tested only a single band for unbound DNA was observed when no helicase was added. Under the conditions investigated, construct 4 (which has a binding region of 2 thymine bases) and construct 5 (which has a binding region of 4 thymine bases) were not observed to allow any helicases to bind at any concentration (see table 14). Construct 6 (which has a binding region of 8 thymine bases see table 14) and construct 1 (which had a binding region of 10 thymine bases) was observed to bind one helicase only (see table 13). Construct 2 which has a binding region of 20 thymine bases allowed two enzymes to bind at the higher concentrations tested and construct 3 which has a binding region of 50 thymine bases allowed up to 6 enzymes to bind at the highest concentrations tested (see FIG. 17 for the gel showing this experiment see table 13). Constructs 1-6 used iSpC3 spacers to prevent binding of the helicase at the junction of the ssDNA/dsDNA region. Constructs 7 and 8 used iSp18 spacers to prevent binding of the helicase at the junction of the ssDNA/dsDNA region. Construct 7 (which has a binding region of 16 thymines) and construct 8 (which has a binding region of 18 thymines) both allowed up to two helicases to bind under the conditions tested (see table 15). Therefore, binding regions greater than 8 thymine bases long allow at least one enzyme to bind to the DNA constructs.

TABLE 13

| DNA Construct | Concentration of T4 Dda - E94C/A360C | | | | |
|---|---|---|---|---|---|
| Entry No | 5000 | 2500 | 1250 | 625 | 312.5 |
| 1 | One enzyme bound only | One enzyme bound only | One enzyme bound only | One enzyme bound only. Faint band for unbound DNA. | One enzyme bound only, Unbound DNA |
| 2 | Two enzymes bound. | Two enzymes bound. | Two enzymes bound. | Two enzymes bound. One enzyme bound. | One enzyme bound only. Unbound DNA |
| 3 (shown in FIG. 17) | Six enzymes bound (lane 1 FIG. 17). | Five enzymes bound (lane 2 FIG. 17). | Faint band for two enzymes bound. Three enzymes bound. Four enzymes bound. Five enzymes bound (lane 3 FIG. 17). | One enzyme bound. Two enzymes bound. Three enzymes bound. Faint band for four enzymes bound (lane 4 FIG. 17). | One enzyme bound. Two enzymes bound. Faint band for three enzymes bound (lane 5 FIG. 17). |

TABLE 14

| DNA Construct | Concentration of T4 Dda - E94C/A360C | | | | |
|---|---|---|---|---|---|
| Entry No | 3750 | 1875 | 938 | 469 | 235 |
| 4 | Unbound DNA only. | Unbound DNA only. | Unbound DNA only. | Unbound DNA only. | Unbound DNA only. |
| 5 | Unbound DNA only. | Unbound DNA only. | Unbound DNA only. | Unbound DNA only. | Unbound DNA only. |
| 6 | One enzyme bound. Faint band for unbound DNA | One enzyme bound. Unbound DNA | Faint band for one enzyme bound. Unbound DNA | Faint band for one enzyme bound. Unbound DNA | Unbound DNA only. |

TABLE 15

| DNA Construct | Concentration of T4 Dda - E94C/A360C | | | | |
|---|---|---|---|---|---|
| Entry No | 2700 | 1350 | 675 | 338 | 169 |
| 7 | Two enzymes bound. | Two enzymes bound. One enzyme bound. Faint band for unbound DNA | Faint band for two enzymes bound. One enzyme bound. Faint band for unbound DNA | One enzyme bound. Unbound DNA. | Faint band for one enzyme bound. Unbound DNA |
| 8 | Two enzymes bound. | Two enzymes bound. Faint band for one enzyme bound. | Faint band for two enzymes bound. One enzyme bound. Unbound DNA | Faint band for one enzyme bound. Unbound DNA | Unbound DNA only. |

Example 9

This Example investigates the concentration of T4 Dda-E94C/A360C helicase which when added to the DNA construct X (described and shown in FIG. 18) results in the binding of two helicases.

Materials and Methods

Two DNA constructs were tested one which has a complementary strand of DNA which is not forked (SEQ ID NO: 42 is hybridised to the DNA construct shown in FIG. 18) and one which is forked (SEQ ID NO: 12 (which has 6 iSp18 spacers attached to the 3' end) is hybridised to the DNA construct shown in FIG. 18). The DNA strands shown in Table 16 were annealed at 1 µM in 25 mM phosphate pH 8.0, 1515.5 mM KCl (a 10% excess of complementary strands SEQ ID NO: 43 (in entries 9 and 10 below) and SEQ ID NO: 12 (entry 10 below) or SEQ ID NO: 42 (entry 9 below) was used).

TABLE 16

| DNA Construct Entry No: | DNA Strands Annealed |
|---|---|
| 9 | 25 SpC3 spacers are attached to the 5' end of SEQ ID NO: 37 which is attached at its 3' end to two iSp18 spacers. The iSp18 spacers are attached to another DNA fragment of SEQ ID NO: 37 which again is attached at its 3' end to the another two iSp18 spacers. The second instance of iSp18 spacers is attached to the 5' end of SEQ ID NO: 10 which is attached its 3' end to four nitroindoles. The four nitroindoles are then attached to the 5' end of SEQ ID NO: 41. SEQ ID NO: 41 is hybridised to the complementary strand SEQ ID NO: 43. SEQ ID NO: 10 is hybridised to the non-forked complementary strand SEQ ID NO: 42. |
| 10 | 25 SpC3 spacers are attached to the 5' end of SEQ ID NO: 37 which is attached at its 3' end to two iSp18 spacers. The iSp18 spacers are attached to another DNA fragment of SEQ ID NO: 37 which again is attached at its 3' end to the another two iSp18 spacers. The second instance of iSp18 spacers is attached to the 5' end of SEQ ID NO: 10 which is attached its 3' end to four nitroindoles. The four nitroindoles are then attached to the 5' end of SEQ ID NO: 41. SEQ ID NO: 41 is hybridised to the complementary strand SEQ ID NO: 43. SEQ ID NO: 10 is hybridised to the forked complementary strand SEQ ID NO: 12 which has 6 iSp18 spacers attached at its 3' end. |

T4 Dda-E94C/A360C was buffer exchanged into 25 mM phosphate pH 8.0, 151.5 mM KCl and serially diluted. The helicase and DNA were then mixed (1:1, v/v) with the DNA construct samples 9 and 10 described above (final concentration DNA=100 nM, helicase concentrations investigated=3800 nM, 1900 nM, 950 nM, 475 nM, 238 nM, 0 nM). The DNA and enzyme volumes were then incubated at ambient temperature for 1.5 hours. Dye free loading buffer (5×, 7.5 µL) was added to each sample (30 µL). Each sample (37.5 µL) was then loaded onto 4-20% TBE gel and run at 160 V for 90 minutes. The gel was then stained using SYBR.

Results and Discussion

The two DNA constructs listed in Table 16 were investigated to determine what concentration of T4 Dda-E94C/A360C helicase is required in order to promote binding of two helicases. For each of the DNA constructs tested only a single band for unbound DNA was observed when no helicase was added. Under the conditions investigated, both constructs 9 (non-forked construct) and 10 (forked) observed binding of one helicase from 238 nM helicase and two enzymes from 475 nM and higher. As the concentration of enzyme was increased the band corresponding to two enzymes bound increased in intensity. The design of the DNA construct shown in FIG. 18 allows the binding of only two enzymes at concentrations as high as 3800 nM. Therefore, the spacers investigated do not allow the helicase to bind to them when the constructs are pre-incubated.

Example 10

This Example shows how the T4 Dda-E94C/A360C is stalled by four iSp18 spacers in free solution until the construct (DNA construct X1) is captured by the nanopore. Upon capture the force of the applied potential moves the enzyme T4 Dda-E94C/A360C past the stalling spacer and allows enzyme controlled DNA movement of the lambda construct through the nanopore.

Materials and Methods

Prior to setting up the experiment, the DNA construct X1 (0.13 µL, 100 nM) and T4 Dda-E94C/A360C (15.6 µL, 250 nM) were pre-incubated together for 1 hour at room temperature in buffer (50 mM potassium phosphate, 253 mM KCl, pH 8.0).

Electrical measurements were acquired at 30° C. (by placing the experimental system on a cooler plate) from single MspA nanopores (MspA-B2C) inserted in block co-polymer in buffer (600 mM KCl, 25 mM potassium phosphate, 75 mM Potassium Ferrocyanide (II), 25 mM Potassium ferricyanide (III), pH 8). After achieving a single pore inserted in the block co-polymer, then buffer (1 mL, 600 mM KCl, 25 mM potassium phosphate, 75 mM Potassium Ferrocyanide (II), 25 mM Potassium ferricyanide (III), pH 8) was flowed through the system to remove any excess MspA nanopores (MspA-B2C). Potassium ferricyanide (III) (200 µM final concentration) was added to the DNA (0.1 nM final concentration) enzyme (3 nM final concentration) pre-mix and left to incubate for one minute before MgCl$_2$ (10 mM final concentration) and ATP (1 mM final concentration) were mixed together with buffer (1260 µL, 600 mM KCl, 25 mM potassium phosphate, 75 mM Potassium Ferrocyanide (II), 25 mM Potassium ferricyanide (III), pH 8). This experimental mix was then added to the single nanopore experimental system. Experiments were carried out for six hours following a potential flip process (+180 mV for 2 s, then 0 V for 2 s, then −120 mV for 3600 s (×6 repeats) applied at the cis side) and helicase-controlled DNA movement was monitored.

Results and Discussion

The DNA construct is shown in FIG. 20. The T4 Dda-E94C/A360C is able to bind on to the region of the construct labelled A (SEQ ID NO: 9) when pre-incubated with the DNA construct. However, the enzyme is not able to motor past the stalling groups (four iSp18 spacers) when in free solution (labelled as black boxes). Therefore, the enzyme is stalled at the iSp18 spacers (labelled B in FIG. 1) until the DNA construct is captured by the nanopore. Once captured by the nanopore, the force of the applied potential moves the enzyme T4 Dda-E94C/A360C past the stalling spacer (four iSp18 spacers) and allows enzyme controlled DNA movement of the DNA construct X1 construct through the nanopore. An example of a helicase-controlled DNA movement is shown in FIG. 21. The section labelled 1 showed when the pT region of SEQ ID NO 38 translocated through the nanopore under control of the helicase. The section labelled 2 showed when the iSp18 spacer translocated through the nanopore under the control of the helicase. The helicase was observed to have a defined start point (resulting from the stalling of the helicase by the iSp18 spacers) as the helicase events observed showed the pT region and the iSp18 signal at the beginning of the helicase controlled DNA movements.

The invention claimed is:

1. A method comprising: (a) providing a complex comprising one or more helicases bound, in an active mode, to a polynucleotide, wherein the polynucleotide comprises one or more spacers that are configured such that movement of the one or more helicases relative to the polynucleotide is stalled: (b) contacting a transmembrane pore, which is present in a membrane, with the complex, wherein the transmembrane pore comprises an opening that permits passage of the polynucleotide, but not the one or more helicases, across the membrane; and (c) applying a potential difference across the membrane such that the polynucleotide moves through the transmembrane pore and such that the one or more helicases pass across the one or more spacers of the polynucleotide.

2. A method of comprising:
(a) providing a target polynucleotide comprising one or more spacers that are configured such that movement of a helicase relative to the target polynucleotide is stalled;
(b) contacting the target polynucleotide with one or more helicases such that the one or more helicases, in an active mode, bind to the target polynucleotide and stall at the one or more spacers;
(c) contacting a transmembrane pore, which is present in a membrane, with the target polynucleotide and the one or more stalled helicases, wherein the transmembrane pore comprises an opening that permits passage of the target polynucleotide, but not the one or more helicases, across the membrane; and
(d) applying a potential difference across the membrane such that the target polynucleotide moves through the transmembrane pore; and such that the one or more helicases pass across the one or more spacers of the target polynucleotide and control the movement of the target polynucleotide through the transmembrane pore.

3. A method according to claim 2, further comprising taking one or more measurements as the target polynucleotide moves with respect to the transmembrane pore wherein the measurements are indicative of one or more characteristics of the target polynucleotide and thereby characterising the target polynucleotide.

4. A method according to claim 3, wherein the one or more characteristics are selected from the group consisting of: (i) the length of the target polynucleotide, (ii) the identity of the target polynucleotide, (iii) the sequence of the target polynucleotide, (iv) the secondary structure of the target polynucleotide, (v) whether or not the target polynucleotide is modified, and (vi) whether or not the target polynucleotide is modified by methylation, by oxidation, by damage, with one or more proteins or with one or more labels, tags or spacers.

5. A method according to claim 3, wherein the one or more characteristics of the target polynucleotide are measured by an electrical measurement and/or optical measurement.

6. A method according to claim 2, wherein (a) the one or more spacers have a different structure from the polynucleotide, (b) the polynucleotide is deoxyribonucleic acid or ribonucleic acid and the one or more spacers comprise peptide nucleic acid, glycerol nucleic acid, threose nucleic acid, locked nucleic acid or a synthetic polymer with nucleotide side chains, (c) the one or more spacers comprise one or more nitroindoles, one or more inosines, one or more acridines, one or more 2-aminopurines, one or more 2-6-diaminopurines, one or more 5-bromo-deoxyuridines, one or more inverted thymidines, one or more inverted dideoxy-thymidines, one or more dideoxy-cytidines, one or more 5-methylcytidines, one or more 5-hydroxymethylcytidines, one or more 2'-O-Methyl RNA bases, one or more Iso-deoxycytidines, one or more Iso-deoxyguanosines, one or more C3 groups, one or more photo-cleavable groups, one or more hexandiol groups, one or more 9-atom spacer groups, one or more 18-atom spacer groups, a polymer or one or more thiol connections, (d) the one or more spacers comprise a polypeptide or a polyethylene glycol, (e) the one or more spacers comprise one or more abasic nucleotides, (f) the one or more spacers comprise one or more chemical groups which cause the one or more helicases to stall, (g) the one or more spacers comprise one or more chemical groups which cause the one or more helicases to stall and the one or more chemical groups are one or more fluorophores, streptavidin and/or biotin, cholesterol, methylene blue, a dinitrophenol, digoxigenin and/or anti-digoxigenin or a dibenzylcyclooctyne group, (h) the one or more spacers are capable of stalling the one or more helicases in the presence of free nucleotides and/or the presence of a helicase cofactor, or (i) the one or more spacers are capable of stalling the one or more helicases in a salt concentration of about 100 mM or lower.

7. A method according to claim 2, wherein the method comprises moving two or more stalled helicases past each spacer or comprises moving two or more helicases that are attached to one another or covalently attached to one another past each spacer.

8. A method according to claim 2, wherein (a) at least a portion of the target polynucleotide is double stranded or (b) at least a portion of the target polynucleotide is double stranded and (i) the one or more spacers are included in a single stranded region or a non-hybridised region of the target polynucleotide or (ii) the one or more spacers are included in a single stranded region of the target polynucleotide and the single stranded region comprises a leader sequence which threads into the transmembrane pore.

9. A method according to claim 8, wherein (a) the two strands of the double stranded portion are linked using a bridging moiety or (b) the two strands of the double stranded portion are linked using a bridging moiety and the one or more spacers are included in the bridging moiety.

10. A method according to claim 2, wherein the one or more helicases are selected from the group consisting of: Hel308 helicases, RecD helicases, XPD helicases, Dda helicases, helicases derived from any of the foregoing helicases, and a combination of any of the foregoing helicases.

11. A method according to claim 2, wherein the transmembrane pore is: (a) a protein pore or a solid state pore; (b) a protein pore derived from one selected from the group consisting of: a hemolysin, leucocidin, *Mycobacterium smegmatis* porin A, MspB, MspC, MspD, lysenin, outer membrane porin F, outer membrane porin G, outer membrane phospholipase A, *Neisseria* autotransporter lipoprotein and WZA; or (c) formed of eight identical subunits as shown in SEQ ID NO: 2 or a variant thereof in which one or more of the eight subunits has at least 50% homology to SEQ ID NO: 2 based on amino acid identity over the entire sequence and retains activity of the transmembrane pore.

12. A method according to claim 5, wherein the one or more characteristics of the target polynucleotide are measured by an electrical measurement, wherein the electrical measurement is selected from the group consisting of: a current measurement, an impedance measurement, a tunneling measurement, and a field effect transistor measurement.

* * * * *

SEQUENCE LISTING

<160> NUMBER OF SEQ ID NOS: 43

<210> SEQ ID NO 1
<211> LENGTH: 558
<212> TYPE: DNA
<213> ORGANISM: Artificial Sequence
<220> FEATURE:
<223> OTHER INFORMATION: Polynucleotide sequence encoding the MS-B1
      mutant MspA monomer

<400> SEQUENCE: 1
atgggtctgg ataatgaact gagcctggtg gacggtcaag atcgtaccct gacggtgcaa      60
caatgggata cctttctgaa tggcgttttt ccgctggatc gtaatcgcct gacccgtgaa     120
tggtttcatt ccggtcgcgc aaaatatatc gtcgcaggcc cgggtgctga cgaattcgaa     180
ggcacgctgg aactgggtta tcagattggc tttccgtggt cactgggcgt tggtatcaac     240
ttctcgtaca ccacgccgaa tattctgatc aacaatggta acattaccgc accgccgttt     300
ggcctgaaca gcgtgattac gccgaacctg tttccgggtg ttagcatctc tgcccgtctg     360
ggcaatggtc cgggcattca agaagtggca acctttagtg tgcgcgtttc cggcgctaaa     420
ggcggtgtcg cggtgtctaa cgcccacggt accgttacgg gcgcggccgg cggtgtcctg     480
ctgcgtccgt tcgcgcgcct gattgcctct accggcgaca gcgttacgac ctatggcgaa     540
ccgtggaata tgaactaa                                                   558

<210> SEQ ID NO 2
<211> LENGTH: 184
<212> TYPE: PRT
<213> ORGANISM: Artificial Sequence
<220> FEATURE:
<223> OTHER INFORMATION: Amino acid sequence of the mature form of the
      MS-B1 mutant of the MspA monomer

<400> SEQUENCE: 2

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asn Asn Gly Asn Ile Thr Ala
                85                  90                  95

Pro Pro Phe Gly Leu Asn Ser Val Ile Thr Pro Asn Leu Phe Pro Gly
            100                 105                 110

Val Ser Ile Ser Ala Arg Leu Gly Asn Gly Pro Gly Ile Gln Glu Val
        115                 120                 125

Ala Thr Phe Ser Val Arg Val Ser Gly Ala Lys Gly Val Ala Val
            130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180

<210> SEQ ID NO 3
<211> LENGTH: 885
<212> TYPE: DNA
<213> ORGANISM: Artificial Sequence
<220> FEATURE:
<223> OTHER INFORMATION: Polynucleotide sequence encoding one monomer of alpha-hemolysin-E111N/K147N

<400> SEQUENCE: 3
atggcagatt ctgatattaa tattaaaacc ggtactacag atattggaag caatactaca    60
gtaaaaacag gtgatttagt cacttatgat aaagaaaatg gcatgcacaa aaaagtattt   120
tatagtttta tcgatgataa aaatcacaat aaaaaactgc tagttattag aacaaaaggt   180
accattgctg gtcaatatag agtttatagc gaagaaggtg ctaacaaaag tggtttagcc   240
tggccttcag cctttaaggt acagttgcaa ctacctgata tgaagtagc tcaaatatct   300 gattactatc caagaaattc gattgataca aaaaactata tgagtacttt aacttatgga   360
ttcaacggta atgttactgg tgatgataca ggaaaaattg gcggccttat tggtgcaaat   420
gtttcgattg gtcatacact gaactatgtt caacctgatt tcaaaacaat tttagagagc   480
ccaactgata aaaagtagg ctggaaagtg atatttaaca atatggtgaa tcaaaattgg   540
ggaccatacg atcgagattc ttggaacccg gtatatggca atcaactttt catgaaaact   600
agaaatggtt ctatgaaagc agcagataac ttccttgatc ctaacaaagc aagttctcta   660
ttatcttcag ggttttcacc agacttcgct acagttatta ctatggatag aaaagcatcc   720
aaacaacaaa caaatataga gtaatatac gaacagttc gtgatgatta ccaattgcat   780
tggacttcaa caaattggaa aggtaccaat actaaagata atggacaga tcgttcttca   840 gaaagatata aaatcgattg ggaaaaagaa gaaatgacaa attaa              885

<210> SEQ ID NO 4
<211> LENGTH: 293
<212> TYPE: PRT
<213> ORGANISM: Artificial Sequence
<220> FEATURE:
<223> OTHER INFORMATION: Amino acid sequence of one monomer of alpha-HL-NN

<400> SEQUENCE: 4

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met His Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
        50                  55                  60

Tyr Arg Val Tyr Ser Glu Glu Gly Ala Asn Lys Ser Gly Leu Ala Trp
65                  70                  75                  80

```
Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Asn Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Asn Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
        290

<210> SEQ ID NO 5
<211> LENGTH: 184
<212> TYPE: PRT
<213> ORGANISM: Mycobacterium smegmatis

<400> SEQUENCE: 5

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
                20                  25                  30

Arg Asn Arg Leu Thr Arg Glu Trp Phe His Ser Gly Arg Ala Lys Tyr
            35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asp Asp Gly Asp Ile Thr Ala
                85                  90                  95

Pro Pro Phe Gly Leu Asn Ser Val Ile Thr Pro Asn Leu Phe Pro Gly
            100                 105                 110

Val Ser Ile Ser Ala Asp Leu Gly Asn Gly Pro Gly Ile Gln Glu Val
        115                 120                 125

Ala Thr Phe Ser Val Asp Val Ser Gly Pro Ala Gly Gly Val Ala Val
    130                 135                 140

Ser Asn Ala His Gly Thr Val Thr Gly Ala Ala Gly Gly Val Leu Leu
```

```
                145                 150                 155                 160
Arg Pro Phe Ala Arg Leu Ile Ala Ser Thr Gly Asp Ser Val Thr Thr
                    165                 170                 175

Tyr Gly Glu Pro Trp Asn Met Asn
            180

<210> SEQ ID NO 6
<211> LENGTH: 184
<212> TYPE: PRT
<213> ORGANISM: Mycobacterium smegmatis

<400> SEQUENCE: 6

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
                20                  25                  30

Arg Asn Arg Leu Thr Arg Glu Trp Phe His Ser Gly Arg Ala Lys Tyr
            35                  40                  45

Ile Val Ala Gly Pro Gly Ala Asp Glu Phe Glu Gly Thr Leu Glu Leu
        50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asp Asp Gly Asp Ile Thr Gly
                85                  90                  95

Pro Pro Phe Gly Leu Glu Ser Val Ile Thr Pro Asn Leu Phe Pro Gly
                100                 105                 110

Val Ser Ile Ser Ala Asp Leu Gly Asn Gly Pro Gly Ile Gln Glu Val
            115                 120                 125

Ala Thr Phe Ser Val Asp Val Ser Gly Pro Ala Gly Gly Val Ala Val
        130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                    165                 170                 175

Tyr Gly Glu Pro Trp Asn Met Asn
            180

<210> SEQ ID NO 7
<211> LENGTH: 183
<212> TYPE: PRT
<213> ORGANISM: Mycobacterium smegmatis

<400> SEQUENCE: 7

Val Asp Asn Gln Leu Ser Val Val Asp Gly Gln Gly Arg Thr Leu Thr
1               5                   10                  15

Val Gln Gln Ala Glu Thr Phe Leu Asn Gly Val Phe Pro Leu Asp Arg
                20                  25                  30

Asn Arg Leu Thr Arg Glu Trp Phe His Ser Gly Arg Ala Thr Tyr His
            35                  40                  45

Val Ala Gly Pro Gly Ala Asp Glu Phe Glu Gly Thr Leu Glu Leu Gly
        50                  55                  60

Tyr Gln Val Gly Phe Pro Trp Ser Leu Gly Val Gly Ile Asn Phe Ser
65                  70                  75                  80

Tyr Thr Thr Pro Asn Ile Leu Ile Asp Gly Gly Asp Ile Thr Gln Pro
                85                  90                  95

Pro Phe Gly Leu Asp Thr Ile Ile Thr Pro Asn Leu Phe Pro Gly Val
```

```
            100                 105                 110
Ser Ile Ser Ala Asp Leu Gly Asn Gly Pro Gly Ile Gln Glu Val Ala
            115                 120                 125

Thr Phe Ser Val Asp Val Lys Gly Ala Lys Gly Ala Val Ala Val Ser
            130                 135             140

Asn Ala His Gly Thr Val Thr Gly Ala Ala Gly Gly Val Leu Leu Arg
145                 150                 155                 160

Pro Phe Ala Arg Leu Ile Ala Ser Thr Gly Asp Ser Val Thr Thr Tyr
                165                 170                 175

Gly Glu Pro Trp Asn Met Asn
            180

<210> SEQ ID NO 8
<211> LENGTH: 439
<212> TYPE: PRT
<213> ORGANISM: Enterobacteria phage T4

<400> SEQUENCE: 8

Met Thr Phe Asp Asp Leu Thr Glu Gly Gln Lys Asn Ala Phe Asn Ile
1               5                   10                  15

Val Met Lys Ala Ile Lys Glu Lys Lys His Val Thr Ile Asn Gly
            20                  25                  30

Pro Ala Gly Thr Gly Lys Thr Thr Leu Thr Lys Phe Ile Ile Glu Ala
            35                  40                  45

Leu Ile Ser Thr Gly Glu Thr Gly Ile Ile Leu Ala Ala Pro Thr His
        50                  55                  60

Ala Ala Lys Lys Ile Leu Ser Lys Leu Ser Gly Lys Glu Ala Ser Thr
65                  70                  75                  80

Ile His Ser Ile Leu Lys Ile Asn Pro Val Thr Tyr Glu Glu Asn Val
                85                  90                  95

Leu Phe Glu Gln Lys Glu Val Pro Asp Leu Ala Lys Cys Arg Val Leu
            100                 105                 110

Ile Cys Asp Glu Val Ser Met Tyr Asp Arg Lys Leu Phe Lys Ile Leu
            115                 120                 125

Leu Ser Thr Ile Pro Pro Trp Cys Thr Ile Ile Gly Ile Gly Asp Asn
        130                 135                 140

Lys Gln Ile Arg Pro Val Asp Pro Gly Glu Asn Thr Ala Tyr Ile Ser
145                 150                 155                 160

Pro Phe Phe Thr His Lys Asp Phe Tyr Gln Cys Glu Leu Thr Glu Val
                165                 170                 175

Lys Arg Ser Asn Ala Pro Ile Ile Asp Val Ala Thr Asp Val Arg Asn
                180                 185                 190

Gly Lys Trp Ile Tyr Asp Lys Val Val Asp Gly His Gly Val Arg Gly
            195                 200                 205

Phe Thr Gly Asp Thr Ala Leu Arg Asp Phe Met Val Asn Tyr Phe Ser
        210                 215                 220

Ile Val Lys Ser Leu Asp Asp Leu Phe Glu Asn Arg Val Met Ala Phe
225                 230                 235                 240

Thr Asn Lys Ser Val Asp Lys Leu Asn Ser Ile Ile Arg Lys Lys Ile
                245                 250                 255

Phe Glu Thr Asp Lys Asp Phe Ile Val Gly Glu Ile Val Met Gln
            260                 265                 270

Glu Pro Leu Phe Lys Thr Tyr Lys Ile Asp Gly Lys Pro Val Ser Glu
            275                 280                 285
```

-continued

```
Ile Ile Phe Asn Asn Gly Gln Leu Val Arg Ile Ile Glu Ala Glu Tyr
    290                 295                 300

Thr Ser Thr Phe Val Lys Ala Arg Gly Val Pro Gly Glu Tyr Leu Ile
305                 310                 315                 320

Arg His Trp Asp Leu Thr Val Glu Thr Tyr Gly Asp Asp Glu Tyr Tyr
                325                 330                 335

Arg Glu Lys Ile Lys Ile Ile Ser Ser Asp Glu Leu Tyr Lys Phe
            340                 345                 350

Asn Leu Phe Leu Gly Lys Thr Ala Glu Thr Tyr Lys Asn Trp Asn Lys
        355                 360                 365

Gly Gly Lys Ala Pro Trp Ser Asp Phe Trp Asp Ala Lys Ser Gln Phe
370                 375                 380

Ser Lys Val Lys Ala Leu Pro Ala Ser Thr Phe His Lys Ala Gln Gly
385                 390                 395                 400

Met Ser Val Asp Arg Ala Phe Ile Tyr Thr Pro Cys Ile His Tyr Ala
                405                 410                 415

Asp Val Glu Leu Ala Gln Gln Leu Leu Tyr Val Gly Val Thr Arg Gly
            420                 425                 430

Arg Tyr Asp Val Phe Tyr Val
        435
```

<210> SEQ ID NO 9
<211> LENGTH: 50
<212> TYPE: DNA
<213> ORGANISM: Artificial Sequence
<220> FEATURE:
<223> OTHER INFORMATION: Polynucleotide sequence used in Example 1, 2, 3, 7 and 8

<400> SEQUENCE: 9
tttttttttt tttttttttt tttttttttt tttttttttt tttttttttt         50

<210> SEQ ID NO 10
<211> LENGTH: 27
<212> TYPE: DNA
<213> ORGANISM: Artificial Sequence
<220> FEATURE:
<223> OTHER INFORMATION: Polynucleotide sequence used in Example 1 and 9

<400> SEQUENCE: 10
ggttgtttct gttggtgctg atattgc                                  27

<210> SEQ ID NO 11
<211> LENGTH: 97138
<212> TYPE: DNA
<213> ORGANISM: Artificial Sequence
<220> FEATURE:
<223> OTHER INFORMATION: Polynucleotide sequence used in Example 1

<400> SEQUENCE: 11
gctccactaa agggccgatt gacgggcggc gacctcgcgg gttttcgcta tttatgaaaa    60
ttttccggtt taaggcgttt ccgttcttct tcgtcataac ttaatgtttt tatttaaaat   120
accctctgaa agaaaggaa acgacaggtg ctgaaagcga ggcttttggg cctctgtcgt    180
ttcctttctc tgtttttgtc cgtggaatga acaatgaag tcaacaaaaa gcagctggct    240
gacattttcg gtgcgagtat ccgtaccatt cagaactggc aggaacaggg aatgcccgtt   300
ctgcgaggcg gtggcaaggg taatgagtg ctttatgact ctgccgccgt cataaaatgg    360
tatgccgaaa gggatgctga aattgagaac gaaaagctgc gccgggaggt tgaagaactg   420
```

```
cggcaggcca gcgaggcaga tctccagcca ggaactattg agtacgaacg ccatcgactt    480
acgcgtgcgc aggccgacgc acaggaactg aagaatgcca gagactccgc tgaagtggtg    540
gaaaccgcat tctgtacttt cgtgctgtcg cggatcgcag gtgaaattgc cagtattctc    600
gacgggctcc ccctgtcggt gcagcggcgt tttccggaac tggaaaaccg acatgttgat    660
ttcctgaaac gggatatcat caaagccatg aacaaagcag ccgcgctgga tgaactgata    720
ccggggttgc tgagtgaata tatcgaacag tcaggttaac aggctgcggc attttgtccg    780
cgccgggctt cgctcactgt tcaggccgga gccacagacc gccgttgaat gggcggatgc    840
taattactat ctcccgaaag aatccgcata ccaggaaggg cgctgggaaa cactgccctt    900
tcagcgggcc atcatgaatg cgatgggcag cgactacatc cgtgaggtga atgtggtgaa    960
gtctgcccgt gtcggttatt ccaaaatgct gctgggtgtt tatgcctact ttatagagca   1020
taagcagcgc aacacccctta tctggttgcc gacggatggt gatgccgaga actttatgaa   1080
aacccacgtt gagccgacta ttcgtgatat tccgtcgctg ctggcgctgg ccccgtggta   1140
tggcaaaaag caccgggata acacgctcac catgaagcgt tcactaatg ggcgtggctt    1200 ctggtgcctg gcggtaaag cggcaaaaaa ctaccgtgaa aagtcggtgg atgtggcggg   1260
ttatgatgaa cttgctgctt ttgatgatga tattgaacag gaaggctctc cgacgttcct   1320
gggtgacaag cgtattgaag gctcggtctg gccaaagtcc atccgtggct ccacgccaaa   1380
agtgagaggc acctgtcaga ttgagcgtgc agccagtgaa tccccgcatt ttatgcgttt   1440
tcatgttgcc tgcccgcatt gcggggagga gcagtatctt aaatttggcg acaaagagac   1500
gccgtttggc ctcaaatgga cgccggatga cccctccagc gtgttttatc tctgcgagca   1560
taatgcctgc gtcatccgcc agcaggagct ggactttact gatgcccgtt atatctgcga   1620
aaagaccggg atctggaccc gtgatggcat tctctggttt tcgtcatccg gtgaagagat   1680
tgagccacct gacagtgtga cctttcacat ctggacagcg tacagcccgt tcaccacctg   1740
ggtgcagatt gtcaaagact ggatgaaaac gaaaggggat acgggaaaac gtaaaacctt   1800
cgtaaacacc acgctcggtg agacgtggga ggcgaaaatt ggcgaacgtc cggatgctga   1860
agtgatggca gagcggaaag agcattattc agcgcccgtt cctgaccgtg tggcttacct   1920
gaccgccggt atcgactccc agctggaccg ctacgaaatg cgcgtatggg gatggggcc   1980 gggtgaggaa agctggctga ttgaccggca gattattatg ggccgccacg acgatgaaca   2040
gacgctgctg cgtgtggatg aggccatcaa taaaacctat acccgccgga atggtgcaga   2100
aatgtcgata tcccgtatct gctgggatac tggcgggatt gacccgacca ttgtgtatga   2160
acgctcgaaa aaacatgggc tgttccgggt gatccccatt aaagggggcat ccgtctacgg   2220 aaagccggtg gccagcatgc cacgtaagcg aaacaaaaac ggggtttacc ttaccgaaat   2280
cggtacggat accgcgaaag agcagattta taaccgcttc acactgacgc cggaaggga   2340 tgaaccgctt cccggtgccg ttcacttccc gaataacccg gatattttg atctgaccga   2400 agcgcagcag ctgactgctg aagagcaggt cgaaaaatgg gtggatggca ggaaaaaat   2460 actgtgggac agcaaaaagc gacgcaatga ggcactcgac tgcttcgttt atgcgctggc   2520
ggcgctgcgc atcagtattt cccgctggca gctggatctc agtgcgctgc tggcgagcct   2580
gcaggaagag gatggtgcag caaccaacaa gaaaacactg gcagattacg cccgtgcctt   2640
atccggagag gatgaatgac gcgacaggaa gaacttgccg ctgcccgtgc ggcactgcat   2700
gacctgatga caggtaaacg ggtggcaaca gtacagaaag acgacgaag ggtggagttt   2760 acggccactt ccgtgtctga cctgaaaaaa tatattgcag agctggaagt gcagaccggc   2820
```

```
atgacacagc gacgcagggg acctgcagga ttttatgtat gaaaacgccc accattccca    2880
cccttctggg gccggacggc atgacatcgc tgcgcgaata tgccggttat cacggcggtg    2940
gcagcggatt tggagggcag ttgcggtcgt ggaacccacc gagtgaaagt gtggatgcag    3000
ccctgttgcc caactttacc cgtggcaatg cccgcgcaga cgatctggta cgcaataacg    3060
gctatgccgc caacgccatc cagctgcatc aggatcatat cgtcgggtct ttttccggc    3120 tcagtcatcg cccaagctgg cgctatctgg gcatcgggga ggaagaagcc cgtgcctttt    3180
cccgcgaggt tgaagcggca tggaaagagt ttgccgagga tgactgctgc tgcattgacg    3240
ttgagcgaaa acgcacgttt accatgatga ttcgggaagg tgtggccatg cacgccttta    3300
acggtgaact gttcgttcag gccacctggg ataccagttc gtcgcggctt tccggacac    3360 agttccggat ggtcagcccg aagcgcatca gcaacccgaa caataccggc gacagccgga    3420
actgccgtgc cggtgtgcag attaatgaca gcggtgcggc gctgggatat acgtcagcg    3480 aggacgggta tcctggctgg atgccgcaga aatggacatg gataccccgt gagttacccg    3540
gcgggcgcgc ctcgttcatt cacgttttg aacccgtgga ggacgggcag actcgcggtg    3600
caaatgtgtt ttacagcgtg atggagcaga tgaagatgct cgacacgctg cagaacacgc    3660
agctgcagag cgccattgtg aaggcgatgt atgccgccac cattgagagt gagctggata    3720
cgcagtcagc gatggatttt attctgggcg cgaacagtca ggagcagcgg gaaaggctga    3780
ccggctggat tggtgaaatt gccgcgtatt acgccgcagc gccggtccgg ctgggaggcg    3840
caaaagtacc gcacctgatg ccgggtgact cactgaacct gcagacggct caggatacgg    3900
ataacggcta ctccgtgttt gagcagtcac tgctgcggta tatcgctgcc gggctgggtg    3960
tctcgtatga gcagctttcc cggaattacg cccagatgag ctactccacg gcacgggcca    4020
gtgcgaacga gtcgtgggcg tactttatgg ggcggcgaaa attcgtcgca tcccgtcagg    4080
cgagccagat gtttctgtgc tggctggaag aggccatcgt tcgccgcgtg gtgacgttac    4140
cttcaaaagc gcgcttcagt tttcaggaag cccgcagtgc ctgggggaac tgcgactgga    4200
taggctccgg tcgtatgcc atcgatggtc tgaaagaagt tcaggaagcg gtgatgctga    4260
tagaagccgg actgagtacc tacgagaaag agtgcgcaaa acgcggtgac gactatcagg    4320
aaatttttgc ccagcaggtc cgtgaaacga tggagcgccg tgcagccggt cttaaaccgc    4380
ccgcctgggc ggctgcagca tttgaatccg ggctgcgaca atcaacgag gaggagaaga    4440 gtgacagcag agctgcgtaa tctcccgcat attgccagca tggcctttaa tgagccgctg    4500
atgcttgaac ccgccatgc gcgggttttc ttttgtgcgc ttgcaggcca gcttgggatc    4560
agcagcctga cggatgcggt gtccggcgac agcctgactg cccaggaggc actcgcgacg    4620
ctggcattat ccgtgatga tgacggacca cgacaggccc gcagttatca ggtcatgaac    4680
ggcatcgccg tgctgccggt gtccggcacg ctggtcagcc ggacgcgggc gctgcagccg    4740
tactcgggga tgaccggtta caacggcatt atcgcccgtc tgcaacaggc tgccagcgat    4800
ccgatggtgg acggcattct gctcgatatg gacacgcccg gcgggatggt ggcggggggca    4860 tttgactgcg ctgacatcat cgcccgtgtg cgtgacataa aaccggtatg ggcgcttgcc    4920
aacgacatga actgcagtgc aggtcagttg cttgccagtg ccgcctcccg gcgtctggtc    4980
acgcagaccg cccggacagg ctccatcggc gtcatgatgg ctcacagtaa ttacggtgct    5040
gcgctggaga aacagggtgt ggaaatcacg ctgattttaca gcggcagcca taaggtggat    5100 ggcaaccct acagccatct tccggatgac gtccgggaga cactgcagtc ccggatggac    5160
```

```
gcaacccgcc agatgtttgc gcagaaggtg tcggcatata ccggcctgtc cgtgcaggtt    5220
gtgctggata ccgaggctgc agtgtacagc ggtcaggagg ccattgatgc cggactggct    5280
gatgaacttg ttaacagcac cgatgcgatc accgtcatgc gtgatgcact ggatgcacgt    5340
aaatcccgtc tctcaggagg gcgaatgacc aaagagactc aatcaacaac tgtttcagcc    5400
actgcttcgc aggctgacgt tactgacgtg gtgccagcga cggagggcga gaacgccagc    5460
gcggcgcagc cggacgtgaa cgcgcagatc accgcagcgg ttgcggcaga aaacagccgc    5520
attatgggga tcctcaactg tgaggaggct cacggacgcg aagaacaggc acgcgtgctg    5580
gcagaaaccc ccggtatgac cgtgaaaacg gcccgccgca ttctggccgc agcaccacag    5640
agtgcacagg cgcgcagtga cactgcgctg atcgtctga tgcaggggc accggcaccg    5700
ctggctgcag gtaacccggc atctgatgcc gttaacgatt tgctgaacac accagtgtaa    5760
gggatgttta tgacgagcaa agaaaccttt acccattacc agccgcaggg caacagtgac    5820
ccggctcata ccgcaaccgc gcccggcgga ttgagtgcga aagcgcctgc aatgaccccg    5880
ctgatgctgg acacctccag ccgtaagctg gttgcgtggg atggcaccac cgacggtgct    5940
gccgttggca ttcttgcggt tgctgctgac cagaccagca ccacgctgac gttctacaag    6000
tccggcacgt tccgttatga ggatgtgctc tggccggagg ctgccagcga cgagacgaaa    6060
aaacggaccg cgtttgccgg aacggcaatc agcatcgttt aactttaccc ttcatcacta    6120
aaggccgcct gtgcggcttt ttttacggga tttttttatg tcgatgtaca caaccgccca    6180
actgctggcg gcaaatgagc agaaatttaa gtttgatccg ctgtttctgc gtctcttttt    6240
ccgtgagagc tatcccttca ccacggagaa agtctatctc tcacaaattc cgggactggt    6300
aaacatggcg ctgtacgttt cgccgattgt ttccggtgag gttatccgtt cccgtggcgg    6360
ctccacctct gaatttacgc cgggatatgt caagccgaag catgaagtga atccgcagat    6420
gaccctgcgt cgcctgccgg atgaagatcc gcagaatctg cggacccgg cttaccgccg    6480
ccgtcgcatc atcatgcaga acatgcgtga cgaagagctg gccattgctc aggtcgaaga    6540
gatgcaggca gtttctgccg tgcttaaggg caaatacacc atgaccggtg aagccttcga    6600
tccggttgag gtggatatgg gccgcagtga ggagaataac atcacgcagt ccggcggcac    6660
ggagtggagc aagcgtgaca gtccacgta tgacccgacc gacgatatcg aagcctacgc    6720
gctgaacgcc agcggtgtgg tgaatatcat cgtgttcgat ccgaaaggct gggcgctgtt    6780
ccgttccttc aaagccgtca aggagaagct ggatacccgt cgtggctcta attccgagct    6840
ggagacagcg gtgaaagacc tgggcaaagc ggtgtcctat aagggatgt atggcgatgt    6900
ggccatcgtc gtgtattccg gacagtacgt ggaaaacggc gtcaaaaaga acttcctgcc    6960
ggacaacacg atggtgctgg ggaacactca ggcacgcgt ctgcgcacct atggctgcat    7020
tcaggatgcg gacgcacagc gcgaaggcat taacgcctct gcccgttacc cgaaaaactg    7080
ggtgaccacc ggcgatccgg cgcgtgagtt caccatgatt cagtcagcac cgctgatgct    7140
gctggctgac cctgatgagt tcgtgtccgt acaactggcg taatcatggc ccttcggggc    7200
cattgttct ctgtggagga gtccatgacg aaagatgaac tgattgcccg tctccgctcg    7260
ctgggtgaac aactgaaccg tgatgtcagc ctgacgggga cgaaagaaga actgcgctc    7320
cgtgtggcag agctgaaaga ggagcttgat gacacggatg aaactgccgg tcaggacacc    7380
cctctcagcc gggaaaatgt gctgaccgga catgaaaatg aggtgggatc agcgcagccg    7440
gataccgtga ttctggatac gtctgaactg gtcacggtcg tggcactggt gaagctgcat    7500
actgatgcac ttcacgccac gcgggatgaa cctgtggcat ttgtgctgcc gggaacggcg    7560
```

```
tttcgtgtct ctgccggtgt ggcagccgaa atgacagagc gcggcctggc cagaatgcaa    7620
taacgggagg cgctgtggct gatttcgata acctgttcga tgctgccatt gcccgcgccg    7680
atgaaacgat acgcgggtac atgggaacgt cagccaccat tacatccggt gagcagtcag    7740
gtgcggtgat acgtggtgtt tttgatgacc ctgaaaatat cagctatgcc ggacagggcg    7800
tgcgcgttga aggctccagc ccgtccctgt ttgtccggac tgatgaggtg cggcagctgc    7860
ggcgtggaga cacgctgacc atcggtgagg aaaatttctg ggtagatcgg gtttcgccgg    7920
atgatggcgg aagttgtcat ctctggcttg acggggcgt accgcctgcc gttaaccgtc     7980
gccgctgaaa gggggatgta tggccataaa aggtcttgag caggccgttg aaaacctcag    8040
ccgtatcagc aaaacggcgg tgcctggtgc cgccgcaatg gccattaacc gcgttgcttc    8100
atccgcgata tcgcagtcgg cgtcacaggt tgcccgtgag acaaaggtac gccggaaact    8160
ggtaaaggaa agggccaggc tgaaaagggc cacggtcaaa aatccgcagg ccagaatcaa    8220
agttaaccgg gggatttgc ccgtaatcaa gctgggtaat gcgcgggttg tcctttcgcg     8280
ccgcaggcgt cgtaaaaagg ggcagcgttc atccctgaaa ggtggcggca gcgtgcttgt    8340
ggtgggtaac cgtcgtattc ccggcgcgtt tattcagcaa ctgaaaaatg gccggtggca    8400
tgtcatgcag cgtgtggctg ggaaaaaccg ttaccccatt gatgtggtga aaatcccgat    8460
ggcggtgccg ctgaccacgg cgtttaaaca aaatattgag cggatacggc gtgaacgtct    8520
tccgaaagag ctgggctatg cgctgcagca tcaactgagg atggtaataa agcgatgaaa    8580
catactgaac tccgtgcagc cgtactggat gcactggaga agcatgacac cggggcgacg    8640 tttttttgatg gtcgccccgc tgttttttgat gaggcggatt ttccggcagt tgccgtttat    8700
ctcaccggcg ctgaatacac gggcgaagag ctggacagcg atacctggca ggcggagctg    8760
catatcgaag ttttcctgcc tgctcaggtg ccggattcag agctggatgc gtggatggag    8820
tcccggattt atccggtgat gagcgatatc ccggcactgt cagatttgat caccagtatg    8880
gtggccagcg gctatgacta ccggcgcgac gatgatgcgg gcttgtggag ttcagccgat    8940
ctgacttatg tcattaccta tgaaatgtga ggacgctatg cctgtaccaa atcctacaat    9000
gccggtgaaa ggtgccggga ccaccctgtg ggtttataag gggagcggtg acccttacgc    9060
gaatccgctt tcagacgttg actggtcgcg tctggcaaaa gttaaagacc tgacgcccgg    9120
cgaactgacc gctgagtcct atgacgacag ctatctcgat gatgaagatg cagactggac    9180
tgcgaccggg caggggcaga atctgccgg agataccagc ttcacgctgg cgtggatgcc     9240
cggagagcag gggcagcagg cgctgctggc gtggtttaat gaaggcgata cccgtgccta    9300
taaaatccgc ttcccgaacg gcacggtcga tgtgttccgt ggctgggtca gcagtatcgg    9360
taaggcggtg acgcgaagg aagtgatcac ccgcacggtg aaagtcacca atgtgggacg     9420
tccgtcgatg gcagaagatc gcagcacggt aacagcggca accggcatga ccgtgacgcc    9480
tgccagcacc tcggtggtga agggcagag caccacgctg accgtggcct tccagccgga     9540
gggcgtaacc gacaagagct tcgtgcggt gtctgcggat aaaacaaaag ccaccgtgtc     9600
ggtcagtggt atgaccatca ccgtgaacg cgttgctgca ggcaaggtca acattccggt     9660
tgtatccggt aatggtgagt ttgctgcggt tgcagaaatt accgtcaccg ccagttaatc    9720
cggagagtca gcgatgttcc tgaaaaccga atcatttgaa cataacggtg tgaccgtcac    9780
gctttctgaa ctgtcagccc tgcagcgcat tgagcatctc gccctgatga acggcaggc    9840 agaacaggcg gagtcagaca gcaaccggaa gtttactgtg gaagacgcca tcagaaccgg    9900
```

```
cgcgtttctg gtggcgatgt ccctgtggca taaccatccg cagaagacgc agatgccgtc      9960
catgaatgaa gccgttaaac agattgagca ggaagtgctt accacctggc ccacggaggc     10020
aatttctcat gctgaaaacg tggtgtaccg gctgtctggt atgtatgagt tgtggtgaa      10080 taatgcccct gaacagacag aggacgccgg gcccgcagag cctgtttctg cgggaaagtg     10140
ttcgacggtg agctgagttt tgccctgaaa ctggcgcgtg agatggggcg acccgactgg     10200
cgtgccatgc ttgccgggat gtcatccacg gagtatgccg actggcaccg cttttacagt     10260
acccattatt ttcatgatgt tctgctggat atgcactttt ccgggctgac gtacaccgtg     10320
ctcagcctgt ttttcagcga tccggatatg catccgctgg atttcagtct gctgaaccgg     10380
cgcgaggctg acgaagagcc tgaagatgat gtgctgatgc agaaagcggc agggcttgcc     10440
ggaggtgtcc gctttggccc ggacgggaat gaagttatcc ccgcttcccc ggatgtggcg     10500
gacatgacgg aggatgacgt aatgctgatg acagtatcag aagggatcgc aggaggagtc     10560
cggtatggct gaaccggtag gcgatctggt cgttgatttg agtctggatg cggccagatt     10620
tgacgagcag atgccagag tcaggcgtca tttttctggt acggaaagtg atgcgaaaaa      10680
aacagcggca gtcgttgaac agtcgctgag ccgacaggcg ctggctgcac agaaagcggg     10740
gatttccgtc gggcagtata agccgccat gcgtatgctg cctgcacagt tcaccgacgt      10800
ggccacgcag cttgcaggcg ggcaaagtcc gtggctgatc ctgctgcaac aggggggca     10860 ggtgaaggac tccttcggcg ggatgatccc catgttcagg gggcttgccg gtgcgatcac     10920
cctgccgatg gtggggggcca cctcgctggc ggtggcgacc ggtgcgctgg cgtatgcctg     10980
gtatcagggc aactcaaccc tgtccgattt caacaaaacg ctggtccttt ccggcaatca     11040
ggcgggactg acggcagatc gtatgctggt cctgtccaga gccgggcagg cggcagggct     11100
gacgtttaac cagaccagcg agtcactcag cgcactggtt aaggcggggg taagcggtga     11160
ggctcagatt gcgtccatca gccagagtgt ggcgcgtttc tcctctgcat ccggcgtgga     11220
ggtggacaag gtcgctgaag ccttcgggaa gctgaccaca gacccgacgt cggggctgac     11280
ggcgatggct cgccagttcc ataacgtgtc ggcggagcag attgcgtatg ttgctcagtt     11340
gcagcgttcc ggcgatgaag ccggggcatt gcaggcggcg aacgaggccg caacgaaagg     11400
gtttgatgac cagacccgcc gcctgaaaga gaacatgggc acgctggaga cctgggcaga     11460
caggactgcg cgggcattca atccatgtg ggatgcggtg ctggatattg tcgtcctga      11520 taccgcgcag gagatgctga ttaaggcaga ggctgcgtat aagaaagcag acgacatctg     11580
gaatctgcgc aaggatgatt attttgttaa cgatgaagcg cgggcgcgtt actgggatga     11640
tcgtgaaaag gcccgtcttg cgcttgaagc cgcccgaaag aaggctgagc agcagactca     11700
acaggacaaa aatgcgcagc agcagagcga taccgaagcg tcacggctga atataccga      11760 agaggcgcag aaggcttacg aacggctgca gacgccgctg gagaaatata ccgcccgtca     11820
ggaagaactg aacaaggcac tgaaagacgg gaaaatcctg caggcggatt acaacacgct     11880
gatggcggcg gcgaaaaagg attatgaagc gacgctgaaa aagccgaaac agtccagcgt     11940
gaaggtgtct gcgggcgatc gtcaggaaga cagtgctcat gctgccctgc tgacgcttca     12000
ggcagaactc cggacgctgg agaagcatgc cggagcaaat gagaaaatca gccagcagcg     12060
ccgggatttg tggaaggcgg agagtcagtt cgcggtactg gaggaggcgg cgcaacgtcg     12120
ccagctgtct gcacaggaga aatccctgct ggcgcataaa gatgagacgc tggagtacaa     12180
acgccagctg gctgcacttg gcgacaaggt tacgtatcag gagcgcctga acgcgctggc     12240
gcagcaggcg gataaattcg cacagcagca acgggcaaaa cgggccgcca ttgatgcgaa     12300
```

```
aagccggggg ctgactgacc ggcaggcaga acgggaagcc acggaacagc gcctgaagga   12360
acagtatggc gataatccgc tggcgctgaa taacgtcatg tcagagcaga aaaagacctg   12420
ggcggctgaa gaccagcttc gcgggaactg gatggcaggc ctgaagtccg gctggagtga   12480
gtgggaagag agcgccacgg acagtatgtc gcaggtaaaa agtgcagcca cgcagacctt   12540
tgatggtatt gcacagaata tggcggcgat gctgaccggc agtgagcaga actggcgcag   12600
cttcacccgt tccgtgctgt ccatgatgac agaaattctg cttaagcagg caatggtggg   12660
gattgtcggg agtatcggca gcgccattgg cggggctgtt ggtggcggcg catccgcgtc   12720
aggcggtaca gccattcagg ccgctgcggc gaaattccat tttgcaaccg gaggatttac   12780
gggaaccggc ggcaaatatg agccagcggg gattgttcac cgtggtgagt ttgtcttcac   12840
gaaggaggca accagccgga ttggcgtggg gaatctttac cggctgatgc gcggctatgc   12900
caccggcggt tatgtcggta caccgggcag catggcagac agccggtcgc aggcgtccgg   12960
gacgtttgag cagaataacc atgtggtgat taacaacgac ggcacgaacg ggcagatagg   13020
tccggctgct ctgaaggcgg tgtatgacat ggcccgcaag ggtgcccgtg atgaaattca   13080
gacacagatg cgtgatggtg gcctgttctc cggaggtgga cgatgaagac cttccgctgg   13140
aaagtgaaac ccggtatgga tgtggcttcg gtcccttctg taagaaaggt gcgctttggt   13200
gatggctatt ctcagcgagc gcctgccggg ctgaatgcca acctgaaaac gtacagcgtg   13260
acgctttctg tcccccgtga ggaggccacg gtactggagt cgtttctgga agagcacggg   13320
ggctggaaat cctttctgtg gacgccgcct tatgagtggc ggcagataaa ggtgacctgc   13380
gcaaaatggt cgtcgcgggt cagtatgctg cgtgttgagt tcagcgcaga gtttgaacag   13440
gtggtgaact gatgcaggat atccggcagg aaacactgaa tgaatgcacc cgtgcggagc   13500
agtcggccag cgtggtgctc tgggaaatcg acctgacaga ggtcggtgga gaacgttatt   13560
ttttctgtaa tgagcagaac gaaaaaggtg agccggtcac ctggcagggg cgacagtatc   13620
agccgtatcc cattcagggg agcggttttg aactgaatgg caaaggcacc agtacgcgcc   13680
ccacgctgac ggtttctaac ctgtacggta tggtcaccgg gatggcggaa gatatgcaga   13740
gtctggtcgg cggaacggtg gtccggcgta aggtttacgc ccgttttctg gatgcggtga   13800
acttcgtcaa cggaaacagt tacgccgatc cggagcagga ggtgatcagc cgctggcgca   13860
ttgagcagtg cagcgaactg agcgcggtga gtgcctcctt tgtactgtcc acgccgacgg   13920
aaacggatgg cgctgttttt ccgggacgta tcatgctggc caacacctgc acctggacct   13980
atcgcgtgna cgagtgcggt tatagcggtc cggctgtcgc ggatgaatat gaccagccaa   14040
cgtccgatat cacgaaggat aaatgcagca aatgcctgag cggttgtaag ttccgcaata   14100
acgtcggcaa ctttggcggc ttcctttcca ttaacaaact ttcgcagtaa atcccatgac   14160
acagacagaa tcagcgattc tggcgcacgc ccggcgatgt gcgccagcgg agtcgtgcgg   14220
cttcgtggta agcacgccgg aggggaaag atatttcccc tgcgtgaata tctccggtga   14280
gccggaggct atttccgtat gtcgccggaa gactggctgc aggcagaaat gcagggtgag   14340
attgtggcgc tggtccacag ccaccccggt ggtctgccct ggctgagtga ggccgaccgg   14400
cggctgcagg tgcagagtga tttgccgtgg tggctggtct gccgggggac gattcataag   14460
ttccgctgtg tgccgcatct caccgggcgg cgctttgagc acggtgtgac ggactgttac   14520
acactgttcc gggatgctta tcatctggcg gggattgaga tgccggactt tcatcgtgag   14580
gatgactggt ggcgtaacgg ccagaatctc tatctggata atctggaggc gacggggctg   14640
```

```
tatcaggtgc cgttgtcagc ggcacagccg ggcgatgtgc tgctgtgctg tttttggttca   14700 tcagtgccga atcacgccgc aatttactgc ggcgacggcg agctgctgca ccatattcct   14760
gaacaactga gcaaacgaga gaggtacacc gacaaatggc agcgacgcac acactccctc   14820
tggcgtcacc gggcatggcg cgcatctgcc tttacgggga tttacaacga tttggtcgcc   14880
gcatcgacct tcgtgtgaaa acggggggctg aagccatccg ggcactggcc acacagctcc   14940
cggcgtttcg tcagaaactg agcgacggct ggtatcaggt acggattgcc gggcgggacg   15000
tcagcacgtc cgggttaacg gcgcagttac atgagactct gcctgatggc gctgtaattc   15060
atattgttcc cagagtcgcc ggggccaagt caggtggcgt attccagatt gtcctggggg   15120
ctgccgccat tgccggatca ttctttaccg ccggagccac ccttgcagca tgggggggcag   15180 ccattgggc cggtggtatg accggcatcc tgttttctct cggtgccagt atggtgctcg   15240
gtggtgtggc gcagatgctg gcaccgaaag ccagaactcc ccgtatacag acaacggata   15300
acggtaagca gaacacctat ttctcctcac tggataacat ggttgcccag ggcaatgttc   15360
tgcctgttct gtacggggaa atgcgcgtgg ggtcacgcgt ggtttctcag gagatcagca   15420
cggcagacga aggggacggt ggtcaggttg tggtgattgg tcgctgatgc aaaatgtttt   15480
atgtgaaacc gcctgcgggc ggttttgtca tttatggagc gtgaggaatg ggtaaaggaa   15540
gcagtaaggg gcataccccg cgcgaagcga aggacaacct gaagtccacg cagttgctga   15600
gtgtgatcga tgccatcagc gaagggccga ttgaaggtcc ggtggatggc ttaaaaagcg   15660
tgctgctgaa cagtacgccg gtgctggaca ctgagggaa taccaacata tccggtgtca   15720
cggtggtgtt ccgggctggt gagcaggagc agactccgcc ggagggattt gaatcctccg   15780
gctccgagac ggtgctgggt acggaagtga aatatgacac gccgatcacc cgcaccatta   15840
cgtctgcaaa catcgaccgt ctgcgcttta ccttcggtgt acaggcactg gtggaaacca   15900
cctcaaaggg tgacaggaat ccgtcggaag tccgcctgct ggttcagata caacgtaacg   15960
gtggctgggt gacggaaaaa gacatcacca ttaagggcaa aaccacctcg cagtatctgg   16020
cctcggtggt gatgggtaac ctgccgccgc gcccgtttaa tatccggatg cgcaggatga   16080
cgccggacag caccacagac cagctgcaga acaaaacgct ctggtcgtca tacactgaaa   16140
tcatcgatgt gaaacagtgc taccccgaaca cggcactggt cggcgtgcag gtggactcgg   16200
agcagttcgg cagccagcag gtgagccgta attatcatct gcgcgggcgt attctgcagg   16260
tgccgtcgaa ctataacccg cagacgcggc aatacagcgg tatctgggac ggaacgttta   16320
aaccggcata cagcaacaac atggcctggt gtctgtggga tatgctgacc catccgcgct   16380
acggcatggg gaaacgtctt ggtgcggcgg atgtggataa atgggcgctg tatgtcatcg   16440
gccagtactg cgaccagtca gtgccggacg gctttggcgg cacggagccg cgcatcacct   16500
gtaatgcgta cctgaccaca cagcgtaagg cgtgggatgt gctcagcgat ttctgctcgg   16560
cgatgcgctg tatgccggta tggaacgggc agacgctgac gttcgtgcag gaccgaccgt   16620
cggataagac gtggacctat aaccgcagta atgtggtgat gccggatgat ggcgcgccgt   16680
tccgctacag cttcagcgcc ctgaaggacc gccataatgc cgttgaggtg aactggattg   16740
acccgaacaa cggctgggag acggcgacag agcttgttga agatacgcag gccattgccc   16800
gttacggtcg taatgttacg aagatggatg cctttggctg taccagccgg gggcaggcac   16860
accgcgccgg gctgtggctg attaaaacag aactgctgga aacgcagacc gtggatttca   16920
gcgtcggcgc agaagggctt cgccatgtac cgggcgatgt tattgaaatc tgcgatgatg   16980
actatgccgg tatcagcacc ggtggtcgtg tgctggcggt gaacagccag acccggacgc   17040
```

```
tgacgctcga ccgtgaaatc acgctgccat cctccggtac cgcgctgata agcctggttg   17100
acggaagtgg caatccggtc agcgtggagg ttcagtccgt caccgacggc gtgaaggtaa   17160
aagtgagccg tgttcctgac ggtgttgctg aatacagcgt atgggagctg aagctgccga   17220
cgctgcgcca gcgactgttc cgctgcgtga gtatccgtga aacgacgac ggcacgtatg    17280 ccatcaccgc cgtgcagcat gtgccggaaa aagaggccat cgtggataac ggggcgcact   17340
ttgacggcga acagagtggc acggtgaatg gtgtcacgcc gccagcggtg cagcacctga   17400
ccgcagaagt cactgcagac agcggggaat atcaggtgct ggcgcgatgg gacacaccga   17460
aggtggtgaa gggcgtgagt ttcctgctcc gtctgaccgt aacagcggac gacggcagtg   17520
agcggctggt cagcacggcc cggacgacgg aaaccacata ccgcttcacg caactggcgc   17580
tggggaacta caggctgaca gtccgggcgg taaatgcgtg ggggcagcag ggcgatccgg   17640
cgtcggtatc gttccggatt gccgcaccgg cagcaccgtc gaggattgag ctgacgccgg   17700
gctattttca gataaccgcc acgccgcatc ttgccgttta tgacccgacg gtacagtttg   17760
agttctggtt ctcggaaaag cagattgcgg atatcagaca ggttgaaacc agcacgcgtt   17820
atcttggtac ggcgctgtac tggatagccg ccagtatcaa tatcaaaccg gccatgatt   17880 attacttta tatccgcagt gtgaacaccg ttggcaaatc ggcattcgtg gaggccgtcg    17940
gtcgggcgag cgatgatgcg gaaggttacc tggatttttt caaaggcaag ataaccgaat   18000
cccatctcgg caaggagctg ctggaaaaag tcgagctgac ggaggataac gccagcagac   18060
tggaggagtt ttcgaaagag tggaaggatg ccagtgataa gtggaatgcc atgtgggctg   18120
tcaaaattga gcagaccaaa gacggcaaac attatgtcgc gggtattggc ctcagcatgg   18180
aggacacgga ggaaggcaaa ctgagccagt ttctggttgc cgccaatcgt atcgcattta   18240
ttgacccggc aaacgggaat gaaacgccga tgtttgtggc gcagggcaac cagatattca   18300
tgaacgacgt gttcctgaag cgcctgacgg cccccaccat taccagcggc ggcaatcctc   18360 cggcctttc cctgacaccg gacggaaagc tgaccgctaa aaatgcggat atcagtggca   18420
gtgtgaatgc gaactccggg acgctcagta atgtgacgat agctgaaaac tgtacgataa   18480
acggtacgct gagggcggaa aaaatcgtcg gggacattgt aaaggcggcg agcgcggctt   18540
ttccgcgcca gcgtgaaagc agtgtggact ggccgtcagg tacccgtact gtcaccgtga   18600
ccgatgacca tccttttgat cgccagatag tggtgcttcc gctgacgttt cgcggaagta   18660
agcgtactgt cagcggcagg acaacgtatt cgatgtgtta tctgaaagta ctgatgaacg   18720
gtgcggtgat ttatgatggc gcggcgaacg aggcggtaca ggtgttctcc cgtattgttg   18780
acatgccagc gggtcgggga aacgtgatcc tgacgttcac gcttacgtcc acacggcatt   18840
cggcagatat tccgccgtat acgtttgcca gcgatgtgca ggttatggtg attaagaaac   18900
aggcgctggg catcagcgtg gtctgagtgt gttacagagg ttcgtccggg aacgggcgtt   18960
ttattataaa acagtgagag gtgaacgatg cgtaatgtgt gtattgccgt tgctgtcttt   19020
gccgcacttg cggtgacagt cactccggcc cgtgcggaag gtggacatgg tacgtttacg   19080
gtgggctatt ttcaagtgaa accgggtaca ttgccgtcgt tgtcgggcgg ggataccggt   19140
gtgagtcatc tgaaagggat taacgtgaag taccgttatg agctgacgga cagtgtgggg   19200
gtgatggctt ccctgggggtt cgccgcgtcg aaaaagagca gcacagtgat gaccggggag   19260
gatacgtttc actatgagag cctgcgtgga cgttatgtga gcgtgatggc cggaccggtt   19320
ttacaaatca gtaagcaggt cagtgcgtac gccatggccg gagtggctca cagtcggtgg   19380
```

```
tccggcagta caatggatta ccgtaagacg gaaatcactc ccgggtatat gaaagagacg   19440
accactgcca gggacgaaag tgcaatgcgg catacctcag tggcgtggag tgcaggtata   19500
cagattaatc cggcagcgtc cgtcgttgtt gatattgctt atgaaggctc cggcagtggc   19560
gactggcgta ctgacggatt catcgttggg gtcggttata aattctgatt agccaggtaa   19620
cacagtgtta tgacagcccg ccggaaccgg tgggcttttt tgtggggtga atatggcagt   19680
aaagatttca ggagtcctga agacggcac aggaaaaccg gtacagaact gcaccattca    19740
gctgaaagcc agacgtaaca gcaccacggt ggtggtgaac acggtgggct cagagaatcc   19800
ggatgaagcc gggcgttaca gcatggatgt ggagtacggt cagtacagtg tcatcctgca   19860
ggttgacggt tttccaccat cgcacgccgg gaccatcacc gtgtatgaag attcacaacc   19920
ggggacgctg aatgattttc tctgtgccat gacggaggat gatgcccggc cggaggtgct   19980
gcgtcgtctt gaactgatgg tggaagaggt ggcgcgtaac gcgtccgtgg tggcacagag   20040
tacggcagac gcgaagaaat cagccggcga tgccagtgca tcagctgctc aggtcgcggc   20100
ccttgtgact gatgcaactg actcagcacg cgccgccagc acgtccgccg gacaggctgc   20160
atcgtcagct caggaagcgt cctccggcgc agaagcggca tcagcaaagg ccactgaagc   20220 ggaaaaagt gccgcagccg cagagtcctc aaaaaacgcg gcggccacca gtgccggtgc    20280
ggcgaaaacg tcagaaacga atgctgcagc gtcacaacaa tcagccgcca cgtctgcctc   20340
caccgcggcc acgaaagcgt cagaggccgc cacttcagca cgagatgcgg tggcctcaaa   20400
agaggcagca aaatcatcag aaacgaacgc atcatcaagt gccggtcgtg cagcttcctc   20460
ggcaacggcg gcagaaaatt ctgccaggac ggcaaaaacg tccgagacga atgccaggtc   20520
atctgaaaca gcagcggaac ggagcgcctc tgccgcggca gacgcaaaaa cagcggcggc   20580 gggagtgcg tcaacggcat ccacgaaggc gacagaggct gcgggaagtg cggtatcagc    20640
atcgcagagc aaaagtgcgg cagaagcggc ggcaatacgt gcaaaaaatt cggcaaaacg   20700
tgcagaagat atagcttcag ctgtcgcgct tgaggatgcg gacacaacga gaaaggggat   20760
agtgcagctc agcagtgcaa ccaacagcac gtctgaaacg cttgctgcaa cgccaaaggc   20820
ggttaaggtg gtaatggatg aaacgaacag aaaagcccac tggacagtcc ggcactgacc   20880
ggaacgccaa cagcaccaac cgcgctcagg gaacaaaca ataccagat tgcgaacacc      20940 gcttttgtac tggccgcgat tgcagatgtt atcgacgcgt cacctgacgc actgaatacg   21000
ctgaatgaac tggccgcagc gctcgggaat gatccagatt ttgctaccac catgactaac   21060
gcgcttgcgg gtaaacaacc gaagaatgcg acactgacgg cgctggcagg gctttccacg   21120
gcgaaaaata aattaccgta ttttgcggaa aatgatgccg ccagcctgac tgaactgact   21180
caggttggca gggatattct ggcaaaaaat tccgttgcag atgttcttga ataccttggg   21240
gccggtgaga attcggcctt tccggcaggt gcgccgatcc cgtggccatc agatatcgtt   21300
ccgtctggct acgtcctgat gcaggggcag gcgtttgaca aatcagccta cccaaaactt   21360
gctgtcgcgt atccatcggg tgtgcttcct gatatgcgag gctggacaat caaggggaaa   21420
cccgccagcg gtcgtgctgt attgtctcag gaacaggatg gaattaagtc gcacacccac   21480
agtgccagtg catccggtac ggatttgggg acgaaaacca catcgtcgtt tgattacggg   21540
acgaaaacaa caggcagttt cgattacggc accaaatcga cgaataacac gggggctcat   21600
gctcacagtc tgagcggttc aacaggggcc gcgggtgctc atgcccacac aagtggttta   21660
aggatgaaca gttctggctg gagtcagtat ggaacagcaa ccattacagg aagtttatcc   21720
acagttaaag gaaccagcac acagggtatt gcttatttat cgaaaacgga cagtcaggc    21780
```

```
agccacagtc actcattgtc cggtacagcc gtgagtgccg gtgcacatgc gcatacagtt    21840
ggtattggtg cgcaccagca tccggttgtt atcggtgctc atgcccattc tttcagtatt    21900
ggttcacacg gacacaccat caccgttaac gctgcgggta acgcggaaaa caccgtcaaa    21960
aacattgcat ttaactatat tgtgaggctt gcataatggc attcagaatg agtgaacaac    22020
cacggaccat aaaaatttat aatctgctgg ccggaactaa tgaatttatt ggtgaaggtg    22080
acgcatatat tccgcctcat accggtctgc ctgcaaacag taccgatatt gcaccgccag    22140
atattccggc tggctttgtg gctgttttca acagtgatga ggcatcgtgg catctcgttg    22200
aagaccatcg gggtaaaacc gtctatgacg tggcttccgg cgacgcgtta tttatttctg    22260
aactcggtcc gttaccggaa aattttacct ggttatcgcc gggagggaa tatcagaagt     22320 ggaacggcac agcctgggtg aaggatacgg aagcagaaaa actgttccgg atccgggagg    22380
cggaagaaac aaaaaaaagc ctgatgcagg tagccagtga gcatattgcg ccgcttcagg    22440
atgctgcaga tctggaaatt gcaacgaagg aagaaacctc gttgctggaa gcctggaaga    22500
agtatcgggt gttgctgaac cgtgttgata catcaactgc acctgatatt gagtggcctg    22560
ctgtccctgt tatggagtaa tcgttttgtg atatgccgca gaaacgttgt atgaaataac    22620
gttctgcggt tagttagtat attgtaaagc tgagtattgg tttatttggc gattattatc    22680
ttcaggagaa taatggaagt tctatgactc aattgttcat agtgtttaca tcaccgccaa    22740
ttgcttttaa gactgaacgc atgaaatatg gttttcgtc atgttttgag tctgctgttg     22800
atatttctaa agtcggtttt ttttcttcgt tttctctaac tattttccat gaaatacatt    22860
tttgattatt atttgaatca attccaatta cctgaagtct ttcatctata attggcattg    22920
tatgtattgg tttattggag tagatgcttg cttttctgag ccatagctct gatatccaaa    22980
tgaagccata ggcatttgtt attttggctc tgtcagctgc ataacgccaa aaaatatatt    23040
tatctgcttg atcttcaaat gttgtattga ttaaatcaat tggatggaat tgtttatcat    23100
aaaaaattaa tgtttgaatg tgataaccgt cctttaaaaa agtcgtttct gcaagcttgg    23160
ctgtatagtc aactaactct tctgtcgaag tgatattttt aggcttatct accagtttta    23220
gacgctcttt aatatcttca ggaattattt tattgtcata ttgtatcatg ctaaatgaca    23280
atttgcttat ggagtaatct tttaatttta aataagttat tctcctggct tcatcaaata    23340
aagagtcgaa tgatgttggc gaaatcacat cgtcacccat tggattgttt atttgtatgc    23400
caagagagtt acagcagtta tacattctgc catagattat agctaaggca tgtaataatt    23460
cgtaatcttt tagcgtatta gcgacccatc gtctttctga tttaataata gatgattcag    23520
ttaaatatga aggtaatttc ttttgtgcaa gtctgactaa cttttttata ccaatgttta    23580
acatactttc atttgtaata aactcaatgt cattttcttc aatgtaagat gaaataagag    23640
tagcctttgc ctcgctatac atttctaaat cgccttgttt ttctatcgta ttgcgagaat    23700
ttttagccca agccattaat ggatcatttt tccatttttc aataacatta ttgttatacc    23760
aaatgtcata tcctataatc tggttttgt ttttttgaat aataaatgtt actgttcttg     23820
cggtttggag gaattgattc aaattcaagc gaaataattc agggtcaaaa tatgtatcaa    23880
tgcagcattt gagcaagtgc gataaatctt taagtcttct ttcccatggt tttttagtca    23940
taaaactctc cattttgata ggttgcatgc tagatgctga tatattttag aggtgataaa    24000
attaactgct taactgtcaa tgtaatacaa gttgtttgat ctttgcaatg attcttatca    24060
gaaaccatat agtaaattag ttacacagga aatttttaat attattatta tcattcatta    24120
```

```
tgtattaaaa ttagagttgt ggcttggctc tgctaacacg ttgctcatag gagatatggt   24180
agagccgcag acacgtcgta tgcaggaacg tgctgcggct ggctggtgaa cttccgatag   24240
tgcgggtgtt gaatgatttc cagttgctac cgattttaca tattttttgc atgagagaat   24300
ttgtaccacc tcccaccgac catctatgac tgtacgccac tgtccctagg actgctatgt   24360
gccggagcgg acattacaaa cgtccttctc ggtgcatgcc actgttgcca atgacctgcc   24420
taggaattgg ttagcaagtt actaccggat tttgtaaaaa cagccctcct catataaaaa   24480
gtattcgttc acttccgata agcgtcgtaa ttttctatct ttcatcatat tctagatccc   24540
tctgaaaaaa tcttccgagt ttgctaggca ctgatacata actcttttcc aataattggg   24600
gaagtcattc aaatctataa taggtttcag atttgcttca ataaattctg actgtagctg   24660
ctgaaacgtt gcggttgaac tatatttcct tataactttt acgaaagagt ttctttgagt   24720
aatcacttca ctcaagtgct tccctgcctc caaacgatac ctgttagcaa tatttaatag   24780
cttgaaatga tgaagagctc tgtgtttgtc ttcctgcctc cagttcgccg ggcattcaac   24840
ataaaaactg atagcacccg gagttccgga aacgaaattt gcatataccc attgctcacg   24900
aaaaaaaatg tccttgtcga tatagggatg aatcgcttgg tgtacctcat ctactgcgaa   24960
aacttgacct ttctctccca tattgcagtc gcggcacgat ggaactaaat taataggcat   25020
caccgaaaat tcaggataat gtgcaatagg aagaaaatga tctatatttt ttgtctgtcc   25080
tatatcacca caaaatggac attttttcacc tgatgaaaca agcatgtcat cgtaatatgt   25140
tctagcgggt ttgttttat ctcggagatt attttcataa agcttttcta atttaaccct   25200
tgtcaggtta ccaactacta aggttgtagg ctcaagaggg tgtgtcctgt cgtaggtaaa   25260
taactgacct gtcgagctta atattctata ttgttgttct ttctgcaaaa aagtggggaa   25320
gtgagtaatg aaattatttc taacatttat ctgcatcata ccttccgagc atttattaag   25380
catttcgcta taagttctcg ctggaagagg tagtttttc attgtacttt accttcatct   25440
ctgttcatta tcatcgcttt taaaacggtt cgaccttcta atcctatctg accattataa   25500 tttttttagaa tggtttcata agaaagctct gaatcaacgg actgcgataa taagtggtgg   25560
tatccagaat ttgtcacttc aagtaaaaac acctcacgag ttaaaacacc taagttctca   25620
ccgaatgtct caatatccgg acggataata tttattgctt ctcttgaccg taggactttc   25680
cacatgcagg attttggaac ctcttgcagt actactgggg aatgagttgc aattattgct   25740
acaccattgc gtgcatcgag taagtcgctt aatgttcgta aaaagcaga gagcaaaggt   25800 ggatgcagat gaacctctgg ttcatcgaat aaaactaatg acttttcgcc aacgacatct   25860
actaatcttg tgatagtaaa taaaacaatt gcatgtccag agctcattcg aagcagatat   25920
ttctggatat tgtcataaaa caatttagtg aatttatcat cgtccacttg aatctgtggt   25980
tcattacgtc ttaactcttc atatttagaa atgaggctga tgagttccat atttgaaaag   26040
ttttcatcac tacttagttt tttgatagct tcaagccaga gttgtctttt tctatctact   26100
ctcatacaac caataaatgc tgaaatgaat tctaagcgga gatcgcctag tgattttaaa   26160
ctattgctgg cagcattctt gagtccaata taaaagtatt gtgtaccttt tgctgggtca   26220
ggttgttctt taggaggagt aaaaggatca aatgcactaa acgaaactga aacaagcgat   26280
cgaaaatatc cctttgggat tcttgactcg ataagtctat tattttcaga gaaaaaatat   26340
tcattgtttt ctgggttggt gattgcacca atcattccat tcaaaattgt tgttttacca   26400
cacccattcc gcccgataaa agcatgaatg ttcgtgctgg gcatagaatt aaccgtcacc   26460
tcaaaaggta tagttaaatc actgaatccg ggagcacttt ttctattaaa tgaaaagtgg   26520
```

```
aaatctgaca attctggcaa accatttaac acacgtgcga actgtccatg aatttctgaa    26580
agagttaccc ctctaagtaa tgaggtgtta aggacgcttt catttcaat gtcggctaat     26640 cgatttggcc atactactaa atcctgaata gctttaagaa ggttatgttt aaaaccatcg    26700
cttaatttgc tgagattaac atagtagtca atgctttcac ctaaggaaaa aaacatttca    26760
gggagttgac tgaattttt atctattaat gaataagtgc ttacttcttc tttttgacct    26820
acaaaaccaa tttaacatt tccgatatcg cattttcac catgctcatc aaagacagta    26880
agataaaaca ttgtaacaaa ggaatagtca ttccaaccat ctgctcgtag gaatgcctta    26940
tttttttcta ctgcaggaat atcccgcct ctttcaataa cactaaactc caacatatag    27000 taaccttaa ttttattaaa ataaccgcaa tttatttggc ggcaacacag gatctctctt    27060
ttaagttact ctctattaca tacgttttcc atctaaaaat tagtagtatt gaacttaacg    27120
gggcatcgta ttgtagtttt ccatatttag cttctgctt ccttttggat aacccactgt    27180
tattcatgtt gcatggtgca ctgtttatac caacgatata gtctattaat gcatatatag    27240
tatcgccgaa cgattagctc ttcaggcttc tgaagaagcg tttcaagtac taataagccg    27300
atagatagcc acggacttcg tagccatttt tcataagtgt taacttccgc tcctcgctca    27360
taacagacat tcactacagt tatggcggaa aggtatgcat gctgggtgtg gggaagtcgt    27420
gaaagaaaag aagtcagctg cgtcgtttga catcactgct atcttcttac tggttatgca    27480
ggtcgtagtg ggtggcacac aaagctttgc actggattgc gaggctttgt gcttctctgg    27540
agtgcgacag gtttgatgac aaaaaattag cgcaagaaga caaaaatcac cttgcgctaa    27600
tgctctgtta caggtcacta ataccatcta agtagttgat tcatagtgac tgcatatgtt    27660 gtgtttaca gtattatgta gtctgttttt tatgcaaaat ctaatttaat atattgatat    27720
ttatatcatt ttacgtttct cgttcagctt ttttatacta agttggcatt ataaaaaagc    27780
attgcttatc aatttgttgc aacgaacagg tcactatcag tcaaaataaa atcattattt    27840
gatttcaatt ttgtcccact ccctgcctct gtcatcacga tactgtgatg ccatggtgtc    27900
cgacttatgc ccgagaagat gttgagcaaa cttatcgctt atctgcttct catagagtct    27960
tgcagacaaa ctgcgcaact cgtgaaaggt aggcggatcc ccttcgaagg aaagacctga    28020
tgcttttcgt gcgcgcataa aataccttga tactgtgccg gatgaaagcg gttcgcgacg    28080
agtagatgca attatggttt ctccgccaag aatctctttg catttatcaa gtgtttcctt    28140
cattgatatt ccgagagcat caatatgcaa tgctgttggg atggcaattt ttacgcctgt    28200 ttgctttgc tcgacataaa gatatccatc tacgatatca gaccacttca tttcgcataa    28260
atcaccaact cgttgcccgg taacaacagc cagttccatt gcaagtctga gccaacatgg    28320
tgatgattct gctgcttgat aaattttcag gtattcgtca gccgtaagtc ttgatctcct    28380
tacctctgat tttgctgcgc gagtggcagc gacatggttt gttgttatat ggccttcagc    28440
tattgcctct cggaatgcat cgctcagtgt tgatctgatt aacttggctg acgccgcctt    28500
gccctcgtct atgtatccat tgagcattgc cgcaatttct tttgtggtga tgtcttcaag    28560
tggagcatca ggcagacccc tccttattgc tttaattttg ctcatgtaat ttatgagtgt    28620
cttctgcttg attcctctgc tggccaggat tttttcgtag cgatcaagcc atgaatgtaa    28680
cgtaacggaa ttatcactgt tgattctcgc tgtcagaggc ttgtgtttgt gtcctgaaaa    28740
taactcaatg ttggcctgta tagcttcagt gattgcgatt cgcctgtctc tgcctaatcc    28800 aaactctta cccgtccttg ggtccctgta gcagtaatat ccattgtttc ttatataaag    28860
```

```
gttaggggt  aaatcccggc  gctcatgact  tcgccttctt  cccatttctg  atcctcttca   28920
aaaggccacc  tgttactggt  cgatttaagt  caacctttac  cgctgattcg  tggaacagat   28980
actctcttcc  atccttaacc  ggaggtggga  atatcctgca  ttcccgaacc  catcgacgaa   29040
ctgtttcaag  gcttcttgga  cgtcgctggc  gtgcgttcca  ctcctgaagt  gtcaagtaca   29100
tcgcaaagtc  tccgcaatta  cacgcaagaa  aaaaccgcca  tcaggcggct  tggtgttctt   29160
tcagttcttc  aattcgaata  ttggttacgt  ctgcatgtgc  tatctgcgcc  catatcatcc   29220
agtggtcgta  gcagtcgttg  atgttctccg  cttcgataac  tctgttgaat  ggctctccat   29280
tccattctcc  tgtgactcgg  aagtgcattt  atcatctcca  taaacaaaa  cccgccgtag   29340
cgagttcaga  taaaataaat  ccccgcgagt  gcgaggattg  ttatgtaata  ttgggtttaa   29400
tcatctatat  gttttgtaca  gagagggcaa  gtatcgtttc  caccgtactc  gtgataataa   29460
ttttgcacgg  tatcagtcat  ttctcgcaca  ttgcagaatg  gggatttgtc  ttcattagac   29520
ttataaacct  tcatggaata  tttgtatgcc  gactctatat  ctataccttc  atctacataa   29580
acaccttcgt  gatgtctgca  tggagacaag  acaccggatc  tgcacaacat  tgataacgcc   29640
caatcttttt  gctcagactc  taactcattg  atactcattt  ataaactcct  tgcaatgtat   29700
gtcgtttcag  ctaaacggta  tcagcaatgt  ttatgtaaag  aaacagtaag  ataatactca   29760
acccgatgtt  tgagtacggt  catcatctga  cactacagac  tctggcatcg  ctgtgaagac   29820
gacgcgaaat  tcagcatttt  cacaagcgtt  atctttaca   aaaccgatct  cactctcctt   29880
tgatgcgaat  gccagcgtca  gacatcatat  gcagatactc  acctgcatcc  tgaacccatt   29940
gacctccaac  cccgtaatag  cgatgcgtaa  tgatgtcgat  agttactaac  gggtcttgtt   30000
cgattaactg  ccgcagaaac  tcttccaggt  caccagtgca  gtgcttgata  acaggagtct   30060
tcccaggatg  gcgaacaaca  agaaactggt  ttccgtcttc  acggacttcg  ttgctttcca   30120
gtttagcaat  acgcttactc  ccatccgaga  taacaccttc  gtaatactca  cgctgctcgt   30180
tgagttttga  ttttgctgtt  tcaagctcaa  cacgcagttt  ccctactgtt  agcgcaatat   30240
cctcgttctc  ctggtcgcgg  cgtttgatgt  attgctggtt  tctttcccgt  tcatccagca   30300
gttccagcac  aatcgatggt  gttaccaatt  catggaaaag  gtctgcgtca  atccccagt   30360
cgtcatgcat  tgcctgctct  gccgcttcac  gcagtgcctg  agagttaatt  tcgctcactt   30420
cgaacctctc  tgtttactga  taagttccag  atcctcctgg  caacttgcac  aagtccgaca   30480
accctgaacg  accaggcgtc  ttcgttcatc  tatcggatcg  ccacactcac  aacaatgagt   30540
ggcagatata  gcctggtggt  tcaggcggcg  catttttatt  gctgtgttgc  gctgtaattc   30600
ttctatttct  gatgctgaat  caatgatgtc  tgccatcttt  cattaatccc  tgaactgttg   30660
gttaatacgc  ttgagggtga  atgcgaataa  taaaaaagga  gcctgtagct  ccctgatgat   30720
tttgcttttc  atgttcatcg  ttccttaaag  acgccgttta  acatgccgat  tgccaggctt   30780
aaatgagtcg  gtgtgaatcc  catcagcgtt  accgttcgc   ggtgcttctt  cagtacgcta   30840
cggcaaatgt  catcgacgtt  tttatccgga  aactgctgtc  tggcttttt   tgatttcaga   30900
attagcctga  cgggcaatgc  tgcgaagggc  gttttcctgc  tgaggtgtca  ttgaacaagt   30960
cccatgtcgg  caagcataag  cacacagaat  atgaagcccg  ctgccagaaa  aatgcattcc   31020
gtggttgtca  tacctggttt  ctctcatctg  cttctgcttt  cgccaccatc  atttccagct   31080
tttgtgaaag  ggatgcggct  aacgtatgaa  attcttcgtc  tgtttctact  ggtattggca   31140
caaacctgat  tccaatttga  gcaaggctat  gtgccatctc  gatactcgtt  cttaactcaa   31200
cagaagatgc  tttgtgcata  cagccctcg   tttattattt  atctcctcag  ccagccgctg   31260
```

```
tgctttcagt ggatttcgga taacagaaag gccgggaaat acccagcctc gctttgtaac   31320
ggagtagacg aaagtgattg cgcctacccg gatattatcg tgaggatgcg tcatcgccat   31380
tgctccccaa atacaaaacc aatttcagcc agtgcctcgt ccatttttc gatgaactcc    31440 ggcacgatct cgtcaaaact cgccatgtac ttttcatccc gctcaatcac gacataatgc   31500
aggccttcac gcttcatacg cgggtcatag ttggcaaagt accaggcatt ttttcgcgtc   31560
acccacatgc tgtactgcac ctgggccatg taagctgact ttatggcctc gaaaccaccg   31620
agccggaact tcatgaaatc ccgggaggta acgggcatt tcagttcaag gccgttgccg    31680
tcactgcata aaccatcggg agagcaggcg gtacgcatac tttcgtcgcg atagatgatc   31740
ggggattcag taacattcac gccggaagtg aattcaaaca gggttctggc gtcgttctcg   31800
tactgttttc cccaggccag tgctttagcg ttaacttccg gagccacacc ggtgcaaacc   31860
tcagcaagca gggtgtggaa gtaggacatt tcatgtcag gccacttctt tccggagcgg    31920
ggttttgcta tcacgttgtg aacttctgaa gcggtgatga cgccgagccg taatttgtgc   31980
cacgcatcat ccccctgttc gacagctctc acatcgatcc cggtacgctg caggataatg   32040
tccggtgtca tgctgccacc ttctgctctg cggctttctg tttcaggaat ccaagagctt   32100
ttactgcttc ggcctgtgtc agttctgacg atgcacgaat gtcgcggcga aatatctggg   32160
aacagagcgg caataagtcg tcatcccatg ttttatccag ggcgatcagc agagtgttaa   32220
tctcctgcat ggtttcatcg ttaaccggag tgatgtcgcg ttccggctga cgttctgcag   32280
tgtatgcagt atttcgaca atgcgctcgg cttcatcctt gtcatagata ccagcaaatc    32340
cgaaggccag acgggcacac tgaatcatgg ctttatgacg taacatccgt ttgggatgcg   32400
actgccacgg ccccgtgatt tctctgcctt cgcgagtttt gaatggttcg cggcggcatt   32460
catccatcca ttcggtaacg cagatcggat gattacggtc cttgcggtaa atccggcatg   32520
tacaggattc attgtcctgc tcaaagtcca tgccatcaaa ctgctggttt tcattgatga   32580
tgcgggacca gccatcaacg cccaccaccg gaacgatgcc attctgctta tcaggaaagg   32640
cgtaaatttc tttcgtccac ggattaaggc cgtactggtt ggcaacgatc agtaatgcga   32700
tgaactgcgc atcgctggca tcacctttaa atgccgtctg gcgaagagtg gtgatcagtt   32760
cctgtgggtc gacagaatcc atgccgacac gttcagccag cttcccagcc agcgttgcga   32820
gtgcagtact cattcgtttt atacctctga atcaatatca acctggtggt gagcaatggt   32880
ttcaaccatg taccggatgt gttctgccat gcgctcctga aactcaacat cgtcatcaaa   32940
cgcacgggta atggattttt tgctggcccc gtggcgttgc aaatgatcga tgcatagcga   33000
ttcaaacagg tgctggggca ggccttttc catgtcgtct gccagttctg cctctttctc    33060
ttcacgggcg agctgctggt agtgacgcgc ccagctctga gcctcaagac gatcctgaat   33120
gtaataagcg ttcatggctg aactcctgaa atagctgtga aatatcgcc cgcgaaatgc    33180 cgggctgatt aggaaaacag gaaaggggggt tagtgaatgc ttttgcttga tctcagtttc   33240
agtattaata tccatttttt ataagcgtcg acggcttcac gaaacatctt ttcatcgcca   33300
ataaaagtgg cgatagtgaa tttagtctgg atagccataa gtgtttgatc cattctttgg   33360
gactcctggc tgattaagta tgtcgataag gcgtttccat ccgtcacgta atttacgggt   33420
gattcgttca agtaaagatt cggaagggca gccagcaaca ggccaccctg caatggcata   33480
ttgcatggtg tgctccttat ttatacataa cgaaaaacgc ctcgagtgaa gcgttattgg   33540
tatgcggtaa aaccgcactc aggcggcctt gatagtcata tcatctgaat caaatattcc   33600
```

```
tgatgtatcg atatcggtaa ttcttattcc ttcgctacca tccattggag gccatccttc   33660
ctgaccattt ccatcattcc agtcgaactc acacacaaca ccatatgcat ttaagtcgct   33720
tgaaattgct ataagcagag catgttgcgc cagcatgatt aatacagcat ttaatacaga   33780
gccgtgttta ttgagtcggt attcagagtc tgaccagaaa ttattaatct ggtgaagttt   33840
ttcctctgtc attacgtcat ggtcgatttc aatttctatt gatgctttcc agtcgtaatc   33900
aatgatgtat ttttgatgt ttgacatctg ttcatatcct cacagataaa aaatcgccct   33960
cacactggag ggcaaagaag atttccaata atcagaacaa gtcggctcct gtttagttac   34020
gagcgacatt gctccgtgta ttcactcgtt ggaatgaata cacagtgcag tgtttattct   34080
gttatttatg ccaaaaataa aggccactat caggcagctt tgttgttctg tttaccaagt   34140
tctctggcaa tcattgccgt cgttcgtatt gcccatttat cgacatattt cccatcttcc   34200
attacaggaa acatttcttc aggcttaacc atgcattccg attgcagctt gcatccattg   34260
catcgcttga attgtccaca ccattgattt ttatcaatag tcgtagtcat acggatagtc   34320
ctggtattgt tccatcacat cctgaggatg ctcttcgaac tcttcaaatt cttcttccat   34380
atatcacctt aaatagtgga ttgcggtagt aaagattgtg cctgtctttt aaccacatca   34440
ggctcggtgg ttctcgtgta cccctacagc gagaaatcgg ataaactatt acaacccta   34500 cagtttgatg agtatagaaa tggatccact cgttattctc ggacgagtgt tcagtaatga   34560
acctctggag agaaccatgt atatgatcgt tatctgggtt ggacttctgc ttttaagccc   34620
agataactgg cctgaatatg ttaatgagag aatcggtatt cctcatgtgt ggcatgtttt   34680
cgtctttgct cttgcatttt cgctagcaat taatgtgcat cgattatcag ctattgccag   34740
cgccagatat aagcgattta agctaagaaa acgcattaag atgcaaaacg ataaagtgcg   34800
atcagtaatt caaaaccta cagaagagca atctatggtt ttgtgcgcag cccttaatga   34860
aggcaggaag tatgtggtta catcaaaaca attcccatac attagtgagt tgattgagct   34920
tggtgtgttg aacaaaactt tttcccgatg gaatggaaag catatattat tccctattga   34980
ggatatttac tggactgaat tagttgccag ctatgatcca tataatattg agataaagcc   35040
aaggccaata tctaagtaac tagataagag gaatcgattt tcccttaatt ttctggcgtc   35100
cactgcatgt tatgccgcgt tcgccaggct tgctgtacca tgtgcgctga ttcttgcgct   35160
caatacgttg caggttgctt tcaatctgtt tgtggtattc agccagcact gtaaggtcta   35220
tcggatttag tgcgctttct actcgtgatt tcggtttgcg attcagcgag agaatagggc   35280
ggttaactgg ttttgcgctt accccaacca acagggatt tgctgctttc cattgagcct   35340
gtttctctgc gcgacgttcg cggcggcgtg tttgtgcatc catctggatt ctcctgtcag   35400
ttagctttgg tggtgtgtgg cagttgtagt cctgaacgaa aaccccccgc gattggcaca   35460
ttggcagcta atccggaatc gcacttacgg ccaatgcttc gtttcgtatc acacacccca   35520
aagccttctg ctttgaatgc tgcccttctt cagggcttaa ttttaagag cgtcaccttc   35580 atggtggtca gtgcgtcctg ctgatgtgct cagtatcacc gccagtggta tttatgtcaa   35640
caccgccaga gataatttat caccgcagat ggttatctgt atgtttttta tatgaattta   35700 tttttttgcag gggggcattg tttggtaggt gagagatctg aattgctatg tttagtgagt   35760
tgtatctatt tattttttcaa taaatacaat tggttatgtg ttttggggggc gatcgtgagg   35820 caaagaaaac ccggcgctga ggccgggtta ttcttgttct ctggtcaaat tatatagttg   35880
gaaaacaagg atgcatatat gaatgaacga tgcagaggca atgccgatgg cgatagtggg   35940
tatcatgtag ccgcttatgc tggaaagaag caataacccg cagaaaaaca aagctccaag   36000
```

```
ctcaacaaaa ctaagggcat agacaataac taccgatgtc atataccat  actctctaat  36060 cttggccagt cggcgcgttc tgcttccgat tagaaacgtc aaggcagcaa tcaggattgc  36120
aatcatggtt cctgcatatg atgacaatgt cgccccaaga ccatctctat gagctgaaaa  36180
agaaacacca ggaatgtagt ggcggaaaag gagatagcaa atgcttacga taacgtaagg  36240
aattattact atgtaaacac caggcatgat tctgttccgc ataattactc ctgataatta  36300
atccttaact ttgcccacct gccttttaaa acattccagt atatcacttt tcattcttgc  36360
gtagcaatat gccatctctt cagctatctc agcattggtg accttgttca gaggcgctga  36420
gagatggcct ttttctgata gataatgttc tgttaaaata tctccggcct catcttttgc  36480
ccgcaggcta atgtctgaaa attgaggtga cgggttaaaa ataatatcct tggcaacctt  36540
ttttatatcc ctttaaatt  ttggcttaat gactatatcc aatgagtcaa aaagctcccc  36600
ttcaatatct gttgcccct  agacctttaa tatatcgcca aatacaggta gcttggcttc  36660
taccttcacc gttgttcggc cgatgaaatg catatgcata acatcgtctt tggtggttcc  36720
cctcatcagt ggctctatct gaacgcgctc tccactgctt aatgacattc ctttcccgat  36780
taaaaaatct gtcagatcgg atgtggtcgg cccgaaaaca gttctggcaa accaatggt   36840 gtcgccttca acaaacaaaa aagatgggaa tcccaatgat tcgtcatctg cgaggctgtt  36900
cttaatatct tcaactgaag ctttagagcg atttatcttc tgaaccagac tcttgtcatt  36960
tgttttggta aagagaaaag ttttt ccatc gattttatga atatacaaat aattggagcc  37020
aacctgcagg tgatgattat cagccagcag agaattaagg aaaacagaca ggtttattga  37080
gcgcttatct ttccctttat ttttgctgcg gtaagtcgca taaaaccat  tcttcataat  37140 tcaatccatt tactatgtta tgttctgagg ggagtgaaaa ttcccctaat tcgatgaaga  37200
ttcttgctca attgttatca gctatgcgcc gaccagaaca ccttgccgat cagccaaacg  37260
tctcttcagg ccactgacta gcgataactt tccccacaac ggaacaactc tcattgcatg  37320
ggatcattgg gtactgtggg tttagtggtt gtaaaaacac ctgaccgcta tccctgatca  37380
gtttcttgaa ggtaaactca tcaccccaa  gtctggctat gcagaaatca cctggctcaa  37440
cagcctgctc agggtcaacg agaattaaca ttccgtcagg aaagcttggc ttggagcctg  37500
ttggtgcggt catggaatta ccttcaacct caagccagaa tgcagaatca ctggcttttt  37560
tggttgtgct tacccatctc tccgcatcac ctttggtaaa ggttctaagc ttaggtgaga  37620
acatccctgc ctgaacatga gaaaaacag  ggtactcata ctcacttcta agtgacggct  37680
gcatactaac cgcttcatac atctcgtaga tttctctggc gattgaaggg ctaaattctt  37740
caacgctaac tttgagaatt tttgtaagca atgcggcgtt ataagcattt aatgcattga  37800
tgccattaaa taaagcacca acgcctgact gccccatccc catcttgtct gcgacagatt  37860
cctgggataa gccaagttca ttttttcttt ttt cataaat tgctttaagg cgacgtgcgt  37920
cctcaagctg ctcttgtgtt aatggtttct ttttgtgct  catacgttaa atctatcacc  37980
gcaagggata aatatctaac accgtgcgtg ttgactattt tacctctggc ggtgataatg  38040
gttgcatgta ctaaggaggt tgtatggaac aacgcataac cctgaaagat tatgcaatgc  38100
gctttgggca aaccaagaca gctaaagatc tcggcgtata tcaaagcgcg atcaacaagg  38160
ccattcatgc aggccgaaag attttttta  ctataaacgc tgatggaagc gtttatgcgg  38220
aagaggtaaa gcccttcccg agtaacaaaa aacaacagc  ataaataacc ccgctcttac  38280
acattccagc cctgaaaaag ggcatcaaat taaaccacac ctatggtgta tgcatttatt  38340
```

```
tgcatacatt caatcaattg ttatctaagg aaatacttac atatggttcg tgcaaacaaa    38400
cgcaacgagg ctctacgaat cgagagtgcg ttgcttaaca aaatcgcaat gcttggaact    38460
gagaagacag cggaagctgt gggcgttgat aagtcgcaga tcagcaggtg gaagagggac    38520
tggattccaa agttctcaat gctgcttgct gttcttgaat gggggtcgt tgacgacgac     38580 atggctcgat tggcgcgaca agttgctgcg attctcacca ataaaaaacg cccggcggca    38640
accgagcgtt ctgaacaaat ccagatggag ttctgaggtc attactggat ctatcaacag    38700
gagtcattat gacaaataca gcaaaaatac tcaacttcgg cagaggtaac tttgccggac    38760
aggagcgtaa tgtggcagat ctcgatgatg gttacgccag actatcaaat atgctgcttg    38820
aggcttattc gggcgcagat ctgaccaagc gacagtttaa agtgctgctt gccattctgc    38880
gtaaaaccta tgggtggaat aaaccaatgg acagaatcac cgattctcaa cttagcgaga    38940
ttacaaagtt acctgtcaaa cggtgcaatg aagccaagtt agaactcgtc agaatgaata    39000
ttatcaagca gcaaggcggc atgtttggac caaataaaaa catctcagaa tggtgcatcc    39060
ctcaaaacga gggaaaatcc cctaaaacga gggataaaac atccctcaaa ttgggggatt    39120
gctatccctc aaaacagggg gacacaaaag acactattac aaaagaaaaa agaaaagatt    39180
attcgtcaga gaattctggc gaatcctctg accagccaga aaacgacctt tctgtggtga    39240
aaccggatgc tgcaattcag agcggcagca agtggggac agcagaagac ctgaccgccg     39300
cagagtggat gtttgacatg gtgaagacta tcgcaccatc agccagaaaa ccgaattttg    39360
ctgggtgggc taacgatatc cgcctgatgc gtgaacgtga cggacgtaac caccgcgaca    39420
tgtgtgtgct gttccgctgg gcatgccagg acaacttctg gtccggtaac gtgctgagcc    39480
cggccaaact ccgcgataag tggacccaac tcgaaatcaa ccgtaacaag caacaggcag    39540
gcgtgacagc cagcaaacca aaactcgacc tgacaaacac agactggatt tacggggtgg    39600
atctatgaaa aacatcgccg cacagatggt taactttgac cgtgagcaga tgcgtcggat    39660
cgccaacaac atgccggaac agtacgacga aaagccgcag gtacagcagg tagcgcagat    39720
catcaacggt gtgttcagcc agttactggc aactttcccg gcgagcctgg ctaaccgtga    39780
ccagaacgaa gtgaacgaaa tccgtcgcca gtgggtctg gcttttcggg aaaacgggat     39840
caccacgatg gaacaggtta acgcaggaat gcgcgtagcc cgtcggcaga atcgaccatt    39900
tctgccatca cccgggcagt tgttgcatg gtgccgggaa gaagcatccg ttaccgccgg     39960
actgccaaac gtcagcgagc tggttgatat ggtttacgag tattgccgga agcgaggcct    40020
gtatccggat gcggagtctt atccgtggaa atcaaacgcg cactactggc tggttaccaa    40080
cctgtatcag aacatgcggg ccaatgcgct tactgatgcg gaattacgcc gtaaggccgc    40140
agatgagctt gtccatatga ctgcgagaat taaccgtggt gaggcgatcc ctgaaccagt    40200
aaaacaactt cctgtcatgg gcggtagacc tctaaatcgt gcacaggctc tggcgaagat    40260
cgcagaaatc aaagctaagt tcggactgaa aggagcaagt gtatgacggg caaagaggca    40320
attattcatt acctggggac gcataatagc ttctgtgcgc cggacgttgc cgcgctaaca    40380
ggcgcaacag taaccagcat aaatcaggcc gcggctaaaa tggcacgggc aggtcttctg    40440
gttatcgaag gtaaggtctg gcgaacggtg tataccggtt tgctaccagg gaagaacgg    40500 gaaggaaaga tgagcacgaa cctggttttt aaggagtgtc gccagagtgc cgcgatgaaa    40560
cgggtattgg cggtatatgg agttaaaaga tgaccatcta cattactgag ctaataacag    40620
gcctgctggt aatcgcaggc cttttatttt gggggagagg gaagtcatga aaaaactaac    40680 cttttgaaatt cgatctccag cacatcagca aaacgctatt cacgcagtac agcaaatcct    40740
```

```
tccagaccca accaaaccaa tcgtagtaac cattcaggaa cgcaaccgca gcttagacca   40800
aaacaggaag ctatgggcct gcttaggtga cgtctctcgt caggttgaat ggcatggtcg   40860
ctggctggat gcagaaagct ggaagtgtgt gtttaccgca gcattaaagc agcaggatgt   40920
tgttcctaac cttgccggga atggctttgt ggtaataggc cagtcaacca gcaggatgcg   40980
tgtaggcgaa tttgcggagc tattagagct tatacaggca ttcggtacag agcgtggcgt   41040
taagtggtca gacgaagcga gactggctct ggagtggaaa gcgagatggg gagacagggc   41100
tgcatgataa atgtcgttag tttctccggt ggcaggacgt cagcatattt gctctggcta   41160
atggagcaaa agcgacgggc aggtaaagac gtgcattacg ttttcatgga tacaggttgt   41220
gaacatccaa tgacatatcg gtttgtcagg gaagttgtga agttctggga tataccgctc   41280
accgtattgc aggttgatat caacccggag cttggacagc caaatggtta tacggtatgg   41340
gaaccaaagg atattcagac gcgaatgcct gttctgaagc catttatcga tatggtaaag   41400
aaatatggca ctccatacgt cggcggcgcg ttctgcactg acagattaaa actcgttccc   41460
ttcaccaaat actgtgatga ccatttcggg cgagggaatt acaccacgtg gattggcatc   41520
agagctgatg aaccgaagcg gctaaagcca aagcctggaa tcagatatct tgctgaactg   41580
tcagactttg agaaggaaga tatcctcgca tggtggaagc aacaaccatt cgatttgcaa   41640
ataccggaac atctcggtaa ctgcatattc tgcattaaaa aatcaacgca aaaaatcgga   41700
cttgcctgca aagatgagga gggattgcag cgtgttttta atgaggtcat cacgggatcc   41760
catgtgcgtg acggacatcg ggaaacgcca aaggagatta tgtaccgagg aagaatgtcg   41820
ctggacggta tcgcgaaaat gtattcagaa aatgattatc aagccctgta tcaggacatg   41880
gtacgagcta aaagattcga taccggctct tgttctgagt catgcgaaat atttggaggg   41940
cagcttgatt tcgacttcgg gagggaagct gcatgatgcg atgttatcgg tgcggtgaat   42000
gcaaagaaga taaccgcttc cgaccaaatc aaccttactg gaatcgatgg tgtctccggt   42060
gtgaaagaac accaacaggg gtgttaccac taccgcagga aaaggaggac gtgtggcgag   42120
acagcgacga gtatcaccg acataatctg cgaaaactgc aaataccttc caacgaaacg   42180
caccagaaat aaacccaagc caatcccaaa agaatctgac gtaaaaacct tcaactacac   42240
ggctcacctg tgggatatcc ggtggctaag acgtcgtgcg aggaaaacaa ggtgattgac   42300
caaaatcgaa gttacgaaca agaaagcgtc gagcgagctt taacgtgcgc taactgcggt   42360
cagaagctgc atgtgctgga agttcacgtg tgtgagcact gctgcgcaga actgatgagc   42420
gatccgaata gctcgatgca cgaggaagaa gatgatggct aaaccagcgc gaagacgatg   42480
taaaaacgat gaatgccggg aatggtttca ccctgcattc gctaatcagt ggtggtgctc   42540
tccagagtgt ggaaccaaga tagcactcga acgacgaagt aaagaacgcg aaaaagcgga   42600
aaaagcagca gagaagaaac gacgacgaga ggagcagaaa cagaaagata aacttaagat   42660
tcgaaaactc gccttaaagc cccgcagtta ctggattaaa caagcccaac aagccgtaaa   42720
cgccttcatc agagaaagag accgcgactt accatgtatc tcgtgcggaa cgctcacgtc   42780
tgctcagtgg gatgccggac attaccggac aactgctgcg gcacctcaac tccgatttaa   42840
tgaacgcaat attcacaagc aatgcgtggt gtgcaaccag cacaaaagcg gaaatctcgt   42900
tccgtatcgc gtcgaactga ttagccgcat cgggcaggaa gcagtagacg aaatcgaatc   42960
aaaccataac cgccatcgct ggactatcga agagtgcaag gcgatcaagg cagagtacca   43020
acagaaactc aaagacctgc gaaatagcag aagtgaggcc gcatgacgtt ctcagtaaaa   43080
```

```
accattccag acatgctcgt tgaaacatac ggaaatcaga cagaagtagc acgcagactg    43140
aaatgtagtc gcggtacggt cagaaaatac gttgatgata aagacgggaa aatgcacgcc    43200
atcgtcaacg acgttctcat ggttcatcgc ggatggagtg aaagagatgc gctattacga    43260
aaaaattgat ggcagcaaat accgaaatat ttgggtagtt ggcgatctgc acggatgcta    43320
cacgaacctg atgaacaaac tggatacgat tggattcgac aacaaaaaag acctgcttat    43380
ctcggtgggc gatttggttg atcgtggtgc agagaacgtt gaatgcctgg aattaatcac    43440
attcccctgg ttcagagctg tacgtggaaa ccatgagcaa atgatgattg atggcttatc    43500
agagcgtgga aacgttaatc actggctgct taatggcggt ggctggttct ttaatctcga    43560
ttacgacaaa gaaattctgg ctaaagctct tgcccataaa gcagatgaac ttccgttaat    43620
catcgaactg gtgagcaaag ataaaaaata tgttatctgc cacgccgatt atcccttga    43680
cgaatacgag tttggaaagc cagttgatca tcagcaggta atctggaacc gcgaacgaat    43740
cagcaactca caaaacggga tcgtgaaaga aatcaaaggc gcggacacgt tcatctttgg    43800
tcatacgcca gcagtgaaac cactcaagtt tgccaaccaa atgtatatcg ataccggcgc    43860
agtgttctgc ggaaacctaa cattgattca ggtacaggga aaggcgcat gagactcgaa    43920
agcgtagcta aatttcattc gccaaaaagc ccgatgatga gcgactcacc acgggccacg    43980
gcttctgact ctcttttccgg tactgatgtg atggctgcta tggggatggc gcaatcacaa    44040
gccggattcg gtatggctgc attctgcggt aagcacgaac tcagccagaa cgacaaacaa    44100
aaggctatca actatctgat gcaatttgca cacaaggtat cggggaaata ccgtggtgtg    44160
gcaaagcttg aaggaaatac taaggcaaag gtactgcaag tgctcgcaac attcgcttat    44220
gcggattatt gccgtagtgc cgcgacgccg ggggcaagat gcagagattg ccatggtaca    44280
ggccgtgcgt tgatattgc caaaacgag ctgtggggga gagttgtcga aaagagtgc    44340
ggaagatgca aaggcgtcgg ctattcaagg atgccagcaa gcgcagcata tcgcgctgtg    44400
acgatgctaa tcccaaacct tacccaaccc acctggtcac gcactgttaa gccgctgtat    44460
gacgctctgg tggtgcaatg ccacaaagaa gagtcaatcg cagacaacat tttgaatgcg    44520
gtcacacgtt agcagcatga ttgccacgga tggcaacata ttaacggcat gatattgact    44580
tattgaataa aattgggtaa atttgactca acgatgggtt aattcgctcg ttgtggtagt    44640
gagatgaaaa gaggcggcgc ttactaccga ttccgcctag ttggtcactt cgacgtatcg    44700
tctggaactc caaccatcgc aggcagagag gtctgcaaaa tgcaatcccg aaacagttcg    44760
caggtaatag ttagagcctg cataacggtt tcgggatttt ttatatctgc acaacaggta    44820
agagcattga gtcgataatc gtgaagagtc ggcgagcctg gttagccagt gctctttccg    44880
ttgtgctgaa ttaagcgaat accggaagca gaaccggatc accaaatgcg tacaggcgtc    44940
atcgccgccc agcaacagca caacccaaac tgagccgtag ccactgtctg tcctgaattc    45000
attagtaata gttacgctgc ggccttttac acatgacctt cgtgaaagcg ggtggcagga    45060
ggtcgcgcta acaacctcct gccgttttgc ccgtgcatat cggtcacgaa caaatctgat    45120
tactaaacac agtagcctgg atttgttcta tcagtaatcg accttattcc taattaaata    45180
gagcaaatcc ccttattggg ggtaagacat gaagatgcca gaaaaacatg acctgttggc    45240
cgccattctc gcggcaaagg aacaaggcat cggggcaatc cttgcgtttg caatggcgta    45300
ccttcgcggc agatataatg gcggtgcgtt tacaaaaaca gtaatcgacg caacgatgtg    45360
cgccattatc gcctagttca ttcgtgacct tctcgacttc gccggactaa gtagcaatct    45420
cgcttatata acgagcgtgt ttatcggcta catcggtact gactcgattg gttcgcttat    45480
```

```
caaacgcttc gctgctaaaa aagccggagt agaagatggt agaaatcaat aatcaacgta   45540
aggcgttcct cgatatgctg gcgtggtcgg agggaactga taacggacgt cagaaaacca   45600
gaaatcatgg ttatgacgtc attgtaggcg gagagctatt tactgattac tccgatcacc   45660
ctcgcaaact tgtcacgcta aacccaaaac tcaaatcaac aggcgccgga cgctaccagc   45720
ttctttcccg ttggtgggat gcctaccgca agcagcttgg cctgaaagac ttctctccga   45780
aaagtcagga cgctgtggca ttgcagcaga ttaaggagcg tggcgcttta cctatgattg   45840
atcgtggtga tatccgtcag gcaatcgacc gttgcagcaa tatctgggct tcactgccgg   45900
gcgctggtta tggtcagttc gagcataagg ctgacagcct gattgcaaaa ttcaaagaag   45960
cgggcggaac ggtcagagag attgatgtat gagcagagtc accgcgatta tctccgctct   46020
ggttatctgc atcatcgtct gcctgtcatg ggctgttaat cattaccgtg ataacgccat   46080
tacctacaaa gcccagcgcg acaaaaatgc cagagaactg aagctggcga acgcggcaat   46140
tactgacatg cagatgcgtc agcgtgatgt tgctgcgctc gatgcaaaat acacgaagga   46200
gttagctgat gctaaagctg aaaatgatgc tctgcgtgat gatgttgccg ctggtcgtcg   46260
tcggttgcac atcaaagcag tctgtcagtc agtgcgtgaa gccaccaccg cctccggcgt   46320
ggataatgca gcctcccccc gactggcaga caccgctgaa cgggattatt tcaccctcag   46380
agagaggctg atcactatgc aaaaacaact ggaaggaacc cagaagtata ttaatgagca   46440
gtgcagatag agttgcccat atcgatgggc aactcatgca attattgtga gcaatacaca   46500
cgcgcttcca gcggagtata aatgcctaaa gtaataaaac cgagcaatcc atttacgaat   46560
gtttgctggg tttctgtttt aacaacattt tctgcgccgc cacaaatttt ggctgcatcg   46620
acagttttct tctgcccaat tccagaaacg aagaaatgat gggtgatggt ttcctttggt   46680
gctactgctg ccggtttgtt ttgaacagta aacgtctgtt gagcacatcc tgtaataagc   46740
agggccagcg cagtagcgag tagcattttt ttcatggtgt tattcccgat gcttttgaa    46800 gttcgcagaa tcgtatgtgt agaaaattaa acaaaccctaa acaatgagt tgaaatttca   46860 tattgttaat atttattaat gtatgtcagg tgcgatgaat cgtcattgta ttcccggatt   46920
aactatgtcc acagccctga cggggaactt ctctgcggga gtgtccggga ataattaaaa   46980
cgatgcacac agggtttagc gcgtacacgt attgcattat gccaacgccc cggtgctgac   47040
acggaagaaa ccggacgtta tgatttagcg tggaaagatt tgtgtagtgt tctgaatgct   47100
ctcagtaaat agtaatgaat tatcaaaggt atagtaatat cttttatgtt catggatatt   47160
tgtaacccat cggaaaactc ctgctttagc aagattttcc ctgtattgct gaaatgtgat   47220
ttctcttgat ttcaacctat cataggacgt ttctataaga tgcgtgtttc ttgagaattt   47280
aacatttaca acctttttaa gtccttttat taacacggtg ttatcgtttt ctaacacgat   47340
gtgaatatta tctgtggcta gatagtaaat ataatgtgag acgttgtgac gttttagttc   47400
agaataaaac aattcacagt ctaaatcttt tcgcacttga tcgaatattt ctttaaaaat   47460
ggcaacctga gccattggta aaaccttcca tgtgatacga gggcgcgtag tttgcattat   47520
cgtttttatc gtttcaatct ggtctgacct ccttgtgttt tgttgatgat ttatgtcaaa   47580
tattaggaat gttttcactt aatagtattg gttgcgtaac aaagtgcggt cctgctggca   47640
ttctggaggg aaatacaacc gacagatgta tgtaaggcca acgtgctcaa atcttcatac   47700
agaaagattt gaagtaatat tttaaccgct agatgaagag caagcgcatg gagcgacaaa   47760
atgaataaag aacaatctgc tgatgatccc tccgtggatc tgattcgtgt aaaaaatatg   47820
```

```
cttaatagca ccatttctat gagttaccct gatgttgtaa ttgcatgtat agaacataag   47880
gtgtctctgg aagcattcag agcaattgag gcagcgttgg tgaagcacga taataatatg   47940
aaggattatt ccctggtggt tgactgatca ccataactgc taatcattca aactatttag   48000
tctgtgacag agccaacacg cagtctgtca ctgtcaggaa agtggtaaaa ctgcaactca   48060
attactgcaa tgccctcgta attaagtgaa tttacaatat cgtcctgttc ggagggaaga   48120
acgcgggatg ttcattcttc atcacttttta attgatgtat atgctctctt ttctgacgtt   48180
agtctccgac ggcaggcttc aatgacccag gctgagaaat tcccgaccc ttttttgctca   48240 agagcgatgt taatttgttc aatcatttgg ttaggaaagc ggatgttgcg ggttgttgtt   48300
ctgcgggttc tgttcttcgt tgacatgagg ttgccccgta ttcagtgtcg ctgatttgta   48360
ttgtctgaag ttgttttttac gttaagttga tgcagatcaa ttaatacgat acctgcgtca   48420
taattgatta tttgacgtgg tttgatggcc tccacgcacg ttgtgatatg tagatgataa   48480
tcattatcac tttacgggtc cttttccggtg atccgacagg ttacggggcg gcgacctcgt   48540
tctgtttatg tttcttgttt gttagccttt tggctaacaa acaagaaaca taaacagaac   48600
gcgtaacctg tcggatcacc ggaaaggacc cgtaaagtga taatgattat catctacata   48660
tcacaacgtg cgtggaggcc atcaaaccac gtcaaataat caattatgac gcaggtatcg   48720
tattaattga tctgcatcaa cttaacgtaa aaacaacttc agacaataca aatcagcgac   48780
actgaatacg gggcaacctc atgtcaacga agaacagaac ccgcagaaca caacccgca   48840 acatccgctt tcctaaccaa atgattgaac aaattaacat cgctcttgag caaaagggt   48900 ccgggaattt ctcagcctgg gtcattgaag cctgccgtcg gagactaacg tcagaaaaga   48960
gagcatatac atcaattaaa agtgatgaag aatgaacatc ccgcgttctt ccctccgaac   49020
aggacgatat tgtaaattca cttaattacg agggcattgc agtaattgag ttgcagtttt   49080
accactttcc tgacagtgac agactgcgtg ttggctctgt cacagactaa atagtttgaa   49140
tgattagcag ttatggtgat cagtcaacca ccagggaata atccttcata ttattatcgt   49200
gcttcaccaa cgctgcctca attgctctga atgcttccag agacacctta tgttctatac   49260
atgcaattac aacatcaggg taactcatag aaatggtgct attaagcata ttttttacac   49320
gaatcagatc cacggaggga tcatcagcag attgttcttt attcattttg tcgctccatg   49380
cgcttgctct tcatctagcg gttaaaatat tacttcaaat cttctgtat gaagatttga   49440 gcacgttggc cttacataca tctgtcggtt gtatttccct ccagaatgcc agcaggaccg   49500
cactttgtta cgcaaccaat actattaagt gaaacattc ctaatatttg acataaatca   49560
tcaacaaaac acaaggaggt cagaccagat tgaaacgata aaaacgataa tgcaaactac   49620
gcgccctcgt atcacatgga aggttttacc aatggctcag gttgccattt ttaaagaaat   49680
attcgatcaa gtgcgaaaag atttagactg tgaattgttt tattctgaac taaaacgtca   49740
caacgtctca cattatattt actatctagc cacagataat attcacatcg tgttagaaaa   49800
cgataacacc gtgttaataa aaggacttaa aaaggttgta aatgttaaat tctcaagaaa   49860
cacgcatctt atagaaacgt cctatgatag gttgaaatca agagaaatca catttcagca   49920
atacagggaa aatcttgcta aagcaggagt ttttccgatgg gttacaaata tccatgaaca   49980
taaaagatat tactatacct ttgataattc attactattt actgagagca ttcagaacac   50040
tacacaaatc tttccacgct aaatcataac gtccggtttc ttccgtgtca gcaccggggc   50100
gttggcataa tgcaatacgt gtacgcgcta aaccctgtgt gcatcgtttt aattattccc   50160
ggacactccc gcagagaagt tccccgtcag ggctgtggac atagttaatc cgggaataca   50220
```

```
atgacgattc atcgcacctg acatacatta ataaatatta acaatatgaa atttcaactc   50280
attgtttagg gtttgtttaa ttttctacac atacgattct gcgaacttca aaaagcatcg   50340
ggaataacac catgaaaaaa atgctactcg ctactgcgct ggccctgctt attacaggat   50400
gtgctcaaca gacgtttact gttcaaaaca aaccggcagc agtagcacca aaggaaacca   50460
tcacccatca tttcttcgtt tctggaattg ggcagaagaa aactgtcgat gcagccaaaa   50520
tttgtggcgg cgcagaaaat gttgttaaaa cagaaaccca gcaaacattc gtaaatggat   50580
tgctcggttt tattacttta ggcatttata ctccgctgga agcgcgtgtg tattgctcac   50640
aataattgca tgagttgccc atcgatatgg gcaactctat ctgcactgct cattaatata   50700
cttctgggtt ccttccagtt gttttttgcat agtgatcagc ctctctctga gggtgaaata   50760
atcccgttca gcggtgtctg ccagtcgggg ggaggctgca ttatccacgc cggaggcggt   50820
ggtggcttca cgcactgact gacagactgc tttgatgtgc aaccgacgac gaccagcggc   50880
aacatcatca cgcagagcat cattttcagc tttagcatca gctaactcct tcgtgtattt   50940
tgcatcgagc gcagcaacat cacgctgacg catctgcatg tcagtaattg ccgcgttcgc   51000
cagcttcagt tctctggcat ttttgtcgcg ctgggctttg taggtaatgg cgttatcacg   51060
gtaatgatta acagcccatg acaggcagac gatgatgcag ataaccagag cggagataat   51120
cgcggtgact ctgctcatac atcaatctct ctgaccgttc cgcccgcttc tttgaatttt   51180
gcaatcaggc tgtcagcctt atgctcgaac tgaccataac cagcgcccgg cagtgaagcc   51240
cagatattgc tgcaacggtc gattgcctga cggatatcac cacgatcaat cataggtaaa   51300
gcgccacgct ccttaatctg ctgcaatgcc acagcgtcct gacttttcgg agagaagtct   51360
ttcaggccaa gctgcttgcg gtaggcatcc caccaacggg aaagaagctg gtagcgtccg   51420
gcgcctgttg atttgagttt tgggtttagc gtgacaagtt tgcgagggtg atcggagtaa   51480
tcagtaaata gctctccgcc tacaatgacg tcataaccat gatttctggt tttctgacgt   51540
ccgttatcag ttccctccga ccacgccagc atatcgagga acgccttacg ttgattattg   51600
atttctacca tcttctactc cggcttttt agcagcgaag cgtttgataa gcgaaccaat   51660
cgagtcagta ccgatgtagc cgataaacac gctcgttata taagcgagat tgctacttag   51720
tccggcgaag tcgagaaggt cacgaatgaa ctaggcgata atggcgcaca tcgttgcgtc   51780
gattactgtt tttgtaaacg caccgccatt atatctgccg cgaaggtacg ccattgcaaa   51840
cgcaaggatt gccccgatgc cttgttcctt tgccgcgaga atggcggcca acaggtcatg   51900
tttttctggc atcttcatgt cttaccccca ataaggggat ttgctctatt taattaggaa   51960
taaggtcgat tactgataga acaaatccag gctactgtgt ttagtaatca gatttgttcg   52020
tgaccgatat gcacgggcaa aacggcagga ggttgttagc gcgacctcct gccaccgct   52080 ttcacgaagg tcatgtgtaa aaggccgcag cgtaactatt actaatgaat tcaggacaga   52140
cagtggctac ggctcagttt gggttgtgct gttgctgggc ggcgatgacg cctgtacgca   52200
tttggtgatc cggttctgct tccggtattc gcttaattca gcacaacgga aagagcactg   52260
gctaaccagg ctcgccgact cttcacgatt atcgactcaa tgctcttacc tgttgtgcag   52320
atataaaaaa tcccgaaacc gttatgcagg ctctaactat tacctgcgaa ctgtttcggg   52380
attgcatttt gcagacctct ctgcctgcga tggttggagt tccagacgat acgtcgaagt   52440
gaccaactag gcggaatcgg tagtaagcgc cgcctctttt catctcacta ccacaacgag   52500
cgaattaacc catcgttgag tcaaatttac ccaatttat tcaataagtc aatatcatgc   52560
```

```
cgttaatatg ttgccatccg tggcaatcat gctgctaacg tgtgaccgca ttcaaaatgt   52620
tgtctgcgat tgactcttct ttgtggcatt gcaccaccag agcgtcatac agcggcttaa   52680
cagtgcgtga ccaggtgggt tgggtaaggt ttgggattag catcgtcaca gcgcgatatg   52740
ctgcgcttgc tggcatcctt gaatagccga cgcctttgca tcttccgcac tctttctcga   52800
caactctccc ccacagctct gttttggcaa tatcaaccgc acggcctgta ccatggcaat   52860
ctctgcatct tgcccccggc gtcgcggcac tacggcaata atccgcataa gcgaatgttg   52920
cgagcacttg cagtaccttt gccttagtat ttccttcaag ctttgccaca ccacggtatt   52980
tccccgatac cttgtgtgca aattgcatca gatagttgat agccttttgt ttgtcgttct   53040
ggctgagttc gtgcttaccg cagaatgcag ccataccgaa tccggcttgt gattgcgcca   53100
tccccatagc agccatcaca tcagtaccgg aaagagagtc agaagccgtg gcccgtggtg   53160
agtcgctcat catcgggctt tttggcgaat gaaatttagc tacgctttcg agtctcatgc   53220
gccttctccc tgtacctgaa tcaatgttag gtttccgcag aacactgcgc cggtatcgat   53280
atacatttgg ttggcaaact tgagtggttt cactgctggc gtatgaccaa agatgaacgt   53340
gtccgcgcct ttgatttctt tcacgatccc gttttgtgag ttgctgattc gttcgcggtt   53400
ccagattacc tgctgatgat caactggctt tccaaactcg tattcgtcaa agggataatc   53460
ggcgtggcag ataacatatt ttttatcttt gctcaccagt tcgatgatta acggaagttc   53520
atctgcttta tgggcaagag cttttagccag aatttctttg tcgtaatcga gattaaagaa   53580
ccagccaccg ccattaagca gccagtgatt aacgtttcca cgctctgata agccatcaat   53640
catcatttgc tcatggtttc cacgtacagc tctgaaccag gggaatgtga ttaattccag   53700
gcattcaacg ttctctgcac cacgatcaac caaatcgccc accgagataa gcaggtcttt   53760
tttgttgtcg aatccaatcg tatccagttt gttcatcagg ttcgtgtagc atccgtgcag   53820
atcgccaact acccaaatat ttcggtattt gctgccatca attttttcgt aatagcgcat   53880
ctctttcact ccatccgcga tgaaccatga gaacgtcgtt gacgatggcg tgcattttcc   53940
cgtctttatc atcaacgtat tttctgaccg taccgcgact acatttcagt ctgcgtgcta   54000
cttctgtctg atttccgtat gtttcaacga gcatgtctgg aatggttttt actgagaacg   54060
tcatgcggcc tcacttctgc tatttcgcag gtctttgagt ttctgttggt actctgcctt   54120
gatcgccttg cactcttcga tagtccagcg atggcggtta tggtttgatt cgatttcgtc   54180
tactgcttcc tgcccgatgc ggctaatcag ttcgacgcga tacggaacga gatttccgct   54240
tttgtgctgg ttgcacacca cgcattgctt gtgaatattg cgttcattaa atcggagttg   54300
aggtgccgca gcagttgtcc ggtaatgtcc ggcatcccac tgagcagacg tgagcgttcc   54360
gcacgagata catggtaagt cgcggtctct ttctctgatg aaggcgttta cggcttgttg   54420
ggcttgttta atccagtaac tgcggggctt taaggcgagt tttcgaatct taagtttatc   54480
tttctgtttc tgctcctctc gtcgtcgttt cttctctgct gcttttttccg cttttttcgcg   54540 ttctttactt cgtcgttcga gtgctatctt ggttccacac tctggagagc accaccactg   54600
attagcgaat gcagggtgaa accattcccg gcattcatcg tttttacatc gtcttcgcgc   54660
tggtttagcc atcatcttct tcctcgtgca tcgagctatt cggatcgctc atcagttctg   54720
cgcagcagtg ctcacacacg tgaacttcca gcacatgcag cttctgaccg cagttagcgc   54780
acgttaaagc tcgctcgacg ctttcttgtt cgtaacttcg attttggtca atcaccttgt   54840
tttcctcgca cgacgtctta gccaccggat atcccacagg tgagccgtgt agttgaaggt   54900
ttttacgtca gattctttg ggattggctt gggtttattt ctggtgcgtt tcgttggaag   54960
```

```
gtatttgcag ttttcgcaga ttatgtcggt gatacttcgt cgctgtctcg ccacacgtcc   55020 tcctttcct gcggtagtgg taacacccct gttggtgttc tttcacaccg gagacaccat    55080
cgattccagt aaggttgatt tggtcggaag cggttatctt ctttgcattc accgcaccga   55140
taacatcgca tcatgcagct tccctcccga agtcgaaatc aagctgccct ccaaatattt   55200
cgcatgactc agaacaagag ccggtatcga atcttttagc tcgtaccatg tcctgataca   55260
gggcttgata atcattttct gaatacattt tcgcgatacc gtccagcgac attcttcctc   55320
ggtacataat ctccttggc gtttcccgat gtccgtcacg cacatgggat cccgtgatga    55380
cctcattaaa aacacgctgc aatccctcct catctttgca ggcaagtccg attttttgcg   55440
ttgatttttt aatgcagaat atgcagttac cgagatgttc cggtatttgc aaatcgaatg   55500
gttgttgctt ccaccatgcg aggatatctt ccttctcaaa gtctgacagt tcagcaagat   55560
atctgattcc aggctttggc tttagccgct tcggttcatc agctctgatg ccaatccacg   55620
tggtgtaatt ccctcgcccg aaatggtcat cacagtattt ggtgaaggga acgagtttta   55680
atctgtcagt gcagaacgcg ccgccgacgt atggagtgcc atatttcttt accatatcga   55740
taaatggctt cagaacaggc attcgcgtct gaatatcctt tggttcccat accgtataac   55800
catttggctg tccaagctcc gggttgatat caacctgcaa tacggtgagc ggtatatccc   55860
agaacttcac aacttccctg acaaaccgat atgtcattgg atgttcacaa cctgtatcca   55920
tgaaaacgta atgcacgtct ttacctgccc gtcgcttttg ctccattagc cagagcaaat   55980
atgctgacgt cctgccaccg gagaaactaa cgacatttat catgcagccc tgtctcccca   56040
tctcgctttc cactccagag ccagtctcgc ttcgtctgac cacttaacgc cacgctctgt   56100
accgaatgcc tgtataagct ctaatagctc cgcaaattcg cctacacgca tcctgctggt   56160
tgactggcct attaccacaa agccattccc ggcaaggtta ggaacaacat cctgctgctt   56220
taatgctgcg gtaaacacac acttccagct ttctgcatcc agccagcgac catgccattc   56280
aacctgacga gagacgtcac ctaagcaggc ccatagcttc ctgttttggt ctaagctgcg   56340
gttgcgttcc tgaatggtta ctacgattgg tttggttggg tctggaagga tttgctgtac   56400
tgcgtgaata gcgttttgct gatgtgctgg agatcgaatt tcaaaggtta gttttttcat   56460
gacttccctc tcccccaaat aaaaaggcct gcgattacca gcaggcctgt tattagctca   56520
gtaatgtaga tggtcatctt ttaactccat ataccgccaa tacccgtttc atcgcggcac   56580
tctggcgaca ctccttaaaa accaggttcg tgctcatctt tccttcccgt tcttccctgg   56640
tagcaaaccg gtaatacacc gttcgccaga ccttaccttc gataaccaga agacctgccc   56700
gtgccatttt agccgcggcc tgatttatgc tggttactgt tgcgcctgtt agcgcggcaa   56760
cgtccggcgc acagaagcta ttatgcgtcc ccaggtaatg aataattgcc tctttgcccg   56820
tcatacactt gctcctttca gtccgaactt agctttgatt tctgcgatct tcgccagagc   56880
ctgtgcacga tttagaggtc taccgcccat gacaggaagt tgttttactg gttcaggaat   56940
cgcctcacca cggttaattc tcgcagtcat atggacaagc tcatctgcgg ccttacggcg   57000
taattccgca tcagtaagcg cattggcccg catgttctga tacaggttgg taaccagcca   57060
gtagtgcgcg tttgatttcc acggataaga ctccgcatcc ggatacaggc ctcgcttccg   57120
gcaatactcg taaaccatat caaccagctc gctgacgttt ggcagtccgg cggtaacgga   57180
tgcttcttcc cggcaccatg caacaaactg cccgggtgat ggcagaaatg gtcgattctg   57240
ccgacgggct acgcgcattc ctgcgttaac ctgttccatc gtggtgatcc cgttttcccg   57300
```

-continued

```
aaaagccaga acccactggc gacggatttc gttcacttcg ttctggtcac ggttagccag   57360
gctcgccggg aaagttgcca gtaactggct gaacacaccg ttgatgatct gcgctacctg   57420
ctgtacctgc ggcttttcgt cgtactgttc cggcatgttg ttggcgatcc gacgcatctg   57480
ctcacggtca aagttaacca tctgtgcggc gatgttttc atagatccac cccgtaaatc    57540
cagtctgtgt tgtcaggtc gagttttggt ttgctggctg tcacgcctgc ctgttgcttg    57600
ttacggttga tttcgagttg ggtccactta tcgcggagtt tggccgggct cagcacgtta   57660
ccggaccaga agttgtcctg gcatgcccag cggaacagca cacacatgtc gcggtggtta   57720
cgtccgtcac gttcacgcat caggcggata tcgttagccc acccagcaaa attcggtttt   57780
ctggctgatg gtgcgatagt cttcaccatg tcaaacatcc actctgcggc ggtcaggtct   57840
tctgctgtcc cccacttgct gccgctctga attgcagcat ccggtttcac cacagaaagg   57900
tcgttttctg gctggtcaga ggattcgcca gaattctctg acgaataatc ttttcttttt   57960
tcttttgtaa tagtgtcttt tgtgtccccc tgttttgagg gatagcaatc ccccaatttg   58020
agggatgttt tatccctcgt tttaggggat tttccctcgt tttgagggat gcaccattct   58080
gagatgtttt tatttggtcc aaacatgccg ccttgctgct tgataatatt cattctgacg   58140
agttctaact tggcttcatt gcaccgtttg acaggtaact ttgtaatctc gctaagttga   58200
gaatcggtga ttctgtccat tggtttattc cacccatagg ttttacgcag aatggcaagc   58260
agcactttaa actgtcgctt ggtcagatct gcgcccgaat aagcctcaag cagcatattt   58320
gatagtctgg cgtaaccatc atcgagatct gccacattac gctcctgtcc ggcaaagtta   58380
cctctgccga agttgagtat ttttgctgta tttgtcataa tgactcctgt tgatagatcc   58440
agtaatgacc tcagaactcc atctggattt gttcagaacg ctcggttgcc gccgggcgtt   58500
ttttattggt gagaatcgca gcaacttgtc gcgccaatcg agccatgtcg tcgtcaacga   58560 cccccattc aagaacagca agcagcattg agaactttgg aatccagtcc ctcttccacc    58620
tgctgatctg cgacttatca acgcccacag cttccgctgt cttctcagtt ccaagcattg   58680
cgattttgtt aagcaacgca ctctcgattc gtagagcctc gttgcgtttg tttgcacgaa   58740
ccatatgtaa gtatttcctt agataacaat tgattgaatg tatgcaaata aatgcataca   58800
ccataggtgt ggtttaattt gatgcccttt ttcagggctg gaatgtgtaa gagcggggtt   58860
atttatgctg ttgttttttt gttactcggg aagggcttta cctcttccgc ataaacgctt   58920
ccatcagcgt ttatagttaa aaaaatcttt cggcctgcat gaatggcctt gttgatcgcg   58980
ctttgatata cgccgagatc tttagctgtc ttggtttgcc caaagcgcat tgcataatct   59040
ttcagggtta tgcgttgttc catacaacct ccttagtaca tgcaaccatt atcaccgcca   59100
gaggtaaaat agtcaacacg cacggtgtta gatatttatc ccttgcggtg atagatttaa   59160
cgtatgagca caaaaaagaa accattaaca caagagcagc ttgaggacgc acgtcgcctt   59220
aaagcaattt atgaaaaaaa gaaaaatgaa cttggcttat cccaggaatc tgtcgcagac   59280
aagatgggga tggggcagtc aggcgttggt gctttattta atggcatcaa tgcattaaat   59340
gcttataacg ccgcattgct tacaaaaatt ctcaaagtta gcgttgaaga atttagccct   59400
tcaatcgcca gagaaatcta cgagatgtat gaagcggtta gtatgcagcc gtcacttaga   59460
agtgagtatg agtaccctgt tttttctcat gttcaggcag ggatgttctc acctaagctt   59520
agaaccttta ccaaaggtga tgcggagaga tgggtaagca caaccaaaaa agccagtgat   59580
tctgcattct ggcttgaggt tgaaggtaat tccatgaccg caccaacagg ctccaagcca   59640
agctttcctg acggaatgtt aattctcgtt gaccctgagc aggctgttga gccaggtgat   59700
```

```
ttctgcatag ccagacttgg gggtgatgag tttaccttca agaaactgat cagggatagc    59760
ggtcaggtgt ttttacaacc actaaaccca cagtacccaa tgatcccatg caatgagagt    59820
tgttccgttg tggggaaagt tatcgctagt cagtggcctg aagagacgtt tggctgatcg    59880
gcaaggtgtt ctggtcggcg catagctgat aacaattgag caagaatctt catcgaatta    59940
ggggaatttt cactcccctc agaacataac atagtaaatg gattgaatta tgaagaatgg    60000 ttttatgcg acttaccgca gcaaaaataa agggaaagat aagcgctcaa taaacctgtc     60060
tgttttcctt aattctctgc tggctgataa tcatcacctg caggttggct ccaattattt    60120
gtatattcat aaaatcgatg gaaaaacttt tctctttacc aaaacaaatg caagagtct     60180 ggttcagaag ataaatcgct ctaaagcttc agttgaagat attaagaaca gcctcgcaga    60240
tgacgaatca ttgggattcc catctttttt gtttgttgaa ggcgacacca ttggttttgc    60300
cagaactgtt ttcgggccga ccacatccga tctgacagat tttttaatcg ggaaaggaat    60360
gtcattaagc agtggagagc gcgttcgat  agagccactg atgagggaa  ccaccaaaga    60420 cgatgttatg catatgcatt tcatcggccg aacaacggtg aaggtagaag ccaagctacc    60480
tgtatttggc gatatattaa aggtcttagg ggcaacagat attgaagggg agcttttga    60540 ctcattggat atagtcatta agccaaaatt taaagggat ataaaaaagg ttgccaagga     60600 tattatttttt aacccgtcac ctcaatttttc agacattagc ctgcgggcaa agatgaggc    60660 cggagatatt ttaacagaac attatctatc agaaaaaggc catctctcag cgcctctgaa    60720
caaggtcacc aatgctgaga tagctgaaga gatggcatat tgctacgcaa gaatgaaaag    60780
tgatatactg gaatgtttta aaaggcaggt gggcaaagtt aaggattaat tatcaggagt    60840
aattatgcgg aacagaatca tgcctggtgt ttacatagta ataattcctt acgttatcgt    60900
aagcatttgc tatctccttt tccgccacta cattcctggt gtttcttttt cagctcatag    60960
agatggtctt ggggcgacat tgtcatcata tgcaggaacc atgattgcaa tcctgattgc    61020
tgccttgacg tttctaatcg gaagcagaac gcgccgactg gccaagatta gagagtatgg    61080
gtatatgaca tcggtagtta ttgtctatgc ccttagtttt gttgagcttg gagctttgtt    61140
tttctgcggg ttattgcttc tttccagcat aagcggctac atgatacca  ctatcgccat    61200 cggcattgcc tctgcatcgt tcattcatat atgcatcctt gttttccaac tatataattt    61260
gaccagagaa caagaataac ccggcctcag cgccggtttt tctttgcctc acgatcgccc    61320
ccaaaacaca taaccaattg tatttattga aaaataaata gatacaactc actaaacata    61380
gcaattcaga tctctcacct accaaacaat gcccccctgc aaaaaataaa ttcatataaa    61440
aaacatacag ataaccatct gcggtgataa attatctctg gcggtgttga cataaatacc    61500
actggcggtg atactgagca catcagcagg acgcactgac caccatgaag gtgacgctct    61560
taaaaattaa gccctgaaga agggcagcat tcaaagcaga aggctttggg gtgtgtgata    61620
cgaaacgaag cattggccgt aagtgcgatt ccggattagc tgccaatgtg ccaatcgcgg    61680
ggggttttcg ttcaggacta caactgccac acaccaccaa agctaactga caggagaatc    61740
cagatggatg cacaaacacg ccgccgcgaa cgtcgcgcag agaaacaggc tcaatggaaa    61800
gcagcaaatc ccctgttggt tgggtaagc  gcaaaaccag ttaaccgccc tattctctcg    61860
ctgaatcgca aaccgaaatc acgagtagaa agcgcactaa atccgataga ccttacagtg    61920
ctggctgaat accacaaaca gattgaaagc aacctgcaac gtattgagcg caagaatcag    61980
cgcacatggt acagcaagcc tggcgaacgc ggcataacat gcagtggacg ccagaaaatt    62040
```

```
aagggaaaat cgattcctct tatctagtta cttagatatt ggccttggct ttatctcaat    62100
attatatgga tcatagctgg caactaattc agtccagtaa atatcctcaa tagggaataa    62160
tatatgcttt ccattccatc gggaaaaagt tttgttcaac acaccaagct caatcaactc    62220
actaatgtat gggaattgtt ttgatgtaac cacatacttc ctgccttcat taagggctgc    62280
gcacaaaacc atagattgct cttctgtaag gttttgaatt actgatcgca ctttatcgtt    62340
ttgcatctta atgcgttttc ttagcttaaa tcgcttatat ctggcgctgg caatagctga    62400
taatcgatgc acattaattg ctagcgaaaa tgcaagagca aagacgaaaa catgccacac    62460
atgaggaata ccgattctct cattaacata ttcaggccag ttatctgggc ttaaaagcag    62520
aagtccaacc cagataacga tcatatacat ggttctctcc agaggttcat tactgaacac    62580
tcgtccgaga ataacgagtg gatccatttc tatactcatc aaactgtagg ggttgtaata    62640
gtttatccga tttctcgctg tagggtaca cgagaaccac cgagcctgat gtggttaaaa    62700
gacaggcaca atctttacta ccgcaatcca ctatttaagg tgatatatgg aagaagaatt    62760
tgaagagttc gaagagcatc ctcaggatgt gatggaacaa taccaggact atccgtatga    62820
ctacgactat tgataaaaat caatggtgtg gacaattcaa gcgatgcaat ggatgcaagc    62880
tgcaatcgga atgcatggtt aagcctgaag aaatgtttcc tgtaatgaa gatgggaaat     62940 atgtcgataa atgggcaata cgaacgacgg caatgattgc cagagaactt ggtaaacaga    63000
acaacaaagc tgcctgatag tggcctttat ttttggcata aataacgaaa taaacactgc    63060
actgtgtatt cattccaacg agtgaataca cggagcaatg tcgctcgtaa ctaaacagga    63120
gccgacttgt tctgattatt ggaaatcttc tttgccctcc agtgtgaggg cgatttttta    63180
tctgtgagga tatgaacaga tgtcaaacat caaaaaatac atcattgatt acgactggaa    63240
agcatcaata gaaattgaaa tcgaccatga cgtaatgaca gaggaaaaac ttcaccagat    63300
taataatttc tggtcagact ctgaataccg actcaataaa cacggctctg tattaaatgc    63360
tgtattaatc atgctggcgc aacatgctct gcttatagca atttcaagcg acttaaatgc    63420
atatggtgtt gtgtgtgagt tcgactggaa tgatggaaat ggtcaggaag gatggcctcc    63480
aatggatggt agcgaaggaa taagaattac cgatatcgat acatcaggaa tatttgattc    63540
agatgatatg actatcaagg ccgcctgagt gcggttttac cgcataccaa taacgcttca    63600
ctcgaggcgt ttttcgttat gtataaataa ggagcacacc atgcaatatg ccattgcagg    63660
gtggcctgtt gctggctgcc cttccgaatc tttacttgaa cgaatcaccc gtaaattacg    63720
tgacggatgg aaacgcctta tcgacatact taatcagcca ggagtcccaa agaatggatc    63780
aaacacttat ggctatccag actaaattca ctatcgccac ttttattggc gatgaaaaga    63840
tgtttcgtga agccgtcgac gcttataaaa aatggatatt aatactgaaa ctgagatcaa    63900
gcaaaagcat tcactaaccc cctttcctgt tttcctaatc agcccggcat ttcgcgggcg    63960
atattttcac agctatttca ggagttcagc catgaacgct tattacattc aggatcgtct    64020
tgaggctcag agctgggcgc gtcactacca gcagctcgcc cgtgaagaga aagaggcaga    64080
actggcagac gacatggaaa aaggcctgcc ccagcacctg tttgaatcgc tatgcatcga    64140
tcatttgcaa cgccacgggg ccagcaaaaa atccattacc cgtgcgtttg atgacgatgt    64200
tgagtttcag gagcgcatgg cagaacacat ccggtacatg gttgaaacca ttgctcacca    64260
ccaggttgat attgattcag aggtataaaa cgaatgagta ctgcactcgc aacgctggct    64320
gggaagctgg ctgaacgtgt cggcatggat tctgtcgacc cacaggaact gatcaccact    64380
cttcgccaga cggcatttaa aggtgatgcc agcgatgcgc agttcatcgc attactgatc    64440
```

```
gttgccaacc agtacggcct taatccgtgg acgaaagaaa tttacgcctt tcctgataag   64500
cagaatggca tcgttccggt ggtgggcgtt gatggctggt cccgcatcat caatgaaaac   64560
cagcagtttg atggcatgga cttcgagcag gacaatgaat cctgtacatg ccggatttac   64620
cgcaaggacc gtaatcatcc gatctgcgtt accgaatgga tggatgaatg ccgccgcgaa   64680
ccattcaaaa ctcgcgaagg cagagaaatc acggggccgt ggcagtcgca tcccaaacgg   64740
atgttacgtc ataaagccat gattcagtgt gcccgtctgg ccttcggatt tgctggtatc   64800
tatgacaagg atgaagccga gcgcattgtc gaaaatactg catacactgc agaacgtcag   64860
ccggaacgcg acatcactcc ggttaacgat gaaaccatgc aggagattaa cactctgctg   64920
atcgccctgg ataaaacatg ggatgacgac ttattgccgc tctgttccca gatatttcgc   64980
cgcgacattc gtgcatcgtc agaactgaca caggccgaag cagtaaaagc tcttggattc   65040
ctgaaacaga agccgcaga gcagaaggtg gcagcatgac accggacatt atcctgcagc   65100
gtaccgggat cgatgtgaga gctgtcgaac aggggatga tgcgtggcac aaattacggc   65160
tcggcgtcat caccgcttca gaagttcaca acgtgatagc aaaacccgc tccggaaaga   65220
agtggcctga catgaaaatg tcctacttcc acaccctgct tgctgaggtt tgcaccggtg   65280
tggctccgga agttaacgct aaagcactgg cctggggaaa acagtacgag aacgacgcca   65340
gaaccctgtt tgaattcact tccggcgtga atgttactga atcccgatc atctatcgcg   65400
acgaaagtat gcgtaccgcc tgctctcccg atggtttatg cagtgacggc aacggccttg   65460
aactgaaatg cccgtttacc tcccgggatt tcatgaagtt ccggctcggt ggtttcgagg   65520
ccataaagtc agcttacatg gcccaggtgc agtacagcat gtgggtgacg cgaaaaaatg   65580
cctggtactt tgccaactat gacccgcgta tgaagcgtga aggcctgcat tatgtcgtga   65640
ttgagcggga tgaaaagtac atggcgagtt ttgacgagat cgtgccggag ttcatcgaaa   65700
aaatggacga ggcactggct gaaattggtt ttgtatttgg ggagcaatgg cgatgacgca   65760
tcctcacgat aatatccggg taggcgcaat cactttcgtc tactccgtta caaagcgagg   65820
ctgggtattt cccggccttt ctgttatccg aaatccactg aaagcacagc ggctggctga   65880
ggagataaat aataaacgag gggctgtatg cacaaagcat cttctgttga gttaagaacg   65940
agtatcgaga tggcacatag ccttgctcaa attggaatca ggtttgtgcc aataccagta   66000
gaaacagacg aagaatttca tacgttagcc gcatcccttt cacaaaagct ggaaatgatg   66060
gtggcgaaag cagaagcaga tgagagaaac caggtatgac aaccacggaa tgcattttc   66120
tggcagcggg cttcatattc tgtgtgctta tgcttgccga catgggactt gttcaatgac   66180
acctcagcag gaaaacgccc ttcgcagcat tgcccgtcag gctaattctg aaatcaaaaa   66240
aagccagaca gcagtttccg gataaaaacg tcgatgacat ttgccgtagc gtactgaaga   66300
agcaccgcga aacggtaacg ctgatgggat tcacaccgac tcatttaagc ctggcaatcg   66360
gcatgttaaa cggcgtcttt aaggaacgat gaacatgaaa agcaaaatca tcagggagct   66420
acaggctcct tttttattat tcgcattcac cctcaagcgt attaaccaac agttcaggga   66480
ttaatgaaag atggcagaca tcattgattc agcatcagaa atagaagaat tacagcgcaa   66540
cacagcaata aaaatgcgcc gcctgaacca ccaggctata tctgccactc attgttgtga   66600
gtgtggcgat ccgatagatg aacgaagacg cctggtcgtt cagggttgtc ggacttgtgc   66660
aagttgccag gaggatctgg aacttatcag taaacagaga ggttcgaagt gagcgaaatt   66720
aactctcagg cactgcgtga agcggcagag caggcaatgc atgacgactg gggatttgac   66780
```

```
gcagaccttt tccatgaatt ggtaacacca tcgattgtgc tggaactgct ggatgaacgg   66840
gaaagaaacc agcaatacat caaacgccgc gaccaggaga acgaggatat tgcgctaaca   66900
gtagggaaac tgcgtgttga gcttgaaaca gcaaaatcaa aactcaacga gcagcgtgag   66960
tattacgaag gtgttatctc ggatgggagt aagcgtattg ctaaactgga aagcaacgaa   67020
gtccgtgaag acggaaacca gtttcttgtt gttcgccatc ctgggaagac tcctgttatc   67080
aagcactgca ctggtgacct ggaagagttt ctgcggcagt taatcgaaca agacccgtta   67140
gtaactatcg acatcattac gcatcgctat tacggggttg gaggtcaatg ggttcaggat   67200
gcaggtgagt atctgcatat gatgtctgac gctggcattc gcatcaaagg agagtgagat   67260
cggttttgta aaagataacg cttgtgaaaa tgctgaattt cgcgtcgtct tcacagcgat   67320
gccagagtct gtagtgtcag atgatgaccg tactcaaaca tcgggttgag tattatctta   67380
ctgtttcttt acataaacat tgctgatacc gtttagctga aacgacatac attgcaagga   67440
gtttataaat gagtatcaat gagttagagt ctgagcaaaa agattgggcg ttatcaatgt   67500
tgtgcagatc cggtgtcttg tctccatgca gacatcacga aggtgtttat gtagatgaag   67560
gtatagatat agagtcggca tacaaatatt ccatgaaggt ttataagtct aatgaagaca   67620
aatccccatt ctgcaatgtg cgagaaatga ctgataccgt gcaaaattat tatcacgagt   67680
acggtggaaa cgatacttgc cctctctgta caaaacatat agatgattaa acccaatatt   67740
acataacaat cctcgcactc gcggggattt attttatctg aactcgctac ggcgggtttt   67800
gttttatgga gatgataaat gcacttccga gtcacaggag aatggaatgg agagccattc   67860
aacagagtta tcgaagcgga gaacatcaac gactgctacg accactggat gatatgggcg   67920
cagatagcac atgcagacgt aaccaatatt cgaattgaag aactgaaaga acaccaagcc   67980
gcctgatggc ggttttttct tgcgtgtaat tgcggagact ttgcgatgta cttgacactt   68040
caggagtgga acgcacgcca gcgacgtcca agaagccttg aaacagttcg tcgatgggtt   68100
cgggaatgca ggatattccc acctccggtt aaggatggaa gagagtatct gttccacgaa   68160
tcagcggtaa aggttgactt aaatcgacca gtaacaggtg gcctttttgaa gaggatcaga   68220 aatgggaaga aggcgaagtc atgagcgccg ggatttaccc cctaaccttt atataagaaa   68280
caatggatat tactgctaca gggacccaag gacgggtaaa gagtttggat taggcagaga   68340
caggcgaatc gcaatcactg aagctataca ggccaacatt gagttatttt caggacacaa   68400
acacaagcct ctgacagcga gaatcaacag tgataattcc gttacgttac attcatggct   68460
tgatcgctac gaaaaaatcc tggccagcag aggaatcaag cagaagacac tcataaatta   68520
catgagcaaa attaaagcaa taaggagggg tctgcctgat gctccacttg aagacatcac   68580
cacaaaagaa attgcggcaa tgctcaatgg atacatagac gagggcaagg cggcgtcagc   68640
caagttaatc agatcaacac tgagcgatgc attccgagag gcaatagctg aaggccatat   68700
aacaacaaac catgtcgctg ccactcgcgc agcaaaatca gaggtaagga gatcaagact   68760
tacggctgac gaataccctga aaatttatca agcagcagaa tcatcaccat gttggctcag   68820
acttgcaatg gaactggctg ttgttaccgg gcaacgagtt ggtgatttat gcgaaatgaa   68880
gtggtctgat atcgtagatg gatatcttta tgtcgagcaa agcaaaacag gcgtaaaaat   68940
tgccatccca acagcattgc atattgatgc tctcggaata tcaatgaagg aaacacttga   69000
taaatgcaaa gagattcttg gcggagaaac cataattgca tctactcgtc gcgaaccgct   69060
ttcatccggc acagtatcaa ggtatttttat gcgcgcacga aaagcatcag gtctttcctt   69120
cgaaggggat ccgcctacct ttcacgagtt gcgcagtttg tctgcaagac tctatgagaa   69180
```

```
gcagataagc gataagtttg ctcaacatct tctcgggcat aagtcggaca ccatggcatc  69240
acagtatcgt gatgacagag gcagggagtg ggacaaaatt gaaatcaaat aatgatttta  69300
ttttgactga tagtgacctg ttcgttgcaa caaattgata agcaatgctt ttttataatg  69360
ccaacttagt ataaaaaagc tgaacgagaa acgtaaaatg atataaatat caatatatta  69420
aattagattt tgcataaaaa acagactaca taatactgta aaacacaaca tatgcagtca  69480
ctatgaatca actacttaga tggtattagt gacctgtaac agagcattag cgcaaggtga  69540
tttttgtctt cttgcgctaa ttttttgtca tcaaacctgt cgcactccag agaagcacaa  69600
agcctcgcaa tccagtgcaa agctttgtgt gccacccact acgacctgca taaccagtaa  69660
gaagatagca gtgatgtcaa acgacgcagc tgacttcttt tctttcacga cttccccaca  69720
cccagcatgc atacctttcc gccataactg tagtgaatgt ctgttatgag cgaggagcgg  69780
aagttaacac ttatgaaaaa tggctacgaa gtccgtggct atctatcggc ttattagtac  69840
ttgaaacgct tcttcagaag cctgaagagc taatcgttcg gcgatactat atatgcatta  69900
atagactata tcgttggtat aaacagtgca ccatgcaaca tgaataacag tgggttatcc  69960
aaaaggaaga agaaagctaa atatggaaaa ctacaaatacg atgccccgtt aagttcaata  70020
ctactaattt ttagatggaa aacgtatgta atagagagta acttaaaaga gagatcctgt  70080
gttgccgcca aataaattgc ggttatttta ataaaattaa gggttactat atgttggagt  70140
ttagtgttat tgaaagaggc gggtatattc ctgcagtaga aaaaaataag gcattcctac  70200
gagcagatgg ttggaatgac tattcctttg ttacaatgtt ttatcttact gtctttgatg  70260
agcatggtga aaaatgcgat atcggaaatg ttaaaattgg ttttgtaggt caaaaagaag  70320
aagtaagcac ttattcatta atagataaaa aattcagtca actccctgaa atgttttttt  70380
ccttaggtga aagcattgac tactatgtta atctcagcaa attaagcgat ggttttaaac  70440
ataaccttct taaagctatt caggatttag tagtatggcc aaatcgatta gccgacattg  70500
aaaatgaaag cgtccttaac acctcattac ttagaggggt aactctttca gaaattcatg  70560
gacagttcgc acgtgtgtta aatggtttgc cagaattgtc agatttccac ttttcattta  70620
atagaaaaag tgctcccgga ttcagtgatt taactatacc ttttgaggtg acggttaatt  70680
ctatgcccag cacgaacatt catgctttta tcgggcggaa tgggtgtggt aaaacaacaa  70740
ttttgaatgg aatgattggt gcaatcacca acccagaaaa caatgaatat ttttctctg   70800 aaaataatag acttatcgag tcaagaatcc caaagggata ttttcgatcg cttgtttcag  70860
tttcgtttag tgcatttgat cctttttactc ctcctaaaga acaacctgac ccagcaaaag  70920
gtacacaata ctttttatatt ggactcaaga atgctgccag caatagttta aaatcactag  70980
gcgatctccg cttagaattc atttcagcat ttattggttg tatgagagta gatagaaaaa  71040
gacaactctg gcttgaagct atcaaaaaac taagtagtga tgaaaacttt tcaaatatgg  71100
aactcatcag cctcatttct aaatatgaag agttaagacg taatgaacca cagattcaag  71160
tggacgatga taaattcact aaattgtttt atgacaatat ccagaaatat ctgcttcgaa  71220
tgagctctgg acatgcaatt gttttatttta ctatcacaag attagtagat gtcgttggcg  71280
aaaagtcatt agttttattc gatgaaccag aggttcatct gcatccacct ttgctctctg  71340
cttttttacg aacattaagc gacttactcg atgcacgcaa tggtgtagca ataattgcaa  71400
ctcattcccc agtagtactg caagaggttc caaaatcctg catgtggaaa gtcctacggt  71460
caagagaagc aataaatatt atccgtccgg atattgagac attcggtgag aacttaggtg  71520
```

```
ttttaactcg tgaggtgttt ttacttgaag tgacaaattc tggataccac cacttattat   71580
cgcagtccgt tgattcagag ctttcttatg aaaccattct aaaaaattat aatggtcaga   71640
taggattaga aggtcgaacc gttttaaaag cgatgataat gaacagagat gaaggtaaag   71700
tacaatgaaa aaactacctc ttccagcgag aacttatagc gaaatgctta ataaatgctc   71760
ggaaggtatg atgcagataa atgttagaaa taatttcatt actcacttcc ccactttttt   71820
gcagaaagaa caacaatata gaatattaag ctcgacaggt cagttattta cctacgacag   71880
gacacaccct cttgagccta caaccttagt agttggtaac ctgacaaagg ttaaattaga   71940
aaagctttat gaaaataatc tccgagataa aaacaaaccc gctagaacat attacgatga   72000
catgcttgtt tcatcaggtg aaaaatgtcc attttgtggt gatataggac agacaaaaaa   72060
tatagatcat tttcttccta ttgcacatta tcctgaattt tcggtgatgc ctattaattt   72120
agttccatcg tgccgcgact gcaatatggg agagaaaggt caagttttcg cagtagatga   72180
ggtacaccaa gcgattcatc cctatatcga caaggacatt ttttttcgtg agcaatgggt   72240
atatgcaaat ttcgtttccg gaactccggg tgctatcagt ttttatgttg aatgcccggc   72300
gaactggagg caggaagaca acacagagc tcttcatcat ttcaagctat taaatattgc   72360
taacaggtat cgtttggagg cagggaagca cttgagtgaa gtgattactc aaagaaactc   72420
tttcgtaaaa gttataagga aatatagttc aaccgcaacg tttcagcagc tacagtcaga   72480
atttattgaa gcaaatctga aacctattat agatttgaat gacttcccca attattggaa   72540
aagagttatg tatcagtgcc tagcaaactc ggaagatttt ttcagaggga tctagaatat   72600
gatgaaagat agaaaattac gacgcttatc ggaagtgaac gaatacttt tatatgagga   72660 gggctgtttt tacaaaatcc ggtagtaact tgctaaccaa ttcctaggca ggtcattggc   72720
aacagtggca tgcaccgaga aggacgtttg taatgtccgc tccggcacat agcagtccta   72780
gggacagtgg cgtacagtca tagatggtcg gtgggaggtg gtacaaattc tctcatgcaa   72840
aaaatatgta aaatcggtag caactggaaa tcattcaaca cccgcactat cggaagttca   72900
ccagccagcc gcagcacgtt cctgcatacg acgtgtctgc ggctctacca tatctcctat   72960
gagcaacgtg ttagcagagc caagccacaa ctctaatttt aatacataat gaatgataat   73020
aataatatta aaaatttcct gtgtaactaa tttactatat ggtttctgat aagaatcatt   73080
gcaaagatca acaacttgt attacattga cagttaagca gttaattta tcacctctaa   73140 aatatatcag catctagcat gcaacctatc aaaatggaga gttttatgac taaaaaacca   73200
tgggaaagaa gacttaaaga tttatcgcac ttgctcaaat gctgcattga tacatatttt   73260
gaccctgaat tatttcgctt gaatttgaat caattcctcc aaaccgcaag aacagtaaca   73320
tttattattc aaaaaaacaa aaaccagatt ataggatatg acatttggta taacaataat   73380
gttattgaaa aatggaaaaa tgatccatta atggcttggg ctaaaaattc tcgcaatacg   73440
atagaaaaac aaggcgattt agaaatgtat agcgaggcaa aggctactct tatttcatct   73500
tacattgaag aaaatgacat tgagtttatt acaaatgaaa gtatgttaaa cattggtata   73560
aaaaagttag tcagacttgc acaaaagaaa ttaccttcat atttaactga atcatctatt   73620
attaaatcag aaagacgatg ggtcgctaat acgctaaaag attacgaatt attacatgcc   73680
ttagctataa tctatggcag aatgtataac tgctgtaact ctcttggcat acaaataaac   73740
aatccaatgg gtgacgatgt gatttcgcca acatcattcg actctttatt tgatgaagcc   73800
aggagaataa cttatttaaa attaaaagat tactccataa gcaaattgtc atttagcatg   73860
atacaatatg acaataaaat aattcctgaa gatattaaag agcgtctaaa actggtagat   73920
```

```
aagcctaaaa atatcacttc gacagaagag ttagttgact atacagccaa gcttgcagaa   73980
acgacttttt taaaggacgg ttatcacatt caaacattaa ttttttatga taaacaattc   74040
catccaattg atttaatcaa tacaacattt gaagatcaag cagataaata tattttttgg   74100
cgttatgcag ctgacagagc caaaataaca aatgcctatg gcttcatttg gatatcagag   74160
ctatggctca gaaaagcaag catctactcc aataaaccaa tacatacaat gccaattata   74220
gatgaaagac ttcaggtaat tggaattgat tcaaataata atcaaaatg tatttcatgg    74280 aaaatagtta gagaaaacga agaaaaaaaa ccgactttag aaatatcaac agcagactca   74340
aaacatgacg aaaaaccata tttcatgcgt tcagtcttaa aagcaattgg cggtgatgta   74400
aacactatga acaattgagt catagaactt ccattattct cctgaagata ataatcgcca   74460
aataaaccaa tactcagctt tacaatatac taactaaccg cagaacgtta tttcatacaa   74520
cgtttctgcg gcatatcaca aaacgattac tccataacag ggacagcagg ccactcaata   74580
tcaggtgcag ttgatgtatc aacacggttc agcaacaccc gatacttctt ccaggcttcc   74640
agcaacgagg tttcttcctt cgttgcaatt tccagatctg cagcatcctg aagcggcgca   74700
atatgctcac tggctacctg catcaggctt ttttttgttt cttccgcctc ccggatccgg   74760
aacagttttt ctgcttccgt atccttcacc caggctgtgc cgttccactt ctgatattcc   74820
cctcccggcg ataaccaggt aaaattttcc ggtaacggac cgagttcaga aataaataac   74880
gcgtcgccgg aagccacgtc atagacggtt ttaccccgat ggtcttcaac gagatgccac   74940
gatgcctcat cactgttgaa aacagccaca aagccagccg gaatatctgg cggtgcaata   75000
tcggtactgt ttgcaggcag accggtatga ggcggaatat atgcgtcacc ttcaccaata   75060
aattcattag ttccggccag cagattataa atttttatgg tccgtggttg ttcactcatt   75120
ctgaatgcca ttatgcaagc ctcacaatat agttaaatgc aatgtttttg acggtgtttt   75180
ccgcgttacc cgcagcgtta acggtgatgg tgtgtccgtg tgaaccaata ctgaaagaat   75240
gggcatgagc accgataaca accggatgct ggtgcgcacc aataccaact gtatgcgcat   75300
gtgcaccggc actcacggct gtaccggaca atgagtgact gtggctgccc tgactgtccg   75360
ttttcgataa ataagcaata ccctgtgtgc tggttccttt aactgtggat aaacttcctg   75420
taatggttgc tgttccatac tgactccagc cagaactgtt catccttaaa ccacttgtgt   75480
gggcatgagc acccgcggcc cctgttgaac cgctcagact gtgagcatga gccccgtgt    75540 tattcgtcga tttggtgccg taatcgaaac tgcctgttgt tttcgtcccg taatcaaacg   75600
acgatgtggt tttcgtcccc aaatccgtac cggatgcact ggcactgtgg gtgtgcgact   75660
taattccatc ctgttcctga gacaatacag cacgaccgct ggcgggtttc cccttgattg   75720
tccagcctcg catatcagga agcacacccg atggatacgc gacagcaagt tttgggtagg   75780
ctgatttgtc aaacgcctgc ccctgcatca ggacgtagcc agacggaacg atatctgatg   75840
gccacgggat cggcgcacct gccggaaagg ccgaattctc accggcccca aggtattcaa   75900
gaacatctgc aacggaattt tttgccagaa tatccctgcc aacctgagtc agttcagtca   75960
ggctggcggc atcatttttcc gcaaaatacg gtaatttatt tttcgccgtg gaaagccctg   76020
ccagcgccgt cagtgtcgca ttcttcggtt gtttaccccgc aagcgcgtta gtcatggtgg   76080
tagcaaaatc tggatcattc ccgagcgctg cggccagttc attcagcgta ttcagtgcgt   76140
caggtgacgc gtcgataaca tctgcaatcg cggccagtac aaaagcggtg ttcgcaatct   76200
gggtattgtt tgttcccctg agcgcggttg gtgctgttgg cgttccggtc agtgccggac   76260
```

```
tgtccagtgg gcttttctgt tcgtttcatc cattaccacc ttaaccgcct ttggcgttgc    76320
agcaagcgtt tcagacgtgc tgttggttgc actgctgagc tgcactatcc cctttctcgt    76380
tgtgtccgca tcctcaagcg cgacagctga agctatatct tctgcacgtt ttgccgaatt    76440
ttttgcacgt attgccgccg cttctgccgc acttttgctc tgcgatgctg ataccgcact    76500
tcccgcagcc tctgtcgcct tcgtggatgc cgttgacgca ctccccgccg ccgctgtttt    76560
tgcgtctgcc gcggcagagg cgctccgttc cgctgctgtt tcagatgacc tggcattcgt    76620
ctcggacgtt tttgccgccc tggcagaatt ttctgccgcc gttgccgagg aagctgcacg    76680
accggcactt gatgatgcgt tcgtttctga tgattttgct gcctcttttg aggccaccgc    76740
atctcgtgct gaagtggcgg cctctgacgc tttcgtggcc gcggtggagg cagacgtggc    76800
ggctgattgt tgtgacgctg cagcattcgt ttctgacgtt ttcgccgcac cggcactggt    76860
ggccgccgcg ttttttgagg actctgcggc tgcggcactt ttttccgctt cagtggcctt    76920
tgctgatgcc gcttctgcgc cggaggacgc ttcctgagct gacgatgcag cctgtccggc    76980
ggacgtgctg gcggcgcgtg ctgagtcagt tgcatcagtc acaagggccg cgacctgagc    77040
agctgatgca ctggcatcgc cggctgattt cttcgcgtct gccgtactct gtgccaccac    77100
ggacgcgtta cgcgccacct cttccaccat cagttcaaga cgacgcagca cctccggccg    77160
ggcatcatcc tccgtcatgg cacagagaaa atcattcagc gtccccggtt gtgaatcttc    77220
atacacggtg atggtcccgg cgtgcgatgg tggaaaaccg tcaacctgca ggatgacact    77280
gtactgaccg tactccacat ccatgctgta acgcccggct tcatccggat tctctgagcc    77340
caccgtgttc accaccaccg tggtgctgtt acgtctggct ttcagctgaa tggtgcagtt    77400
ctgtaccggt tttcctgtgc cgtctttcag gactcctgaa atctttactg ccatattcac    77460
cccacaaaaa agcccaccgg ttccggcggg ctgtcataac actgtgttac ctggctaatc    77520
agaatttata accgacccca acgatgaatc cgtcagtacg ccagtcgcca ctgccggagc    77580
cttcataagc aatatcaaca acgacggacg ctgccggatt aatctgtata cctgcactcc    77640
acgccactga ggtatgccgc attgcacttt cgtccctggc agtggtcgtc tctttcatat    77700
acccgggagt gatttccgtc ttacggtaat ccattgtact gccggaccac cgactgtgag    77760
ccactccggc catggcgtac gcactgacct gcttactgat ttgtaaaacc ggtccggcca    77820
tcacgctcac ataacgtcca cgcaggctct catagtgaaa cgtatcctcc ccggtcatca    77880
ctgtgctgct cttttcgac gcggcgaacc ccagggaagc catcaccccc acactgtccg    77940
tcagctcata acgtacttc acgttaatcc ctttcagatg actcacaccg gtatccccgc    78000
ccgacaacga cggcaatgta cccggtttca cttgaaaata gcccaccgta aacgtaccat    78060
gtccaccttc cgcacgggcc ggagtgactg tcaccgcaag tgcggcaaag acagcaacgg    78120
caatacacac attcgcatc gttcacctct cactgttta taataaaacg cccgttcccg    78180
gacgaacctc tgtaacacac tcagaccacg ctgatgccca cgcctgttt cttaatcacc    78240
ataacctgca catcgctggc aaacgtatac ggcggaatat ctgccgaatg ccgtgtggac    78300
gtaagcgtga acgtcaggat cacgtttccc cgacccgctg gcatgtcaac aatacgggag    78360
aacacctgta ccgcctcgtt cgccgcgcca tcataaatca ccgcaccgtt catcagtact    78420
ttcagataac acatcgaata cgttgtcctg ccgctgacag tacgcttact tccgcgaaac    78480
gtcagcggaa gcaccactat ctggcgatca aaaggatggt catcggtcac ggtgacagta    78540
cgggtacctg acgccagtc cacactgctt tcacgctggc gcggaaaagc cgcgctcgcc    78600
gcctttacaa tgtccccgac gatttttcc gccctcagcg taccgtttat cgtacagttt    78660
```

```
tcagctatcg tcacattact gagcgtcccg gagttcgcat tcacactgcc actgatatcc   78720
gcatttttag cggtcagctt tccgtccggt gtcagggaaa aggccggagg attgccgccg   78780
ctggtaatgg tgggggccgt caggcgcttc aggaacacgt cgttcatgaa tatctggttg   78840
ccctgcgcca caaacatcgg cgtttcattc ccgtttgccg ggtcaataaa tgcgatacga   78900
ttggcggcaa ccagaaactg gctcagtttg ccttcctccg tgtcctccat gctgaggcca   78960
atacccgcga cataatgttt gccgtctttg gtctgctcaa ttttgacagc ccacatggca   79020
ttccacttat cactggcatc cttccactct ttcgaaaact cctccagtct gctggcgtta   79080
tcctccgtca gctcgacttt ttccagcagc tccttgccga gatgggattc ggttatcttg   79140
cctttgaaaa aatccaggta accttccgca tcatcgctcg cccgaccgac ggcctccacg   79200
aatgccgatt tgccaacggt gttcacactg cggatataaa agtaataatc atggcccggt   79260
ttgatattga tactggcggc tatccagtac agcgccgtac caagataacg cgtgctggtt   79320
tcaacctgtc tgatatccgc aatctgcttt tccgagaacc agaactcaaa ctgtaccgtc   79380
gggtcataaa cggcaagatg cggcgtggcg gttatctgaa aatagcccgg cgtcagctca   79440
atcctcgacg gtgctgccgg tgcggcaatc cggaacgata ccgacgccgg atcgccctgc   79500
tgcccccacg catttaccgc ccggactgtc agcctgtagt tccccagcgc cagttgcgtg   79560
aagcggtatg tggtttccgt cgtccgggcc gtgctgacca gccgctcact gccgtcgtcc   79620
gctgttacgg tcagacggag caggaaactc acgcccttca ccaccttcgg tgtgtcccat   79680
cgcgccagca cctgatattc cccgctgtct gcagtgactt ctgcggtcag gtgctgcacc   79740
gctggcggcg tgacaccatt caccgtgcca ctctgttcgc cgtcaaagtg cgccccgtta   79800
tccacgatgg cctctttttc cggcacatgc tgcacggcgg tgatggcata cgtgccgtcg   79860
tcgttctcac ggatactcac gcagcggaac agtcgctggc gcagcgtcgg cagcttcagc   79920
tcccatacgc tgtattcagc aacaccgtca ggaacacggc tcacttttac cttcacgccg   79980
tcggtgacgg actgaacctc cacgctgacc ggattgccac ttccgtcaac caggcttatc   80040
agcgcggtac cggaggatgg cagcgtgatt tcacggtcga gcgtcagcgt ccgggtctgg   80100
ctgttcaccg ccagcacacg accaccggtg ctgataccgg catagtcatc atcgcagatt   80160
tcaataacat cgcccggtac atggcgaagc ccttctgcgc cgacgctgaa atccacggtc   80220
tgcgtttcca gcagttctgt tttaatcagc cacagcccgg cgcggtgtgc ctgccccgg    80280
ctggtacagc caaaggcatc catcttcgta acattacgac cgtaacgggc aatggcctgc   80340
gtatcttcaa caagctctgt cgccgtctcc cagccgttgt tcgggtcaat ccagttcacc   80400
tcaacggcat tatggcggtc cttcagggcg ctgaagctgt agcggaacgg cgcgccatca   80460
tccggcatca ccacattact gcggttatag gtccacgtct tatccgacgg tcggtcctgc   80520
acgaacgtca gcgtctgccc gttccatacc ggcatacagc gcatcgccga gcagaaatcg   80580
ctgagcacat cccacgcctt acgctgtgtg gtcaggtacg cattacaggt gatgcgcggc   80640
tccgtgccgc caaagccgtc cggcactgac tggtcgcagt actggccgat gacatacagc   80700
gcccatttat ccacatccgc cgcaccaaga cgtttcccca tgccgtagcg cggatgggtc   80760
agcatatccc acagacacca ggccatgttg ttgctgtatg ccggtttaaa cgttccgtcc   80820
cagataccgc tgtattgccg cgtctgcggg ttatagttcg acggcacctg cagaatacgc   80880
ccgcgcagat gataattacg gctcacctgc tggctgccga actgctccga gtccacctgc   80940
acgccgacca gtgccgtgtt cgggtagcac tgtttcacat cgatgatttc agtgtatgac   81000
```

```
gaccagagcg ttttgttctg cagctggtct gtggtgctgt ccggcgtcat cctgcgcatc   81060
cggatattaa acgggcgcgg cggcaggtta cccatcacca ccgaggccag atactgcgag   81120
gtggttttgc ccttaatggt gatgtctttt tccgtcaccc agccaccgtt acgttgtatc   81180
tgaaccagca ggcggacttc cgacggattc ctgtcaccct ttgaggtggt ttccaccagt   81240
gcctgtacac cgaaggtaaa gcgcagacgg tcgatgtttg cagacgtaat ggtgcgggtg   81300
atcggcgtgt catatttcac ttccgtaccc agcaccgtct cggagccgga ggattcaaat   81360
ccctccggcg gagtctgctc ctgctcacca gcccggaaca ccaccgtgac accggatatg   81420
ttggtattcc cctcagtgtc cagcaccggc gtactgttca gcagcacgct ttttaagcca   81480
tccaccggac cttcaatcgg cccttcgctg atggcatcga tcacactcag caactgcgtg   81540
gacttcaggt tgtccttcgc ttcgcgcggg gtatgcccct tactgcttcc tttacccatt   81600
cctcacgctc cataaatgac aaaaccgccc gcaggcggtt tcacataaaa cattttgcat   81660
cagcgaccaa tcaccacaac ctgaccaccg tccccttcgt ctgccgtgct gatctcctga   81720
gaaaccacgc gtgaccccac gcgcatttcc ccgtacagaa caggcagaac attgccctgg   81780
gcaaccatgt tatccagtga ggagaaatag gtgttctgct taccgttatc cgttgtctgt   81840
atacggggag ttctggcttt cggtgccagc atctgcgcca caccaccgag caccatactg   81900
gcaccgagag aaaacaggat gccggtcata ccaccggccc caatggctgc cccccatgct   81960
gcaagggtgg ctccggcggt aaagaatgat ccggcaatgg cggcagcccc caggacaatc   82020
tggaatacgc cacctgactt ggccccggcg actctgggaa caatatgaat tacagcgcca   82080
tcaggcagag tctcatgtaa ctgcgccgtt aacccgacg tgctgacgtc ccgcccggca   82140
atccgtacct gataccagcc gtcgctcagt ttctgacgaa cgccgggag ctgtgtggcc   82200 agtgcccgga tggcttcagc ccccgttttc acacgaaggt cgatgcggcg accaaatcgt   82260
tgtaaatccc cgtaaaggca gatgcgcgcc atgcccggtg acgccagagg gagtgtgtgc   82320
gtcgctgcca tttgtcggtg tacctctctc gtttgctcag ttgttcagga atatggtgca   82380
gcagctcgcc gtcgccgcag taaattgcgg cgtgattcgg cactgatgaa ccaaaacagc   82440
acagcagcac atcgcccggc tgtgccgctg acaacggcac ctgatacagc cccgtcgcct   82500
ccagattatc cagatagaga ttctggccgt tacgccacca gtcatcctca cgatgaaagt   82560
ccggcatctc aatccccgcc agatgataag catcccggaa cagtgtgtaa cagtccgtca   82620
caccgtgctc aaagcgccgc ccggtgagat gcggcacaca gcggaactta tgaatcgtcc   82680
cccggcagac cagccaccac ggcaaatcac tctgcacctg cagccgccgg tcggcctcac   82740
tcagccaggg cagaccaccg gggtggctgt ggaccagcgc cacaatctca ccctgcattt   82800
ctgcctgcag ccagtcttcc ggcgacatac ggaaatagcc tccggctcac cggagatatt   82860
cacgcagggg aaatatcttt cccctccgg cgtgcttacc acgaagccgc acgactccgc   82920
tggcgcacat cgccgggcgt gcgccagaat cgctgattct gtctgtgtca tgggatttac   82980
tgcgaaagtt tgttaatgga aaggaagccg ccaaagttgc cgacgttatt gcggaactta   83040
caaccgctca ggcatttgct gcatttatcc ttcgtgatat cggacgttgg ctggtcatat   83100
tcatccgcga cagccggacc gctataaccg cactcgtcac cgcgataggt ccaggtcag   83160 gtgttggcca gcatgatacg tccggaaaaa acagcgccat ccgtttccgt cggcgtggac   83220
agtacaaagg aggcactcac cgcgctcagt tcgctgcact gctcaatgcg cagcggctg   83280 atcacctcct gctccggatc ggcgtaactg tttccgttga cgaagttcac cgcatccaga   83340
aaacgggcgt aaaccttacg ccggaccacc gttccgccga ccagactctg catatcttcc   83400
```

```
gccatcccgg tgaccatacc gtacaggtta gaaaccgtca gcgtggggcg cgtactggtg    83460
cctttgccat tcagttcaaa accgctcccc tgaatgggat acggctgata ctgtcgcccc    83520
tgccaggtga ccggctcacc tttttcgttc tgctcattac agaaaaaata acgttctcca    83580
ccgacctctg tcaggtcgat ttcccagagc accacgctgg ccgactgctc cgcacgggtg    83640
cattcattca gtgtttcctg ccggatatcc tgcatcagtt caccacctgt tcaaactctg    83700
cgctgaactc aacacgcagc atactgaccc gcgacgacca ttttgcgcag gtcaccttta    83760
tctgccgcca ctcataaggc ggcgtccaca gaaaggattt ccagccccg tgctcttcca    83820 gaaacgactc cagtaccgtg gcctcctcac gggggacaga aagcgtcacg ctgtacgttt    83880
tcaggttggc attcagcccg gcaggcgctc gctgagaata gccatcacca aagcgcacct    83940
ttcttacaga agggaccgaa gccacatcca taccgggttt cactttccag cggaaggtct    84000
tcatcgtcca cctccggaga acaggccacc atcacgcatc tgtgtctgaa tttcatcacg    84060
ggcacccttg cgggccatgt catacaccgc cttcagagca gccggaccta tctgccgtt    84120 cgtgccgtcg ttgttaatca ccacatggtt attctgctca aacgtcccgg acgcctgcga    84180
ccggctgtct gccatgctgc ccggtgtacc gacataaccg ccggtggcat agccgcgcat    84240
cagccggtaa agattcccca cgccaatccg gctggttgcc tccttcgtga agacaaactc    84300
accacggtga acaatcccg ctggctcata tttgccgccg gttcccgtaa atcctccggt    84360
tgcaaaatgg aatttcgccg cagcggcctg aatggctgta ccgcctgacg cggatgcgcc    84420
gccaccaaca gccccgccaa tggcgctgcc gatactcccg acaatcccca ccattgcctg    84480
cttaagcaga atttctgtca tcatggacag cacggaacgg gtgaagctgc gccagttctg    84540
ctcactgccg gtcagcatcg ccgccatatt ctgtgcaata ccatcaaagg tctgcgtggc    84600 tgcactttt acctgcgaca tactgtccgt ggcgctctct tcccactcac tccagccgga    84660
cttcaggcct gccatccagt tcccgcgaag ctggtcttca gccgcccagg tcttttctg    84720 ctctgacatg acgttattca gcgccagcgg attatcgcca tactgttcct tcaggcgctg    84780
ttccgtggct tcccgttctg cctgccggtc agtcagcccc cggcttttcg catcaatggc    84840
ggcccgtttt gcccgttgct gctgtgcgaa tttatccgcc tgctgcgcca gcgcgttcag    84900
gcgctcctga tacgtaacct tgtcgccaag tgcagccagc tggcgtttgt actccagcgt    84960
ctcatcttta tgcgccagca gggatttctc ctgtgcagac agctggcgac gttgcgccgc    85020
ctcctccagt accgcgaact gactctccgc cttccacaaa tcccggcgct gctggctgat    85080
tttctcattt gctccggcat gcttctccag cgtccggagt tctgcctgaa gcgtcagcag    85140
ggcagcatga gcactgtctt cctgacgatc gcccgcagac accttcacgc tggactgttt    85200 cggcttttc agcgtcgctt cataatcctt tttcgccgcc gccatcagcg tgttgtaatc    85260
cgcctgcagg attttcccgt ctttcagtgc cttgttcagt tcttcctgac gggcggtata    85320
tttctccagc ggcgtctgca gccgttcgta agccttctgc gcctcttcgg tatatttcag    85380
ccgtgacgct tcggtatcgc tctgctgctg cgcattttg tcctgttgag tctgctgctc    85440
agccttcttt cgggcggctt caagcgcaag acgggccttt tcacgatcat cccagtaacg    85500
cgcccgcgct tcatcgttaa caaaataatc atccttgcgc agattccaga tgtcgtctgc    85560
tttcttatac gcagcctctg ccttaatcag catctcctgc gcggtatcag gacgaccaat    85620
atccagcacc gcatcccaca tggatttgaa tgccgcgca gtcctgtctg cccaggtctc    85680
cagcgtgccc atgttctctt tcaggcggcg ggtctggtca tcaaacccctt tcgttgcggc    85740
```

```
ctcgttcgcc gcctgcaatg ccccggcttc atcgccggaa cgctgcaact gagcaacata   85800
cgcaatctgc tccgccgaca cgttatggaa ctggcgagcc atcgccgtca gccccgacgt   85860
cgggtctgtg gtcagcttcc cgaaggcttc agcgaccttg tccacctcca cgccggatgc   85920
agaggagaaa cgcgccacac tctggctgat ggacgcaatc tgagcctcac cgcttacccc   85980
cgccttaacc agtgcgctga gtgactcgct ggtctggtta acgtcagcc ctgccgcctg    86040 cccggctctg gacaggacca gcatacgatc tgccgtcagt cccgcctgat tgccggaaag   86100
gaccagcgtt ttgttgaaat cggacagggt tgagttgccc tgataccagg catacgccag   86160
cgcaccggtc gccaccgcca gcgaggtggc ccccaccatc ggcagggtga tcgcaccggc   86220 aagcccctg aacatgggga tcatcccgcc gaaggagtcc ttcacctgcc ccccctgttg    86280
cagcaggatc agccacggac tttgcccgcc tgcaagctgc gtggccacgt cggtgaactg   86340
tgcaggcagc atacgcatgg cggctttata ctgcccgacg gaaatccccg ctttctgtgc   86400
agccagcgcc tgtcggctca gcgactgttc aacgactgcc gctgttttt tcgcatcact   86460 ttccgtacca gaaaaatgac gcctgactct ggccatctgc tcgtcaaatc tggccgcatc   86520
cagactcaaa tcaacgacca gatcgcctac cggttcagcc ataccggact cctcctgcga   86580
tcccttctga tactgtcatc agcattacgt catcctccgt catgtccgcc acatccgggg   86640
aagcggggat aacttcattc ccgtccgggc caaagcggac acctccggca agccctgccg   86700 cttttctgcat cagcacatca tcttcaggct cttcgtcagc ctcgcgccgg ttcagcagac   86760
tgaaatccag cggatgcata tccggatcgc tgaaaaacag gctgagcacg gtgtacgtca   86820
gcccggaaaa gtgcatatcc agcagaacat catgaaaata atgggtactg taaaagcggt   86880
gccagtcggc atactccgtg gatgacatcc cggcaagcat ggcacgccag tcgggtcgcc   86940
ccatctcacg cgccagtttc agggcaaaac tcagctcacc gtcgaacact ttcccgcaga   87000
aacaggctct gcgggcccgg cgtcctctgt ctgttcaggg gcattattca ccacaaactc   87060
atacatacca gacagccggt acaccacgtt ttcagcatga gaaattgcct ccgtgggcca   87120
ggtggtaagc acttcctgct caatctgttt aacggcttca ttcatggacg gcatctgcgt   87180
cttctgcgga tggttatgcc acagggacat cgccaccaga aacgcgccgg ttctgatggc   87240
gtcttccaca gtaaacttcc ggttgctgtc tgactccgcc tgttctgcct gccgtttcat   87300
cagggcgaga tgctcaatgc gctgcagggc tgacagttca gaaagcgtga cggtcacacc   87360
gttatgttca aatgattcgg ttttcaggaa catcgctgac tctccggatt aactggcggt   87420
gacggtaatt tctgcaaccg cagcaaactc accattaccg gatacaaccg gaatgttgac   87480
cttgcctgca gcaacgccgt tcacggtgat ggtcatacca ctgaccgaca cggtggcttt   87540
tgttttatcc gcagacaccg cacgaaagct cttgtcggtt acgccctccg gctggaaggc   87600
cacggtcagc gtggtgctct gccctttcac caccgaggtg ctggcaggcg tcacggtcat   87660
gccggttgcc gctgttaccg tgctgcgatc ttctgccatc gacggacgtc ccacattggt   87720
gactttcacc gtgcgggtga tcacttcctt cgccgtcacc gccttaccga tactgctgac   87780
ccagccacgg aacacatcga ccgtgccgtt cgggaagcgg attttatagg cacgggtatc   87840
gccttcatta aaccacgcca gcagcgcctg ctgcccctgc tctccgggca tccacgccag   87900
cgtgaagctg gtatctccgg cagatttctg cccctgcccg gtcgcagtcc agtctgcatc   87960
ttcatcatcg agatagctgt cgtcatagga ctcagcggtc agttcgccgg gcgtcaggtc   88020
tttaactttt gccagacgcg accagtcaac gtctgaaagc ggattcgcgt aagggtcacc   88080
gctcccctta taaacccaca gggtggtccc ggcacctttc accggcattg taggatttgg   88140
```

```
tacaggcata gcgtcctcac atttcatagg taatgacata agtcagatcg gctgaactcc   88200
acaagcccgc atcatcgtcg cgccggtagt catagccgct ggccaccata ctggtgatca   88260
aatctgacag tgccgggata tcgctcatca ccggataaat ccgggactcc atccacgcat   88320
ccagctctga atccggcacc tgagcaggca ggaaaacttc gatatgcagc tccgcctgcc   88380
aggtatcgct gtccagctct tcgcccgtgt attcagcgcc ggtgagataa acggcaactg   88440
ccggaaaatc cgcctcatca aaaacagcgg ggcgaccatc aaaaaacgtc gccccggtgt   88500
catgcttctc cagtgcatcc agtacggctg cacggagttc agtatgtttc atcgctttat   88560
taccatcctc agttgatgct gcagcgcata gcccagctct ttcggaagac gttcacgccg   88620
tatccgctca atattttgtt taaacgccgt ggtcagcggc accgccatcg ggattttcac   88680
cacatcaatg gggtaacggt ttttcccagc cacacgctgc atgacatgcc accggccatt   88740
tttcagttgc tgaataaacg cgccgggaat acgacggtta cccaccacaa gcacgctgcc   88800
gccacctttc agggatgaac gctgcccctt tttacgacgc ctgcggcgcg aaaggacaac   88860
ccgcgcatta cccagcttga ttacgggcaa atcccccccgg ttaactttga ttctggcctg   88920
cggattttg accgtggccc ttttcagcct ggccttttcc tttaccagtt ccgcgtac    88980
ctttgtctca cgggcaacct gtgacgccga ctgcgatatc gcggatgaag caacgcggtt   89040
aatggccatt gcggcggcac caggcaccgc cgttttgctg atacggctga ggttttcaac   89100
ggcctgctca agaccttta tggccataca tccccctttc agcggcgacg gttaacggca   89160
ggcggtacgc cccgtccaag ccagagatga caacttccgc catcatccgg cgaaacccga   89220
tctacccaga aattttcctc accgatggtc agcgtgtctc cacgccgcag ctgccgcacc   89280
tcatcagtcc ggacaaacag ggacgggctg gagccttcaa cgcgcacgcc ctgtccggca   89340
tagctgatat tttcagggtc atcaaaaaca ccacgtatca ccgcacctga ctgctcaccg   89400
gatgtaatgg tggctgacgt tcccatgtac ccgcgtatcg tttcatcggc gcgggcaatg   89460
gcagcatcga acaggttatc gaaatcagcc acagcgcctc ccgttattgc attctggcca   89520
ggccgcgctc tgtcatttcg gctgccacac cggcagagac acgaaacgcc gttcccggca   89580
gcacaaatgc cacaggttca tcccgcgtgg cgtgaagtgc atcagtatgc agcttcacca   89640
gtgccacgac cgtgaccagt tcagacgtat ccagaatcac ggtatccggc tgcgctgatc   89700
ccacctcatt ttcatgtccg gtcagcacat tttcccggct gagaggggtg tcctgaccgg   89760
cagtttcatc cgtgtcatca agctcctctt tcagctctgc cacacggagc gccagttctt   89820
ctttcgtccc cgtcaggctg acatcacggt tcagttgttc acccagcgag cggagacggg   89880
caatcagttc atctttcgtc atggactcct ccacagagaa acaatggccc gaagggcca    89940
tgattacgcc agttgtacgg acacgaactc atcagggtca gccagcagca tcagcggtgc   90000
tgactgaatc atggtgaact cacgcgccgg atcgccggtg gtcacccagt ttttcgggta   90060
acgggcagag gcgttaatgc cttcgcgctg tgcgtccgca tcctgaatgc agccataggt   90120
gcgcagaccg cgtgcctgag tgttccccag caccatcgtg ttgtccggca ggaagttctt   90180
tttgacgccg ttttccacgt actgtccgga atacacgacg atggccacat cgccatacat   90240
cccctatag acaccgcctt tgcccaggtc tttcaccgct gtctccagct cggaattaga   90300
gccacgacgg gtatccagct tctccttgac ggctttgaag gaacggaaca gcgcccagcc   90360
tttcggatca aacacgatga tattcaccac accgctggcg ttcagcgcgt aggcttcgat   90420
atcgtcggtc gggtcatacg tggacttgtc acgcttgctc cactccgtgc cgccggactg   90480
```

```
cgtgatgtta ttctcctcac tgcggcccat atccacctca accggatcga aggcttcacc    90540
ggtcatggtg tatttgccct taagcacggc agaaactgcc tgcatctctt cgacctgagc    90600
aatggccagc tcttcgtcac gcatgttctg catgatgatg cgacggcggc ggtaagccgg    90660
gtccgccaga ttctgcggat cttcatccgg caggcgacgc agggtcatct gcggattcac    90720
ttcatgcttc ggcttgacat atcccggcgt aaattcagag gtggagccgc cacgggaacg    90780
gataacctca ccggaaacaa tcggcgaaac gtacagcgcc atgtttacca gtcccggaat    90840
ttgtgagaga tagactttct ccgtggtgaa gggatagctc tcacggaaaa agagacgcag    90900
aaacagcgga tcaaacttaa atttctgctc atttgccgcc agcagttggg cggttgtgta    90960
catcgacata aaaaaatccc gtaaaaaaag ccgcacaggc ggcctttagt gatgaagggt    91020
aaagttaaac gatgctgatt gccgttccgg caaacgcggt ccgttttttc gtctcgtcgc    91080
tggcagcctc cggccagagc acatcctcat aacggaacgt gccggacttg tagaacgtca    91140
gcgtggtgct ggtctggtca gcagcaaccg caagaatgcc aacggcagca ccgtcggtgg    91200
tgccatccca cgcaaccagc ttacggctgg aggtgtccag catcagcggg gtcattgcag    91260
gcgctttcgc actcaatccg ccgggcgcgg ttgcggtatg agccgggtca ctgttgccct    91320
gcggctggta atgggtaaag gtttctttgc tcgtcataaa catcccttac actggtgtgt    91380
tcagcaaatc gttaacggca tcagatgccg ggttacctgc agccagcggt gccggtgccc    91440
cctgcatcag acgatccagc gcagtgtcac tgcgcgcctg tgcactctgt ggtgctgcgg    91500
ccagaatgcg gcgggccgtt tcacggtca taccgggggt ttctgccagc acgcgtgcct    91560
gttcttcgcg tccgtgagcc tcctcacagt tgaggatccc cataatgcgg ctgttttctg    91620
ccgcaaccgc tgcggtgatc tgcgcgttca cgtccggctg cgccgcgctg gcgttctcgc    91680
cctccgtcgc tggcaccacg tcagtaacgt cagcctgcga agcagtggct gaaacagttg    91740
ttgattgagt ctctttggtc attcgccctc ctgagagacg ggatttacgt gcatccagtg    91800
catcacgcat gacggtgatc gcatcggtgc tgttaacaag ttcatcagcc agtccggcat    91860
caatggcctc ctgaccgctg tacactgcag cctcggtatc cagcacaacc tgcacggaca    91920
ggccggtata tgccgacacc ttctgcgcaa acatctggcg ggttgcgtcc atccgggact    91980
gcagtgtctc ccggacgtca tccggaagat ggctgtaggg gttgccatcc accttatggc    92040
tgccgctgta atcagcgtg atttccacac cctgtttctc cagcgcagca ccgtaattac    92100
tgtgagccat catgacgccg atggagcctg tccgggcggt ctgcgtgacc agacgccggg    92160
aggcggcact ggcaagcaac tgacctgcac tgcagttcat gtcgttggca agcgcccata    92220
ccggttttat gtcacgcaca cgggcgatga tgtcagcgca gtcaaatgcc cccgccacca    92280
tcccgccggg cgtgtccata tcgagcagaa tgccgtccac catcggatcg ctggcagcct    92340
gttgcagacg ggcgataatg ccgttgtaac cggtcatccc cgagtacggc tgcagcgccc    92400
gcgtccggct gaccagcgtg ccggacaccg gcagcacggc gatgccgttc atgacctgat    92460
aactgcgggc ctgtcgtggt ccgtcatcat caccggataa tgccagcgtc gcgagtgcct    92520
cctgggcagt caggctgtcg ccggacaccg catccgtcag gctgctgatc ccaagctggc    92580
ctgcaagcgc acaaaagaaa acccgcgcat aggcgggttc aagcatcagc ggctcattaa    92640
aggccatgct ggcaatatgc gggagattac gcagctctgc tgtcactctt ctcctcctct    92700
gttgattgtc gcagcccgga ttcaaatgct gcagccgccc aggcgggcgg tttaagaccg    92760
gctgcacggc gctccatcgt ttcacggacc tgctgggcaa aaatttcctg atagtcgtca    92820
ccgcgttttg cgcactcttt ctcgtaggta ctcagtccgg cttctatcag catcaccgct    92880
```

```
tcctgaactt ctttcagacc atcgatggcc atacgaccgg agcctatcca gtcgcagttc   92940
ccccaggcac tgcgggcttc ctgaaaactg aagcgcgctt ttgaaggtaa cgtcaccacg   93000
cggcgaacga tggcctcttc cagccagcac agaaacatct ggctcgcctg acgggatgcg   93060
acgaattttc gccgcccat aaagtacgcc cacgactcgt tcgcactggc ccgtgccgtg    93120
gagtagctca tctgggcgta attccgggaa agctgctcat acgagacacc cagcccggca   93180
gcgatatacc gcagcagtga ctgctcaaac acggagtagc cgttatccgt atcctgagcc   93240
gtctgcaggt tcagtgagtc acccggcatc aggtgcggta cttttgcgcc tcccagccgg   93300
accggcgctg cggcgtaata cgcggcaatt tcaccaatcc agccggtcag cctttcccgc   93360
tgctcctgac tgttcgcgcc cagaataaaa tccatcgctg actgcgtatc cagctcactc   93420
tcaatggtgg cggcatacat cgccttcaca atggcgctct gcagctgcgt gttctgcagc   93480
gtgtcgagca tcttcatctg ctccatcacg ctgtaaaaca catttgcacc gcgagtctgc   93540
ccgtcctcca cgggttcaaa aacgtgaatg aacgaggcgc gcccgccggg taactcacgg   93600
ggtatccatg tccatttctg cggcatccag ccaggatacc cgtcctcgct gacgtaatat   93660
cccagcgccg caccgctgtc attaatctgc acaccggcac ggcagttccg gctgtcgccg   93720
gtattgttcg ggttgctgat gcgcttcggg ctgaccatcc ggaactgtgt ccggaaaagc   93780
cgcgacgaac tggtatccca ggtggcctga cgaacagtt caccgttaaa ggcgtgcatg    93840
gccacacctt cccgaatcat catggtaaac gtgcgttttc gctcaacgtc aatgcagcag   93900
cagtcatcct cggcaaactc tttccatgcc gcttcaacct cgcgggaaaa ggcacgggct   93960
tcttcctccc cgatgcccag atagcgccag cttgggcgat gactgagccg gaaaaaagac   94020
ccgacgatat gatcctgatg cagctggatg gcgttggcgg catagccgtt attgcgtacc   94080
agatcgtctg cgcgggcatt gccacgggta agttgggca acagggctgc atccacactt    94140
tcactcggtg ggttccacga ccgcaactgc cctccaaatc cgctgccacc gccgtgataa   94200
ccggcatatt cgcgcagcga tgtcatgccg tccggcccca aagggtggg aatggtgggc    94260 gttttcatac ataaaatcct gcaggtcccc tgcgtcgctg tgtcatgccg gtctgcactt   94320
ccagctctgc aatatatttt ttcaggtcag acacggaagt ggccgtaaac tccacccttc   94380 gtccgtctt ctgtactgtt gccacccgtt tacctgtcat caggtcatgc agtgccgcac     94440
gggcagcggc aagttcttcc tgtcgcgtca ttcatcctct ccggataagg cacgggcgta   94500
atctgccagt gttttcttgt tggttgctgc accatcctct tcctgcaggc tcgccagcag   94560
cgcactgaga tccagctgcc agcgggaaat actgatgcgc agcgccgcca gcgcataaac   94620
gaagcagtcg agtgcctcat tgcgtcgctt tttgctgtcc cacagtattt ttttcctgcc   94680
atccacccat ttttcgacct gctcttcagc agtcagctgc tgcgcttcgg tcagatcaaa   94740
aatatccggg ttattcggga agtgaacggc accgggaagc ggttcatccc cttccggcgt   94800
cagtgtgaag cggttataaa tctgctcttt cgcggtatcc gtaccgattt cggtaaggta   94860
aaccccgttt ttgtttcgct tacgtggcat gctggccacc ggctttccgt agacggatgc   94920 cccctttaatg gggatcaccc ggaacagccc atgttttttc gagcgttcat acacaatggt   94980
cgggtcaatc ccgccagtat cccagcagat acggatatc gacatttctg caccattccg    95040
gcgggtatag gttttattga tggcctcatc cacacgcagc agcgtctgtt catcgtcgtg   95100
gcggcccata ataatctgcc ggtcaatcag ccagctttcc tcacccggcc cccatcccca   95160
tacgcgcatt tcgtagcggt ccagctggga gtcgataccg gcggtcaggt aagccacacg   95220
```

```
gtcaggaacg ggcgctgaat aatgctcttt ccgctctgcc atcacttcag catccggacg    95280
ttcgccaatt ttcgcctccc acgtctcacc gagcgtggtg tttacgaagg ttttacgttt    95340
tcccgtatcc cctttcgttt tcatccagtc tttgacaatc tgcacccagg tggtgaacgg    95400
gctgtacgct gtccagatgt gaaaggtcac actgtcaggt ggctcaatct cttcaccgga    95460
tgacgaaaac cagagaatgc catcacgggt ccagatcccg gtcttttcgc agatataacg    95520
ggcatcagta aagtccagct cctgctggcg gatgacgcag gcattatgct cgcagagata    95580
aaacacgctg gagggtcat ccggcgtcca tttgaggcca aacggcgtct ctttgtcgcc    95640
aaatttaaga tactgctcct ccccgcaatg cgggcaggca acatgaaaac gcataaaatg    95700
cggggattca ctggctgcac gctcaatctg acaggtgcct ctcacttttg gcgtggagcc    95760
acggatggac tttggccaga ccgagccttc aatacgcttg tcacccagga acgtcggaga    95820
gccttcctgt tcaatatcat catcaaaagc agcaagttca tcataacccg ccacatccac    95880
cgacttttca cggtagtttt ttgccgcttt accgcccagg caccagaagc cacgcccatt    95940
agtgaaacgc ttcatggtga gcgtgttatc ccggtgcttt ttgccatacc acggggccag    96000
cgccagcagc gacggaatat cacgaatagt cggctcaacg tgggttttca taaagttctc    96060
ggcatcacca tccgtcggca accagataag ggtgttgcgc tgcttatgct ctataaagta    96120
ggcataaaca cccagcagca ttttggaata accgacacgg gcagacttca ccacattcac    96180
ctcacggatg tagtcgctgc ccatcgcatt catgatggcc cgctgaaagg gcagtgtttc    96240
ccagcgccct tcctggtatg cggattcttt cgggagatag taattagcat ccgcccattc    96300
aacggcggtc tgtggctccg gcctgaacag tgagcgaagc ccggcgcgga caaaatgccg    96360
cagcctgtta acctgactgt tcgatatatt cactcagcaa ccccggtatc agttcatcca    96420
gcgcggctgc tttgttcatg gctttgatga tatcccgttt caggaaatca acatgtcggt    96480
tttccagttc cggaaaacgc cgctgcaccg acaggggag cccgtcgaga atactggcaa    96540
tttcacctgc gatccgcgac agcacgaaag tacagaatgc ggtttccacc acttcagcgg    96600
agtctctggc attcttcagt tcctgtgcgt cggcctgcgc acgcgtaagt cgatggcgtt    96660
cgtactcaat agttcctggc tggagatctg cctcgctggc ctgccgcagt tcttcaacct    96720
cccggcgcag cttttcgttc tcaatttcag catccctttc ggcataccat tttatgacgg    96780
cggcagagtc ataaagcacc tcattaccct tgccaccgcc tcgcagaacg ggcattccct    96840
gttcctgcca gttctgaatg gtacggatac tcgcaccgaa aatgtcagcc agctgctttt    96900
tgttgacttc cattgttcat tccacggaca aaaacagaga aaggaaacga cagaggccaa    96960
aaagcctcgc tttcagcacc tgtcgtttcc tttcttttca gagggtattt taaataaaaa    97020
cattaagtta tgacgaagaa gaacggaaac gccttaaacc ggaaaatttt cataaatagc    97080
gaaaacccgc gaggtcgccg cccaggtcgc cgcccgtcaa tcggcccttt agtggagc      97138
```

<210> SEQ ID NO 12
<211> LENGTH: 28
<212> TYPE: DNA
<213> ORGANISM: Artificial Sequence
<220> FEATURE:
<223> OTHER INFORMATION: Polynucleotide sequence used in Examples 1 and
      9

<400> SEQUENCE: 12
gcaatatcag caccaacaga aacaacct                                        28

<210> SEQ ID NO 13

<211> LENGTH: 48502
<212> TYPE: DNA
<213> ORGANISM: Enterobacteria phage lambda

<400> SEQUENCE: 13

```
gggcggcgac ctcgcgggtt ttcgctattt atgaaaattt tccggtttaa ggcgtttccg      60
ttcttcttcg tcataactta atgtttttat ttaaaatacc ctctgaaaag aaaggaaacg     120
acaggtgctg aaagcgaggc ttttggcct ctgtcgtttc cttctctgt ttttgtccgt      180
ggaatgaaca atggaagtca acaaaaagca gctggctgac attttcggtg cgagtatccg     240
taccattcag aactggcagg aacagggaat gcccgttctg cgaggcggtg caagggtaa      300
tgaggtgctt tatgactctg ccgccgtcat aaaatggtat gccgaaaggg atgctgaaat     360
tgagaacgaa aagctgcgcc gggaggttga agaactgcgg caggccagcg aggcagatct     420
ccagccagga actattgagt acgaacgcca tcgacttacg cgtgcgcagg ccgacgcaca     480
ggaactgaag aatgccagag actccgctga agtggtggaa accgcattct gtactttcgt     540
gctgtcgcgg atcgcaggtg aaattgccag tattctcgac gggctccccc tgtcggtgca     600
gcggcgtttt ccggaactgg aaaaccgaca tgttgatttc ctgaaacggg atatcatcaa     660
agccatgaac aaagcagccg cgctggatga actgataccg gggttgctga gtgaatatat     720
cgaacagtca ggttaacagg ctgcggcatt ttgtccgcgc cgggcttcgc tcactgttca     780
ggccggagcc acagaccgcc gttgaatggg cggatgctaa ttactatctc ccgaaagaat     840
ccgcatacca ggaagggcgc tgggaaacac tgccctttca gcgggccatc atgaatgcga     900
tgggcagcga ctacatccgt gaggtgaatg tggtgaagtc tgcccgtgtc ggttattcca     960
aaatgctgct gggtgtttat gcctacttta tagagcataa gcagcgcaac cccttatct     1020
ggttgccgac ggatggtgat gccgagaact ttatgaaaac ccacgttgag ccgactattc     1080
gtgatattcc gtcgctgctg gcgctggccc cgtggtatgg caaaaagcac cgggataaca     1140
cgctcaccat gaagcgtttc actaatgggc gtggcttctg gtgcctgggc ggtaaagcgg     1200
caaaaaacta ccgtgaaaag tcggtggatg tggcgggtta tgatgaactt gctgcttttg     1260
atgatgatat tgaacaggaa ggctctccga cgttcctggg tgacaagcgt attgaaggct     1320
cggtctggcc aaagtccatc cgtggctcca cgccaaaagt gagaggcacc tgtcagattg     1380
agcgtgcagc cagtgaatcc ccgcatttta tgcgttttca tgttgcctgc ccgcattgcg     1440
gggaggagca gtatcttaaa tttggcgaca agagacgcc gtttggcctc aaatggacgc     1500
cggatgaccc ctccagcgtg ttttatctct gcgagcataa tgcctgcgtc atccgccagc     1560
aggagctgga ctttactgat gcccgttata tctgcgaaaa gaccgggatc tggacccgtg     1620
atggcattct ctggttttcg tcatccggtg aagagattga ccacctgac agtgtgacct     1680
ttcacatctg gacagcgtac agcccgttca ccacctgggt gcagattgtc aaagactgga     1740
tgaaaacgaa aggggatacg ggaaaacgta aaccttcgt aaacaccacg ctcggtgaga     1800
cgtgggaggc gaaaattggc gaacgtccgg atgctgaagt gatggcagag cggaaagagc     1860
attattcagc gcccgttcct gaccgtgtgg cttacctgac cgccggtatc gactcccagc     1920
tggaccgcta cgaaatgcgc gtatggggat ggggccggg tgaggaaagc tggctgattg     1980
accggcagat tattatgggc cgccacgacg atgaacagac gctgctgcgt gtggatgagg     2040
ccatcaataa aacctatacc cgccggaatg gtgcagaaat gtcgatatcc cgtatctgct     2100
gggatactgg cggattgac ccgaccattg tgtatgaacg ctcgaaaaaa catgggctgt     2160
tccgggtgat ccccattaaa ggggcatccg tctacggaaa gccggtggcc agcatgccac     2220
```

```
gtaagcgaaa caaaaacggg gtttaccttg ccgaaatcgg tacgatacc gcgaaagagc    2280 agatttataa ccgcttcaca ctgacgccgg aagggatga accgcttccc ggtgccgttc    2340
acttcccgaa taacccggat atttttgatc tgaccgaagc gcagcagctg actgctgaag   2400
agcaggtcga aaatgggtg gatggcagga aaaaatact gtgggacagc aaaaagcgac     2460
gcaatgaggc actcgactgc ttcgtttatg cgctggcggc gctgcgcatc agtatttccc   2520
gctggcagct ggatctcagt gcgctgctgg cgagcctgca ggaagaggat ggtgcagcaa   2580
ccaacaagaa aacactggca gattacgccc gtgccttatc cggagaggat gaatgacgcg   2640
acaggaagaa cttgccgctg cccgtgcggc actgcatgac ctgatgacag gtaaacgggt   2700
ggcaacagta cagaaagacg gacgaagggt ggagtttacg gccacttccg tgtctgacct   2760
gaaaaaatat attgcagagc tggaagtgca gaccggcatg acacagcgac gcaggggacc   2820
tgcaggattt tatgtatgaa aacgcccacc attcccaccc ttctggggcc ggacggcatg   2880
acatcgctgc gcgaatatgc cggttatcac ggcggtggca gcggatttgg agggcagttg   2940
cggtcgtgga acccaccgag tgaaagtgtg gatgcagccc tgttgcccaa ctttacccgt   3000
ggcaatgccc gcgcagacga tctggtacgc aataacggct atgccgccaa cgccatccag   3060
ctgcatcagg atcatatcgt cgggtctttt ttccggctca gtcatcgccc aagctggcgc   3120
tatctgggca tcggggagga agaagcccgt gccttttccc gcgaggttga agcggcatgg   3180
aaagagtttg ccgaggatga ctgctgctgc attgacgttg agcgaaaacg cacgtttacc   3240
atgatgattc gggaaggtgt ggccatgcac gcctttaacg tgaactgtt cgttcaggcc    3300 acctgggata ccagttcgtc gcggcttttc cggacacagt tccggatggt cagcccgaag   3360
cgcatcagca acccgaacaa taccggcgac agccggaact gccgtgccgg tgtgcagatt   3420
aatgacagcg gtgcggcgct gggatattac gtcagcgagg acgggtatcc tggctggatg   3480
ccgcagaaat ggacatggat acccgtgag ttacccggcg ggcgcgcctc gttcattcac    3540
gtttttgaac ccgtggagga cgggcagact cgcggtgcaa atgtgtttta cagcgtgatg   3600
gagcagatga agatgctcga cacgctgcag aacacgcagc tgcagagcgc cattgtgaag   3660
gcgatgtatg ccgccaccat tgagagtgag ctggatacgc agtcagcgat ggattttatt   3720
ctgggcgcga acagtcagga gcagcgggaa aggctgaccg gctggattgg tgaaattgcc   3780
gcgtattacg ccgcagcgcc ggtccggctg ggaggcgcaa aagtaccgca cctgatgccg   3840
ggtgactcac tgaacctgca gacggctcag gatacggata acggctactc cgtgtttgag   3900
cagtcactgc tgcggtatat cgctgccggg ctgggtgtct cgtatgagca gctttcccgg   3960
aattacgccc agatgagcta ctccacggca cgggccagtg cgaacgagtc gtgggcgtac   4020
tttatggggc ggcgaaaatt cgtcgcatcc cgtcaggcga ccagatgtt tctgtgctgg    4080 ctggaagagg ccatcgttcg ccgcgtggtg acgttacctt caaaagcgcg cttcagtttt   4140
caggaagccc gcagtgcctg ggggaactgc gactggatag gctccggtcg tatgccatc    4200 gatggtctga agaagttca ggaagcggtg atgctgatag aagccggact gagtacctac    4260
gagaaagagt gcgcaaaacg cggtgacgac tatcaggaaa ttttgcccca gcaggtccgt   4320
gaaacgatgg agcgccgtgc agccggtctt aaaccgcccg cctgggcggc tgcagcattt   4380
gaatccgggc tgcgacaatc aacagaggag gagaagagtg acagcagagc tgcgtaatct   4440
cccgcatatt gccagcatgg cctttaatga gccgctgatg cttgaacccg cctatgcgcg   4500 ggttttctttt tgtgcgcttg caggccagct tgggatcagc agcctgacgg atgcggtgtc   4560
```

```
cggcgacagc ctgactgccc aggaggcact cgcgacgctg gcattatccg gtgatgatga    4620
cggaccacga caggcccgca gttatcaggt catgaacggc atcgccgtgc tgccggtgtc    4680
cggcacgctg gtcagccgga cgcgggcgct gcagccgtac tcggggatga ccggttacaa    4740
cggcattatc gcccgtctgc aacaggctgc cagcgatccg atggtggacg cattctgct     4800
cgatatggac acgcccggcg ggatggtggc ggggcattt gactgcgctg acatcatcgc     4860
ccgtgtgcgt gacataaaac cggtatgggc gcttgccaac gacatgaact gcagtgcagg    4920
tcagttgctt gccagtgccg cctcccggcg tctggtcacg cagaccgccc ggacaggctc    4980
catcggcgtc atgatggctc acagtaatta cggtgctgcg ctggagaaac agggtgtgga    5040
aatcacgctg atttacagcg gcagccataa ggtggatggc aacccctaca gccatcttcc    5100
ggatgacgtc cgggagacac tgcagtcccg gatggacgca acccgccaga tgtttgcgca    5160
gaaggtgtcg gcatataccg gcctgtccgt gcaggttgtg ctggataccg aggctgcagt    5220
gtacagcggt caggaggcca ttgatgccgg actggctgat gaacttgtta acagcaccga    5280
tgcgatcacc gtcatgcgtg atgcactgga tgcacgtaaa tcccgtctct caggagggcg    5340
aatgaccaaa gagactcaat caacaactgt ttcagccact gcttcgcagg ctgacgttac    5400
tgacgtggtg ccagcgacgg agggcgagaa cgccagcgcg gcgcagccgg acgtgaacgc    5460
gcagatcacc gcagcggttg cggcagaaaa cagccgcatt atgggatcc tcaactgtga    5520
ggaggctcac ggacgcgaag aacaggcacg cgtgctggca gaaaccccg gtatgaccgt    5580
gaaaacggcc cgccgcattc tggccgcagc accacagagt gcacaggcgc gcagtgacac    5640
tgcgctggat cgtctgatgc aggggcacc ggcaccgctg gctgcaggta acccggcatc    5700
tgatgccgtt aacgatttgc tgaacacacc agtgtaaggg atgtttatga cgagcaaaga    5760
aaccttacc cattaccagc cgcagggcaa cagtgacccg gctcataccg caaccgcgcc    5820
cggcggattg agtgcgaaag cgcctgcaat gaccccgctg atgctggaca cctccagccg    5880
taagctggtt gcgtgggatg gcaccaccga cggtgctgcc gttggcattc ttgcggttgc    5940
tgctgaccag accagcacca cgctgacgtt ctacaagtcc ggcacgttcc gttatgagga    6000
tgtgctctgg ccggaggctg ccagcgacga gacgaaaaaa cggaccgcgt ttgccggaac    6060
ggcaatcagc atcgtttaac tttacccttc atcactaaag gccgcctgtg cggctttttt    6120
tacgggattt ttttatgtcg atgtacacaa ccgcccaact gctggcggca atgagcaga    6180
aatttaagtt tgatccgctg tttctgcgtc tcttttttccg tgagagctat cccttcacca    6240
cggagaaagt ctatctctca caaattccgg gactggtaaa catggcgctg tacgtttcgc    6300
cgattgtttc cggtgaggtt atccgttccc gtggcggctc cacctctgaa tttacgccgg    6360
gatatgtcaa gccgaagcat gaagtgaatc cgcagatgac cctgcgtcgc ctgccggatg    6420
aagatccgca gaatctggcg gacccggctt accgccgccg tcgcatcatc atgcagaaca    6480
tgcgtgacga agagctggcc attgctcagg tcgaagagat gcaggcagtt tctgccgtgc    6540
ttaagggcaa atacaccatg accggtgaag ccttcgatcc ggttgaggtg gatatgggcc    6600
gcagtgagga gaataacatc acgcagtccg gcggcacgga gtggagcaag cgtgacaagt    6660
ccacgtatga cccgaccgac gatatcgaag cctacgcgct gaacgccagc ggtgtggtga    6720
atatcatcgt gttcgatccg aaaggctggg cgctgttccg ttccttcaaa gccgtcaagg    6780
agaagctgga tacccgtcgt ggctctaatt ccgagctgga gacagcggtg aaagacctgg    6840
gcaaagcggt gtcctataag gggatgtatg gcgatgtggc catcgtcgtg tattccggac    6900
agtacgtgga aaacggcgtc aaaaagaact tcctgccgga caacacgatg gtgctgggga    6960
```

```
acactcaggc acgcggtctg cgcacctatg gctgcattca ggatgcggac gcacagcgcg   7020
aaggcattaa cgcctctgcc cgttacccga aaaactgggt gaccaccggc gatccggcgc   7080
gtgagttcac catgattcag tcagcaccgc tgatgctgct ggctgaccct gatgagttcg   7140
tgtccgtaca actggcgtaa tcatggccct tcggggccat tgtttctctg tggaggagtc   7200
catgacgaaa gatgaactga ttgcccgtct ccgctcgctg ggtgaacaac tgaaccgtga   7260
tgtcagcctg acgggacga aagaagaact ggcgctccgt gtggcagagc tgaaagagga   7320
gcttgatgac acggatgaaa ctgccggtca ggacacccct ctcagccggg aaaatgtgct   7380
gaccggacat gaaaatgagg tgggatcagc gcagccggat accgtgattc tggatacgtc   7440
tgaactggtc acggtcgtgg cactggtgaa gctgcatact gatgcacttc acgccacgcg   7500
ggatgaacct gtggcatttg tgctgccggg aacggcgttt cgtgtctctg ccggtgtggc   7560
agccgaaatg acagagcgcg gcctggccag aatgcaataa cgggaggcgc tgtggctgat   7620
ttcgataacc tgttcgatgc tgccattgcc cgcgccgatg aaacgatacg cgggtacatg   7680
ggaacgtcag ccaccattac atccggtgag cagtcaggtg cggtgatacg tggtgttttt   7740
gatgaccctg aaaatatcag ctatgccgga cagggcgtgc gcgttgaagg ctccagcccg   7800
tccctgtttg tccggactga tgaggtgcgg cagctgcggc gtggagacac gctgaccatc   7860
ggtgaggaaa atttctgggt agatcgggtt tcgccggatg atggcggaag ttgtcatctc   7920
tggcttggac ggggcgtacc gcctgccgtt aaccgtcgcc gctgaaaggg ggatgtatgg   7980
ccataaaagg tcttgagcag gccgttgaaa acctcagccg tatcagcaaa acggcggtgc   8040
ctggtgccgc cgcaatggcc attaaccgcg ttgcttcatc cgcgatatcg cagtcggcgt   8100
cacaggttgc ccgtgagaca aaggtacgcc ggaaactggt aaaggaaagg gccaggctga   8160
aaagggccac ggtcaaaaat ccgcaggcca gaatcaaagt taaccggggg gatttgcccg   8220
taatcaagct gggtaatgcg cggggttgtcc tttcgcgccg caggcgtcgt aaaaaggggc   8280
agcgttcatc cctgaaaggt ggcggcagcg tgcttgtggt gggtaaccgt cgtattcccg   8340
gcgcgtttat tcagcaactg aaaaatggcc ggtggcatgt catgcagcgt gtggctggga   8400
aaaaccgtta ccccattgat gtggtgaaaa tcccgatggc ggtgccgctg accacggcgt   8460
ttaaacaaaa tattgagcgg atacggcgtg aacgtcttcc gaaagagctg gctatgcgc    8520 tgcagcatca actgaggatg gtaataaagc gatgaaacat actgaactcc gtgcagccgt   8580
actggatgca ctggagaagc atgacaccgg ggcgacgttt tttgatggtc gccccgctgt   8640
ttttgatgag gcggattttc cggcagttgc cgtttatctc accggcgctg aatacacggg   8700
cgaagagctg acagcgata cctggcaggc ggagctgcat atcgaagttt tcctgcctgc    8760
tcaggtgccg gattcagagc tggatgcgtg gatggagtcc cggatttatc cggtgatgag   8820
cgatatcccg gcactgtcag atttgatcac cagtatggtg gccagcggct atgactaccg   8880
gcgcgacgat gatgcgggct gtggagttc agccgatctg acttatgtca ttacctatga    8940
aatgtgagga cgctatgcct gtaccaaatc ctacaatgcc ggtgaaaggt gccgggacca   9000
ccctgtgggg ttataagggg agcggtgacc cttacgcgaa tccgctttca gacgttgact   9060
ggtcgcgtct ggcaaaagtt aaagacctga cgcccgcgca actgaccgct gagtcctatg   9120
acgacagcta tctcgatgat gaagatgcag actggactgc gaccgggcag gggcagaaat   9180
ctgccggaga taccagcttc acgctggcgt ggatgcccgg agagcagggg cagcaggcgc   9240
tgctggcgtg gtttaatgaa ggcgataccc gtgcctataa aatccgcttc ccgaacggca   9300
```

-continued

```
cggtcgatgt gttccgtggc tgggtcagca gtatcggtaa ggcggtgacg gcgaaggaag   9360
tgatcacccg cacggtgaaa gtcaccaatg tgggacgtcc gtcgatggca gaagatcgca   9420
gcacggtaac agcggcaacc ggcatgaccg tgacgcctgc cagcacctcg gtggtgaaag   9480
ggcagagcac cacgctgacc gtggccttcc agcggagggg cgtaaccgac aagagctttc   9540
gtgcggtgtc tgcggataaa acaaaagcca ccgtgtcggt cagtggtatg accatcaccg   9600
tgaacggcgt tgctgcaggc aaggtcaaca ttccggttgt atccggtaat ggtgagtttg   9660
ctgcggttgc agaaattacc gtcaccgcca gttaatccgg agagtcagcg atgttcctga   9720
aaaccgaatc atttgaacat aacggtgtga ccgtcacgct ttctgaactg tcagccctgc   9780
agcgcattga gcatctcgcc ctgatgaaac ggcaggcaga acaggcggag tcagacagca   9840
accggaagtt tactgtggaa gacgccatca gaaccggcgc gttctggtg gcgatgtccc    9900 tgtggcataa ccatccgcag aagacgcaga tgccgtccat gaatgaagcc gttaaacaga   9960
ttgagcagga agtgcttacc acctggccca cggaggcaat ttctcatgct gaaaacgtgg  10020
tgtaccggct gtctggtatg tatgagtttg tggtgaataa tgcccctgaa cagacagagg  10080
acgccgggcc cgcagagcct gtttctgcgg gaaagtgttc gacggtgagc tgagttttgc  10140
cctgaaactg gcgcgtgaga tggggcgacc cgactggcgt gccatgcttg ccgggatgtc  10200
atccacggag tatgccgact ggcaccgctt ttacagtacc cattattttc atgatgttct  10260
gctggatatg cacttttccg ggctgacgta caccgtgctc agcctgtttt tcagcgatcc  10320
ggatatgcat ccgctggatt tcagtctgct gaaccggcgc gaggctgacg aagagcctga  10380
agatgatgtg ctgatgcaga aagcggcagg gcttgccgga ggtgtccgct ttggcccgga  10440
cgggaatgaa gttatccccg cttccccgga tgtggcggac atgacggagg atgacgtaat  10500
gctgatgaca gtatcagaag ggatcgcagg aggagtccgg tatggctgaa ccggtaggcg  10560
atctggtcgt tgatttgagt ctggatgcgg ccagatttga cgagcagatg ccagagtca   10620 ggcgtcattt ttctggtacg gaaagtgatg cgaaaaaaac agcggcagtc gttgaacagt  10680
cgctgagccg acaggcgctg ctgcacagaa aagcgggat ttccgtcggg cagtataaag   10740
ccgccatgcg tatgctgcct gcacagttca ccgacgtggc cacgcagctt gcaggcgggc  10800
aaagtccgtg gctgatcctg ctgcaacagg gggcaggt gaaggactcc ttcggcggga    10860
tgatccccat gttcaggggg cttgccggtg cgatcaccct gccgatggtg ggggccacct  10920
cgctggcggt ggcgaccggt gcgctggcgt atgcctggta tcagggcaac tcaaccctgt  10980
ccgatttcaa caaaacgctg gtccttttccg gcaatcaggc gggactgacg gcagatcgta  11040
tgctggtcct gtccagagcc gggcaggcgg cagggctgac gtttaaccag accagcgagt  11100
cactcagcgc actggttaag gcggggtaa gcgtgaggc tcagattgcg tccatcagcc    11160
agagtgtggc gcgtttctcc tctgcatccg gcgtggaggt ggacaaggtc gctgaagcct  11220 tcggaagct gaccacagac ccgacgtcgg ggctgacggc gatggctcgc cagttccata   11280
acgtgtcggc ggagcagatt gcgtatgttg ctcagttgca gcgttccggc gatgaagccg  11340
gggcattgca ggcggcgaac gaggccgcaa cgaaagggtt tgatgaccag acccgccgcc  11400
tgaaagagaa catgggcacg ctggagacct gggcagacag gactgcgcgg gcattcaaat  11460
ccatgtggga tgcggtgctg gatattggtc gtcctgatac cgcgcaggag atgctgatta  11520
aggcagaggc tgcgtataag aaagcagacg acatctggaa tctgcgcaag gatgattatt  11580 tgttaacga tgaagcgcgg gcgcgttact gggatgatcg tgaaaaggcc cgtcttgcgc    11640
ttgaagccgc ccgaaagaag gctgagcagc agactcaaca ggacaaaaat gcgcagcagc  11700
```

```
agagcgatac cgaagcgtca cggctgaaat ataccgaaga ggcgcagaag gcttacgaac   11760
ggctgcagac gccgctggag aaatataccg cccgtcagga agaactgaac aaggcactga   11820
aagacgggaa aatcctgcag gcggattaca acacgctgat ggcggcggcg aaaaaggatt   11880
atgaagcgac gctgaaaaag ccgaaacagt ccagcgtgaa ggtgtctgcg ggcgatcgtc   11940
aggaagacag tgctcatgct gccctgctga cgcttcaggc agaactccgg acgctggaga   12000
agcatgccgg agcaaatgag aaaatcagcc agcagcgccg ggatttgtgg aaggcggaga   12060
gtcagttcgc ggtactggag gaggcggcgc aacgtcgcca gctgtctgca caggagaaat   12120
ccctgctggc gcataaagat gagacgctgg agtacaaacg ccagctggct gcacttggcg   12180
acaaggttac gtatcaggag cgcctgaacg cgctggcgca gcaggcggat aaattcgcac   12240
agcagcaacg ggcaaaacgg gccgccattg atgcgaaaag ccggggggctg actgaccggc   12300 aggcagaacg ggaagccacg gaacagcgcc tgaaggaaca gtatggcgat aatccgctgg   12360
cgctgaataa cgtcatgtca gagcagaaaa agacctgggc ggctgaagac cagcttcgcg   12420
ggaactggat ggcaggcctg aagtccggct ggagtgagtg ggaagagagc gccacggaca   12480
gtatgtcgca ggtaaaaagt gcagccacgc agacctttga tggtattgca cagaatatgg   12540
cggcgatgct gaccggcagt gagcagaact ggcgcagctt cacccgttcc gtgctgtcca   12600
tgatgacaga aattctgctt aagcaggcaa tggtggggat tgtcgggagt atcggcagcg   12660
ccattggcgg ggctgttggt ggcggcgcat ccgcgtcagg cggtacagcc attcaggccg   12720
ctgcggcgaa attccatttt gcaaccggag gatttacggg aaccggcggc aaatatgagc   12780
cagcggggat tgttcaccgt ggtgagtttg tcttcacgaa ggaggcaacc agccggattg   12840
gcgtggggaa tctttaccgg ctgatgcgcg gctatgccac cggcggttat gtcggtacac   12900
cgggcagcat ggcagacagc cggtcgcagg cgtccgggac gtttgagcag aataaccatg   12960
tggtgattaa caacgacggc acgaacgggc agataggtcc ggctgctctg aaggcggtgt   13020
atgacatggc ccgcaagggt gcccgtgatg aaattcagac acagatgcgt gatggtggcc   13080
tgttctccgg aggtgacgga tgaagacctt ccgctgaaaa gtgaaacccg gtatggatgt   13140
ggcttcggtc ccttctgtaa gaaaggtgcg ctttggtgat ggctattctc agcgagcgcc   13200
tgccgggctg aatgccaacc tgaaaacgta cagcgtgacg cttctgtcc cccgtgagga   13260 ggccacggta ctggagtcgt ttctggaaga gcacggggc tggaaatcct ttctgtggac   13320
gccgccttat gagtggcggc agataaaggt gacctgcgca aaatggtcgt cgcgggtcag   13380
tatgctgcgt gttgagttca gcgcagagtt tgaacaggtg gtgaactgat gcaggatatc   13440
cggcaggaaa cactgaatga atgcacccgt gcggagcagt cggccagcgt ggtgctctgg   13500
gaaatcgacc tgacagaggt cggtggagaa cgttattttt tctgtaatga gcagaacgaa   13560
aaaggtgagc cggtcacctg gcaggggcga cagtatcagc cgtatcccat tcaggggagc   13620
ggttttgaac tgaatggcaa aggcaccagt acgcgcccca cgctgacggt ttctaacctg   13680
tacggtatgg tcaccgggat ggcggaagat atgcagagtc tggtcggcgg aacggtggtc   13740
cggcgtaagg tttacgcccg ttttctggat gcggtgaact tcgtcaacgg aaacagttac   13800
gccgatccgg agcaggaggt gatcagccgc tggcgcattg agcagtgcag cgaactgagc   13860
gcggtgagtg cctcctttgt actgtccacg ccgacggaaa cggatggcgc tgttttccg   13920 ggacgtatca tgctggccaa cacctgcacc tggacctatc gcggtgacga gtgcggttat   13980
agcggtccgg ctgtcgcgga tgaatatgac cagccaacgt ccgatatcac gaaggataaa   14040
```

```
tgcagcaaat gcctgagcgg ttgtaagttc cgcaataacg tcggcaactt tggcggcttc   14100
ctttccatta acaaactttc gcagtaaatc ccatgacaca gacagaatca gcgattctgg   14160
cgcacgcccg gcgatgtgcg ccagcggagt cgtgcggctt cgtggtaagc acgccggagg   14220
gggaaagata tttcccctgc gtgaatatct ccggtgagcc ggaggctatt tccgtatgtc   14280
gccggaagac tggctgcagg cagaaatgca gggtgagatt gtggcgctgg tccacagcca   14340
ccccggtggt ctgccctggc tgagtgaggc cgaccggcgg ctgcaggtgc agagtgattt   14400
gccgtggtgg ctggtctgcc ggggacgat tcataagttc cgctgtgtgc cgcatctcac   14460
cgggcggcgc tttgagcacg gtgtgacgga ctgttacaca ctgttccggg atgcttatca   14520
tctggcgggg attgagatgc cggactttca tcgtgaggat gactggtggc gtaacggcca   14580
gaatctctat ctggataatc tggaggcgac ggggctgtat caggtgccgt tgtcagcggc   14640
acagccgggg gatgtgctgc tgtgctgttt tggttcatca gtgccgaatc acgccgcaat   14700
ttactgcggc gacggcgagc tgctgcacca tattcctgaa caactgagca acgagagag   14760 gtacaccgac aaatggcagc gacgcacaca ctccctctgg cgtcaccggg catggcgcgc   14820
atctgccttt acggggattt acaacgattt ggtcgccgca tcgaccttcg tgtgaaaacg   14880
ggggctgaag ccatccgggc actggccaca cagctcccgg cgtttcgtca gaaactgagc   14940
gacggctggt atcaggtacg gattgccggg cgggacgtca gcacgtccgg gttaacggcg   15000
cagttacatg agactctgcc tgatggcgct gtaattcata ttgttcccag agtcgccggg   15060
gccaagtcag gtggcgtatt ccagattgtc ctggggggctg ccgccattgc cggatcattc   15120
tttaccgccg gagccaccct tgcagcatgg ggggcagcca ttggggccgg tggtatgacc   15180
ggcatcctgt tttctctcgg tgccagtatg gtgctcggtg gtgtggcgca gatgctggca   15240
ccgaaagcca gaactccccg tatacagaca acggataacg gtaagcagaa cacctatttc   15300
tcctcactgg ataacatggt tgcccagggc aatgttctgc ctgttctgta cggggaaatg   15360
cgcgtggggt cacgcgtggt ttctcaggag atcagcacgg cagacgaagg ggacggtggt   15420
caggttgtgg tgattggtcg ctgatgcaaa atgtttatg tgaaaccgcc tgcgggcggt   15480
tttgtcattt atggagcgtg aggaatgggt aaaggaagca gtaaggggca taccccgcgc   15540
gaagcgaagg acaacctgaa gtccacgcag ttgctgagtg tgatcgatgc catcagcgaa   15600
gggccgattg aaggtccggt ggatggctta aaaagcgtgc tgctgaacag tacgccggtg   15660
ctggacactg aggggaatac caacatatcc ggtgtcacgg tggtgttccg ggctggtgag   15720
caggagcaga ctccgccgga gggatttgaa tcctccggct ccgagacggt gctgggtacg   15780
gaagtgaaat atgacacgcc gatcacccgc accattacgt ctgcaaacat cgaccgtctg   15840
cgctttacct tcggtgtaca ggcactggtg gaaaccacct caaagggtga caggaatccg   15900
tcggaagtcc gcctgctggt tcagatacaa cgtaacggtg gctgggtgac ggaaaaagac   15960
atcaccatta agggcaaaac cacctcgcag tatctggcct cggtggtgat gggtaacctg   16020
ccgccgcgcc cgtttaatat ccggatgcgc aggatgacgc cggacagcac cacagaccag   16080
ctgcagaaca aaacgctctg gtcgtcatac actgaaatca tcgatgtgaa acagtgctac   16140
ccgaacacgg cactggtcgg cgtgcaggtg gactcggagc agttcggcag ccagcaggtg   16200
agccgtaatt atcatctgcg cgggcgtatt ctgcaggtgc cgtcgaacta taacccgcag   16260
acgcggcaat acagcggtat ctgggacgga acgtttaaac cggcatacag caacaacatg   16320
gcctggtgtc tgtgggatat gctgacccat ccgcgctacg gcatgggggaa acgtcttggt   16380 gcggcggatg tggataaatg ggcgctgtat gtcatcggcc agtactgcga ccagtcagtg   16440
```

```
ccggacggct ttggcggcac ggagccgcgc atcacctgta atgcgtacct gaccacacag   16500
cgtaaggcgt gggatgtgct cagcgatttc tgctcggcga tgcgctgtat gccggtatgg   16560
aacgggcaga cgctgacgtt cgtgcaggac cgaccgtcgg ataagacgtg gacctataac   16620
cgcagtaatg tggtgatgcc ggatgatggc gcgccgttcc gctacagctt cagcgccctg   16680
aaggaccgcc ataatgccgt tgaggtgaac tggattgacc cgaacaacgg ctgggagacg   16740
gcgacagagc ttgttgaaga tacgcaggcc attgcccgtt acggtcgtaa tgttacgaag   16800
atggatgcct ttggctgtac cagccggggg caggcacacc gcgccgggct gtggctgatt   16860
aaaacagaac tgctggaaac gcagaccgtg gatttcagcg tcggcgcaga agggcttcgc   16920
catgtaccgg gcgatgttat tgaaatctgc gatgatgact atgccggtat cagcaccggt   16980
ggtcgtgtgc tggcggtgaa cagccagacc cggacgctga cgctcgaccg tgaaatcacg   17040
ctgccatcct ccggtaccgc gctgataagc ctggttgacg gaagtggcaa tccggtcagc   17100
gtggaggttc agtccgtcac cgacggcgtg aaggtaaaag tgagccgtgt tcctgacggt   17160
gttgctgaat acagcgtatg ggagctgaag ctgccgacgc tgcgccagcg actgttccgc   17220
tgcgtgagta tccgtgagaa cgacgacggc acgtatgcca tcaccgccgt gcagcatgtg   17280
ccggaaaaag aggccatcgt ggataacggg gcgcactttg acggcgaaca gagtggcacg   17340
gtgaatggtg tcacgccgcc agcggtgcag cacctgaccg cagaagtcac tgcagacagc   17400
ggggaatatc aggtgctggc gcgatgggac acaccgaagg tggtgaaggg cgtgagtttc   17460
ctgctccgtc tgaccgtaac agcggacgac ggcagtgagc ggctggtcag cacggcccgg   17520
acgacggaaa ccacataccg cttcacgcaa ctggcgctgg ggaactacag gctgacagtc   17580
cgggcggtaa atgcgtgggg gcagcagggc gatccggcgt cggtatcgtt ccggattgcc   17640
gcaccggcag caccgtcgag gattgagctg acgccgggct attttcagat aaccgccacg   17700
ccgcatcttg ccgtttatga cccgacggta cagtttgagt tctggttctc ggaaaagcag   17760
attgcggata tcagacaggt tgaaaccagc acgcgttatc ttggtacggc gctgtactgg   17820
atagccgcca gtatcaatat caaaccgggc catgattatt acttttatat ccgcagtgtg   17880
aacaccgttg gcaaatcggc attcgtggag gccgtcggtc gggcgagcga tgatgcggaa   17940
ggttacctgg atttttttcaa aggcaagata accgaatccc atctcggcaa ggagctgctg   18000
gaaaaagtcg agctgacgga ggataacgcc agcagactgg aggagttttc gaaagagtgg   18060
aaggatgcca gtgataagtg gaatgccatg tgggctgtca aaattgagca gaccaaagac   18120
ggcaaacatt atgtcgcggg tattggcctc agcatggagg acacggagga aggcaaactg   18180
agccagtttc tggttgccgc caatcgtatc gcatttattg acccggcaaa cgggaatgaa   18240
acgccgatgt ttgtggcgca gggcaaccag atattcatga cgacgtgtt cctgaagcgc   18300 ctgacggccc ccaccattac cagcggcggc aatcctccgg cctttcccct gacaccggac   18360
ggaaagctga ccgctaaaaa tgcggatatc agtggcagtg tgaatgcgaa ctccgggacg   18420
ctcagtaatg tgacgatagc tgaaaactgt acgataaacg gtacgctgag gcggaaaaa   18480 atcgtcgggg acattgtaaa ggcggcgagc gcggcttttc cgcgccagcg tgaaagcagt   18540
gtggactggc cgtcaggtac ccgtactgtc accgtgaccg atgaccatcc ttttgatcgc   18600
cagatagtgg tgcttccgct gacgtttcgc ggaagtaagc gtactgtcag cggcaggaca   18660
acgtattcga tgtgttatct gaaagtactg atgaacggtg cggtgattta tgatggcgcg   18720
gcgaacgagg cggtacaggt gttctcccgt attgttgaca tgccagcggg tcggggaaac   18780
```

-continued

```
gtgatcctga cgttcacgct tacgtccaca cggcattcgg cagatattcc gccgtatacg    18840
tttgccagcg atgtgcaggt tatggtgatt aagaaacagg cgctgggcat cagcgtggtc    18900
tgagtgtgtt acagaggttc gtccgggaac gggcgtttta ttataaaaca gtgagaggtg    18960
aacgatgcgt aatgtgtgta ttgccgttgc tgtctttgcc gcacttgcgg tgacagtcac    19020
tccggcccgt gcggaaggtg gacatggtac gtttacggtg ggctattttc aagtgaaacc    19080
gggtacattg ccgtcgttgt cgggcgggga taccggtgtg agtcatctga aagggattaa    19140
cgtgaagtac cgttatgagc tgacggacag tgtgggggtg atggcttccc tggggttcgc    19200
cgcgtcgaaa aagagcagca cagtgatgac cggggaggat acgtttcact atgagagcct    19260
gcgtggacgt tatgtgagcg tgatggccgg accggtttta caaatcagta agcaggtcag    19320
tgcgtacgcc atggccggag tggctcacag tcggtggtcc ggcagtacaa tggattaccg    19380
taagacggaa atcactcccg ggtatatgaa agagacgacc actgccaggg acgaaagtgc    19440
aatgcggcat acctcagtgg cgtggagtgc aggtatacag attaatccgg cagcgtccgt    19500
cgttgttgat attgcttatg aaggctccgg cagtggcgac tggcgtactg acggattcat    19560
cgttggggtc ggttataaat tctgattagc caggtaacac agtgttatga cagcccgccg    19620
gaaccggtgg gctttttttgt ggggtgaata tggcagtaaa gatttcagga gtcctgaaag    19680
acggcacagg aaaaccggta cagaactgca ccattcagct gaaagccaga cgtaacagca    19740
ccacggtggt ggtgaacacg gtgggctcag agaatccgga tgaagccggg cgttacagca    19800
tggatgtgga gtacggtcag tacagtgtca tcctgcaggt tgacggtttt ccaccatcgc    19860
acgccgggac catcaccgtg tatgaagatt cacaaccggg gacgctgaat gattttctct    19920
gtgccatgac ggaggatgat gcccggccgg aggtgctgcg tcgtcttgaa ctgatggtgg    19980
aagaggtggc gcgtaacgcg tccgtggtgg cacagagtac ggcagacgcg aagaaatcag    20040
ccggcgatgc cagtgcatca gctgctcagg tcgcggccct tgtgactgat gcaactgact    20100
cagcacgcgc cgccagcacg tccgccggac aggctgcatc gtcagctcag gaagcgtcct    20160
ccggcgcaga agcggcatca gcaaaggcca ctgaagcgga aaaaagtgcc gcagccgcag    20220
agtcctcaaa aaacgcggcg gccaccagtg ccggtgcggc gaaaacgtca gaaacgaatg    20280
ctgcagcgtc acaacaatca gccgccacgt ctgcctccac cgcggccacg aaagcgtcag    20340
aggccgccac ttcagcacga gatgcggtgg cctcaaaaga ggcagcaaaa tcatcagaaa    20400
cgaacgcatc atcaagtgcc ggtcgtgcag cttcctcggc aacggcggca gaaaattctg    20460
ccagggcggg aaaaacgtcc gagacgaatg ccaggtcatc tgaaacagca gcggaacgga    20520
gcgcctctgc cgcggcagac gcaaaaacag cggcggcggg gagtgcgtca acggcatcca    20580
cgaaggcgac agaggctgcg ggaagtgcgg tatcagcatc gcagagcaaa agtgcggcag    20640
aagcggcggc aatacgtgca aaaaattcgg caaaacgtgc agaagatata gcttcagctg    20700
tcgcgcttga ggatgcggac acaacagaaa aggggatagt gcagctcagc agtgcaacca    20760
acagcacgtc tgaaacgctt gctgcaacgc caaaggcggt taaggtggta atggatgaaa    20820
cgaacagaaa agcccactgg acagtccggc actgaccgga acgccaacag caccaaccgc    20880
gctcagggga acaaacaata cccagattgc gaacaccgct tttgtactgg ccgcgattgc    20940
agatgttatc gacgcgtcac ctgacgcact gaatacgctg aatgaactgg ccgcagcgct    21000
cgggaatgat ccagattttg ctaccaccat gactaacgcg cttgcgggta acaaccgaa    21060
gaatgcgaca ctgacggcgc tggcagggct ttccacggcg aaaaataaat taccgtattt    21120
tgcggaaaat gatgccgcca gcctgactga actgactcag gttggcaggg atattctggc    21180
```

```
aaaaaattcc gttgcagatg ttcttgaata ccttggggcc ggtgagaatt cggcctttcc   21240
ggcaggtgcg ccgatcccgt ggccatcaga tatcgttccg tctggctacg tcctgatgca   21300
ggggcaggcg tttgacaaat cagcctaccc aaaacttgct gtcgcgtatc catcgggtgt   21360
gcttcctgat atgcgaggct ggacaatcaa ggggaaaccc gccagcggtc gtgctgtatt   21420
gtctcaggaa caggatggaa ttaagtcgca cacccacagt gccagtgcat ccggtacgga   21480
tttggggacg aaaaccacat cgtcgtttga ttacgggacg aaaacaacag gcagtttcga   21540
ttacggcacc aaatcgacga ataacacggg ggctcatgct cacagtctga gcggttcaac   21600
aggggccgcg ggtgctcatg cccacacaag tggtttaagg atgaacagtt ctggctggag   21660
tcagtatgga acagcaacca ttacaggaag tttatccaca gttaaaggaa ccagcacaca   21720
gggtattgct tatttatcga aaacggacag tcagggcagc cacagtcact cattgtccgg   21780
tacagccgtg agtgccggtg cacatgcgca tacagttggt attggtgcgc accagcatcc   21840
ggttgttatc ggtgctcatg cccattcttt cagtattggt tcacacggac acaccatcac   21900
cgttaacgct gcgggtaacg cggaaaacac cgtcaaaaac attgcattta actatattgt   21960
gaggcttgca taatggcatt cagaatgagt gaacaaccac ggaccataaa aatttataat   22020
ctgctggccg gaactaatga atttattggt gaaggtgacg catatattcc gcctcatacc   22080
ggtctgcctg caaacagtac cgatattgca ccgccagata ttccggctgg ctttgtggct   22140
gttttcaaca gtgatgaggc atcgtggcat ctcgttgaag accatcgggg taaaaccgtc   22200
tatgacgtgg cttccggcga cgcgttattt atttctgaac tcggtccgtt accggaaaat   22260
tttacctggt tatcgccggg agggaatat cagaagtgga acggcacagc ctgggtgaag   22320
gatacgaaag cagaaaaact gttccggatc cgggaggcgg aagaaacaaa aaaaagcctg   22380
atgcaggtag ccagtgagca tattgcgccg cttcaggatg ctgcagatct ggaaattgca   22440
acgaaggaag aaacctcgtt gctggaagcc tggaagaagt atcgggtgtt gctgaaccgt   22500
gttgatacat caactgcacc tgatattgag tggcctgctg tccctgttat ggagtaatcg   22560
ttttgtgata tgccgcagaa acgttgtatg aaataacgtt ctgcggttag ttagtatatt   22620
gtaaagctga gtattggttt atttggcgat tattatcttc aggagaataa tggaagttct   22680
atgactcaat tgttcatagt gtttacatca ccgccaattg cttttaagac tgaacgcatg   22740
aaatatggtt tttcgtcatg ttttgagtct gctgttgata tttctaaagt cggttttttt   22800
tcttcgtttt ctctaactat tttccatgaa atacattttt gattattatt tgaatcaatt   22860
ccaattacct gaagtctttc atctataatt ggcattgtat gtattggttt attggagtag   22920
atgcttgctt ttctgagcca tagctctgat atccaaatga agccataggc atttgttatt   22980
ttggctctgt cagctgcata acgccaaaaa atatatttat ctgcttgatc ttcaaatgtt   23040
gtattgatta aatcaattgg atggaattgt ttatcataaa aaattaatgt tgaatgtga   23100 taaccgtcct ttaaaaaagt cgtttctgca agcttggctg tatagtcaac taactcttct   23160
gtcgaagtga tattttagg cttatctacc agttttagac gctctttaat atcttcagga   23220
attattttat tgtcatattg tatcatgcta aatgacaatt tgcttatgga gtaatctttt   23280
aattttaaat aagttattct cctggcttca tcaaataaag agtcgaatga tgttggcgaa   23340
atcacatcgt cacccattgg attgtttatt tgtatgccaa gagagttaca gcagttatac   23400
attctgccat agattatagc taaggcatgt aataattcgt aatcttttag cgtattagcg   23460
acccatcgtc tttctgattt aataaatagat gattcagtta aatatgaagg taatttcttt   23520
```

```
tgtgcaagtc tgactaactt ttttatacca atgtttaaca tactttcatt tgtaataaac    23580
tcaatgtcat tttcttcaat gtaagatgaa ataagagtag cctttgcctc gctatacatt    23640
tctaaatcgc cttgtttttc tatcgtattg cgagaatttt tagcccaagc cattaatgga    23700 tcattttttcc attttttcaat aacattattg ttataccaaa tgtcatatcc tataatctgg    23760
tttttgtttt tttgaataat aaatgttact gttcttgcgg tttggaggaa ttgattcaaa    23820
ttcaagcgaa ataattcagg gtcaaaatat gtatcaatgc agcatttgag caagtgcgat    23880
aaatctttaa gtcttctttc ccatggtttt ttagtcataa aactctccat tttgataggt    23940
tgcatgctag atgctgatat attttagagg tgataaaatt aactgcttaa ctgtcaatgt    24000
aatacaagtt gtttgatctt tgcaatgatt cttatcagaa accatatagt aaattagtta    24060
cacaggaaat ttttaatatt attattatca ttcattatgt attaaaatta gagttgtggc    24120
ttggctctgc taacacgttg ctcataggag atatggtaga gccgcagaca cgtcgtatgc    24180
aggaacgtgc tgcggctggc tggtgaactt ccgatagtgc gggtgttgaa tgatttccag    24240
ttgctaccga ttttacatat ttttttgcatg agagaatttg taccacctcc caccgaccat    24300
ctatgactgt acgccactgt ccctaggact gctatgtgcc ggagcggaca ttacaaacgt    24360
ccttctcggt gcatgccact gttgccaatg acctgcctag gaattggtta gcaagttact    24420
accggatttt gtaaaaacag ccctcctcat ataaaaagta ttcgttcact tccgataagc    24480
gtcgtaattt tctatctttc atcatattct agatccctct gaaaaaatct tccgagtttg    24540
ctaggcactg atacataact cttttccaat aattggggaa gtcattcaaa tctataatag    24600
gtttcagatt tgcttcaata aattctgact gtagctgctg aaacgttgcg gttgaactat    24660
atttccttat aacttttacg aaagagtttc tttgagtaat cacttcactc aagtgcttcc    24720
ctgcctccaa acgatacctg ttagcaatat ttaatagctt gaaatgatga agagctctgt    24780
gtttgtcttc ctgcctccag ttcgccgggc attcaacata aaaactgata gcacccggag    24840
ttccggaaac gaaatttgca tacccatt gctcacgaaa aaaaatgtcc ttgtcgatat    24900
agggatgaat cgcttggtgt acctcatcta ctgcgaaaac ttgacctttc tctcccatat    24960
tgcagtcgcg gcacgatgga actaaattaa taggcatcac cgaaaattca ggataatgtg    25020
caataggaag aaaatgatct atatttttg tctgtcctat atcaccacaa aatggacatt    25080
tttcacctga tgaaacaagc atgtcatcgt aatatgttct agcgggtttg ttttatctc    25140 ggagattatt ttcataaagc ttttctaatt taaccttgt caggttacca actactaagg    25200
ttgtaggctc aagagggtgt gtcctgtcgt aggtaaataa ctgacctgtc gagcttaata    25260
ttctatattg ttgttctttc tgcaaaaaag tggggaagtg agtaatgaaa ttatttctaa    25320
catttatctg catcataacct tccgagcatt tattaagcat ttcgctataa gttctcgctg    25380
gaagaggtag ttttttcatt gtactttacc ttcatctctg ttcattatca tcgcttttaa    25440
aacggttcga ccttctaatc ctatctgacc attataattt tttagaatgg tttcataaga    25500
aagctctgaa tcaacggact gcgataataa gtggtggtat ccagaatttg tcacttcaag    25560
taaaaacacc tcacgagtta aaacacctaa gttctcaccg aatgtctcaa tatccggacg    25620
gataatattt attgcttctc ttgaccgtag gactttccac atgcaggatt ttggaacctc    25680
ttgcagtact actggggaat gagttgcaat tattgctaca ccattgcgtg catcgagtaa    25740
gtcgcttaat gttcgtaaaa aagcagagag caaggtgga tgcagatgaa cctctggttc    25800
atcgaataaa actaatgact tttcgccaac gacatctact aatcttgtga tagtaaataa    25860
aacaattgca tgtccagagc tcattcgaag cagatatttc tggatattgt cataaaacaa    25920
```

-continued

```
tttagtgaat ttatcatcgt ccacttgaat ctgtggttca ttacgtctta actcttcata   25980
tttagaaatg aggctgatga gttccatatt tgaaaagttt tcatcactac ttagttttttt   26040
gatagcttca agccagagtt gtcttttttct atctactctc atacaaccaa taaatgctga   26100
aatgaattct aagcggagat cgcctagtga ttttaaacta ttgctggcag cattcttgag   26160
tccaatataa aagtattgtg taccttttgc tgggtcaggt tgttctttag gaggagtaaa   26220
aggatcaaat gcactaaacg aaactgaaac aagcgatcga aaatatccct ttgggattct   26280
tgactcgata agtctattat tttcagagaa aaaatattca ttgttttctg ggttggtgat   26340
tgcaccaatc attccattca aaattgttgt tttaccacac ccattccgcc cgataaaagc   26400
atgaatgttc gtgctgggca tagaattaac cgtcacctca aaaggtatag ttaaatcact   26460
gaatccggga gcacttttc tattaaatga aaagtggaaa tctgacaatt ctggcaaacc   26520
atttaacaca cgtgcgaact gtccatgaat ttctgaaaga gttacccctc taagtaatga   26580
ggtgttaagg acgctttcat tttcaatgtc ggctaatcga tttggccata ctactaaatc   26640
ctgaatagct ttaagaaggt tatgtttaaa accatcgctt aatttgctga gattaacata   26700
gtagtcaatg ctttcaccta aggaaaaaaa catttcaggg agttgactga attttttatc   26760
tattaatgaa taagtgctta cttcttcttt ttgacctaca aaaccaattt taacatttcc   26820
gatatcgcat ttttcaccat gctcatcaaa gacagtaaga taaaacattg taacaaagga   26880
atagtcattc caaccatctg ctcgtaggaa tgccttattt ttttctactg caggaatata   26940
cccgcctctt tcaataacac taaactccaa catatagtaa cccttaattt tattaaaata   27000
accgcaattt atttggcggc aacacaggat ctctctttta agttactctc tattacatac   27060
gttttccatc taaaaattag tagtattgaa cttaacgggg catcgtattg tagttttcca   27120
tatttagctt tctgcttcct tttggataac ccactgttat tcatgttgca tggtgcactg   27180
tttataccaa cgatatagtc tattaatgca tatatagtat cgccgaacga ttagctcttc   27240
aggcttctga agaagcgttt caagtactaa taagccgata gatagccacg gacttcgtag   27300
ccatttttca taagtgttaa cttccgctcc tcgctcataa cagacattca ctacagttat   27360
ggcggaaagg tatgcatgct gggtgtgggg aagtcgtgaa agaaaagaag tcagctgcgt   27420
cgtttgacat cactgctatc ttcttactgg ttatgcaggt cgtagtgggt ggcacacaaa   27480
gctttgcact ggattgcgag gctttgtgct tctctggagt gcgacaggtt tgatgacaaa   27540
aaattagcgc aagaagacaa aaatcacctt gcgctaatgc tctgttacag gtcactaata   27600
ccatctaagt agttgattca tagtgactgc atatgttgtg ttttacagta ttatgtagtc   27660
tgttttttat gcaaaatcta atttaatata ttgatattta tatcatttta cgtttctcgt   27720
tcagcttttt tatactaagt tggcattata aaaaagcatt gcttatcaat ttgttgcaac   27780
gaacaggtca ctatcagtca aaataaaatc attatttgat ttcaattttg tcccactccc   27840
tgcctctgtc atcacgatac tgtgatgcca tggtgtccga cttatgcccg agaagatgtt   27900
gagcaaactt atcgcttatc tgcttctcat agagtcttgc agacaaactg cgcaactcgt   27960
gaaaggtagg cggatcccct tcgaaggaaa gacctgatgc ttttcgtgcg cgcataaaat   28020
accttgatac tgtgccggat gaaagcggtt cgcgacgagt agatgcaatt atggtttctc   28080
cgccaagaat ctctttgcat ttatcaagtg tttccttcat tgatattccg agagcatcaa   28140
tatgcaatgc tgttgggatg gcaatttttta cgcctgtttt gctttgctcg acataaagat   28200
atccatctac gatatcagac cacttcattt cgcataaatc accaactcgt tgcccggtaa   28260
```

```
caacagccag ttccattgca agtctgagcc aacatggtga tgattctgct gcttgataaa   28320
ttttcaggta ttcgtcagcc gtaagtcttg atctccttac ctctgatttt gctgcgcgag   28380
tggcagcgac atggtttgtt gttatatggc cttcagctat tgcctctcgg aatgcatcgc   28440
tcagtgttga tctgattaac ttggctgacg ccgccttgcc ctcgtctatg tatccattga   28500
gcattgccgc aatttctttt gtggtgatgt cttcaagtgg agcatcaggc agacccctcc   28560
ttattgcttt aattttgctc atgtaattta tgagtgtctt ctgcttgatt cctctgctgg   28620
ccaggatttt ttcgtagcga tcaagccatg aatgtaacgt aacggaatta tcactgttga   28680
ttctcgctgt cagaggcttg tgtttgtgtc ctgaaaataa ctcaatgttg gcctgtatag   28740
cttcagtgat tgcgattcgc ctgtctctgc ctaatccaaa ctctttaccc gtccttgggt   28800
ccctgtagca gtaatatcca ttgtttctta tataaaggtt aggggtaaa tcccggcgct   28860 catgacttcg ccttcttccc atttctgatc ctcttcaaaa ggccacctgt tactggtcga   28920
tttaagtcaa cctttaccgc tgattcgtgg aacagatact ctcttccatc cttaaccgga   28980
ggtgggaata tcctgcattc ccgaacccat cgacgaactg tttcaaggct tcttggacgt   29040
cgctggcgtg cgttccactc ctgaagtgtc aagtacatcg caaagtctcc gcaattacac   29100
gcaagaaaaa accgccatca ggcggcttgg tgttctttca gttcttcaat tcgaatattg   29160
gttacgtctg catgtgctat ctgcgcccat atcatccagt ggtcgtagca gtcgttgatg   29220
ttctccgctt cgataactct gttgaatggc tctccattcc attctcctgt gactcggaag   29280
tgcatttatc atctccataa aacaaaaccc gccgtagcga gttcagataa aataaatccc   29340
cgcgagtgcg aggattgtta tgtaatattg ggtttaatca tctatatgtt ttgtacagag   29400
agggcaagta tcgtttccac cgtactcgtg ataataattt tgcacggtat cagtcatttc   29460
tcgcacattg cagaatgggg atttgtcttc attagactta taaaccttca tggaatattt   29520
gtatgccgac tctatatcta taccttcatc tacataaaca ccttcgtgat gtctgcatgg   29580
agacaagaca ccggatctgc acaacattga taacgcccaa tcttttttgct cagactctaa   29640 ctcattgata ctcatttata aactccttgc aatgtatgtc gtttcagcta acggtatca   29700 gcaatgttta tgtaaagaaa cagtaagata atactcaacc cgatgtttga gtacggtcat   29760
catctgacac tacagactct ggcatcgctg tgaagacgac gcgaaattca gcattttcac   29820
aagcgttatc ttttacaaaa ccgatctcac tctccttttga tgcgaatgcc agcgtcagac   29880
atcatatgca gatactcacc tgcatcctga acccattgac ctccaacccc gtaatagcga   29940
tgcgtaatga tgtcgatagt tactaacggg tcttgttcga ttaactgccg cagaaactct   30000
tccaggtcac cagtgcagtg cttgataaca ggagtcttcc caggatggcg aacaacaaga   30060
aactggtttc cgtcttcacg gacttcgttg cttttccagtt tagcaatacg cttactccca   30120
tccgagataa caccttcgta atactcacgc tgctcgttga gttttgattt tgctgtttca   30180
agctcaacac gcagtttccc tactgttagc gcaatatcct cgttctcctg gtcgcggcgt   30240
ttgatgtatt gctggtttct ttcccgttca tccagcagtt ccagcacaat cgatggtgtt   30300
accaattcat ggaaaaggtc tgcgtcaaat ccccagtcgt catgcattgc ctgctctgcc   30360
gcttcacgca gtgcctgaga gttaatttcg ctcacttcga acctctctgt ttactgataa   30420
gttccagatc ctcctggcaa cttgcacaag tccgacaacc ctgaacgacc aggcgtcttc   30480
gttcatctat cggatcgcca cactcacaac aatgagtggc agatatagcc tggtggttca   30540
ggcggcgcat ttttattgct gtgttgcgct gtaattcttc tatttctgat gctgaatcaa   30600
tgatgtctgc catctttcat taatccctga actgttggtt aatacgcttg agggtgaatg   30660
```

```
cgaataataa aaaaggagcc tgtagctccc tgatgatttt gcttttcatg ttcatcgttc    30720
cttaaagacg ccgtttaaca tgccgattgc caggcttaaa tgagtcggtg tgaatcccat    30780
cagcgttacc gtttcgcggt gcttcttcag tacgctacgg caaatgtcat cgacgttttt    30840
atccggaaac tgctgtctgg ctttttttga tttcagaatt agcctgacgg caatgctgc    30900 gaagggcgtt ttcctgctga ggtgtcattg aacaagtccc atgtcggcaa gcataagcac    30960
acagaatatg aagcccgctg ccagaaaaat gcattccgtg gttgtcatac ctggtttctc    31020
tcatctgctt ctgctttcgc caccatcatt ccagcttttt gtgaaaggga tgcggctaac    31080
gtatgaaatt cttcgtctgt ttctactggt attggcacaa acctgattcc aatttgagca    31140
aggctatgtg ccatctcgat actcgttctt aactcaacag aagatgcttt gtgcatacag    31200
cccctcgttt attatttatc tcctcagcca gccgctgtgc tttcagtgga tttcggataa    31260
cagaaaggcc gggaaatacc cagcctcgct ttgtaacgga gtagacgaaa gtgattgcgc    31320
ctacccggat attatcgtga ggatgcgtca tcgccattgc tccccaaata caaaaccaat    31380
ttcagccagt gcctcgtcca ttttttcgat gaactccggc acgatctcgt caaaactcgc    31440
catgtacttt tcatcccgct caatcacgac ataatgcagg ccttcacgct tcatacgcgg    31500
gtcatagttg gcaaagtacc aggcattttt tcgcgtcacc cacatgctgt actgcacctg    31560
ggccatgtaa gctgacttta tggcctcgaa accaccgagc cggaacttca tgaaatcccg    31620
ggaggtaaac gggcatttca gttcaaggcc gttgccgtca ctgcataaac catcgggaga    31680
gcaggcggta cgcatacttt cgtcgcgata gatgatcggg gattcagtaa cattcacgcc    31740
ggaagtgaat tcaaacaggg ttctggcgtc gttctcgtac tgttttcccc aggccagtgc    31800
tttagcgtta acttccggag ccacaccggt gcaaacctca gcaagcaggg tgtggaagta    31860
ggacattttc atgtcaggcc acttctttcc ggagcggggt tttgctatca cgttgtgaac    31920
ttctgaagcg gtgatgacgc cgagccgtaa tttgtgccac gcatcatccc cctgttcgac    31980
agctctcaca tcgatcccgg tacgctgcag gataatgtcc ggtgtcatgc tgccaccttc    32040
tgctctgcgg cttctgtttt caggaatcca agagctttta ctgcttcggc ctgtgtcagt    32100
tctgacgatg cacgaatgtc gcggcgaaat atctgggaac agagcggcaa taagtcgtca    32160
tcccatgttt tatccagggc gatcagcaga gtgttaatct cctgcatggt ttcatcgtta    32220
accggagtga tgtcgcgttc cggctgacgt tctgcagtgt atgcagtatt ttcgacaatg    32280
cgctcggctt catccttgtc atagatacca gcaaatccga aggccagacg ggcacactga    32340
atcatggctt tatgacgtaa catccgtttg ggatgcgact gccacggccc cgtgatttct    32400
ctgccttcgc gagttttgaa tggttcgcgg cggcattcat ccatccattc ggtaacgcag    32460
atcggatgat tacggtcctt gcggtaaatc cggcatgtac aggattcatt gtcctgctca    32520
aagtccatgc catcaaactg ctggttttca ttgatgatgc gggaccagcc atcaacgccc    32580
accaccggaa cgatgccatt ctgcttatca ggaaaggcgt aaatttcttt cgtccacgga    32640
ttaaggccgt actggttggc aacgatcagt aatgcgatga actgcgcatc gctggcatca    32700
cctttaaatg ccgtctggcg aagagtggtg atcagttcct gtgggtcgac agaatccatg    32760
ccgacacgtt cagccagctt cccagccagc gttgcgagtg cagtactcat tcgtttt ata    32820 cctctgaatc aatatcaacc tggtggtgag caatggtttc aaccatgtac cggatgtgtt    32880
ctgccatgcg ctcctgaaac tcaacatcgt catcaaacgc acgggtaatg gatttttgc     32940 tggccccgtg gcgttgcaaa tgatcgatgc atagcgattc aaacaggtgc tggggcaggc    33000
```

```
cttttttccat gtcgtctgcc agttctgcct ctttctcttc acgggcgagc tgctggtagt    33060
gacgcgccca gctctgagcc tcaagacgat cctgaatgta ataagcgttc atggctgaac    33120
tcctgaaata gctgtgaaaa tatcgcccgc gaaatgccgg gctgattagg aaaacaggaa    33180 aggggttag tgaatgcttt tgcttgatct cagtttcagt attaatatcc atttttata    33240 agcgtcgacg gcttcacgaa acatcttttc atcgccaata aaagtggcga tagtgaattt    33300
agtctggata gccataagtg tttgatccat tctttgggac tcctggctga ttaagtatgt    33360
cgataaggcg tttccatccg tcacgtaatt tacgggtgat tcgttcaagt aaagattcgg    33420
aagggcagcc agcaacaggc caccctgcaa tggcatattg catggtgtgc tccttattta    33480
tacataacga aaaacgcctc gagtgaagcg ttattggtat gcggtaaaac cgcactcagg    33540
cggccttgat agtcatatca tctgaatcaa atattcctga tgtatcgata tcggtaattc    33600
ttattccttc gctaccatcc attggaggcc atccttcctg accatttcca tcattccagt    33660
cgaactcaca cacaacacca tatgcattta agtcgcttga aattgctata agcagagcat    33720
gttgcgccag catgattaat acagcattta atacagagcc gtgtttattg agtcggtatt    33780
cagagtctga ccagaaatta ttaatctggt gaagttttttc ctctgtcatt acgtcatggt    33840 cgattttcaat ttctattgat gctttccagt cgtaatcaat gatgtatttt ttgatgtttg    33900
acatctgttc atatcctcac agataaaaaa tcgccctcac actggagggc aaagaagatt    33960
tccaataatc agaacaagtc ggctcctgtt tagttacgag cgacattgct ccgtgtattc    34020
actcgttgga atgaatacac agtgcagtgt ttattctgtt atttatgcca aaaataaagg    34080
ccactatcag gcagctttgt tgttctgttt accaagttct ctggcaatca ttgccgtcgt    34140
tcgtattgcc catttatcga catatttccc atcttccatt acaggaaaca tttcttcagg    34200
cttaaccatg cattccgatt gcagcttgca tccattgcat cgcttgaatt gtccacacca    34260
ttgattttta tcaatagtcg tagtcatacg gatagtcctg gtattgttcc atcacatcct    34320
gaggatgctc ttcgaactct tcaaattctt cttccatata tcaccttaaa tagtggattg    34380
cggtagtaaa gattgtgcct gtcttttaac cacatcaggc tcggtggttc tcgtgtaccc    34440
ctacagcgag aaatcggata aactattaca acccctacag tttgatgagt atagaaatgg    34500
atccactcgt tattctcgga cgagtgttca gtaatgaacc tctggagaga accatgtata    34560
tgatcgttat ctgggttgga cttctgcttt taagcccaga taactggcct gaatatgtta    34620
atgagagaat cggtattcct catgtgtggc atgttttcgt ctttgctctt gcattttcgc    34680
tagcaattaa tgtgcatcga ttatcagcta ttgccagcgc cagatataag cgatttaagc    34740
taagaaaacg cattaagatg caaaacgata aagtgcgatc agtaattcaa aaccttacag    34800
aagagcaatc tatggttttg tgcgcagccc ttaatgaagg caggaagtat gtggttacat    34860
caaaacaatt cccatacatt agtgagttga ttgagcttgg tgtgttgaac aaaactttttt    34920 cccgatggaa tggaaagcat atattattcc ctattgagga tatttactgg actgaattag    34980
ttgccagcta tgatccatat aatattgaga taaagccaag gccaatatct aagtaactag    35040
ataagaggaa tcgattttcc cttaattttc tggcgtccac tgcatgttat gccgcgttcg    35100
ccaggcttgc tgtaccatgt gcgctgatte ttgcgctcaa tacgttgcag gttgctttca    35160
atctgtttgt ggtattcagc cagcactgta aggtctatcg gatttagtgc gctttctact    35220
cgtgatttcg gtttgcgatt cagcgagaga ataggggcggt taactggttt tgcgcttacc    35280
ccaaccaaca ggggatttgc tgctttccat tgagcctgtt tctctgcgcg acgttcgcgg    35340
cggcgtgttt gtgcatccat ctggattctc ctgtcagtta gctttggtgg tgtgtggcag    35400
```

```
ttgtagtcct gaacgaaaac cccccgcgat tggcacattg gcagctaatc cggaatcgca    35460
cttacggcca atgcttcgtt tcgtatcaca caccccaaag ccttctgctt tgaatgctgc    35520
ccttcttcag ggcttaattt ttaagagcgt caccttcatg gtggtcagtg cgtcctgctg    35580
atgtgctcag tatcaccgcc agtggtattt atgtcaacac cgccagagat aatttatcac    35640
cgcagatggt tatctgtatg tttttatat gaatttattt tttgcagggg ggcattgttt    35700
ggtaggtgag agatctgaat tgctatgttt agtgagttgt atctatttat ttttcaataa    35760
atacaattgg ttatgtgttt tggggcgat cgtgaggcaa agaaaacccg gcgctgaggc    35820
cgggttattc ttgttctctg gtcaaattat atagttggaa acaaggatg catatatgaa    35880 tgaacgatgc agaggcaatg ccgatggcga tagtgggtat catgtagccg cttatgctgg    35940
aaagaagcaa taacccgcag aaaaacaaag ctccaagctc aacaaaacta agggcataga    36000
caataactac cgatgtcata tacccatact ctctaatctt ggccagtcgg cgcgttctgc    36060
ttccgattag aaacgtcaag gcagcaatca ggattgcaat catggttcct gcatatgatg    36120
acaatgtcgc cccaagacca tctctatgag ctgaaaaaga aacaccagga atgtagtggc    36180
ggaaaaggag atagcaaatg cttacgataa cgtaaggaat tattactatg taaacaccag    36240
gcatgattct gttccgcata attactcctg ataattaatc cttaactttg cccacctgcc    36300
ttttaaaaca ttccagtata tcacttttca ttcttgcgta gcaatatgcc atctcttcag    36360
ctatctcagc attggtgacc ttgttcagag gcgctgagag atggccttt tctgatagat    36420 aatgttctgt taaatatct ccggcctcat cttttgcccg caggctaatg tctgaaaatt    36480
gaggtgacgg gttaaaaata atatccttgg caaccttttt tatatcccct ttaaattttg    36540
gcttaatgac tatatccaat gagtcaaaaa gctccccttc aatatctgtt gcccctaaga    36600
cctttaatat atcgccaaat acaggtagct tggcttctac cttcaccgtt gttcggccga    36660
tgaaatgcat atgcataaca tcgtctttgg tggttcccct catcagtggc tctatctgaa    36720
cgcgctctcc actgcttaat gacattcctt tcccgattaa aaaatctgtc agatcggatg    36780
tggtcggccc gaaaacagtt ctggcaaaac caatggtgtc gccttcaaca aacaaaaaag    36840
atgggaatcc caatgattcg tcatctgcga ggctgttctt aatatcttca actgaagctt    36900
tagagcgatt tatcttctga accagactct tgtcatttgt tttggtaaag agaaaagttt    36960
ttccatcgat tttatgaata tacaaataat tggagccaac ctgcaggtga tgattatcag    37020
ccagcagaga attaaggaaa acagacaggt ttattgagcg cttatctttc cctttatttt    37080
tgctgcggta agtcgcataa aaaccattct tcataattca atccatttac tatgttatgt    37140
tctgagggga gtgaaaattc ccctaattcg atgaagattc ttgctcaatt gttatcagct    37200
atgcgccgac cagaacacct tgccgatcag ccaaacgtct cttcaggcca ctgactagcg    37260
ataactttcc ccacaacgga acaactctca ttgcatggga tcattgggta ctgtgggttt    37320
agtggttgta aaaacacctg accgctatcc ctgatcagtt tcttgaaggt aaactcatca    37380
cccccaagtc tggctatgca gaaatcacct ggctcaacag cctgctcagg gtcaacgaga    37440
attaacattc cgtcaggaaa gcttggcttg gagcctgttg gtgcggtcat ggaattacct    37500
tcaacctcaa gccagaatgc agaatcactg gcttttttgg ttgtgcttac ccatctctcc    37560
gcatcacctt tggtaaaggt tctaagctta ggtgagaaca tccctgcctg aacatgagaa    37620
aaaacagggt actcatactc acttctaagt gacggctgca tactaaccgc ttcatacatc    37680
tcgtagattt ctctggcgat tgaagggcta aattcttcaa cgctaacttt gagaattttt    37740
```

```
gtaagcaatg cggcgttata agcatttaat gcattgatgc cattaaataa agcaccaacg    37800
cctgactgcc ccatccccat cttgtctgcg acagattcct gggataagcc aagttcattt    37860
ttcttttttt cataaattgc tttaaggcga cgtgcgtcct caagctgctc ttgtgttaat    37920
ggtttctttt ttgtgctcat acgttaaatc tatcaccgca agggataaat atctaacacc    37980
gtgcgtgttg actattttac ctctggcggt gataatggtt gcatgtacta aggaggttgt    38040
atggaacaac gcataaccct gaaagattat gcaatgcgct ttgggcaaac caagacagct    38100
aaagatctcg gcgtatatca agcgcgatc aacaaggcca ttcatgcagg ccgaaagatt    38160
tttttaacta taaacgctga tggaagcgtt tatgcggaag aggtaaagcc cttcccgagt    38220
aacaaaaaaa caacagcata ataaccccg ctcttacaca ttccagccct gaaaaagggc    38280
atcaaattaa accacaccta tggtgtatgc atttatttgc atacattcaa tcaattgtta    38340
tctaaggaaa tacttacata tggttcgtgc aaacaaacgc aacgaggctc tacgaatcga    38400
gagtgcgttg cttaacaaaa tcgcaatgct tggaactgag aagacagcgg aagctgtggg    38460
cgttgataag tcgcagatca gcaggtggaa gagggactgg attccaaagt tctcaatgct    38520
gcttgctgtt cttgaatggg gggtcgttga cgacgacatg gctcgattgg cgcgacaagt    38580
tgctgcgatt ctcaccaata aaaaacgccc ggcggcaacc gagcgttctg aacaaatcca    38640
gatggagttc tgaggtcatt actggatcta tcaacaggag tcattatgac aaatacagca    38700
aaaatactca acttcggcag aggtaacttt gccggacagg agcgtaatgt ggcagatctc    38760
gatgatggtt acgccagact atcaaatatg ctgcttgagg cttattcggg cgcagatctg    38820
accaagcgac agtttaaagt gctgcttgcc attctgcgta aaacctatgg gtggaataaa    38880
ccaatggaca gaatcaccga ttctcaactt agcgagatta caagttacc tgtcaaacgg    38940 tgcaatgaag ccaagttaga actcgtcaga atgaatatta tcaagcagca aggcggcatg    39000
tttggaccaa ataaaaacat ctcagaatgg tgcatccctc aaaacgaggg aaaatcccct    39060
aaaacgaggg ataaaacatc cctcaaattg ggggattgct atccctcaaa acaggggac    39120 acaaaagaca ctattacaaa agaaaaaaga aaagattatt cgtcagagaa ttctggcgaa    39180
tcctctgacc agccagaaaa cgacctttct gtggtgaaac cggatgctgc aattcagagc    39240
ggcagcaagt gggggacagc agaagacctg accgccgcag agtggatgtt tgacatggtg    39300
aagactatcg caccatcagc cagaaaaccg aattttgctg ggtgggctaa cgatatccgc    39360
ctgatgcgtg aacgtgacgg acgtaaccac cgcgacatgt gtgtgctgtt ccgctgggca    39420
tgccaggaca cttctggtc cggtaacgtg ctgagcccgg ccaaactccg cgataagtgg    39480
acccaactcg aaatcaaccg taacaagcaa caggcaggcg tgacagccag caaaccaaaa    39540
ctcgacctga caaacacaga ctggatttac ggggtggatc tatgaaaaac atcgccgcac    39600
agatggttaa ctttgaccgt gagcagatgc gtcggatcgc caacaacatg ccggaacagt    39660
acgacgaaaa gccgcaggta cagcaggtag cgcagatcat caacggtgtg ttcagccagt    39720
tactggcaac tttcccggcg agcctggcta accgtgacca gaacgaagtg aacgaaatcc    39780
gtcgccagtg ggttctggct tttcgggaaa acgggatcac cacgatggaa caggttaacg    39840
caggaatgcg cgtagcccgt cggcagaatc gaccatttct gccatcaccc gggcagtttg    39900
ttgcatggtg ccgggaagaa gcatccgtta ccgccggact gccaaacgtc agcgagctgg    39960
ttgatatggt ttacgagtat tgccggaagc gaggcctgta tccggatgcg gagtcttatc    40020
cgtggaaatc aaacgcgcac tactggctgg ttaccaacct gtatcagaac atgcgggcca    40080
atgcgcttac tgatgcggaa ttacgccgta aggccgcaga tgagcttgtc catatgactg    40140
```

```
cgagaattaa ccgtggtgag gcgatccctg aaccagtaaa acaacttcct gtcatgggcg    40200
gtagacctct aaatcgtgca caggctctgg cgaagatcgc agaaatcaaa gctaagttcg    40260
gactgaaagg agcaagtgta tgacgggcaa agaggcaatt attcattacc tggggacgca    40320
taatagcttc tgtgcgccgg acgttgccgc gctaacaggc gcaacagtaa ccagcataaa    40380
tcaggccgcg gctaaaatgg cacgggcagg tcttctggtt atcgaaggta aggtctggcg    40440
aacggtgtat taccggtttg ctaccaggga agaacgggaa ggaaagatga gcacgaacct    40500 ggttttaag gagtgtcgcc agagtgccgc gatgaaacgg gtattggcgg tatatggagt    40560
taaaagatga ccatctacat tactgagcta ataacaggcc tgctggtaat cgcaggcctt    40620
tttatttggg ggagagggaa gtcatgaaaa aactaacctt tgaaattcga tctccagcac    40680
atcagcaaaa cgctattcac gcagtacagc aaatccttcc agacccaacc aaaccaatcg    40740
tagtaaccat tcaggaacgc aaccgcagct tagaccaaaa caggaagcta tgggcctgct    40800
taggtgacgt ctctcgtcag gttgaatggc atggtcgctg gctggatgca gaaagctgga    40860
agtgtgtgtt taccgcagca ttaaagcagc aggatgttgt tcctaacctt gccgggaatg    40920
gctttgtggt aataggccag tcaaccagca ggatgcgtgt aggcgaattt gcggagctat    40980
tagagcttat acaggcattc ggtacagagc gtggcgttaa gtggtcagac gaagcgagac    41040
tggctctgga gtggaaagcg agatggggag acagggctgc atgataaatg tcgttagttt    41100
ctccggtggc aggacgtcag catatttgct ctggctaatg gagcaaaagc gacgggcagg    41160
taaagacgtg cattacgttt tcatggatac aggttgtgaa catccaatga catatcggtt    41220
tgtcagggaa gttgtgaagt tctgggatat accgctcacc gtattgcagg ttgatatcaa    41280
cccggagctt ggacagccaa atggttatac ggtatgggaa ccaaaggata ttcagacgcg    41340
aatgcctgtt ctgaagccat ttatcgatat ggtaaagaaa tatggcactc catacgtcgg    41400
cggcgcgttc tgcactgaca gattaaaact cgttcccttc accaaatact gtgatgacca    41460
tttcgggcga gggaattaca ccacgtggat tggcatcaga gctgatgaac cgaagcggct    41520
aaagccaaag cctggaatca gatatcttgc tgaactgtca gactttgaga aggaagatat    41580
cctcgcatgg tggaagcaac aaccattcga tttgcaaata ccggaacatc tcggtaactg    41640
catattctgc attaaaaaat caacgcaaaa aatcggactt gcctgcaaag atgaggaggg    41700
attgcagcgt gtttttaatg aggtcatcac gggatcccat gtgcgtgacg gacatcggga    41760
aacgccaaag gagattatgt accgaggaag aatgtcgctg gacggtatcg cgaaaatgta    41820
ttcagaaaat gattatcaag ccctgtatca ggacatggta cgagctaaaa gattcgatac    41880
cggctcttgt tctgagtcat gcgaaatatt tggagggcag cttgatttcg acttcgggag    41940
ggaagctgca tgatgcgatg ttatcggtgc ggtgaatgca aagaagataa ccgcttccga    42000
ccaaatcaac cttactggaa tcgatggtgt ctccggtgtg aaagaacacc aacagggtgt    42060
ttaccactac cgcaggaaaa ggaggacgtg tggcagaca cgcacgaagt atcaccgaca    42120
taatctgcga aaactgcaaa taccttccaa cgaaacgcac cagaaataaa cccaagccaa    42180
tcccaaaaga atctgacgta aaaaccttca actacacggc tcacctgtgg gatatccggt    42240
ggctaagacg tcgtgcgagg aaaacaaggt gattgaccaa aatcgaagtt acgaacaaga    42300
aagcgtcgag cgagctttaa cgtgcgctaa ctgcggtcag aagctgcatg tgctggaagt    42360
tcacgtgtgt gagcactgct gcgcagaact gatgagcgat ccgaatagct cgatgcacga    42420
ggaagaagat gatggctaaa ccagcgcgaa gacgatgtaa aaacgatgaa tgccgggaat    42480
```

```
ggtttcaccc tgcattcgct aatcagtggt ggtgctctcc agagtgtgga accaagatag   42540
cactcgaacg acgaagtaaa gaacgcgaaa aagcggaaaa agcagcagag aagaaacgac   42600
gacgagagga gcagaaacag aaagataaac ttaagattcg aaaactcgcc ttaaagcccc   42660
gcagttactg gattaaacaa gcccaacaag ccgtaaacgc cttcatcaga gaaagagacc   42720
gcgacttacc atgtatctcg tgcggaacgc tcacgtctgc tcagtgggat gccggacatt   42780
accggacaac tgctgcggca cctcaactcc gatttaatga acgcaatatt cacaagcaat   42840
gcgtggtgtg caaccagcac aaaagcggaa atctcgttcc gtatcgcgtc gaactgatta   42900
gccgcatcgg gcaggaagca gtagacgaaa tcgaatcaaa ccataaccgc catcgctgga   42960
ctatcgaaga gtgcaaggcg atcaaggcag agtaccaaca gaaactcaaa gacctgcgaa   43020
atagcagaag tgaggccgca tgacgttctc agtaaaaacc attccagaca tgctcgttga   43080
aacatacgga aatcagacag aagtagcacg cagactgaaa tgtagtcgcg gtacggtcag   43140
aaaatacgtt gatgataaag acgggaaaat gcacgccatc gtcaacgacg ttctcatggt   43200
tcatcgcgga tggagtgaaa gagatgcgct attacgaaaa aattgatggc agcaaatacc   43260
gaaatatttg ggtagttggc gatctgcacg gatgctacac gaacctgatg aacaaactgg   43320
atacgattgg attcgacaac aaaaaagacc tgcttatctc ggtgggcgat ttggttgatc   43380
gtggtgcaga aacgttgaa tgcctggaat taatcacatt ccctggttc agagctgtac   43440 gtggaaacca tgagcaaatg atgattgatg cttatcaga gcgtggaaac gttaatcact   43500
ggctgcttaa tggcggtggc tggttcttta atctcgatta cgacaaagaa attctggcta   43560
aagctcttgc ccataaagca gatgaacttc cgttaatcat cgaactggtg agcaaagata   43620
aaaaatatgt tatctgccac gccgattatc cctttgacga atacgagttt ggaaagccag   43680
ttgatcatca gcaggtaatc tggaaccgcg aacgaatcag caactcacaa aacgggatcg   43740
tgaaagaaat caaaggcgcg gacacgttca tctttggtca tacgccagca gtgaaaccac   43800
tcaagtttgc caaccaaatg tatatcgata ccggcgcagt gttctgcgga aacctaacat   43860
tgattcaggt acagggagaa ggcgcatgag actcgaaagc gtagctaaat tcattcgcc   43920 aaaaagcccg atgatgagcg actcaccacg ggccacggct tctgactctc tttccggtac   43980
tgatgtgatg gctgctatgg ggatggcgca atcacaagcc ggattcggta tggctgcatt   44040
ctgcggtaag cacgaactca gccagaacga caaacaaaag gctatcaact atctgatgca   44100
atttgcacac aaggtatcgg ggaaataccg tggtgtggca aagcttgaag gaaatactaa   44160
ggcaaaggta ctgcaagtgc tcgcaacatt cgcttatgcg gattattgcc gtagtgccgc   44220
gacgccgggg gcaagatgca gagattgcca tggtacaggc cgtgcggttg atattgccaa   44280
aacagagctg tgggggagag ttgtcgagaa agagtgcgga agatgcaaag gcgtcggcta   44340
ttcaaggatg ccagcaagcg cagcatatcg cgctgtgacg atgctaatcc caaaccttac   44400
ccaacccacc tggtcacgca ctgttaagcc gctgtatgac gctctggtgg tgcaatgcca   44460
caaagaagag tcaatcgcag acaacatttt gaatgcggtc acacgttagc agcatgattg   44520
ccacggatgg caacatatta acggcatgat attgacttat tgaataaaat tgggtaaatt   44580
tgactcaacg atgggttaat tcgctcgttg tggtagtgag atgaaaagag gcggcgctta   44640
ctaccgattc cgcctagttg gtcacttcga cgtatcgtct ggaactccaa ccatcgcagg   44700
cagagaggtc tgcaaaatgc aatcccgaaa cagttcgcag gtaatagtta gagcctgcat   44760
aacggtttcg ggatttttta tatctgcaca acaggtaaga gcattgagtc gataatcgtg   44820
aagagtcggc gagcctggtt agccagtgct ctttccgttg tgctgaatta agcgaatacc   44880
```

```
ggaagcagaa ccggatcacc aaatgcgtac aggcgtcatc gccgcccagc aacagcacaa    44940
cccaaactga gccgtagcca ctgtctgtcc tgaattcatt agtaatagtt acgctgcggc    45000
cttttacaca tgaccttcgt gaaagcgggt ggcaggaggt cgcgctaaca acctcctgcc    45060
gttttgcccg tgcatatcgg tcacgaacaa atctgattac taaacacagt agcctggatt    45120
tgttctatca gtaatcgacc ttattcctaa ttaaatagag caaatcccct tattggggt     45180 aagacatgaa gatgccagaa aaacatgacc tgttggccgc cattctcgcg gcaaaggaac    45240
aaggcatcgg ggcaatcctt gcgtttgcaa tggcgtacct tcgcggcaga tataatggcg    45300
gtgcgtttac aaaaacagta atcgacgcaa cgatgtgcgc cattatcgcc tagttcattc    45360
gtgaccttct cgacttcgcc ggactaagta gcaatctcgc ttatataacg agcgtgttta    45420
tcggctacat cggtactgac tcgattggtt cgcttatcaa acgcttcgct gctaaaaaag    45480
ccggagtaga agatggtaga aatcaataat caacgtaagg cgttcctcga tatgctggcg    45540
tggtcggagg gaactgataa cggacgtcag aaaaccagaa atcatggtta tgacgtcatt    45600
gtaggcggag agctatttac tgattactcc gatcaccctc gcaaacttgt cacgctaaac    45660
ccaaaactca aatcaacagg cgccggacgc taccagcttc tttcccgttg gtgggatgcc    45720
taccgcaagc agcttggcct gaaagacttc tctccgaaaa gtcaggacgc tgtggcattg    45780
cagcagatta aggagcgtgg cgctttacct atgattgatc gtggtgatat ccgtcaggca    45840
atcgaccgtt gcagcaatat ctgggcttca ctgccgggcg ctggttatgg tcagttcgag    45900
cataaggctg acagcctgat tgcaaaattc aaagaagcgg gcggaacggt cagagagatt    45960
gatgtatgag cagagtcacc gcgattatct ccgctctggt tatctgcatc atcgtctgcc    46020
tgtcatgggc tgttaatcat taccgtgata acgccattac ctacaaagcc cagcgcgaca    46080
aaaatgccag agaactgaag ctggcgaacg cggcaattac tgacatgcag atgcgtcagc    46140
gtgatgttgc tgcgctcgat gcaaaataca cgaaggagtt agctgatgct aaagctgaaa    46200
atgatgctct gcgtgatgat gttgccgctg gtcgtcgtcg gttgcacatc aaagcagtct    46260
gtcagtcagt gcgtgaagcc accaccgcct ccggcgtgga taatgcagcc tcccccgac    46320 tggcagacac cgctgaacgg gattatttca ccctcagaga gaggctgatc actatgcaaa    46380
aacaactgga aggaacccag aagtatatta atgagcagtg cagatagagt tgcccatatc    46440
gatgggcaac tcatgcaatt attgtgagca atacacacgc gcttccagcg gagtataaat    46500
gcctaaagta ataaaaccga gcaatccatt tacgaatgtt tgctgggttt ctgttttaac    46560 aacatttttct gcgccgccac aaattttggc tgcatcgaca gttttcttct gcccaattcc    46620
agaaacgaag aaatgatggg tgatggtttc ctttggtgct actgctgccg gtttgttttg    46680
aacagtaaac gtctgttgag cacatcctgt aataagcagg gccagcgcag tagcgagtag    46740
catttttttc atggtgttat tcccgatgct ttttgaagtt cgcagaatcg tatgtgtaga    46800
aaattaaaca aaccctaaac aatgagttga aatttcatat tgttaatatt tattaatgta    46860
tgtcaggtgc gatgaatcgt cattgtattc ccggattaac tatgtccaca gccctgacgg    46920
ggaacttctc tgcgggagtg tccgggaata attaaaacga tgcacacagg gtttagcgcg    46980
tacacgtatt gcattatgcc aacgccccgg tgctgacacg gaagaaaccg gacgttatga    47040
tttagcgtgg aaagatttgt gtagtgttct gaatgctctc agtaaatagt aatgaattat    47100
caaaggtata gtaatatctt ttatgttcat ggatatttgt aacccatcgg aaaactcctg    47160
ctttagcaag attttccctg tattgctgaa atgtgatttc tcttgatttc aacctatcat    47220
```

```
aggacgtttc tataagatgc gtgtttcttg agaatttaac atttacaacc ttttaagtc    47280 cttttattaa cacggtgtta tcgttttcta acacgatgtg aatattatct gtggctagat    47340
agtaaatata atgtgagacg ttgtgacgtt ttagttcaga ataaaacaat tcacagtcta    47400
aatcttttcg cacttgatcg aatatttctt taaaaatggc aacctgagcc attggtaaaa    47460
ccttccatgt gatacgaggg cgcgtagttt gcattatcgt ttttatcgtt tcaatctggt    47520
ctgacctcct tgtgttttgt tgatgattta tgtcaaatat taggaatgtt ttcacttaat    47580
agtattggtt gcgtaacaaa gtgcggtcct gctggcattc tggagggaaa tacaaccgac    47640
agatgtatgt aaggccaacg tgctcaaatc ttcatacaga aagatttgaa gtaatatttt    47700
aaccgctaga tgaagagcaa gcgcatggag cgacaaaatg aataaagaac aatctgctga    47760
tgatccctcc gtggatctga ttcgtgtaaa aaatatgctt aatagcacca tttctatgag    47820
ttaccctgat gttgtaattg catgtataga acataaggtg tctctggaag cattcagagc    47880
aattgaggca gcgttggtga agcacgataa taatatgaag gattattccc tggtggttga    47940
ctgatcacca taactgctaa tcattcaaac tatttagtct gtgacagagc caacacgcag    48000
tctgtcactg tcaggaaagt ggtaaaactg caactcaatt actgcaatgc cctcgtaatt    48060
aagtgaattt acaatatcgt cctgttcgga gggaagaacg cgggatgttc attcttcatc    48120
acttttaatt gatgtatatg ctctctttc tgacgttagt ctccgacggc aggcttcaat    48180
gacccaggct gagaaattcc cggacccttt ttgctcaaga gcgatgttaa tttgttcaat    48240
catttggtta ggaaagcgga tgttgcgggt tgttgttctg cgggtctgt tcttcgttga    48300 catgaggttg ccccgtattc agtgtcgctg atttgtattg tctgaagttg ttttacgtt    48360 aagttgatgc agatcaatta atacgatacc tgcgtcataa ttgattattt gacgtggttt    48420
gatggcctcc acgcacgttg tgatatgtag atgataatca ttatcacttt acgggtcctt    48480
tccggtgatc cgacaggtta cg                                             48502

<210> SEQ ID NO 14
<211> LENGTH: 77
<212> TYPE: DNA
<213> ORGANISM: Artificial Sequence
<220> FEATURE:
<223> OTHER INFORMATION: Polynucleotide sequence used in Examples 2 and
      3

<400> SEQUENCE: 14
tttttttttt tttttttttt tttttttttt tttttttttt tttttttttt ggttgtttct    60
gttggtgctg atattgc                                                   77

<210> SEQ ID NO 15
<211> LENGTH: 50
<212> TYPE: DNA
<213> ORGANISM: Artificial Sequence
<220> FEATURE:
<223> OTHER INFORMATION: Polynucleotide sequence used in Examples 2 and
      3

<400> SEQUENCE: 15
gttttcgcat ttatcgtgaa acgctttcgc gtttttcgtg cgccgcttca                50

<210> SEQ ID NO 16
<211> LENGTH: 29
<212> TYPE: DNA
<213> ORGANISM: Artificial Sequence
<220> FEATURE:
<223> OTHER INFORMATION: Polynucleotide sequence used in Examples 2 and
```

<400> SEQUENCE: 16
gcaatatcag caccaacaga aacaacctt                                    29

<210> SEQ ID NO 17
<211> LENGTH: 970
<212> TYPE: PRT
<213> ORGANISM: Citromicrobium bathyomarinum

<400> SEQUENCE: 17

```
Met Leu Ser Val Ala Asn Val Arg Ser Pro Ser Ala Ala Ser Tyr
1               5                  10                  15

Phe Ala Ser Asp Asn Tyr Tyr Ala Ser Ala Asp Ala Asp Arg Ser Gly
                20                  25                  30

Gln Trp Ile Gly Asp Gly Ala Lys Arg Leu Gly Leu Glu Gly Lys Val
            35                  40                  45

Glu Ala Arg Ala Phe Asp Ala Leu Leu Arg Gly Glu Leu Pro Asp Gly
    50                  55                  60

Ser Ser Val Gly Asn Pro Gly Gln Ala His Arg Pro Gly Thr Asp Leu
65                  70                  75                  80

Thr Phe Ser Val Pro Lys Ser Trp Ser Leu Ala Leu Val Gly Lys
                85                  90                  95

Asp Glu Arg Ile Ile Ala Ala Tyr Arg Glu Ala Val Val Glu Ala Leu
            100                 105                 110

His Trp Ala Glu Lys Asn Ala Ala Glu Thr Arg Val Val Glu Lys Gly
        115                 120                 125

Met Val Val Thr Gln Ala Thr Gly Asn Leu Ala Ile Gly Leu Phe Gln
130                 135                 140

His Asp Thr Asn Arg Asn Gln Glu Pro Asn Leu His Phe His Ala Val
145                 150                 155                 160

Ile Ala Asn Val Thr Gln Gly Lys Asp Gly Lys Trp Arg Thr Leu Lys
                165                 170                 175

Asn Asp Arg Leu Trp Gln Leu Asn Thr Thr Leu Asn Ser Ile Ala Met
            180                 185                 190

Ala Arg Phe Arg Val Ala Val Glu Lys Leu Gly Tyr Glu Pro Gly Pro
        195                 200                 205

Val Leu Lys His Gly Asn Phe Glu Ala Arg Gly Ile Ser Arg Glu Gln
    210                 215                 220

Val Met Ala Phe Ser Thr Arg Arg Lys Glu Val Leu Glu Ala Arg Arg
225                 230                 235                 240

Gly Pro Gly Leu Asp Ala Gly Arg Ile Ala Ala Leu Asp Thr Arg Ala
                245                 250                 255

Ser Lys Glu Gly Ile Glu Asp Arg Ala Thr Leu Ser Lys Gln Trp Ser
            260                 265                 270

Glu Ala Ala Gln Ser Ile Gly Leu Asp Leu Lys Pro Leu Val Asp Arg
        275                 280                 285

Ala Arg Thr Lys Ala Leu Gly Gln Gly Met Glu Ala Thr Arg Ile Gly
    290                 295                 300

Ser Leu Val Glu Arg Gly Arg Ala Trp Leu Ser Arg Phe Ala Ala His
305                 310                 315                 320

Val Arg Gly Asp Pro Ala Asp Pro Leu Val Pro Ser Val Leu Lys
                325                 330                 335

Gln Asp Arg Gln Thr Ile Ala Ala Ala Gln Ala Val Ala Ser Ala Val
            340                 345                 350
```

```
Arg His Leu Ser Gln Arg Glu Ala Ala Phe Glu Arg Thr Ala Leu Tyr
            355                 360                 365

Lys Ala Ala Leu Asp Phe Gly Leu Pro Thr Thr Ile Ala Asp Val Glu
370                 375                 380

Lys Arg Thr Arg Ala Leu Val Arg Ser Gly Asp Leu Ile Ala Gly Lys
385                 390                 395                 400

Gly Glu His Lys Gly Trp Leu Ala Ser Arg Asp Ala Val Val Thr Glu
            405                 410                 415

Gln Arg Ile Leu Ser Glu Val Ala Ala Gly Lys Gly Asp Ser Ser Pro
            420                 425                 430

Ala Ile Thr Pro Gln Lys Ala Ala Ser Val Gln Ala Ala Leu
            435                 440                 445

Thr Gly Gln Gly Phe Arg Leu Asn Glu Gly Gln Leu Ala Ala Ala Arg
            450                 455                 460

Leu Ile Leu Ile Ser Lys Asp Arg Thr Ile Ala Val Gln Gly Ile Ala
465                 470                 475                 480

Gly Ala Gly Lys Ser Ser Val Leu Lys Pro Val Ala Glu Val Leu Arg
            485                 490                 495

Asp Glu Gly His Pro Val Ile Gly Leu Ala Ile Gln Asn Thr Leu Val
            500                 505                 510

Gln Met Leu Glu Arg Asp Thr Gly Ile Gly Ser Gln Thr Leu Ala Arg
            515                 520                 525

Phe Leu Gly Gly Trp Asn Lys Leu Leu Asp Asp Pro Gly Asn Val Ala
            530                 535                 540

Leu Arg Ala Glu Ala Gln Ala Ser Leu Lys Asp His Val Leu Val Leu
545                 550                 555                 560

Asp Glu Ala Ser Met Val Ser Asn Glu Asp Lys Glu Lys Leu Val Arg
            565                 570                 575

Leu Ala Asn Leu Ala Gly Val His Arg Leu Val Leu Ile Gly Asp Arg
            580                 585                 590

Lys Gln Leu Gly Ala Val Asp Ala Gly Lys Pro Phe Ala Leu Leu Gln
            595                 600                 605

Arg Ala Gly Ile Ala Arg Ala Glu Met Ala Thr Asn Leu Arg Ala Arg
            610                 615                 620

Asp Pro Val Val Arg Glu Ala Gln Ala Ala Gln Ala Gly Asp Val
625                 630                 635                 640

Arg Lys Ala Leu Arg His Leu Lys Ser His Thr Val Glu Ala Arg Gly
            645                 650                 655

Asp Gly Ala Gln Val Ala Ala Glu Thr Trp Leu Ala Leu Asp Lys Glu
            660                 665                 670

Thr Arg Ala Arg Thr Ser Ile Tyr Ala Ser Gly Arg Ala Ile Arg Ser
            675                 680                 685

Ala Val Asn Ala Ala Val Gln Gln Gly Leu Leu Ala Ser Arg Glu Ile
            690                 695                 700

Gly Pro Ala Lys Met Lys Leu Glu Val Leu Asp Arg Val Asn Thr Thr
705                 710                 715                 720

Arg Glu Glu Leu Arg His Leu Pro Ala Tyr Arg Ala Gly Arg Val Leu
            725                 730                 735

Glu Val Ser Arg Lys Gln Gln Ala Leu Gly Leu Phe Ile Gly Glu Tyr
            740                 745                 750

Arg Val Ile Gly Gln Asp Arg Lys Gly Lys Leu Val Glu Val Glu Asp
            755                 760                 765
```

```
Lys Arg Gly Lys Arg Phe Arg Phe Asp Pro Ala Arg Ile Arg Ala Gly
770                 775                 780
Lys Gly Asp Asp Asn Leu Thr Leu Leu Glu Pro Arg Lys Leu Glu Ile
785                 790                 795                 800
His Glu Gly Asp Arg Ile Arg Trp Thr Arg Asn Asp His Arg Arg Gly
                805                 810                 815
Leu Phe Asn Ala Asp Gln Ala Arg Val Val Glu Ile Ala Asn Gly Lys
            820                 825                 830
Val Thr Phe Glu Thr Ser Lys Gly Asp Leu Val Glu Leu Lys Lys Asp
        835                 840                 845
Asp Pro Met Leu Lys Arg Ile Asp Leu Ala Tyr Ala Leu Asn Val His
    850                 855                 860
Met Ala Gln Gly Leu Thr Ser Asp Arg Gly Ile Ala Val Met Asp Ser
865                 870                 875                 880
Arg Glu Arg Asn Leu Ser Asn Gln Lys Thr Phe Leu Val Thr Val Thr
                885                 890                 895
Arg Leu Arg Asp His Leu Thr Leu Val Val Asp Ser Ala Asp Lys Leu
            900                 905                 910
Gly Ala Ala Val Ala Arg Asn Lys Gly Glu Lys Ala Ser Ala Ile Glu
        915                 920                 925
Val Thr Gly Ser Val Lys Pro Thr Ala Thr Lys Gly Ser Gly Val Asp
    930                 935                 940
Gln Pro Lys Ser Val Glu Ala Asn Lys Ala Glu Lys Glu Leu Thr Arg
945                 950                 955                 960
Ser Lys Ser Lys Thr Leu Asp Phe Gly Ile
                965                 970

<210> SEQ ID NO 18
<211> LENGTH: 55
<212> TYPE: DNA
<213> ORGANISM: Artificial Sequence
<220> FEATURE:
<223> OTHER INFORMATION: Polynucleotide sequence used in Example 3
<220> FEATURE:
<221> NAME/KEY: modified_base
<222> LOCATION: (1)..(5)
<223> OTHER INFORMATION: n is I

<400> SEQUENCE: 18
nnnnntgaag cggcgcacga aaacgcgaaa gcgtttcac gataaatgcg aaaac         55

<210> SEQ ID NO 19
<211> LENGTH: 54
<212> TYPE: DNA
<213> ORGANISM: Artificial Sequence
<220> FEATURE:
<223> OTHER INFORMATION: Polynucleotide sequence used in Example 2

<400> SEQUENCE: 19
gatcugaagc ggcgcacgaa aaacgcgaaa gcgtttcacg ataaatgcga aaac          54

<210> SEQ ID NO 20
<211> LENGTH: 49
<212> TYPE: DNA
<213> ORGANISM: Artificial Sequence
<220> FEATURE:
<223> OTHER INFORMATION: Polynucleotide sequence used in Example 2

<400> SEQUENCE: 20
gaagcggcgc acgaaaaacg cgaaagcgtt tcacgataaa tgcgaaaac               49
```

<210> SEQ ID NO 21

<400> SEQUENCE: 21

000

<210> SEQ ID NO 22

<400> SEQUENCE: 22

000

<210> SEQ ID NO 23
<211> LENGTH: 73
<212> TYPE: DNA
<213> ORGANISM: Artificial Sequence
<220> FEATURE:
<223> OTHER INFORMATION: Polynucleotide sequence used in Example 4

<400> SEQUENCE: 23
tttttttttt tttttttttt tttttttttt tttttttttt tttttggtt gtttctgttg    60 gtgctgatat tgc                                                        73

<210> SEQ ID NO 24
<211> LENGTH: 606
<212> TYPE: DNA
<213> ORGANISM: Artificial Sequence
<220> FEATURE:
<223> OTHER INFORMATION: Polynucelotide sequence used in Example 9

<400> SEQUENCE: 24
gccatcagat tgtgtttgtt agtcgctttt ttttttggga attttttttt tggaatttt     60 tttttgacgc tcagtaatgt gacgatagct gaaaactgta cgataaacgg tacgctgagg    120
gcggaaaaaa tcgtcgggga cattgtaaag gcggcgagcg cggcttttcc gcgccagcgt    180
gaaagcagtg tggactggcc gtcaggtacc cgtactgtca ccgtgaccga tgaccatcct    240
tttgatcgcc agatagtggt gcttccgctg acgtttcgcg gaagtaagcg tactgtcagc    300
ggcaggacaa cgtattcgat gtgttatctg aaagtactga tgaacggtgc ggtgatttat    360
gatggcgcgg cgaacgaggc ggtacaggtg ttctcccgta ttgttgacat gccagcgggt    420
cggggaaacg tgatcctgac gttcacgctt acgtccacac ggcattcggc agatattccg    480
ccgtatacgt ttgccagcga tgtgcaggtt atggtgatta agaaacaggc gctgggcatc    540
agcgtggtct gagtgtgaaa aaaaaggtac caaaaaaaac atcgtcgtga gtagtgaacc    600
gtaagc                                                                606

<210> SEQ ID NO 25
<211> LENGTH: 60
<212> TYPE: DNA
<213> ORGANISM: Artificial Sequence
<220> FEATURE:
<223> OTHER INFORMATION: Polynucleotide sequence used in Example 5

<400> SEQUENCE: 25
ctattctgtt tatgtttctt gtttgttagc cctattctgt cccccccccc acccccccc     60

<210> SEQ ID NO 26
<211> LENGTH: 40
<212> TYPE: DNA
<213> ORGANISM: Artificial Sequence
<220> FEATURE:
<223> OTHER INFORMATION: Polynucleotide sequence used in Examples 5 and

6

<400> SEQUENCE: 26
acagaatagg gctaacaaac aagaaacata aacagaatag                                    40

<210> SEQ ID NO 27
<211> LENGTH: 40
<212> TYPE: DNA
<213> ORGANISM: Artificial Sequence
<220> FEATURE:
<223> OTHER INFORMATION: Polynucleotide sequence used in Examples 5 and
      6

<400> SEQUENCE: 27
ctattctgtt tatgtttctt gtttgttagc cctattctgt                                    40

<210> SEQ ID NO 28
<211> LENGTH: 760
<212> TYPE: PRT
<213> ORGANISM: Methanococcoides burtonii

<400> SEQUENCE: 28

Met Met Ile Arg Glu Leu Asp Ile Pro Arg Asp Ile Ile Gly Phe Tyr
 1               5                  10                  15

Glu Asp Ser Gly Ile Lys Glu Leu Tyr Pro Pro Gln Ala Glu Ala Ile
             20                  25                  30

Glu Met Gly Leu Leu Glu Lys Lys Asn Leu Leu Ala Ala Ile Pro Thr
         35                  40                  45

Ala Ser Gly Lys Thr Leu Leu Ala Glu Leu Ala Met Ile Lys Ala Ile
     50                  55                  60

Arg Glu Gly Gly Lys Ala Leu Tyr Ile Val Pro Leu Arg Ala Leu Ala
 65                  70                  75                  80

Ser Glu Lys Phe Glu Arg Phe Lys Glu Leu Ala Pro Phe Gly Ile Lys
                 85                  90                  95

Val Gly Ile Ser Thr Gly Asp Leu Asp Ser Arg Ala Asp Trp Leu Gly
            100                 105                 110

Val Asn Asp Ile Ile Val Ala Thr Ser Glu Lys Thr Asp Ser Leu Leu
        115                 120                 125

Arg Asn Gly Thr Ser Trp Met Asp Glu Ile Thr Thr Val Val Val Asp
    130                 135                 140

Glu Ile His Leu Leu Asp Ser Lys Asn Arg Gly Pro Thr Leu Glu Val
145                 150                 155                 160

Thr Ile Thr Lys Leu Met Arg Leu Asn Pro Asp Val Gln Val Val Ala
                165                 170                 175

Leu Ser Ala Thr Val Gly Asn Ala Arg Glu Met Ala Asp Trp Leu Gly
            180                 185                 190

Ala Ala Leu Val Leu Ser Glu Trp Arg Pro Thr Asp Leu His Glu Gly
        195                 200                 205

Val Leu Phe Gly Asp Ala Ile Asn Phe Pro Gly Ser Gln Lys Lys Ile
    210                 215                 220

Asp Arg Leu Glu Lys Asp Asp Ala Val Asn Leu Val Leu Asp Thr Ile
225                 230                 235                 240

Lys Ala Glu Gly Gln Cys Leu Val Phe Glu Ser Ser Arg Arg Asn Cys
                245                 250                 255

Ala Gly Phe Ala Lys Thr Ala Ser Ser Lys Val Ala Lys Ile Leu Asp
            260                 265                 270

Asn Asp Ile Met Ile Lys Leu Ala Gly Ile Ala Glu Glu Val Glu Ser

```
            275                 280                 285
Thr Gly Glu Thr Asp Thr Ala Ile Val Leu Ala Asn Cys Ile Arg Lys
    290                 295                 300
Gly Val Ala Phe His His Ala Gly Leu Asn Ser Asn His Arg Lys Leu
305                 310                 315                 320
Val Glu Asn Gly Phe Arg Gln Asn Leu Ile Lys Val Ile Ser Ser Thr
                325                 330                 335
Pro Thr Leu Ala Ala Gly Leu Asn Leu Pro Ala Arg Arg Val Ile Ile
                340                 345                 350
Arg Ser Tyr Arg Arg Phe Asp Ser Asn Phe Gly Met Gln Pro Ile Pro
                355                 360                 365
Val Leu Glu Tyr Lys Gln Met Ala Gly Arg Ala Gly Arg Pro His Leu
    370                 375                 380
Asp Pro Tyr Gly Glu Ser Val Leu Leu Ala Lys Thr Tyr Asp Glu Phe
385                 390                 395                 400
Ala Gln Leu Met Glu Asn Tyr Val Glu Ala Asp Ala Glu Asp Ile Trp
                405                 410                 415
Ser Lys Leu Gly Thr Glu Asn Ala Leu Arg Thr His Val Leu Ser Thr
                420                 425                 430
Ile Val Asn Gly Phe Ala Ser Thr Arg Gln Glu Leu Phe Asp Phe Phe
                435                 440                 445
Gly Ala Thr Phe Phe Ala Tyr Gln Gln Asp Lys Trp Met Leu Glu Glu
    450                 455                 460
Val Ile Asn Asp Cys Leu Glu Phe Leu Ile Asp Lys Ala Met Val Ser
465                 470                 475                 480
Glu Thr Glu Asp Ile Glu Asp Ala Ser Lys Leu Phe Leu Arg Gly Thr
                485                 490                 495
Arg Leu Gly Ser Leu Val Ser Met Leu Tyr Ile Asp Pro Leu Ser Gly
                500                 505                 510
Ser Lys Ile Val Asp Gly Phe Lys Asp Ile Gly Lys Ser Thr Gly Gly
                515                 520                 525
Asn Met Gly Ser Leu Glu Asp Asp Lys Gly Asp Asp Ile Thr Val Thr
    530                 535                 540
Asp Met Thr Leu Leu His Leu Val Cys Ser Thr Pro Asp Met Arg Gln
545                 550                 555                 560
Leu Tyr Leu Arg Asn Thr Asp Tyr Thr Ile Val Asn Glu Tyr Ile Val
                565                 570                 575
Ala His Ser Asp Glu Phe His Glu Ile Pro Asp Lys Leu Lys Glu Thr
                580                 585                 590
Asp Tyr Glu Trp Phe Met Gly Glu Val Lys Thr Ala Met Leu Leu Glu
                595                 600                 605
Glu Trp Val Thr Glu Val Ser Ala Glu Asp Ile Thr Arg His Phe Asn
    610                 615                 620
Val Gly Glu Gly Asp Ile His Ala Leu Ala Asp Thr Ser Glu Trp Leu
625                 630                 635                 640
Met His Ala Ala Ala Lys Leu Ala Glu Leu Leu Gly Val Glu Tyr Ser
                645                 650                 655
Ser His Ala Tyr Ser Leu Glu Lys Arg Ile Arg Tyr Gly Ser Gly Leu
                660                 665                 670
Asp Leu Met Glu Leu Val Gly Ile Arg Gly Val Gly Arg Val Arg Ala
                675                 680                 685
Arg Lys Leu Tyr Asn Ala Gly Phe Val Ser Val Ala Lys Leu Lys Gly
    690                 695                 700
```

```
Ala Asp Ile Ser Val Leu Ser Lys Leu Val Gly Pro Lys Val Ala Tyr
705                 710                 715                 720

Asn Ile Leu Ser Gly Ile Gly Val Arg Val Asn Asp Lys His Phe Asn
            725                 730                 735

Ser Ala Pro Ile Ser Ser Asn Thr Leu Asp Thr Leu Leu Asp Lys Asn
        740                 745                 750

Gln Lys Thr Phe Asn Asp Phe Gln
    755                 760
```

```
<210> SEQ ID NO 29
<211> LENGTH: 20
<212> TYPE: DNA
<213> ORGANISM: Artificial Sequence
<220> FEATURE:
<223> OTHER INFORMATION: Polynucleotide sequence used in Example 5

<400> SEQUENCE: 29
cccccccccc acccccccccc                                                  20

<210> SEQ ID NO 30
<211> LENGTH: 19
<212> TYPE: DNA
<213> ORGANISM: Artificial Sequence
<220> FEATURE:
<223> OTHER INFORMATION: Polynucleotide sequence used in Example 6

<400> SEQUENCE: 30
ccccccccca ccccccccc                                                    19

<210> SEQ ID NO 31
<211> LENGTH: 16
<212> TYPE: DNA
<213> ORGANISM: Artificial Sequence
<220> FEATURE:
<223> OTHER INFORMATION: Polynucleotide sequence used in Example 6

<400> SEQUENCE: 31
ccccccaccc cccccc                                                       16

<210> SEQ ID NO 32
<211> LENGTH: 80
<212> TYPE: DNA
<213> ORGANISM: Artificial Sequence
<220> FEATURE:
<223> OTHER INFORMATION: Polynucleotide sequence used in Example 6

<400> SEQUENCE: 32
ctattctgtt tatgtttctt gtttgttagc cctattctgt cccccccccc acccccccc        60 accccccccc accccccccc                                                   80

<210> SEQ ID NO 33
<211> LENGTH: 50
<212> TYPE: DNA
<213> ORGANISM: Artificial Sequence
<220> FEATURE:
<223> OTHER INFORMATION: Polynucleotide sequence used in Example 6

<400> SEQUENCE: 33
ctattctgtt tatgtttctt gtttgttagc cctattctgt cccccccccc                  50

<210> SEQ ID NO 34
<211> LENGTH: 83
<212> TYPE: DNA
```

```
<213> ORGANISM: Artificial Sequence
<220> FEATURE:
<223> OTHER INFORMATION: Polynucleotide sequence used in Example 7

<400> SEQUENCE: 34
tttttttttt tttttttttt tttttttttt tttttttttt tttttttttt tcgctgctcc      60
acaggtctca gcttgagcag cga                                              83

<210> SEQ ID NO 35
<211> LENGTH: 33
<212> TYPE: DNA
<213> ORGANISM: Artificial Sequence
<220> FEATURE:
<223> OTHER INFORMATION: Polynucleotide sequence used in Examples 7 and
      8

<400> SEQUENCE: 35
tcgctgctca agctgagacc tgtggagcag cga                                   33

<210> SEQ ID NO 36
<211> LENGTH: 33
<212> TYPE: DNA
<213> ORGANISM: Artificial Sequence
<220> FEATURE:
<223> OTHER INFORMATION: Polynucleotide sequence used in Examples 7 and
      8

<400> SEQUENCE: 36
tcgctgctcc acaggtctca gcttgagcag cga                                   33

<210> SEQ ID NO 37
<211> LENGTH: 10
<212> TYPE: DNA
<213> ORGANISM: Artificial Sequence
<220> FEATURE:
<223> OTHER INFORMATION: Polynucleotide sequence used in Examples 7, 8
      and 9

<400> SEQUENCE: 37
tttttttttt                                                             10

<210> SEQ ID NO 38
<211> LENGTH: 20
<212> TYPE: DNA
<213> ORGANISM: Artificial Sequence
<220> FEATURE:
<223> OTHER INFORMATION: Polynucleotide sequence used in Examples 8 and
      10

<400> SEQUENCE: 38
tttttttttt tttttttttt                                                  20

<210> SEQ ID NO 39
<211> LENGTH: 16
<212> TYPE: DNA
<213> ORGANISM: Artificial Sequence
<220> FEATURE:
<223> OTHER INFORMATION: Polynucleotide sequence used in Example 8

<400> SEQUENCE: 39
tttttttttt tttttt                                                      16

<210> SEQ ID NO 40
<211> LENGTH: 18
<212> TYPE: DNA
<213> ORGANISM: Artificial Sequence
```

```
<220> FEATURE:
<223> OTHER INFORMATION: Polynucleotide sequence used in Example 8

<400> SEQUENCE: 40
tttttttttt ttttttt                                                          18

<210> SEQ ID NO 41
<211> LENGTH: 27
<212> TYPE: DNA
<213> ORGANISM: Artificial Sequence
<220> FEATURE:
<223> OTHER INFORMATION: Polynucleotide sequence used in Example 9

<400> SEQUENCE: 41
gccatcagat tgtgtttgtt agtcgct                                               27

<210> SEQ ID NO 42
<211> LENGTH: 27
<212> TYPE: DNA
<213> ORGANISM: Artificial Sequence
<220> FEATURE:
<223> OTHER INFORMATION: Polynucleotide sequence used in Example 9

<400> SEQUENCE: 42
gcaatatcag caccaacaga aacaacc                                               27

<210> SEQ ID NO 43
<211> LENGTH: 27
<212> TYPE: DNA
<213> ORGANISM: Artificial Sequence
<220> FEATURE:
<223> OTHER INFORMATION: Polynucleotide sequence used in Example 9

<400> SEQUENCE: 43
agcgactaac aaacacaatc tgatggc                                               27
```

UNITED STATES PATENT AND TRADEMARK OFFICE
CERTIFICATE OF CORRECTION

| | |
|---|---|
| PATENT NO. | : 10,221,450 B2 |
| APPLICATION NO. | : 14/773164 |
| DATED | : March 5, 2019 |
| INVENTOR(S) | : Andrew John Heron et al. |

It is certified that error appears in the above-identified patent and that said Letters Patent is hereby corrected as shown below:

In the Claims
At Column 211, Claim 2, Line 54:
"A method of comprising:"
Should read:
—A method comprising:—

Signed and Sealed this
Seventh Day of May, 2019

Andrei Iancu
*Director of the United States Patent and Trademark Office*